United States Patent
Ampolini et al.

(10) Patent No.: US 9,833,019 B2
(45) Date of Patent: Dec. 5, 2017

(54) METHOD FOR ASSEMBLING A CARTRIDGE FOR A SMOKING ARTICLE

(71) Applicant: R.J. Reynolds Tobacco Company, Winston-Salem, NC (US)

(72) Inventors: Frederic Philippe Ampolini, Winston-Salem, NC (US); Timothy Brian Nestor, Advance, NC (US); Jack Gray Flinchum, Jr., Clemmons, NC (US); Wayne Douglas Brown, Walnut Cove, NC (US); Nicholas Harrison Watson, Westfield, NC (US); Charles Jacob Novak, III, Winston-Salem, NC (US); Paul A. Brinkley, Winston-Salem, NC (US); James Robert Covino, Haverhill, MA (US); John DePiano, Burlington, MA (US); Edward Louis Dickinson, Leicester, MA (US); Eugene R. Harris, Groton, MA (US); Kevin Edward Keough, Canton, MA (US); David Jay Smith, Needham, MA (US); John Hook, Temple, NH (US); Michael LaCourse, Manchester, NH (US); Robert Metcalf, Peterborough, NH (US); Steven Hart, Acton, MA (US); David Pelletier, Chelmsford, MA (US); Marc Bourque, Weare, NH (US); Nathaniel Cambray, Litchfield, NH (US); John William Wolber, Nashua, NH (US); James William McClellan, Hollis, NH (US); Steven R. Mongillo, Oneonta, NY (US); Frank S. Silveira, Wilmington, MA (US); Michael Laine, Newburyport, MA (US); Quentin Paul Guenther, Jr., Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 679 days.

(21) Appl. No.: 14/227,159

(22) Filed: Mar. 27, 2014

(65) Prior Publication Data
US 2015/0223522 A1    Aug. 13, 2015

Related U.S. Application Data

(60) Provisional application No. 61/939,446, filed on Feb. 13, 2014.

(51) Int. Cl.
A24F 47/00     (2006.01)
B23P 11/00     (2006.01)
(Continued)

(52) U.S. Cl.
CPC ........... *A24F 47/008* (2013.01); *A61M 15/06* (2013.01); *B23P 11/005* (2013.01); *B23P 19/04* (2013.01);
(Continued)

(58) Field of Classification Search
CPC . A24F 47/008; A61M 15/06; A61M 2207/00; A61M 2207/10;
(Continued)

(56) References Cited

U.S. PATENT DOCUMENTS

| | | | |
|---|---|---|---|
| 1,771,366 A | 7/1930 | Wyss et al. | |
| 2,057,353 A | 10/1936 | Whittemore, Jr. | |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

Invitation to Pay Additional Fees and Results of the Partial International Search for corresponding International Application No. PCT/US2015/015878 dated May 13, 2015.

(Continued)

*Primary Examiner* — Christopher Belser
*Assistant Examiner* — Matthew P Travers
(74) *Attorney, Agent, or Firm* — Womble Bond Dickinson (US) LLP

(57) ABSTRACT

The present disclosure relates to systems, apparatuses, and methods for assembling cartridges for aerosol delivery devices. The cartridges may be assembled by transporting (Continued)

carriages between various substations at which parts are added to a base. In another assembly method, the base may be moved between a plurality of robots which direct the base downwardly into contact with components to couple the components therewith. An inspection system may inspect the cartridges at various stages of completion.

6 Claims, 94 Drawing Sheets

(51) Int. Cl.
   *B23P 19/04* (2006.01)
   *A61M 15/06* (2006.01)
   *G01R 31/02* (2006.01)
   *B61B 13/04* (2006.01)
   *A24C 5/34* (2006.01)

(52) U.S. Cl.
   CPC ............ *B61B 13/04* (2013.01); *G01R 31/025* (2013.01); *A24C 5/34* (2013.01); *A61M 2207/00* (2013.01); *A61M 2207/10* (2013.01); *Y10T 29/49913* (2015.01)

(58) Field of Classification Search
   CPC ......... B23P 11/005–11/02; B23P 19/02; B23P 19/04; B23P 19/12; Y10T 29/49913
   See application file for complete search history.

(56) References Cited

U.S. PATENT DOCUMENTS

| | | |
|---|---|---|
| 2,104,266 A | 1/1938 | McCormick |
| 2,805,669 A | 9/1957 | Meriro |
| 3,200,819 A | 8/1965 | Gilbert |
| 3,316,919 A | 5/1967 | Green et al. |
| 3,398,754 A | 8/1968 | Tughan |
| 3,419,015 A | 12/1968 | Wochnowski |
| 3,424,171 A | 1/1969 | Rooker |
| 3,476,118 A | 11/1969 | Luttich |
| 4,054,145 A | 10/1977 | Berndt et al. |
| 4,131,117 A | 12/1978 | Kite et al. |
| 4,150,677 A | 4/1979 | Osborne |
| 4,190,046 A | 2/1980 | Virag |
| 4,219,032 A | 8/1980 | Tabatznik et al. |
| 4,259,970 A | 4/1981 | Green, Jr. |
| 4,284,089 A | 8/1981 | Ray |
| 4,303,083 A | 12/1981 | Burruss, Jr. |
| 4,449,541 A | 5/1984 | Mays et al. |
| 4,506,682 A | 3/1985 | Muller |
| 4,635,651 A | 1/1987 | Jacobs |
| 4,674,519 A | 6/1987 | Keritsis et al. |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,776,353 A | 10/1988 | Lilja et al. |
| 4,793,365 A | 12/1988 | Sensabaugh, Jr. et al. |
| 4,800,903 A | 1/1989 | Ray et al. |
| 4,819,665 A | 4/1989 | Roberts et al. |
| 4,821,749 A | 4/1989 | Toft et al. |
| 4,830,028 A | 5/1989 | Lawson et al. |
| 4,836,224 A | 6/1989 | Lawson et al. |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,880,018 A | 11/1989 | Graves, Jr. et al. |
| 4,887,619 A | 12/1989 | Burcham, Jr. et al. |
| 4,907,606 A | 3/1990 | Lilja et al. |
| 4,913,168 A | 4/1990 | Potter et al. |
| 4,917,119 A | 4/1990 | Potter et al. |
| 4,917,128 A | 4/1990 | Clearman et al. |
| 4,922,901 A | 5/1990 | Brooks et al. |
| 4,924,888 A | 5/1990 | Perfetti et al. |
| 4,928,714 A | 5/1990 | Shannon |
| 4,938,236 A | 7/1990 | Banerjee et al. |
| 4,941,483 A | 7/1990 | Ridings et al. |
| 4,941,484 A | 7/1990 | Clapp et al. |
| 4,945,931 A | 8/1990 | Gori |
| 4,947,874 A | 8/1990 | Brooks et al. |
| 4,947,875 A | 8/1990 | Brooks et al. |
| 4,972,854 A | 11/1990 | Kiernan et al. |
| 4,972,855 A | 11/1990 | Kuriyama et al. |
| 4,986,286 A | 1/1991 | Roberts et al. |
| 4,987,906 A | 1/1991 | Young et al. |
| 5,005,593 A | 4/1991 | Fagg |
| 5,019,122 A | 5/1991 | Clearman et al. |
| 5,022,416 A | 6/1991 | Watson |
| 5,042,510 A | 8/1991 | Curtiss et al. |
| 5,056,537 A | 10/1991 | Brown et al. |
| 5,060,669 A | 10/1991 | White et al. |
| 5,060,671 A | 10/1991 | Counts et al. |
| 5,065,775 A | 11/1991 | Fagg |
| 5,072,744 A | 12/1991 | Luke et al. |
| 5,074,319 A | 12/1991 | White et al. |
| 5,076,296 A | 12/1991 | Nystrom et al. |
| 5,093,894 A | 3/1992 | Deevi et al. |
| 5,095,921 A | 3/1992 | Losee et al. |
| 5,097,850 A | 3/1992 | Braunshteyn et al. |
| 5,099,862 A | 3/1992 | White et al. |
| 5,099,864 A | 3/1992 | Young et al. |
| 5,101,839 A | 4/1992 | Jakob et al. |
| 5,103,842 A | 4/1992 | Strang et al. |
| 5,121,757 A | 6/1992 | White et al. |
| 5,129,409 A | 7/1992 | White et al. |
| 5,131,415 A | 7/1992 | Munoz et al. |
| 5,143,097 A | 9/1992 | Sohn et al. |
| 5,144,962 A | 9/1992 | Counts et al. |
| 5,146,934 A | 9/1992 | Deevi et al. |
| 5,154,192 A | 10/1992 | Sprinkel et al. |
| 5,159,940 A | 11/1992 | Hayward et al. |
| 5,159,942 A | 11/1992 | Brinkley et al. |
| 5,179,966 A | 1/1993 | Losee et al. |
| 5,211,684 A | 5/1993 | Shannon et al. |
| 5,220,930 A | 6/1993 | Gentry |
| 5,224,498 A | 7/1993 | Deevi et al. |
| 5,228,460 A | 7/1993 | Sprinkel, Jr. et al. |
| 5,230,354 A | 7/1993 | Smith et al. |
| 5,235,992 A | 8/1993 | Sensabaugh |
| 5,243,999 A | 9/1993 | Smith |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,293,883 A | 3/1994 | Edwards |
| 5,301,694 A | 4/1994 | Raymond |
| 5,303,720 A | 4/1994 | Banerjee et al. |
| 5,318,050 A | 6/1994 | Gonzalez-Parra et al. |
| 5,322,075 A | 6/1994 | Deevi et al. |
| 5,322,076 A | 6/1994 | Brinkley et al. |
| 5,339,838 A | 8/1994 | Young et al. |
| 5,345,951 A | 9/1994 | Serrano et al. |
| 5,353,813 A | 10/1994 | Deevi et al. |
| 5,357,984 A | 10/1994 | Farrier et al. |
| 5,360,023 A | 11/1994 | Blakley et al. |
| 5,369,723 A | 11/1994 | Counts et al. |
| 5,372,148 A | 12/1994 | McCafferty et al. |
| 5,377,698 A | 1/1995 | Litzinger et al. |
| 5,388,574 A | 2/1995 | Ingebrethsen et al. |
| 5,388,594 A | 2/1995 | Counts et al. |
| 5,408,574 A | 4/1995 | Deevi et al. |
| 5,435,325 A | 7/1995 | Clapp et al. |
| 5,445,169 A | 8/1995 | Brinkley et al. |
| 5,468,266 A | 11/1995 | Bensalem et al. |
| 5,468,936 A | 11/1995 | Deevi et al. |
| 5,479,948 A | 1/1996 | Counts et al. |
| 5,498,850 A | 3/1996 | Das |
| 5,498,855 A | 3/1996 | Deevi et al. |
| 5,499,636 A | 3/1996 | Baggett, Jr. et al. |
| 5,501,237 A | 3/1996 | Young et al. |

(56) References Cited

U.S. PATENT DOCUMENTS

| | | | |
|---|---|---|---|
| 5,505,214 | A * | 4/1996 | Collins ................. A24F 47/008 128/202.21 |
| 5,515,842 | A | 5/1996 | Ramseyer et al. |
| 5,530,225 | A | 6/1996 | Hajaligol |
| 5,551,450 | A | 9/1996 | Hemsley |
| 5,551,451 | A | 9/1996 | Riggs et al. |
| 5,564,442 | A | 10/1996 | MacDonald et al. |
| 5,573,692 | A | 11/1996 | Das et al. |
| 5,591,368 | A | 1/1997 | Fleischhauer et al. |
| 5,593,792 | A | 1/1997 | Farrier et al. |
| 5,595,577 | A | 1/1997 | Bensalem et al. |
| 5,596,706 | A | 1/1997 | Sikk et al. |
| 5,611,360 | A | 3/1997 | Tang |
| 5,613,504 | A | 3/1997 | Collins et al. |
| 5,613,505 | A | 3/1997 | Campbell et al. |
| 5,649,552 | A | 7/1997 | Cho et al. |
| 5,649,554 | A | 7/1997 | Sprinkel et al. |
| 5,659,656 | A | 8/1997 | Das |
| 5,665,262 | A | 9/1997 | Hajaligol et al. |
| 5,666,976 | A | 9/1997 | Adams et al. |
| 5,666,977 | A | 9/1997 | Higgins et al. |
| 5,666,978 | A | 9/1997 | Counts et al. |
| 5,687,746 | A | 11/1997 | Rose et al. |
| 5,692,525 | A | 12/1997 | Counts et al. |
| 5,692,526 | A | 12/1997 | Adams et al. |
| 5,708,258 | A | 1/1998 | Counts et al. |
| 5,711,320 | A | 1/1998 | Martin |
| 5,726,421 | A | 3/1998 | Fleischhauer et al. |
| 5,727,571 | A | 3/1998 | Meiring et al. |
| 5,730,158 | A | 3/1998 | Collins et al. |
| 5,750,964 | A | 5/1998 | Counts et al. |
| 5,799,663 | A | 9/1998 | Gross et al. |
| 5,816,263 | A | 10/1998 | Counts et al. |
| 5,819,756 | A | 10/1998 | Mielordt |
| 5,829,453 | A | 11/1998 | White et al. |
| 5,865,185 | A | 2/1999 | Collins et al. |
| 5,865,186 | A | 2/1999 | Volsey, II |
| 5,878,752 | A | 3/1999 | Adams et al. |
| 5,880,439 | A | 3/1999 | Deevi et al. |
| 5,894,841 | A | 4/1999 | Voges |
| 5,901,444 | A * | 5/1999 | Bove ....................... B23P 19/04 29/447 |
| 5,902,431 | A * | 5/1999 | Wilkinson ................ A24C 5/20 156/159 |
| 5,915,387 | A | 6/1999 | Baggett, Jr. et al. |
| 5,934,289 | A | 8/1999 | Watkins et al. |
| 5,954,979 | A | 9/1999 | Counts et al. |
| 5,967,148 | A | 10/1999 | Harris et al. |
| 6,026,820 | A | 2/2000 | Baggett, Jr. et al. |
| 6,033,623 | A | 3/2000 | Deevi et al. |
| 6,040,560 | A | 3/2000 | Fleischhauer et al. |
| 6,053,176 | A | 4/2000 | Adams et al. |
| 6,089,857 | A | 7/2000 | Matsuura et al. |
| 6,095,153 | A | 8/2000 | Kessler et al. |
| 6,116,247 | A | 9/2000 | Banyasz et al. |
| 6,119,700 | A | 9/2000 | Fleischhauer et al. |
| 6,125,853 | A | 10/2000 | Susa et al. |
| 6,125,855 | A | 10/2000 | Nevett et al. |
| 6,125,866 | A | 10/2000 | Nichols et al. |
| 6,155,268 | A | 12/2000 | Takeuchi |
| 6,164,287 | A | 12/2000 | White |
| 6,182,670 | B1 | 2/2001 | White |
| 6,196,218 | B1 | 3/2001 | Voges |
| 6,196,219 | B1 | 3/2001 | Hess et al. |
| 6,216,706 | B1 | 4/2001 | Kumar et al. |
| 6,289,898 | B1 | 9/2001 | Fournier et al. |
| 6,349,728 | B1 | 2/2002 | Pham |
| 6,357,671 | B1 | 3/2002 | Cewers |
| 6,418,938 | B1 | 7/2002 | Fleischhauer et al. |
| 6,446,426 | B1 | 9/2002 | Sweeney et al. |
| 6,532,965 | B1 | 3/2003 | Abhulimen et al. |
| 6,598,607 | B2 | 7/2003 | Adiga et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,701,936 | B2 | 3/2004 | Shafer et al. |
| 6,715,494 | B1 | 4/2004 | McCoy |
| 6,730,832 | B1 | 5/2004 | Dominguez et al. |
| 6,772,756 | B2 | 8/2004 | Shayan |
| 6,803,545 | B2 | 10/2004 | Blake et al. |
| 6,803,550 | B2 | 10/2004 | Sharpe et al. |
| 6,810,883 | B2 | 11/2004 | Felter et al. |
| 6,854,461 | B2 | 2/2005 | Nichols |
| 6,854,470 | B1 | 2/2005 | Pu |
| 6,994,096 | B2 | 2/2006 | Rostami et al. |
| 7,011,096 | B2 | 3/2006 | Li et al. |
| 7,017,585 | B2 | 3/2006 | Li et al. |
| 7,025,066 | B2 | 4/2006 | Lawson et al. |
| 7,040,314 | B2 | 5/2006 | Nguyen et al. |
| 7,117,867 | B2 | 10/2006 | Cox et al. |
| 7,163,015 | B2 | 1/2007 | Moffitt |
| 7,173,222 | B2 | 2/2007 | Cox et al. |
| 7,185,659 | B2 | 3/2007 | Sharpe et al. |
| 7,234,470 | B2 | 6/2007 | Yang |
| 7,234,471 | B2 * | 6/2007 | Fitzgerald ................ A24D 1/02 131/365 |
| 7,290,549 | B2 | 11/2007 | Banerjee et al. |
| 7,293,565 | B2 | 11/2007 | Griffin et al. |
| 7,392,809 | B2 | 7/2008 | Larson et al. |
| 7,513,253 | B2 | 4/2009 | Kobayashi et al. |
| 7,647,932 | B2 | 1/2010 | Cantrell et al. |
| 7,690,385 | B2 | 4/2010 | Moffitt |
| 7,692,123 | B2 | 4/2010 | Baba et al. |
| 7,726,320 | B2 | 6/2010 | Robinson et al. |
| 7,753,056 | B2 | 7/2010 | Borschke et al. |
| 7,775,459 | B2 | 8/2010 | Martens, III et al. |
| 7,810,505 | B2 | 10/2010 | Yang |
| 7,832,410 | B2 | 11/2010 | Hon |
| 7,836,897 | B2 | 11/2010 | Borschke et al. |
| 7,845,359 | B2 | 12/2010 | Montaser |
| 7,878,209 | B2 | 2/2011 | Newbery et al. |
| 7,896,006 | B2 | 3/2011 | Hamano et al. |
| 8,066,010 | B2 | 11/2011 | Newbery et al. |
| 8,079,371 | B2 | 12/2011 | Robinson et al. |
| 8,127,772 | B2 | 3/2012 | Montaser |
| 8,156,944 | B2 | 4/2012 | Han |
| 8,314,591 | B2 | 11/2012 | Terry et al. |
| 8,365,742 | B2 | 2/2013 | Hon |
| 8,375,957 | B2 | 2/2013 | Hon |
| 8,393,331 | B2 | 3/2013 | Hon |
| 8,402,976 | B2 | 3/2013 | Fernando et al. |
| 8,464,726 | B2 | 6/2013 | Sebastian et al. |
| 8,469,035 | B2 | 6/2013 | Banerjee et al. |
| 8,499,766 | B1 | 8/2013 | Newton |
| 8,528,569 | B1 | 9/2013 | Newton |
| 8,550,069 | B2 | 10/2013 | Alelov |
| 8,616,217 | B2 | 12/2013 | Tsurizumi et al. |
| 8,915,255 | B2 | 12/2014 | Poget et al. |
| 9,484,155 | B2 | 11/2016 | Peckerar et al. |
| 2002/0146242 | A1 | 10/2002 | Vieira |
| 2003/0131859 | A1 | 7/2003 | Li et al. |
| 2003/0226837 | A1 | 12/2003 | Blake et al. |
| 2004/0020500 | A1 | 2/2004 | Wrenn et al. |
| 2004/0118401 | A1 | 6/2004 | Smith et al. |
| 2004/0129280 | A1 | 7/2004 | Woodson et al. |
| 2004/0149296 | A1 | 8/2004 | Rostami et al. |
| 2004/0200488 | A1 | 10/2004 | Felter et al. |
| 2004/0226568 | A1 | 11/2004 | Takeuchi et al. |
| 2004/0255965 | A1 | 12/2004 | Perfetti et al. |
| 2005/0016549 | A1 | 1/2005 | Banerjee et al. |
| 2005/0016550 | A1 | 1/2005 | Katase |
| 2005/0066986 | A1 | 3/2005 | Nestor et al. |
| 2005/0172976 | A1 | 8/2005 | Newman et al. |
| 2005/0274390 | A1 | 12/2005 | Banerjee et al. |
| 2006/0016453 | A1 | 1/2006 | Kim |
| 2006/0070633 | A1 | 4/2006 | Rostami et al. |
| 2006/0162733 | A1 | 7/2006 | McGrath et al. |
| 2006/0185687 | A1 | 8/2006 | Hearn et al. |
| 2006/0196518 | A1 | 9/2006 | Hon |
| 2007/0052748 | A1 | 3/2007 | Sarnoff et al. |
| 2007/0074734 | A1 | 4/2007 | Braunshteyn et al. |
| 2007/0102013 | A1 | 5/2007 | Adams et al. |
| 2007/0212269 | A1 * | 9/2007 | Kobayashi ............. B23P 11/005 422/168 |

(56) References Cited

U.S. PATENT DOCUMENTS

| | | |
|---|---|---|
| 2007/0215167 A1 | 9/2007 | Crooks et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0320863 A1 | 12/2009 | Fernando et al. |
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0258139 A1 | 10/2010 | Onishi et al. |
| 2010/0300467 A1 | 12/2010 | Kuistilla et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120482 A1 | 5/2011 | Brenneise |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0180082 A1 | 7/2011 | Banerjee et al. |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0145169 A1 | 6/2012 | Wu |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0133675 A1 | 5/2013 | Shinozaki et al. |
| 2013/0192619 A1 | 8/2013 | Tucker et al. |
| 2013/0213419 A1 | 8/2013 | Tucker et al. |
| 2013/0232779 A1 | 9/2013 | Mori et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2015/0027471 A1 | 1/2015 | Feldman et al. |
| 2015/0289565 A1 | 10/2015 | Cadieux et al. |
| 2015/0291301 A1 | 10/2015 | Cadieux et al. |
| 2015/0327598 A1 | 11/2015 | Xiang |
| 2016/0044962 A1* | 2/2016 | Thorens ............... A24F 47/008 392/395 |

FOREIGN PATENT DOCUMENTS

| | | |
|---|---|---|
| CA | 2 752 255 | 8/2010 |
| CH | 635232 A5 | 3/1983 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 202 262 413 | 6/2012 |
| CN | 103 355 745 | 10/2013 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 1808087 A1 | 7/2007 |
| EP | 2113177 A1 | 11/2009 |
| EP | 2 316 286 | 5/2011 |
| EP | 2 338 361 | 6/2011 |
| EP | 2 468 116 | 6/2012 |
| EP | 2550879 A1 | 1/2013 |
| EP | 2 754 359 | 7/2014 |
| EP | 2 779 786 | 9/2014 |
| GB | 1444461 | 7/1976 |
| GB | 2469850 | 11/2010 |
| WO | WO 86/02528 | 5/1986 |
| WO | WO 97/48293 | 12/1997 |
| WO | 9857556 A1 | 12/1998 |
| WO | WO 02/37990 | 5/2002 |
| WO | WO 03/034847 A1 | 5/2003 |
| WO | WO 2004/043175 | 5/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO 2011/081558 | 7/2011 |
| WO | WO 2012/072762 | 6/2012 |
| WO | WO 2012/100523 | 8/2012 |
| WO | 2012164077 A1 | 12/2012 |
| WO | WO 2013/089551 | 6/2013 |
| WO | 2013098380 A1 | 7/2013 |
| WO | 2013098405 A2 | 7/2013 |
| WO | 2013098410 A2 | 7/2013 |
| WO | 2013104914 A1 | 7/2013 |
| WO | 2014151040 A2 | 9/2014 |
| WO | WO 2015/011565 | 1/2015 |
| WO | 2015106604 A1 | 7/2015 |
| WO | WO 2015/117701 | 8/2015 |
| WO | 2015139186 A1 | 9/2015 |
| WO | 2015172383 A1 | 11/2015 |
| WO | 2015172384 A1 | 11/2015 |
| WO | 2015172387 A1 | 11/2015 |

(56) References Cited

FOREIGN PATENT DOCUMENTS

| WO | 2015172389 A1 | 11/2015 |
| WO | 2015172390 A1 | 11/2015 |
| WO | 2015180145 A1 | 12/2015 |
| WO | 2015196367 A1 | 12/2015 |
| WO | 2016079533 A1 | 5/2016 |
| WO | 2016116755 A1 | 7/2016 |

OTHER PUBLICATIONS

Anonymous; "The Latest Trend in Liquid Filling: E-Cigarette Cartridges and Containers Part 2"; Filamatic of Baltimore, MD; May 24, 2013 (3 pgs.) URL: http://www.filamatic.com/blog/409.

International Search Report and Written Opinion of the International Searching Authority for corresponding International Application No. PCT/US2015/015878 dated Oct. 23, 2015.

Freedom Smokeless Press Release; *Electronic Cigarettes U.S. Automated Filling, Assembly & Packaging*, Feb. 12, 2014 (2 pgs.) http://www.freedomsmokeless.com/20120212_pressrelease.pdf.

Freedom Smokeless; Manufacturing: Component Manufacturing, Manufacturing Audits, and Automations Systems and QC; site visited Mar. 27, 2014 (4 pgs.) http://www.freedomsmokeless.com/manufacturing.php.

Freedom Smokeless Video on Vimeo; site visited May 14, 2014 (screenshots—42 pgs.) http://vimeo.com/85109379.

\* cited by examiner

```
┌────────────────────────────────────────────────────────────────┐
│   PROVIDE A RESERVOIR SUBSTRATE EXTENDING AT LEAST PARTIALLY ABOUT   │──3702
│                         AN ATOMIZER                             │
└────────────────────────────────────────────────────────────────┘
                                │
                                ▼
┌────────────────────────────────────────────────────────────────┐
│  PROVIDE AN OUTER BODY CONFIGURED TO AT LEAST PARTIALLY RECEIVE │──3704
│     THE RESERVOIR SUBSTRATE AND THE ATOMIZER THEREIN            │
└────────────────────────────────────────────────────────────────┘
                                │
                                ▼
┌────────────────────────────────────────────────────────────────┐
│ INSERT THE RESERVOIR SUBSTRATE THROUGH A TOOL INTO THE OUTER BODY, THE TOOL │──3706
│  DEFINING A FUNNEL PORTION CONFIGURED TO REDUCE AN OUTER DIMENSION OF THE   │
│      RESERVOIR SUBSTRATE SUCH THAT THE OUTER DIMENSION OF THE RESERVOIR     │
│     SUBSTRATE IS LESS THAN OR EQUAL TO AN INTERNAL DIMENSION OF THE OUTER   │
│  BODY TO FACIALITATE INSERTION OF THE RESERVOIR SUBSTRATE INTO THE OUTER BODY │
└────────────────────────────────────────────────────────────────┘
```

FIG. 88

| PROVIDE A CARTRIDGE FOR AN AEROSOL DELIVERY DEVICE COMPRISING A RESERVOIR SUBSTRATE POSITIONED IN AN OUTER BODY | ⟵ 4002 |

| SEQUENTIALLY POSITION AN OUTLET OF A FILLING DEVICE IN PROXIMITY TO A PLURALITY OF ANGULAR PORTIONS OF THE RESERVOIR SUBSTRATE | ⟵ 4004 |

| DIRECT A FLOW OF AN AEROSOL PRECURSOR COMPOSITION THROUGH THE OUTLET OF THE FILLING DEVICE AT EACH OF THE ANGULAR PORTIONS OF THE RESERVOIR SUBSTRATE | ⟵ 4006 |

*FIG. 90*

METHOD FOR ASSEMBLING A CARTRIDGE FOR A SMOKING ARTICLE

CROSS-REFERENCE TO RELATED APPLICATIONS

This application claims the benefit of U.S. Provisional Application No. 61/939,446, filed Feb. 13, 2014, which is entirely incorporated herein by reference in its entirety.

FIELD OF THE DISCLOSURE

The present disclosure relates to a cartridge for aerosol delivery devices such as smoking articles, and more particularly to methods for assembling a cartridge for smoking articles including an atomizer. The atomizer may be configured to heat an aerosol precursor, which may be made or derived from tobacco or otherwise incorporate tobacco, to form an inhalable substance for human consumption.

BACKGROUND

Cigarettes, cigars and pipes are popular smoking articles that employ tobacco in various forms. For example, a traditional type of cigarette has a substantially cylindrical rod-shaped structure and includes a charge, roll or column of smokable material, such as shredded tobacco (e.g., in cut filler form), surrounded by a paper wrapper, thereby forming a so-called "smokable rod", "tobacco rod" or "cigarette rod." Normally, such a cigarette has a cylindrical filter element aligned in an end-to-end relationship with the tobacco rod. Preferably, a filter element comprises plasticized cellulose acetate tow circumscribed by a paper material known as "plug wrap." Preferably, the filter element is attached to one end of the tobacco rod using a circumscribing wrapping material known as "tipping paper." It also has become desirable to perforate the tipping material and plug wrap, in order to provide dilution of drawn mainstream smoke with ambient air. Descriptions of cigarettes and the various components thereof are set forth in Tobacco Production, Chemistry and Technology, Davis et al. (Eds.) (1999); which is incorporated herein by reference in its entirety. A traditional type of cigarette is employed by a smoker by lighting one end of the tobacco rod. The smoker then receives mainstream smoke into his/her mouth by drawing on the opposite end (e.g., the filter end or mouth end) of the burning cigarette.

Through the years, efforts have been made to improve upon the components, construction and performance of smoking articles that require combustion of tobacco for smoke generation. Many of the improvements that have been proposed purportedly attempt to provide the sensations associated with cigarette, cigar or pipe smoking, but without delivering considerable quantities of incomplete combustion and pyrolysis products that result from burning tobacco. See, for example, the various references described, discussed, or referenced in U.S. Pat. No. 7,753,056 to Borschke et al.; which is incorporated herein by reference in its entirety.

Certain types of cigarettes that employ carbonaceous fuel elements have been commercially marketed under the brand names "Premier" and "Eclipse" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette recently has been marketed in Japan by Japan Tobacco Inc. under the brand name "Steam Hot One." Furthermore, various types of smoking products incorporating carbonaceous fuel elements for heat generation and aerosol formation recently have been set forth in the patent literature. See, for example, the types of smoking products proposed in U.S. Pat. No. 7,836,897 to Borschke et al.; U.S. Pat. No. 8,469,035 to Banerjee et al. and U.S. Pat. No. 8,464,726 to Sebastian et al.; US Pat. Pub. Nos. 2012/0042885 to Stone et al.; 2013/0019888 to Tsuruizumi et al; 2013/0133675 to Shinozaki et al. and 2013/0146075 to Poget et al.; PCT WO Nos. 2012/0164077 to Gladden et al.; 2013/098380 to Raether et al.; 2013/098405 to Zuber et al.; 2013/098410 to Zuber et al. and 2013/104914 to Woodcock; EP 1808087 to Baba et al. and EP 2550879 to Tsuruizumi et al.; which are incorporated herein by reference in their entirety.

In recent years, there have been proposed numerous smoking products, flavor generators and medicinal inhalers that utilize electrical energy to heat and vaporize volatile materials, or otherwise attempt to provide many of the sensations of smoking, without burning tobacco to any significant degree. See, for example, the various types of aerosol generation devices described, discussed, or referenced in U.S. Pat. No. 7,726,320 to Robinson et al., U.S. patent application Ser. No. 13/826,929, filed Mar. 14, 2013, to Ampolini et al., Ser. No. 14/011,992, filed Aug. 28, 2013, to Davis et al., and Ser. No. 14/170,838, filed Feb. 3, 2014, to Bless et al.; which are incorporated herein by reference in their entireties.

In this regard, certain tobacco products that have employed electrical energy to produce heat for smoke or aerosol formation, and in particular, certain products that have been referred to as electronic cigarette products, have become commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Additional manufacturers, designers, and/or assignees of components and related technologies that may be employed in aerosol delivery device include Shenzhen Jieshibo Technology of Shenzhen, China; Shenzhen First Union Technology of Shenzhen City, China; Safe Cig of Los Angeles, Calif.; Janty Asia Company of the Philippines; Joyetech Changzhou Electronics of Shenzhen, China; SIS Resources; B2B International Holdings of Dover, Del.; Evolv LLC of OH; Montrade of Bologna, Italy; Shenzhen Bauway Technology of Shenzhen, China; Global Vapor Trademarks Inc. of Pompano Beach, Fla.; Vapor Corp. of Fort Lauderdale, Fla.; Nemtra GMBH of Raschau-Markersbach, Germany; Perrigo L. Co. of Allegan, Mich.; Needs Co., Ltd.; Smokefree Innotec of Las Vegas, Nev.; McNeil AB of Helsingborg, Sweden; Chong Corp; Alexza Pharmaceuticals of Mountain View, Calif.; BLEC, LLC of Charlotte, N.C.; Gaitrend Sarl of Rohrbach-lès-Bitche, France; FeelLife Bioscience International of Shenzhen, China; Vishay Electronic BMGH of Selb, Germany; Shenzhen Smaco Technology Ltd. of Shenzhen, China; Vapor Systems International of Boca Raton, Fla.; Exonoid Medical Devices of Israel; Shenzhen Nowotech Electronic of Shenzhen, China; Minilogic Device Corporation of Hong Kong, China; Shenzhen Kontle Electronics of Shenzhen, China, and Fuma International, LLC of Medina, Ohio, and 21st Century Smoke of Beloit, Wis.

However, embodiments of electronic smoking articles may be difficult to manufacture. In this regard, for example, the various components in electronic smoking articles may be relatively small and/or fragile. Thus, advances with respect to manufacturing electronic smoking articles would be desirable.

BRIEF SUMMARY OF THE DISCLOSURE

The present disclosure relates to assembly of aerosol delivery devices configured to produce aerosol. In one aspect a method for assembling a cartridge for an aerosol delivery device is provided. The method may include providing a reservoir substrate extending at least partially about an atomizer, providing an outer body configured to at least partially receive the reservoir substrate and the atomizer therein, and inserting the reservoir substrate through a tool into the outer body, the tool defining a funnel portion configured to reduce an outer dimension of the reservoir substrate such that the outer dimension of the reservoir substrate is less than or equal to an internal dimension of the outer body to facilitate insertion of the reservoir substrate into the outer body.

In some embodiments the method may further comprise twisting the tool relative to the reservoir substrate while inserting the reservoir substrate through the tool into the outer body. Providing the reservoir substrate extending at least partially about the atomizer may comprise wrapping the reservoir substrate at least partially about the atomizer prior to inserting the reservoir substrate through the tool into the outer body. Wrapping the reservoir substrate at least partially about the atomizer may comprise directing a flow of air at the reservoir substrate.

In some embodiments the method may further comprise engaging the reservoir substrate with one or more fingers such that the reservoir substrate remains at least partially wrapped about the atomizer when beginning to insert the reservoir substrate through the tool into the outer body. The method may further comprise releasing the one or more fingers from the reservoir substrate when the reservoir substrate is inserted to a predetermined depth in the tool. Releasing the one or more fingers may comprise deflecting the one or more fingers away from the reservoir substrate by contacting the one or more fingers with the tool. Releasing the one or more fingers may comprise sequentially releasing the fingers. The method may further comprise coupling the atomizer to a base prior to wrapping the reservoir substrate at least partially about the atomizer, and coupling the outer body to the base after inserting the reservoir substrate through the tool into the outer body. Additionally, the method may include supplying the reservoir substrate from a substantially continuous reservoir substrate input and controlling a tension in the substantially continuous reservoir substrate input.

In an additional aspect a method for assembling an atomizer for an aerosol delivery device is provided. The method may comprise providing a first heating terminal, a second heating terminal, and a heating element, determining a position of the first heating terminal and the second heating terminal, determining a position of the heating element, and affixing the heating element to the first heating terminal and the second heating terminal based on the position of the first heating terminal and the second heating terminal and the position of the heating element.

In some embodiments determining the position of the first heating terminal and the second heating terminal may comprise determining a midpoint between a first heating terminal tab and a second heating terminal tab. The heating element may comprise a first contact portion and a second contact portion, and determining the position of the heating element may comprise determining a midpoint between the first contact portion and the second contact portion. The method may further comprise aligning the midpoint between the first heating terminal tab and the second heating terminal tab with the midpoint between the first contact portion and the second contact portion, engaging the first contact portion with the first heating terminal tab, and engaging the second contact portion with the second heating terminal tab.

In some embodiments the method may further comprise clamping the first heating terminal and the second heating terminal such that the first heating terminal tab and the second heating terminal tab are substantially coplanar. Clamping the first heating terminal and the second heating terminal may comprise adjusting a spacing between the first heating terminal and the second heating terminal. Affixing the heating element to the first heating terminal and the second heating terminal may comprise directing a laser beam at the first heating terminal tab and at the second heating terminal tab. Directing the laser beam at the first heating terminal tab and at the second heating terminal tab may comprise directing the laser beam at a backside of the first heating terminal tab and the second heating terminal tab opposite from the heating element.

The method may further comprise inserting the heating element, the first heating terminal, and the second heating terminal into a substantially sealed chamber before directing the laser beam at the first heating terminal tab and at the second heating terminal tab. Providing the heating element may comprise supplying the heating element from a substantially continuous heating element input and controlling a tension in the substantially continuous heating element input. The method may further comprise coupling the heating element to a liquid transport element. Providing the first heating terminal and the second heating terminal may comprise supplying the first heating terminal from a substantially continuous first heating terminal input and supplying the second heating terminal from a substantially continuous second heating terminal input. The heating element may comprise a wire wound about a liquid transport element. The wire may comprise two contact portions, a center portion, and two outer portions positioned outside of the contact portions, the two contact portions and the center portion of the wire defining the heating element, wherein the contact portions define a first coil spacing, the center portion defines a second coil spacing, and the outer portions define a third coil spacing, the third coil spacing being greater than the second coil spacing and the second coil spacing being greater than the first coil spacing, and affixing the heating element to the first heating terminal and the second heating terminal may comprise affixing the contact portions to the first heating terminal and the second heating terminal.

In an additional aspect, a test fixture is provided. The test fixture may comprise a receptacle configured to engage a base of a cartridge, first and second electrical contacts coupled to the receptacle and configured to engage first and second heating terminals of an atomizer of the cartridge, and a controller configured to communicate with the cartridge through the electrical contacts when the base of the cartridge is engaged with the receptacle to test the cartridge. The controller may be configured to determine a resistance of the atomizer of the cartridge and compare the resistance to a desired resistance.

In some embodiments the controller may be further configured to determine if the atomizer is shorted to an outer body of the cartridge. The test fixture may further comprise a third electrical contact coupled to the receptacle and configured to engage a control component terminal of the cartridge. The controller may be configured to transmit program code instructions to an electronic control component of the cartridge through the third electrical contact and the control component terminal. The controller may be further configured to read program code instructions stored on the electronic control component and determine whether the program code instructions stored on the electronic control component correspond to desired program code instructions. The test fixture may further comprise a slot positioned on opposing sides of the receptacle, the slot being configured to receive a gripper such that the gripper may grasp beneath the base to remove the cartridge from the receptacle. The test fixture may further comprise an aperture configured to provide for a flow of air through the base of the cartridge.

In an additional aspect a cartridge filling method is provided. The method may include providing a cartridge for an aerosol delivery device comprising a reservoir substrate positioned in an outer body, sequentially positioning an outlet of a filling device in proximity to a plurality of angular portions of the reservoir substrate, and directing a flow of an aerosol precursor composition through the outlet of the filling device at each of the angular portions of the reservoir substrate.

In some embodiments the outlet of the filling device may remain out of contact with the reservoir substrate. The method may further comprise transporting the cartridge between a plurality of filling stations, wherein the flow of the aerosol precursor composition is directed to at least one of the angular portions of the reservoir substrate at each of the filling stations. The flow of the aerosol precursor composition may be directed at each of the angular portions of the reservoir substrate at a first one of the filling stations. The flow of the aerosol precursor composition may be respectively directed to one of the angular portions of the reservoir substrate at a remainder of the filing stations. The method may further comprise controlling an ambient environment in which the cartridge is filled such that the ambient environment defines a relative humidity of less than about 40%.

In an additional aspect a method for assembling a cartridge for an aerosol delivery device is provided. The method may comprise grasping a base, providing a plurality of components configured to engage the base, the components being provided in a stationary position, and coupling the components to the base by directing the base into contact with the components in the stationary position.

In some embodiments grasping the base may comprise grasping an internal surface of an attachment end of the base configured to engage a control body. Directing the base into contact with the components in the stationary position may comprise directing the base downwardly into contact with the components. The method may further comprise inserting the base into a fixture, and inspecting a position of first and second heating terminals coupled to the base through the fixture.

In an additional aspect, a transport system configured to transport a cartridge for a smoking article during assembly thereof is provided. The transport system may comprise a rail, a carriage configured to engage the rail and move therealong, the carriage comprising a clamping mechanism configured to engage one or more components of a cartridge during assembly thereof, and a locking apparatus configured to temporarily restrain movement of the carriage along the rail.

In some embodiments the clamping mechanism may be configured to engage a base of the cartridge. The locking apparatus may comprise a locator mechanism coupled to the carriage and an engagement mechanism configured to engage the locator mechanism. The locator mechanism may comprise a plurality of pegs. The engagement mechanism may comprise a roller.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
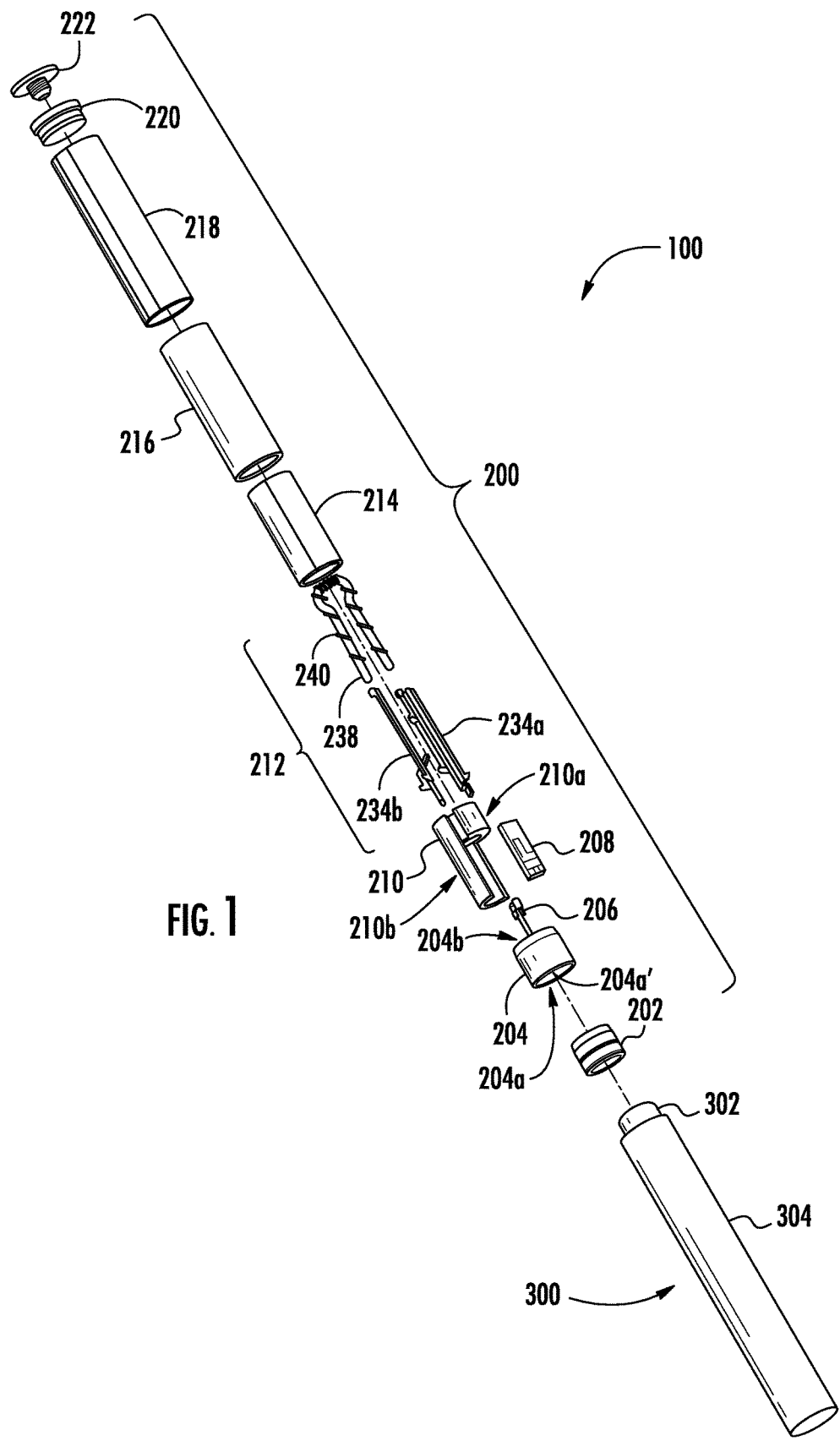
Figure 2:
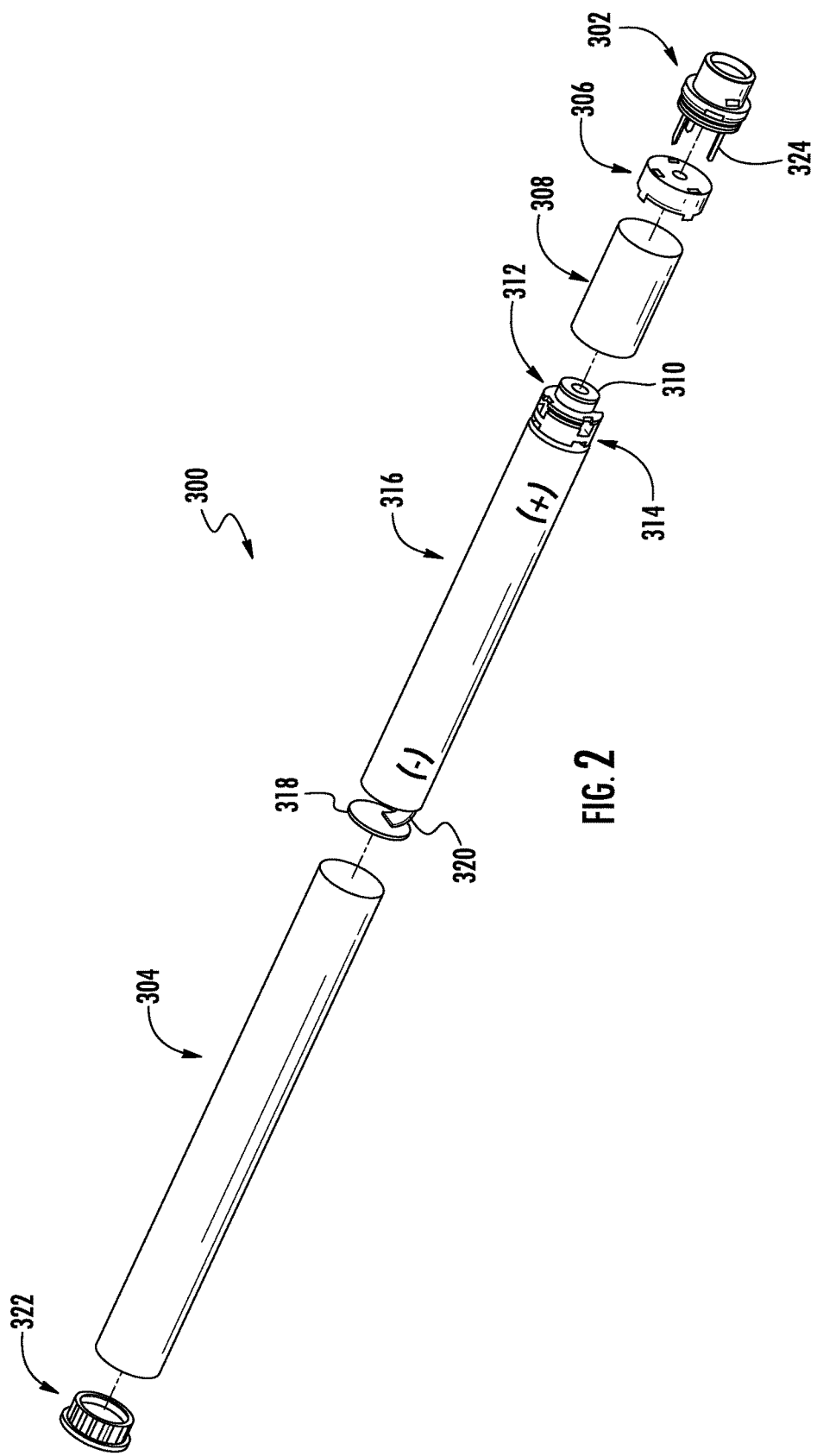
Figure 3:
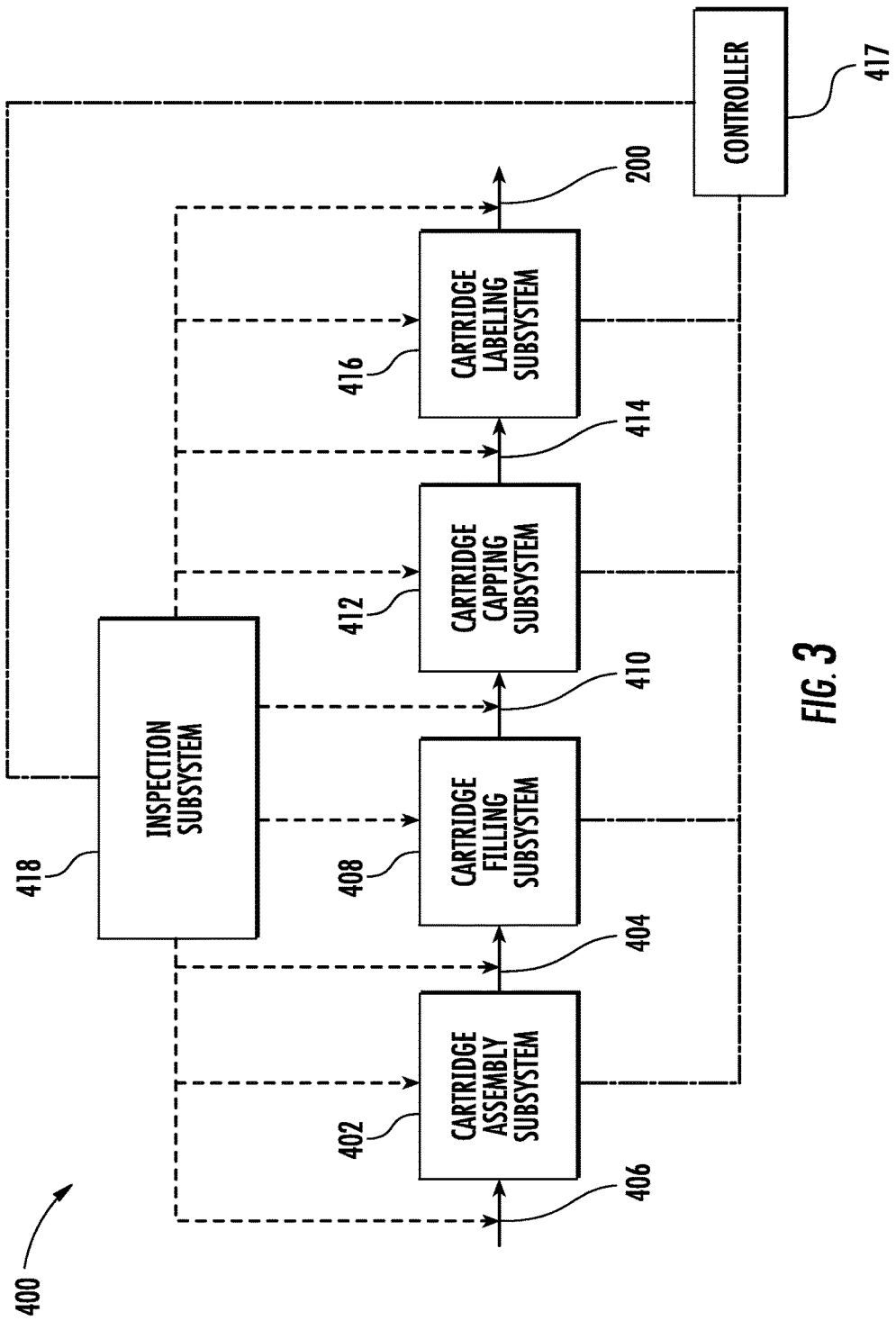
Figure 4:
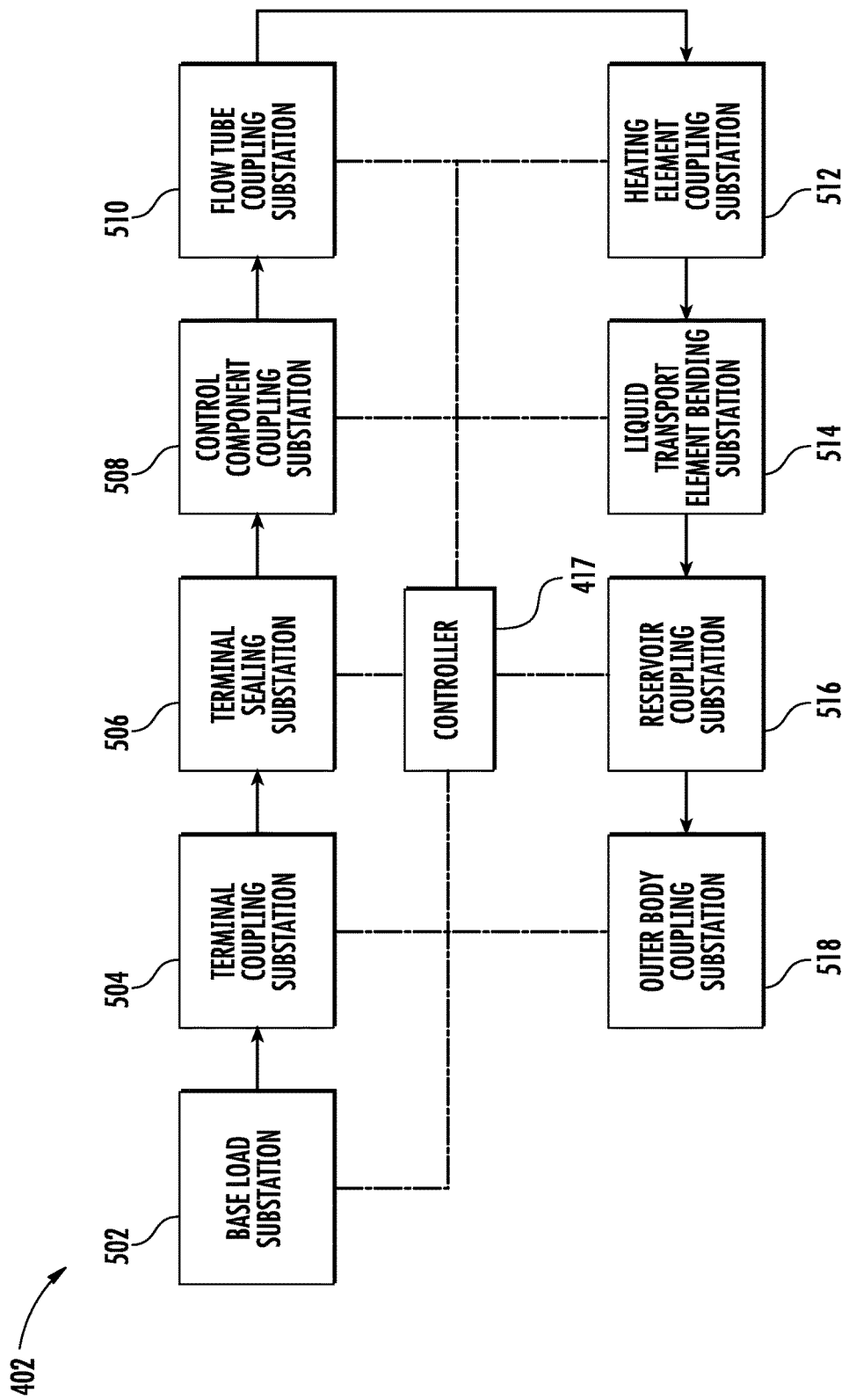
Figure 5:
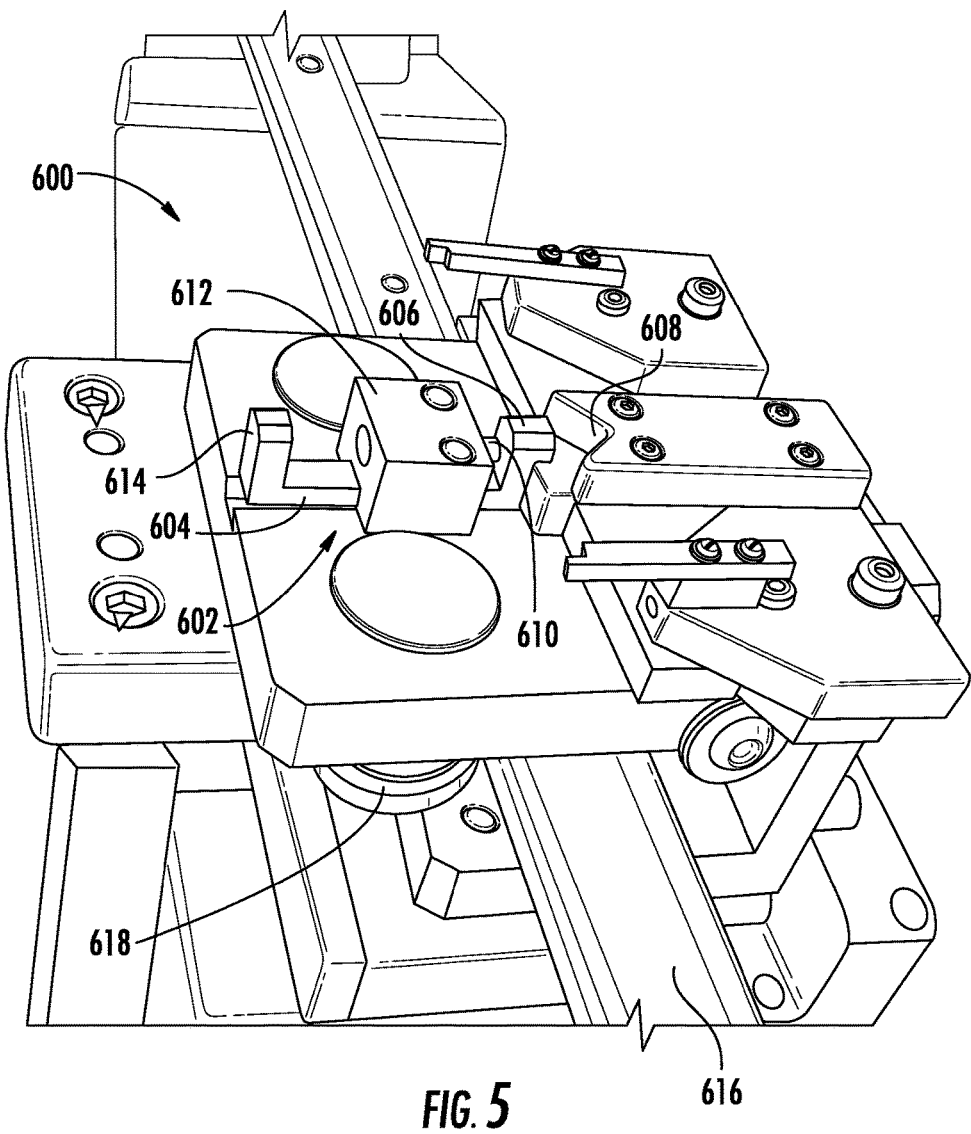
Figure 6:
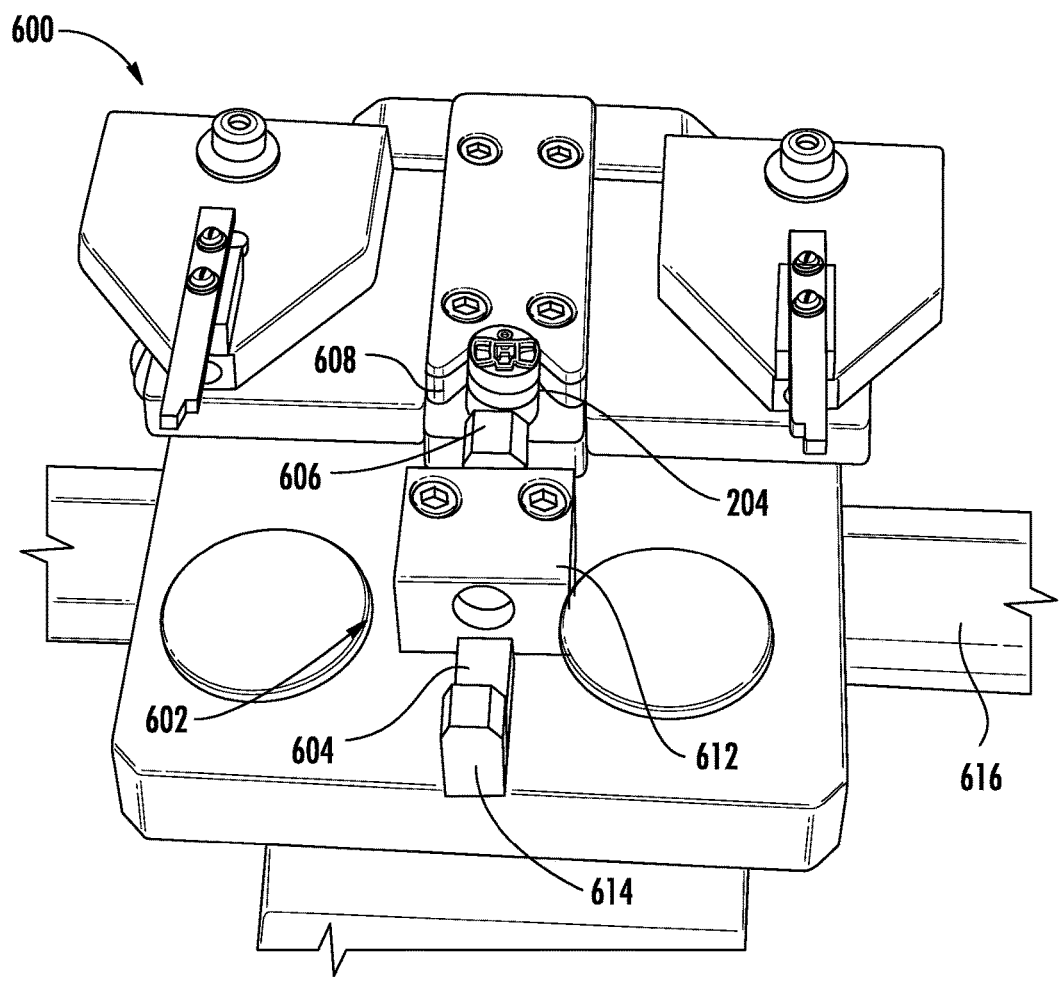
Figure 7:
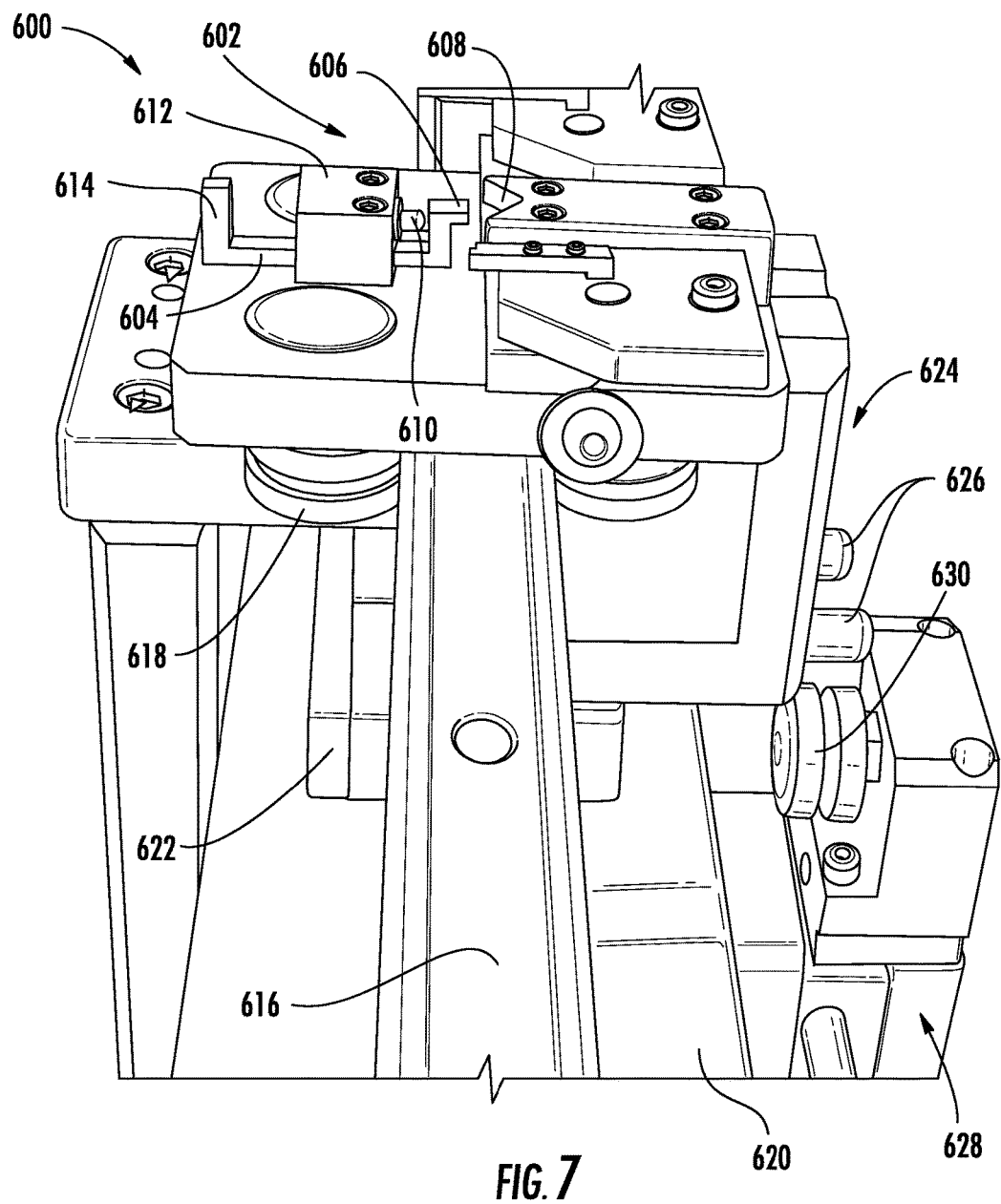
Figure 8:
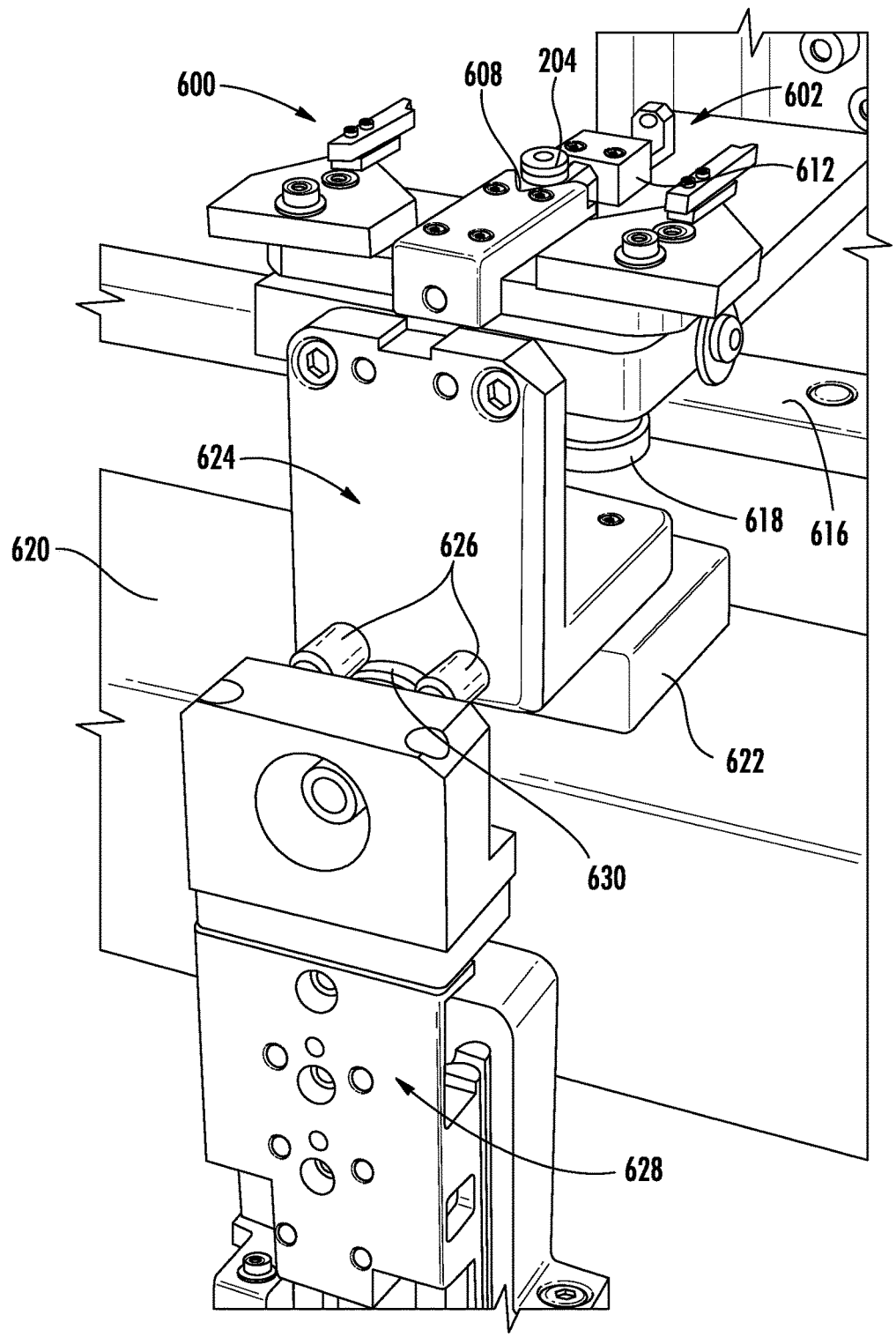
Figure 9:
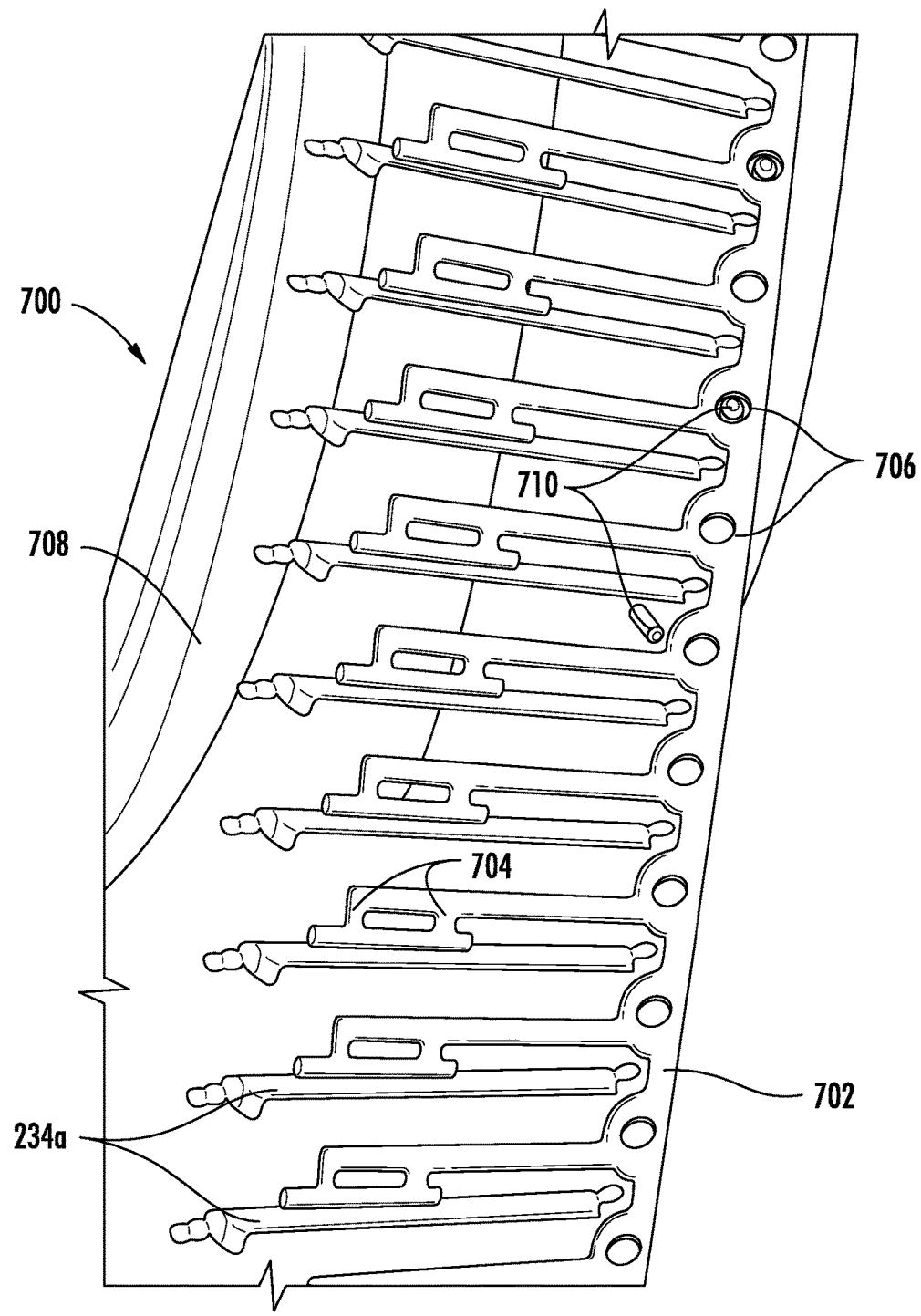
Figure 10:
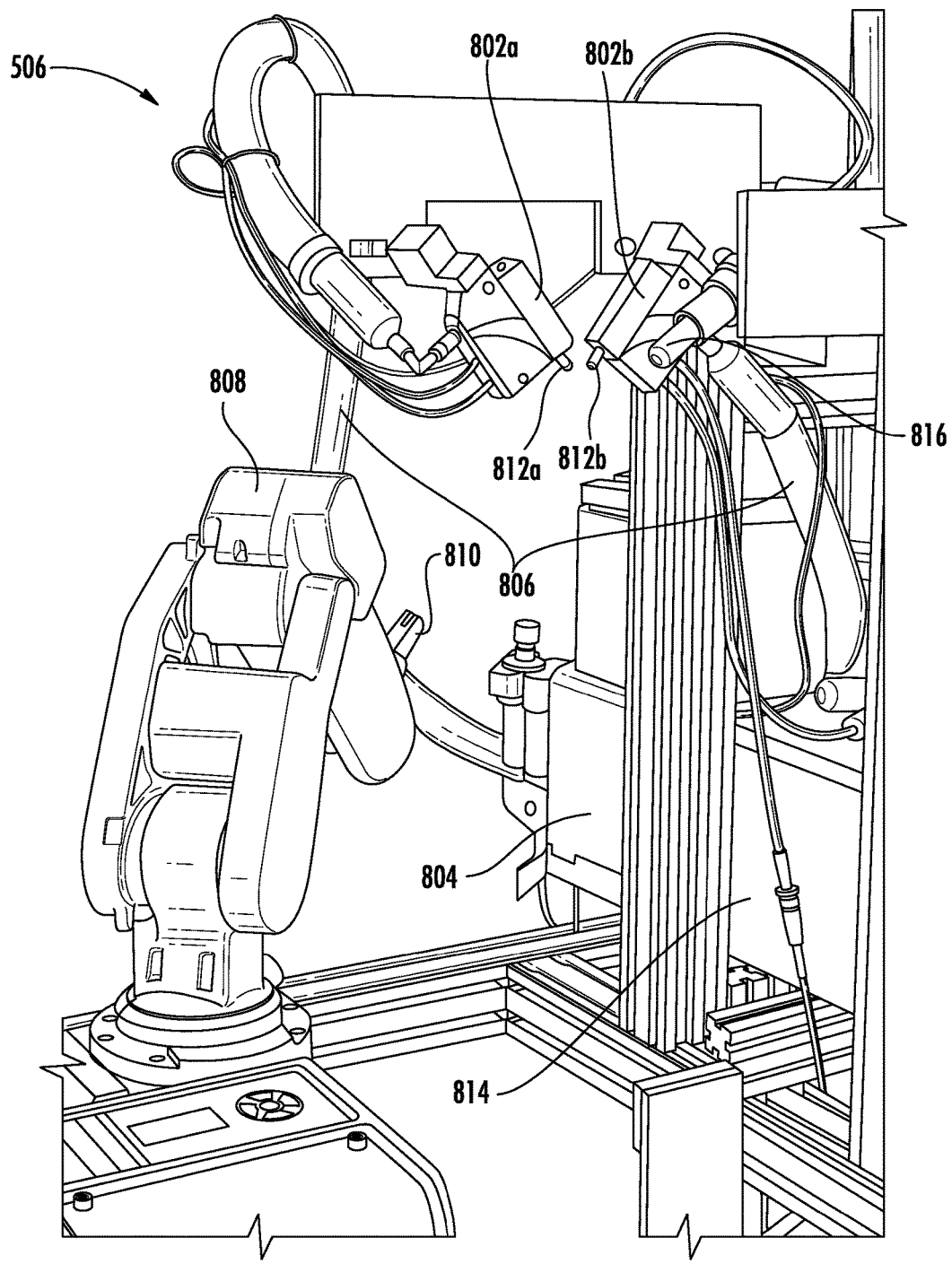
Figure 11:
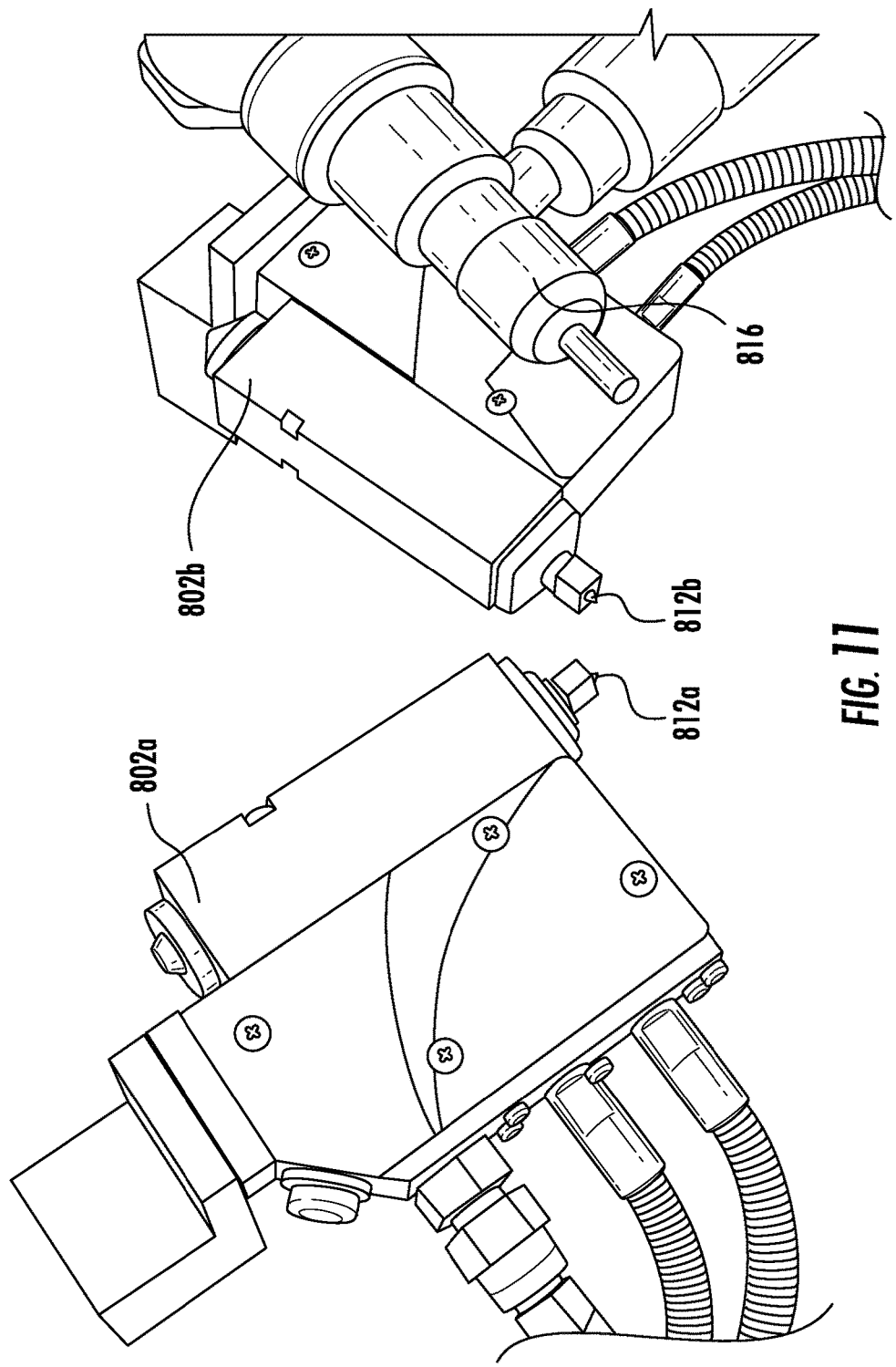
Figure 12:
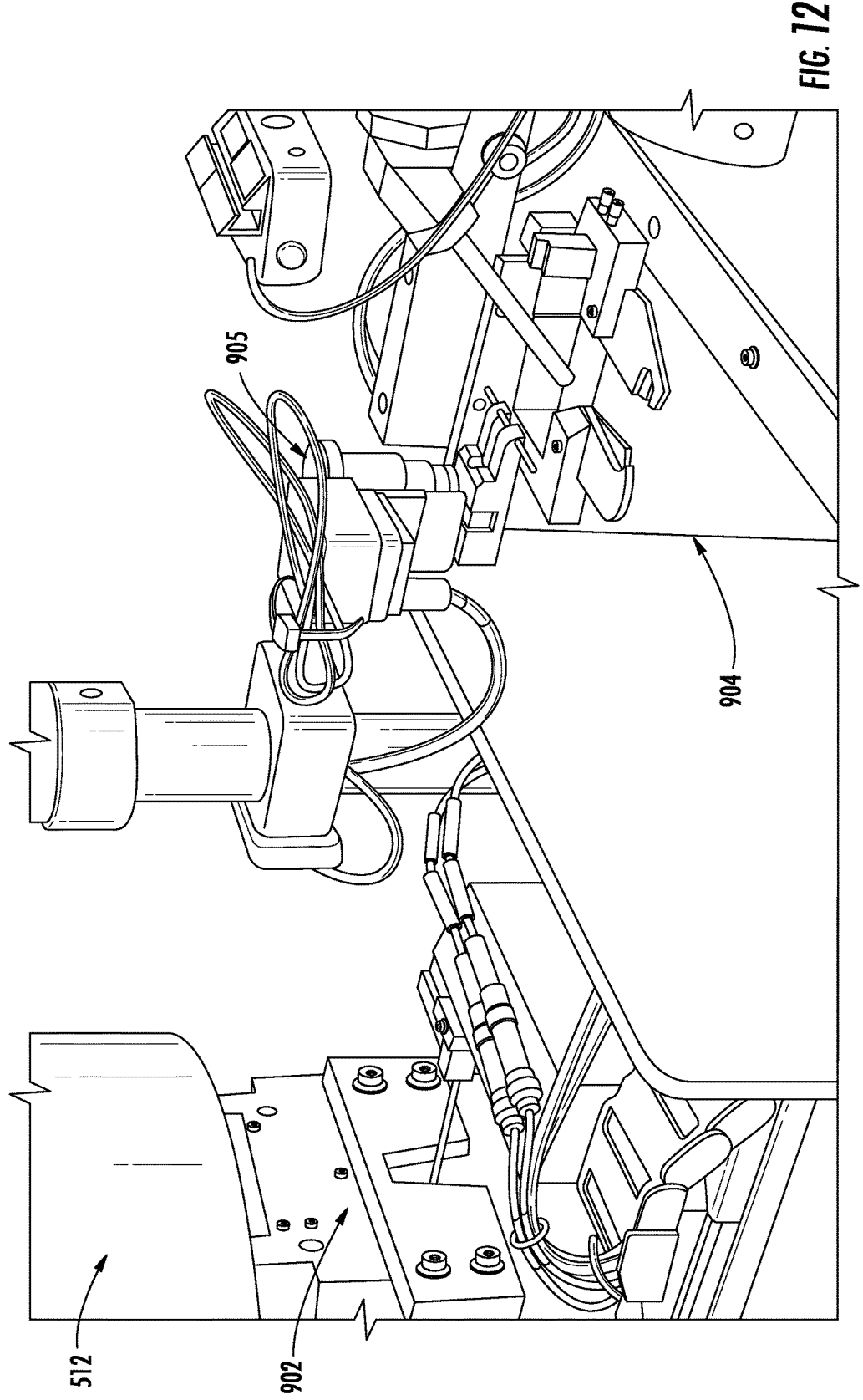
Figure 13:
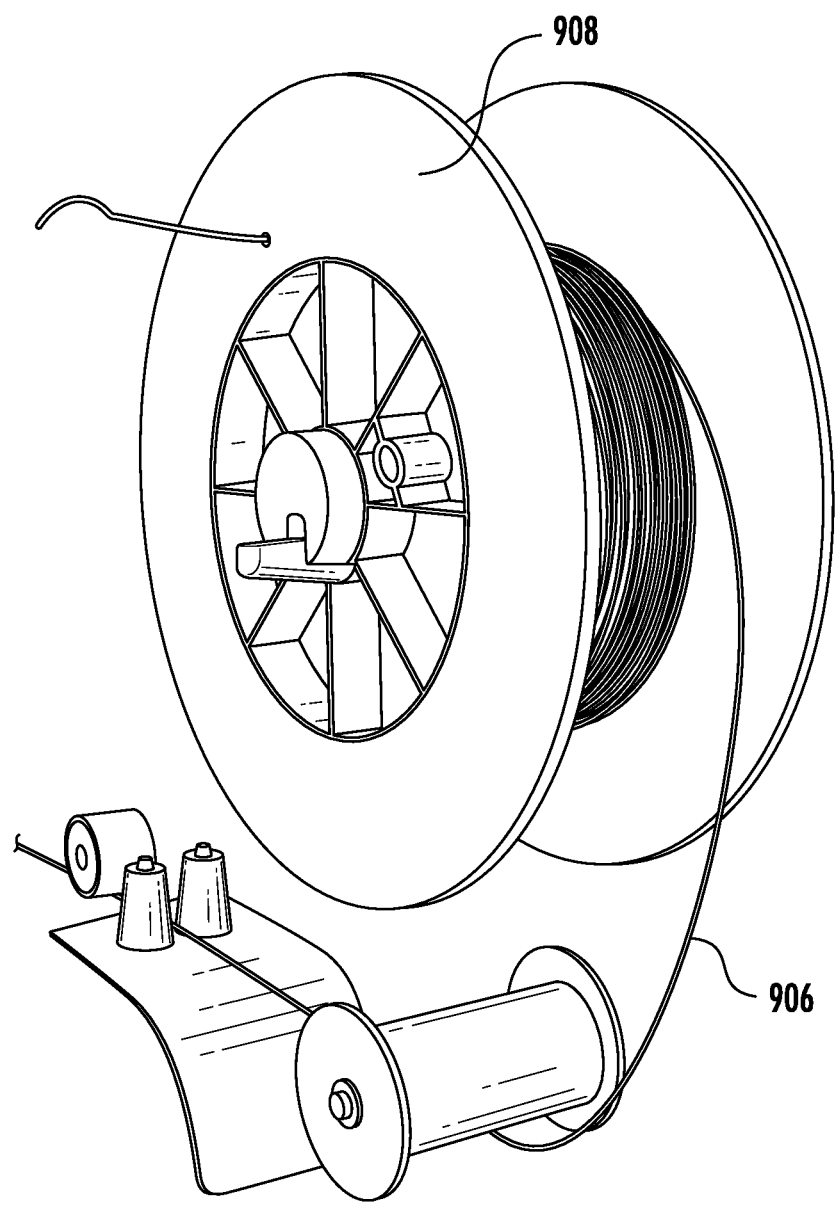
Figure 14:
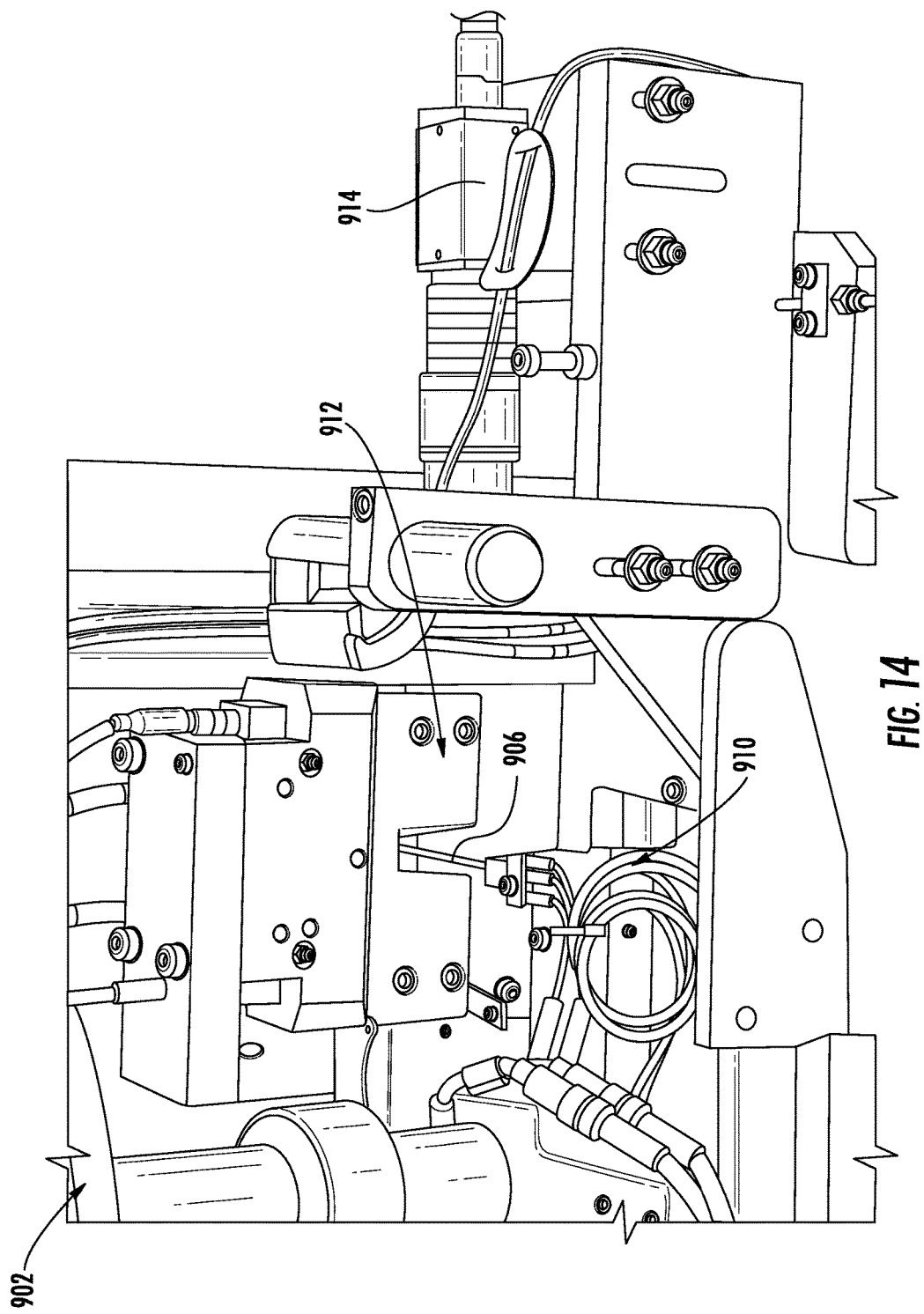
Figure 15:
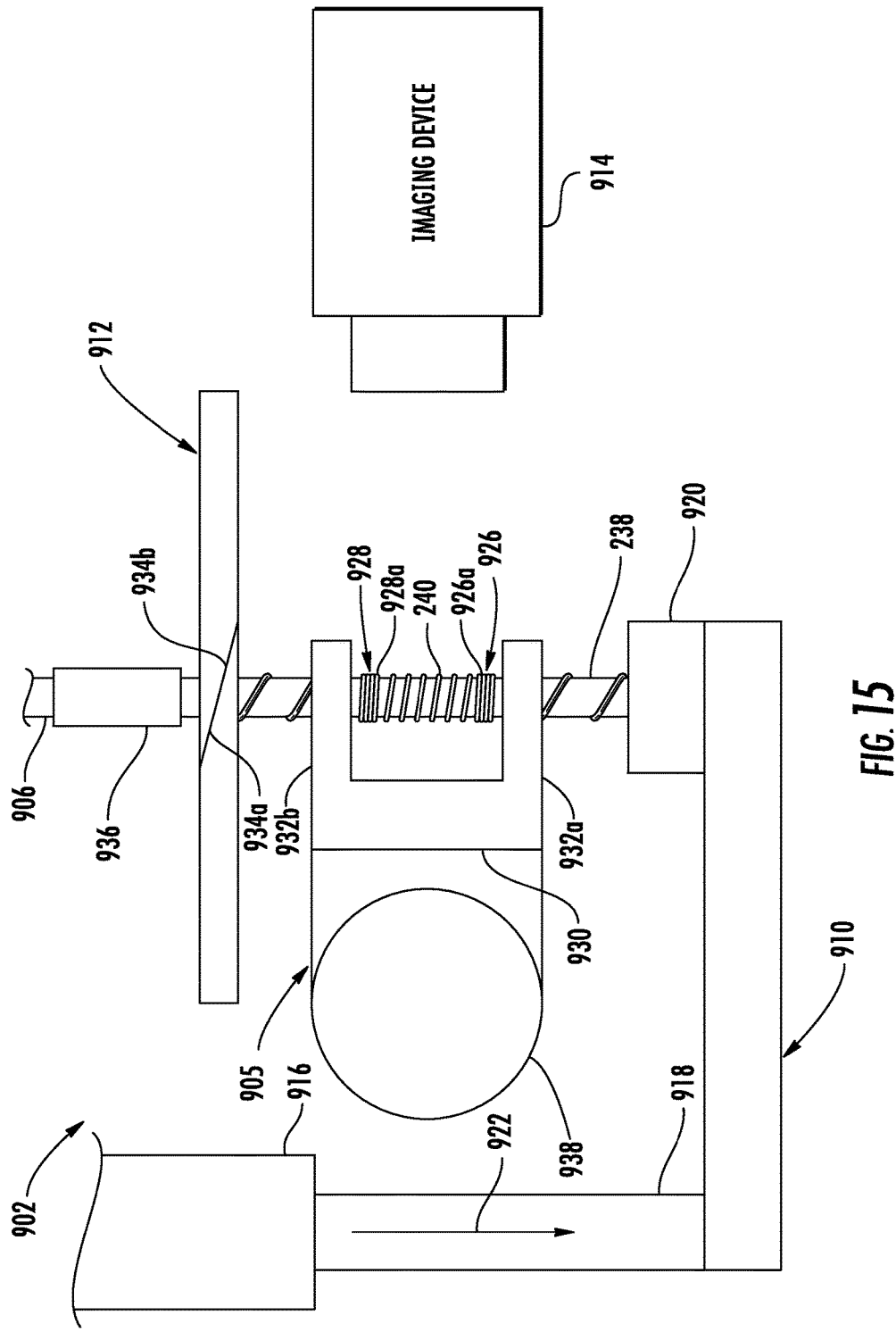
Figure 16:
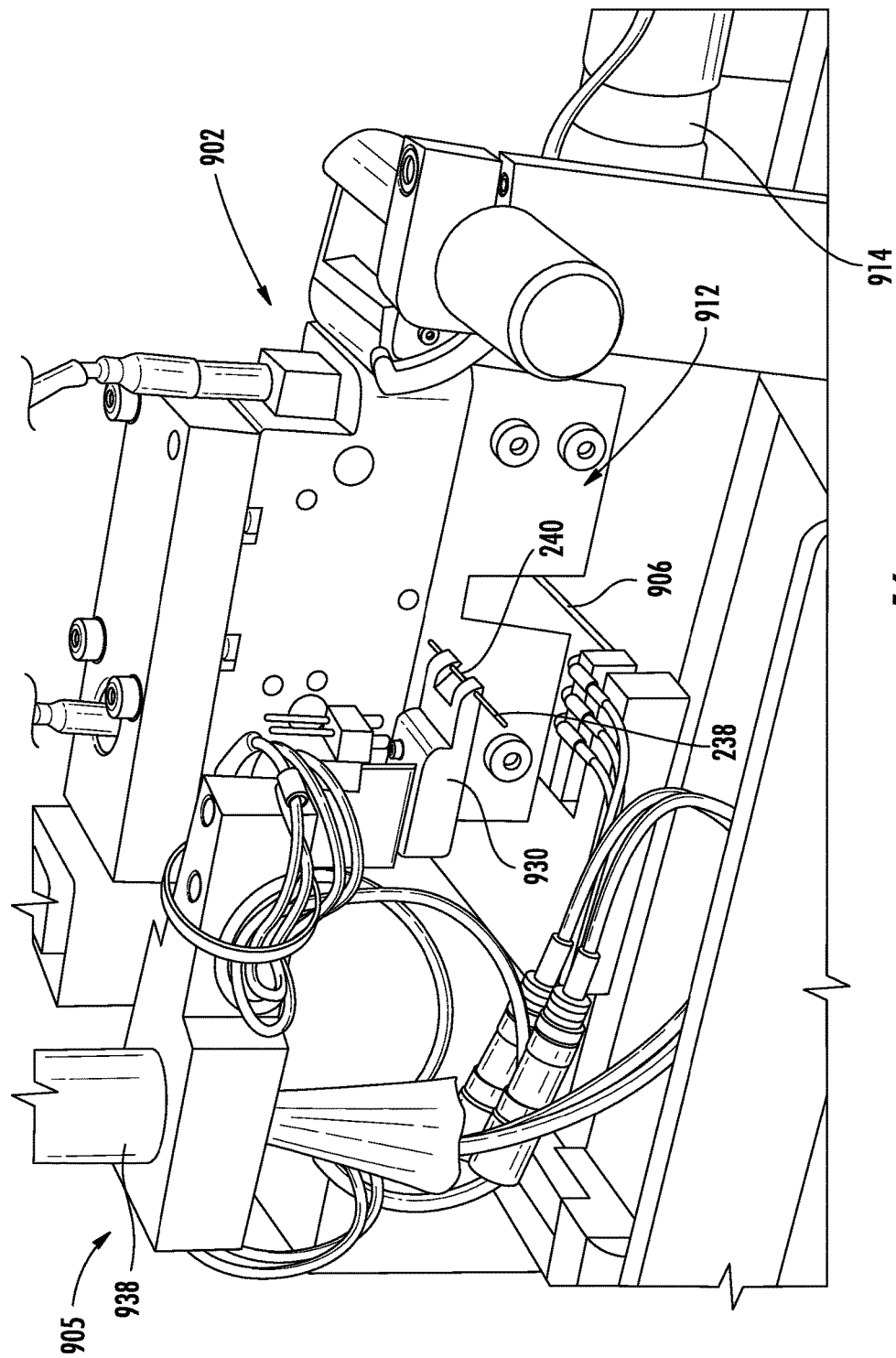
Figure 17:
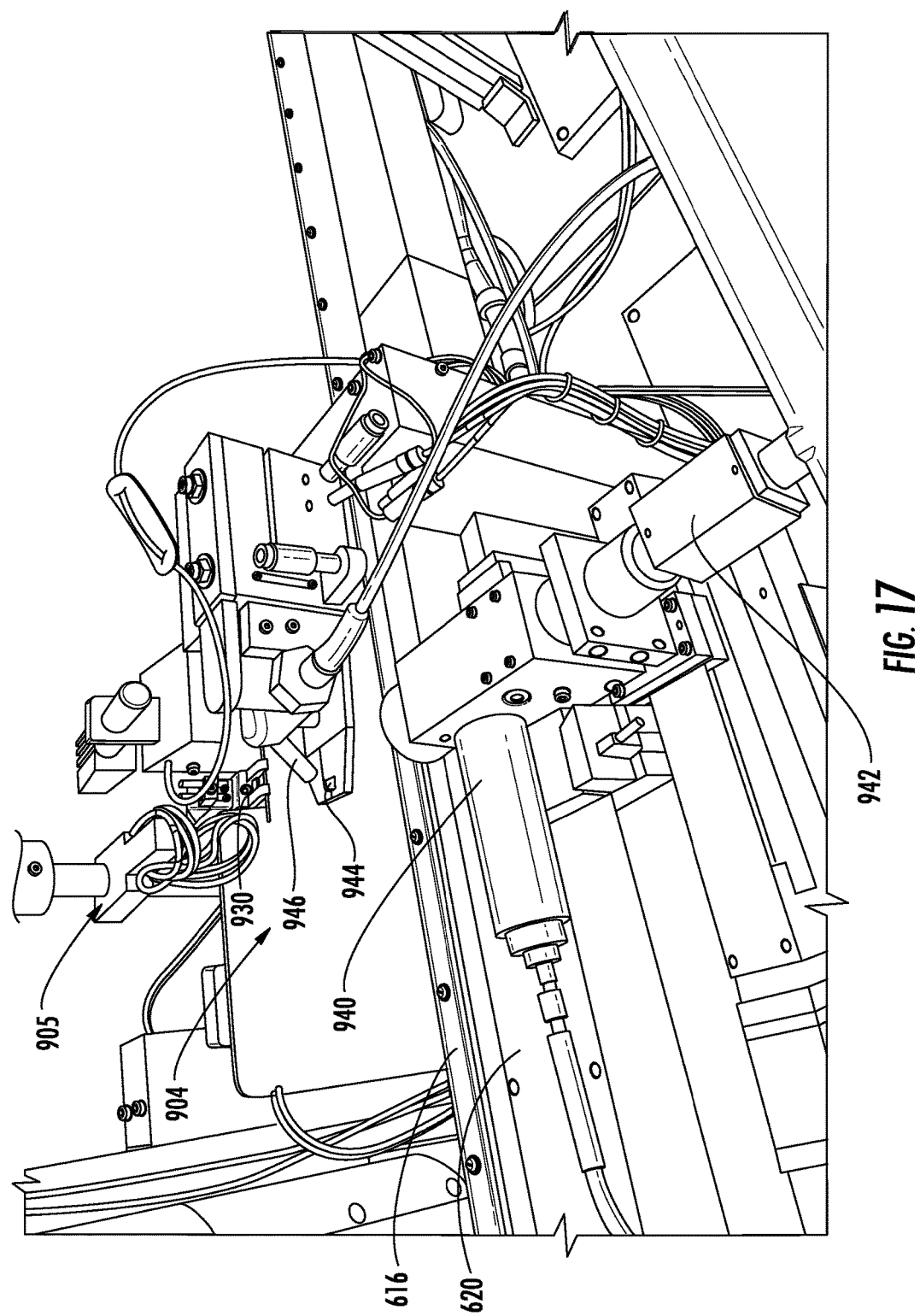
Figure 18:
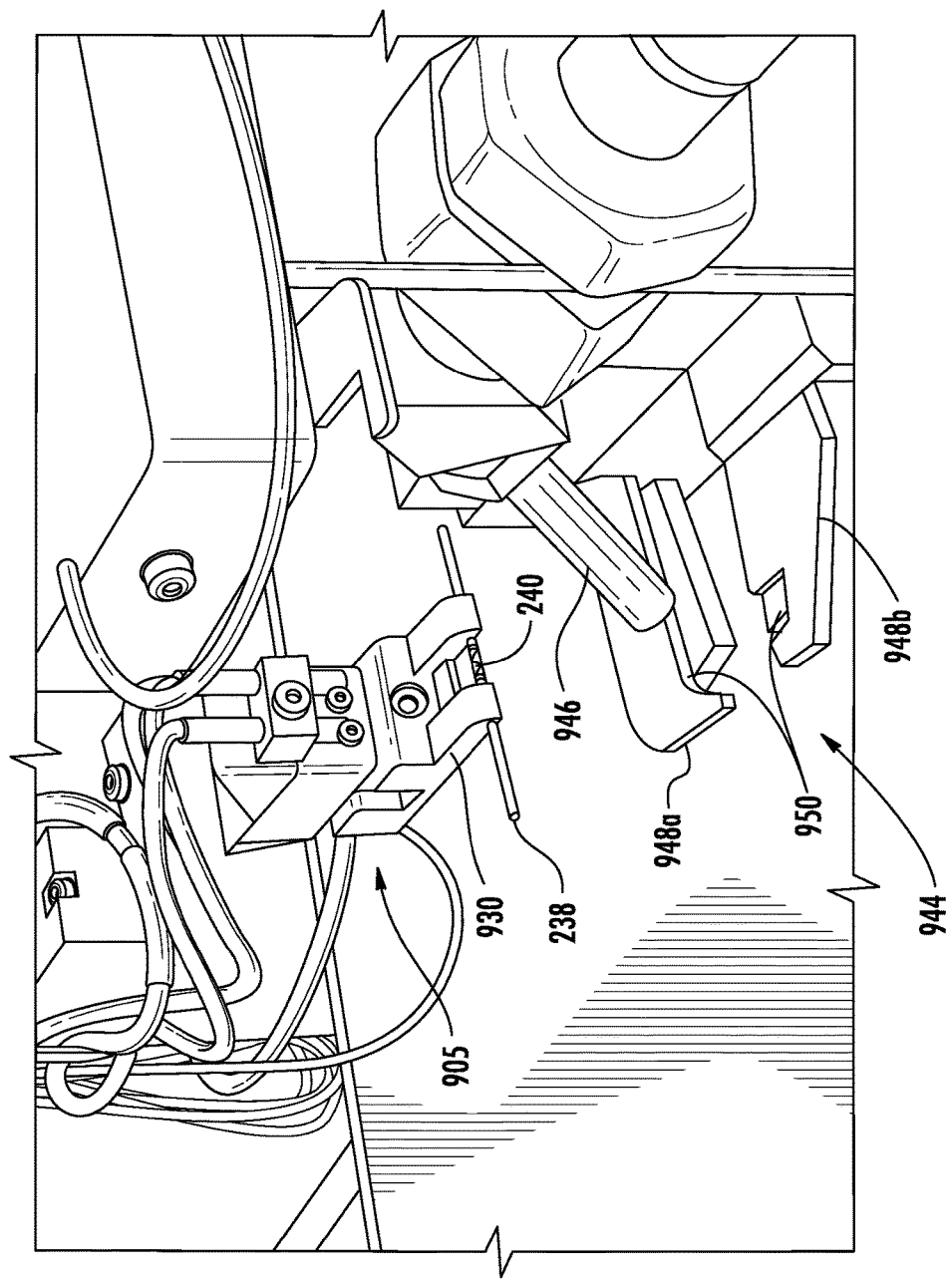
Figure 19:
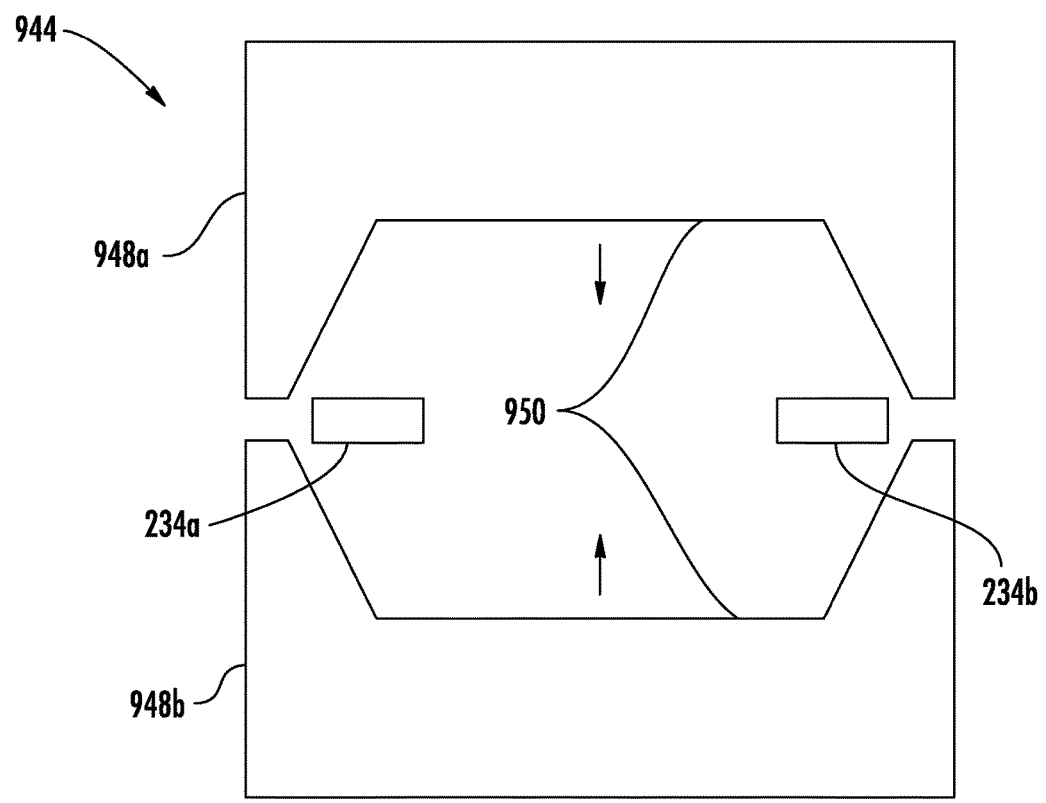
Figure 20:
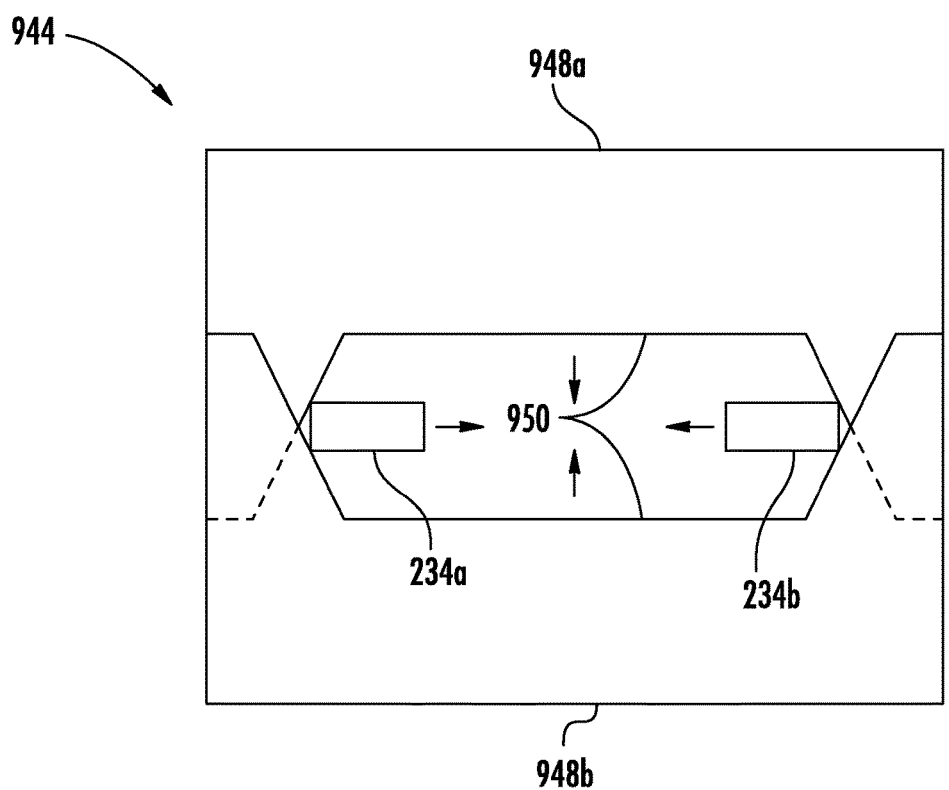
Figure 21:
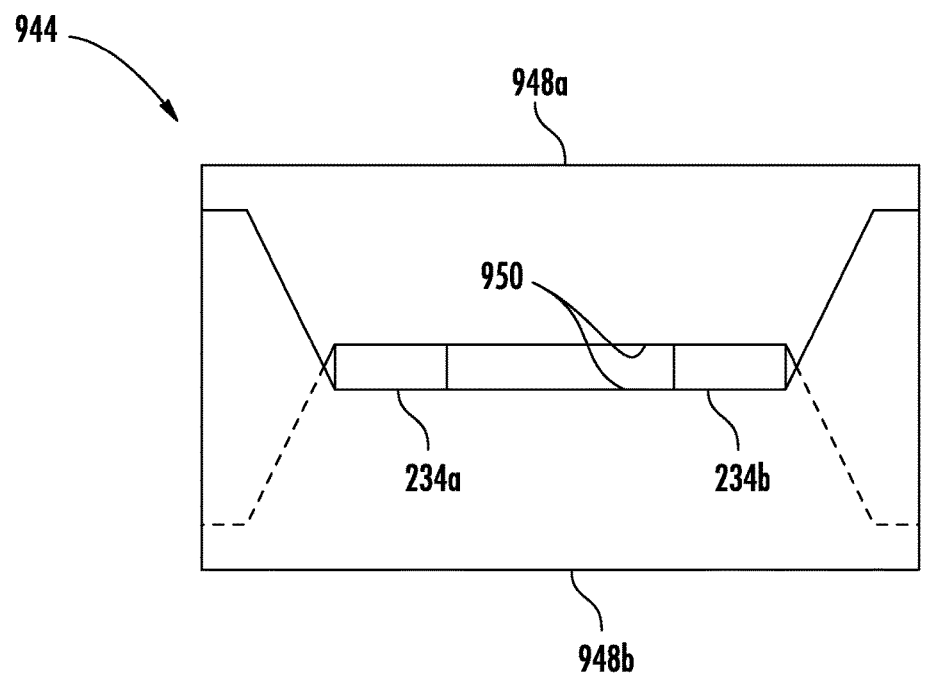
Figure 22:
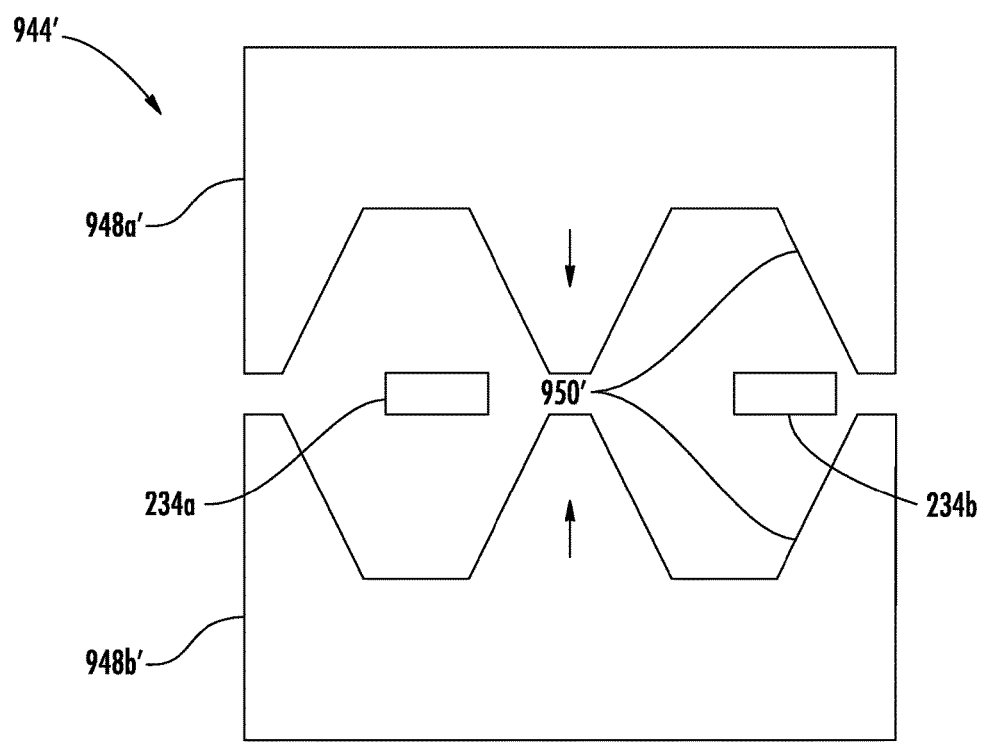
Figure 23:
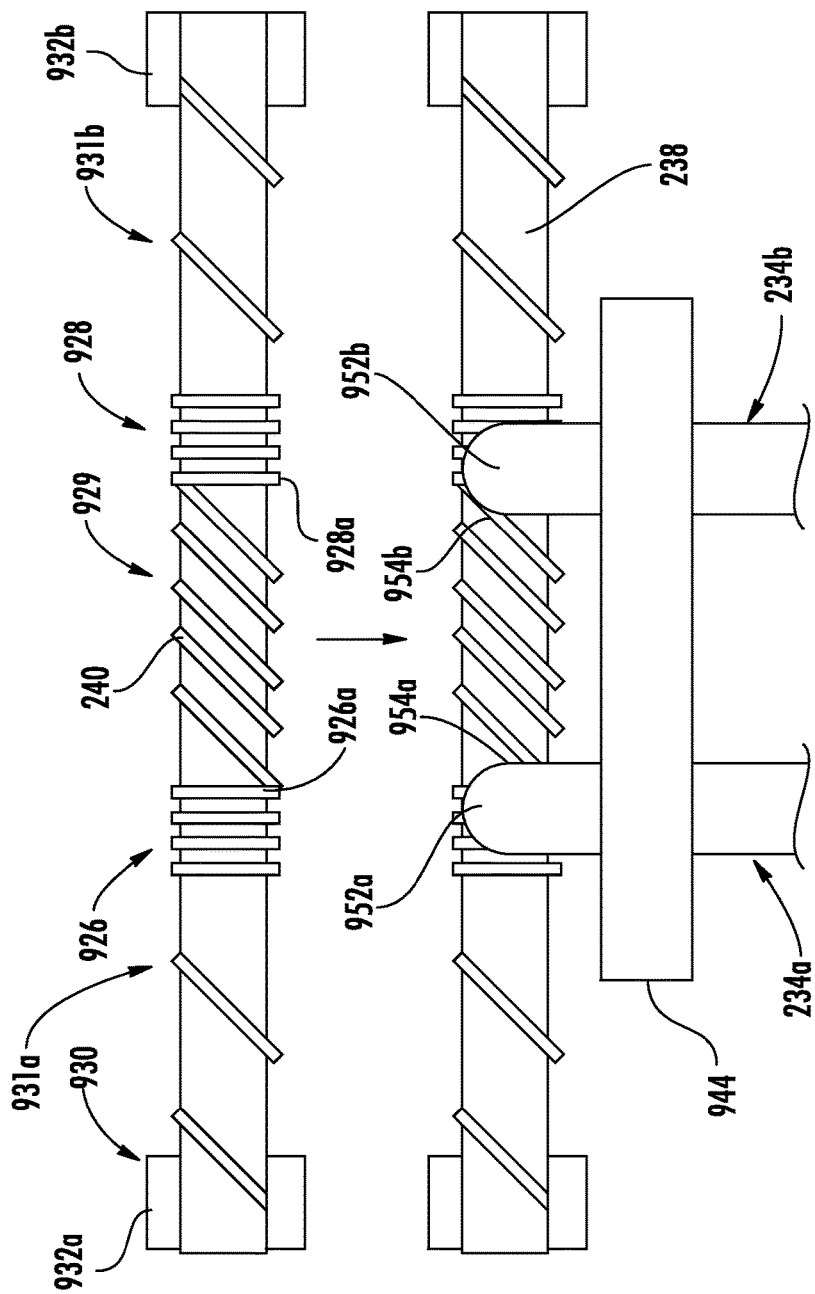
Figure 24:
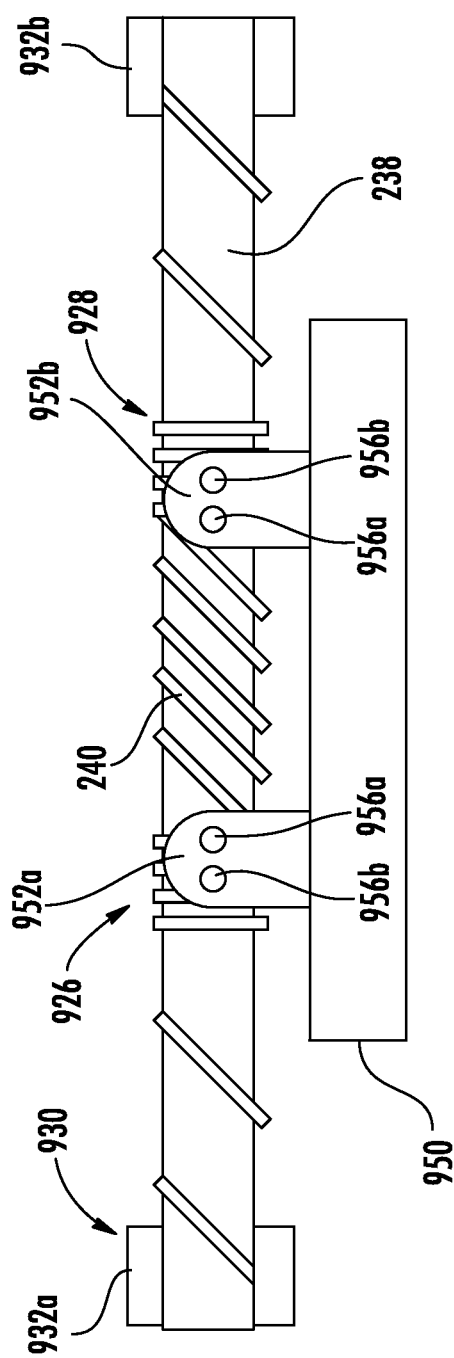
Figure 25:
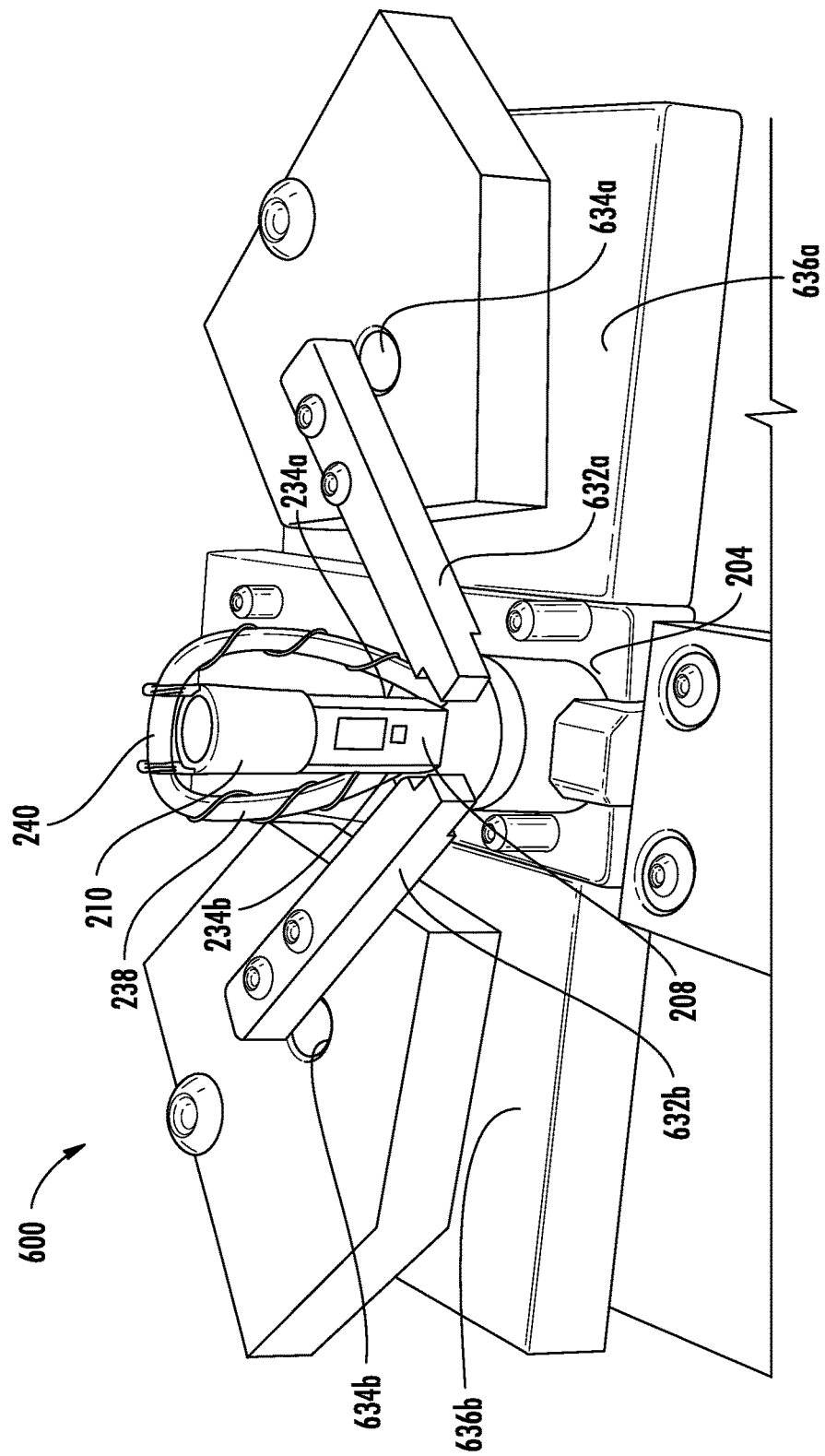
Figure 26:
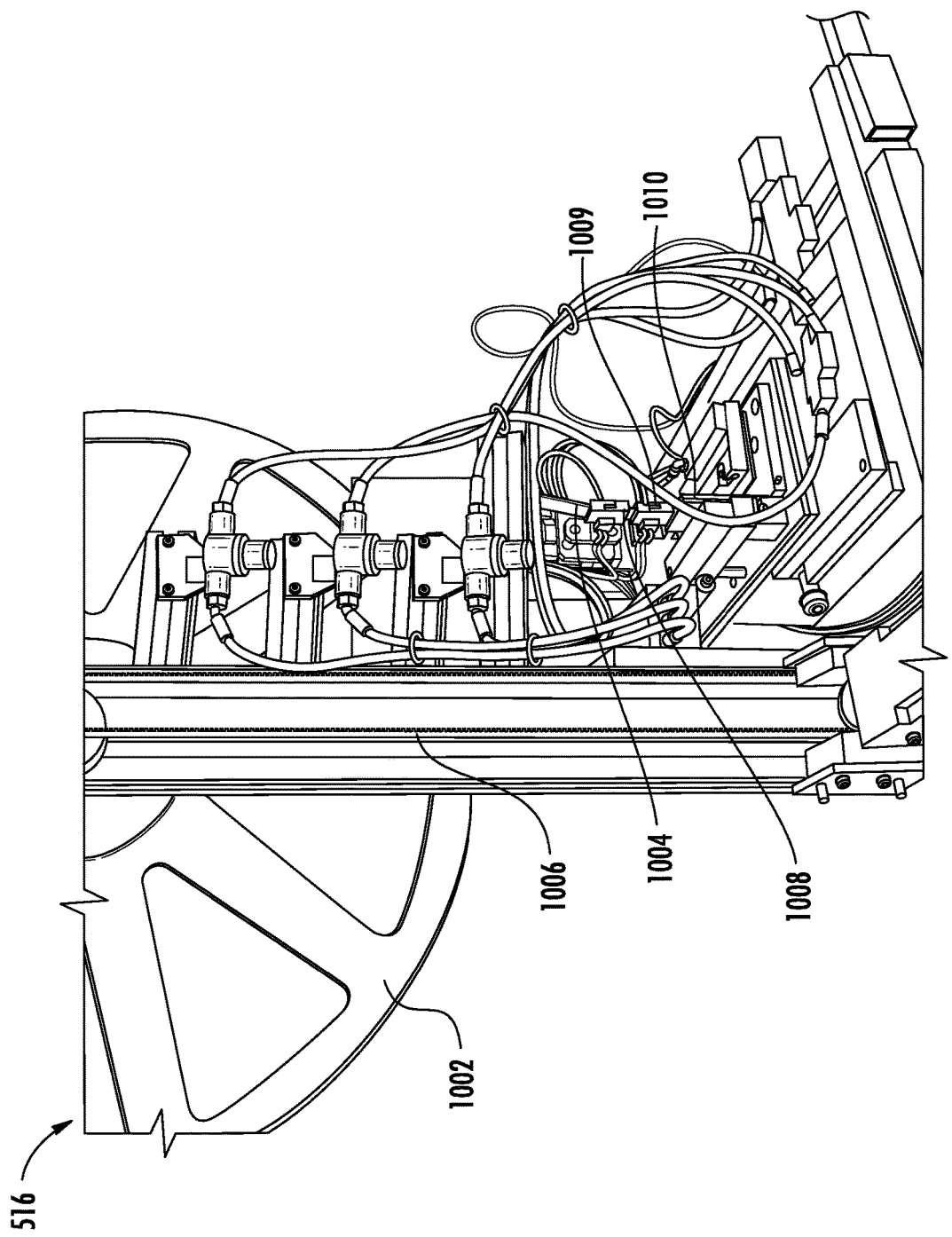
Figure 27:
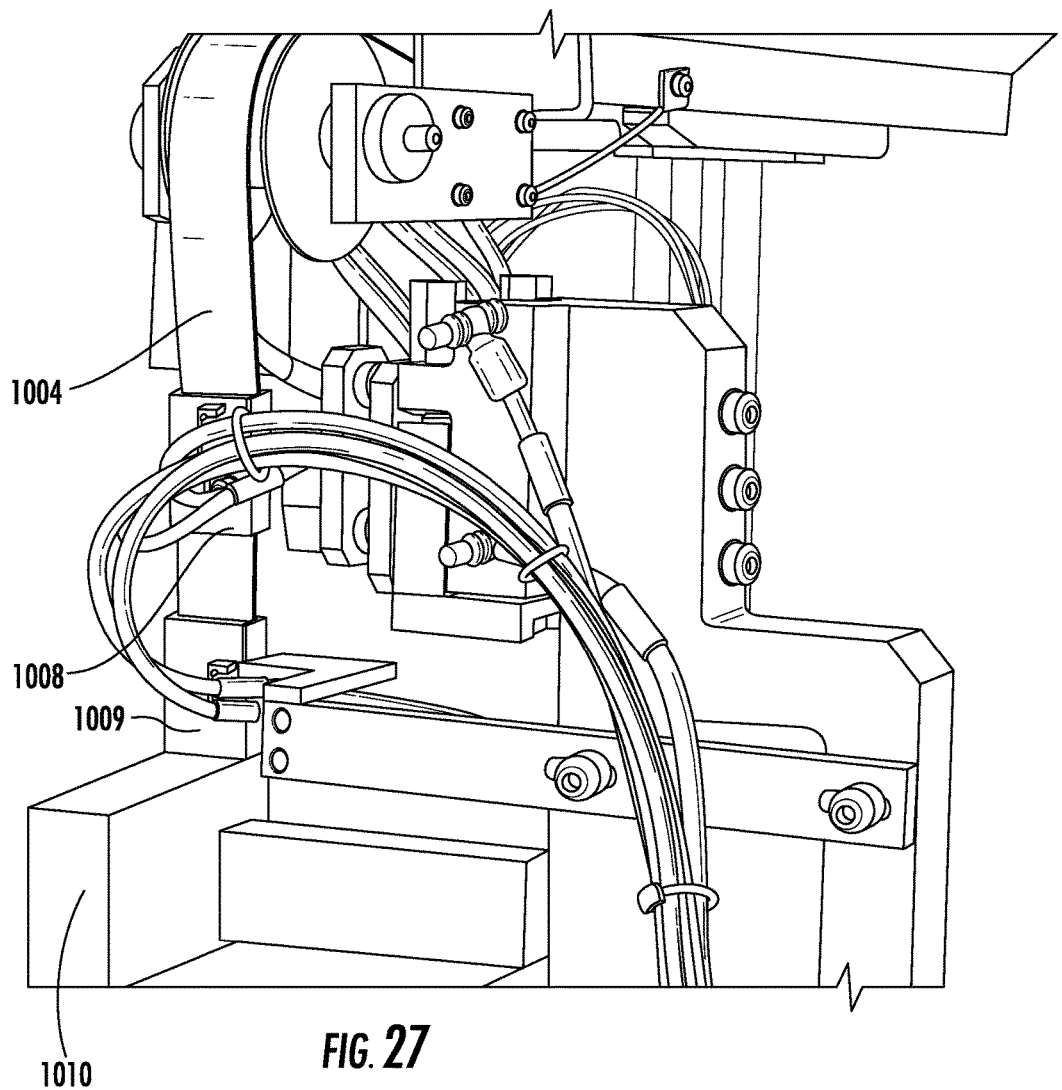
Figure 28:
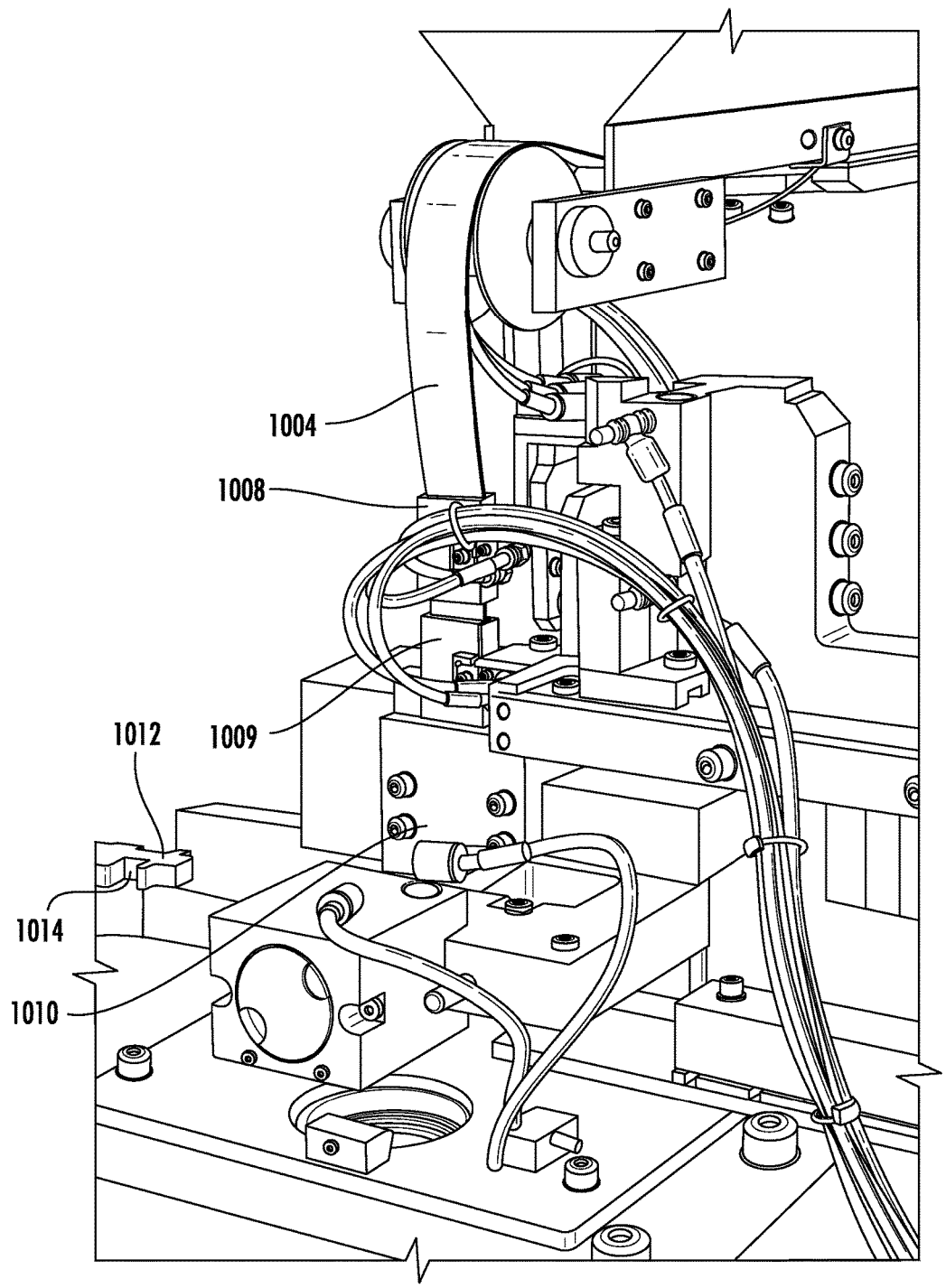
Figure 29:
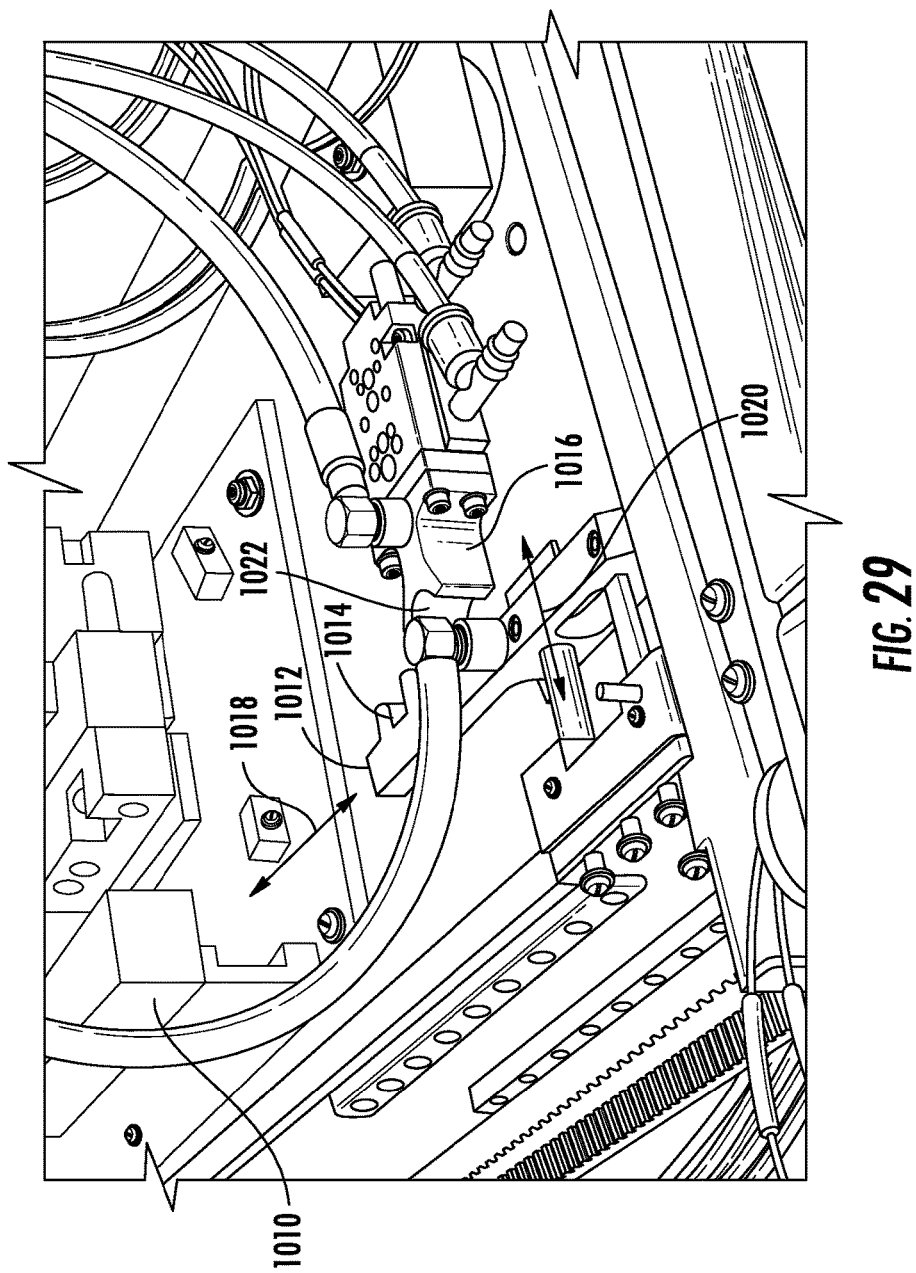
Figure 30:
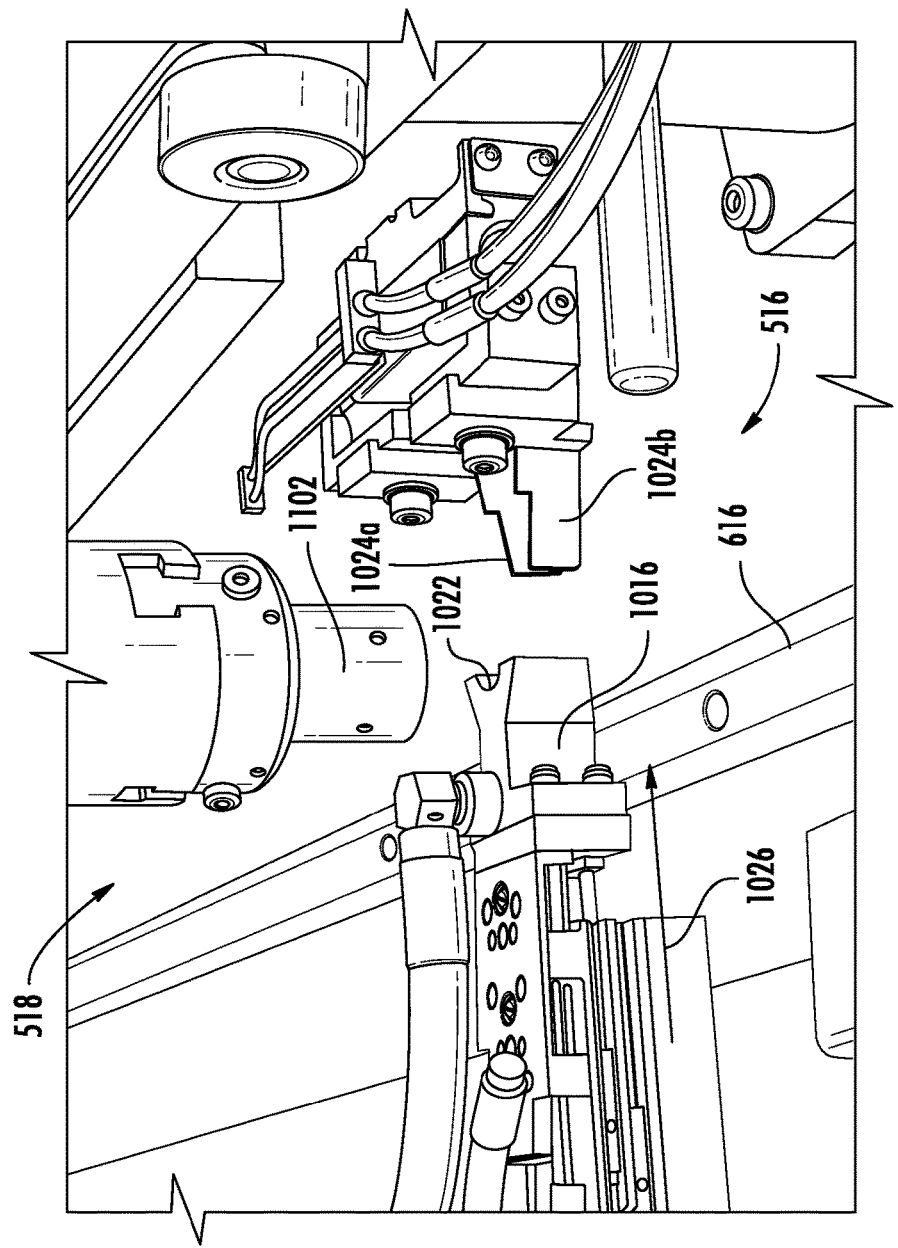
Figure 31:
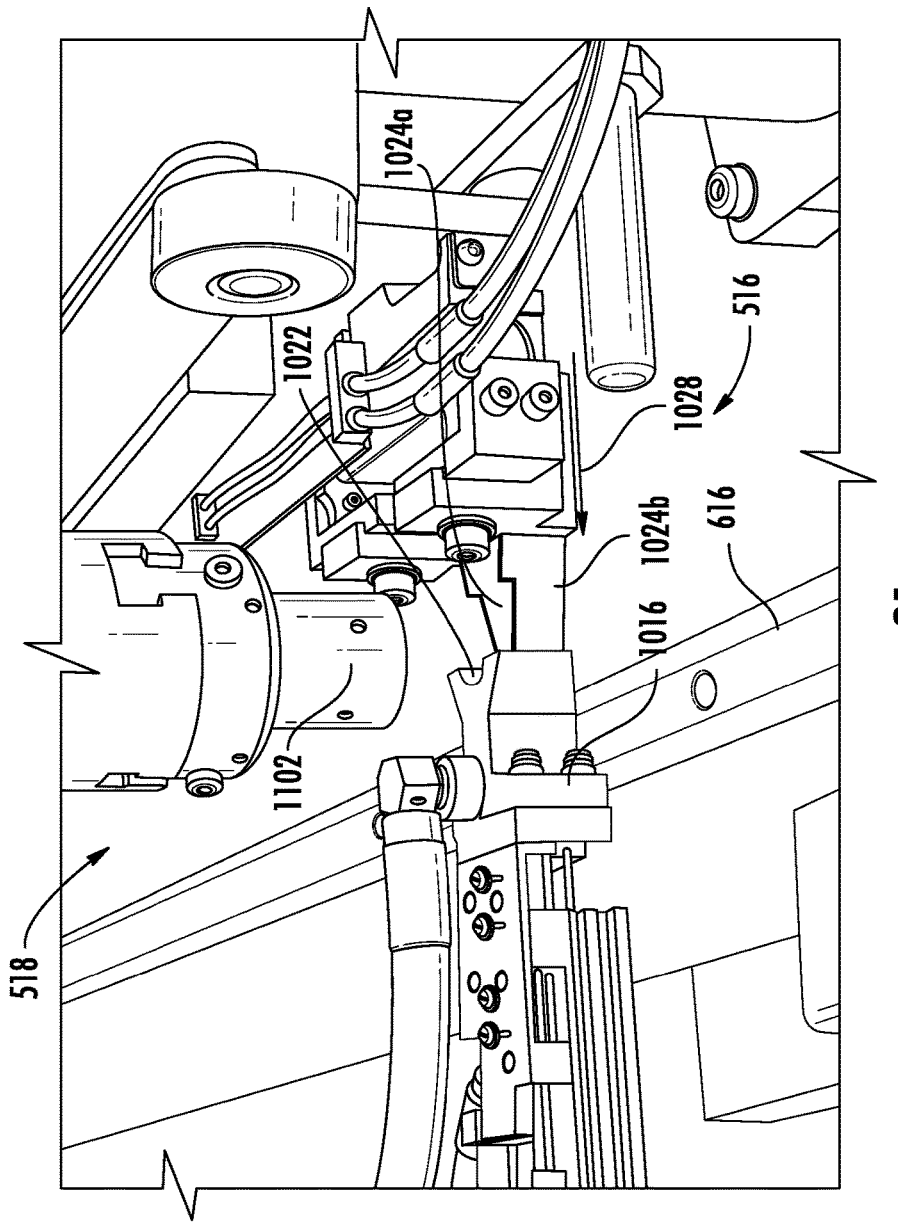
Figure 32:
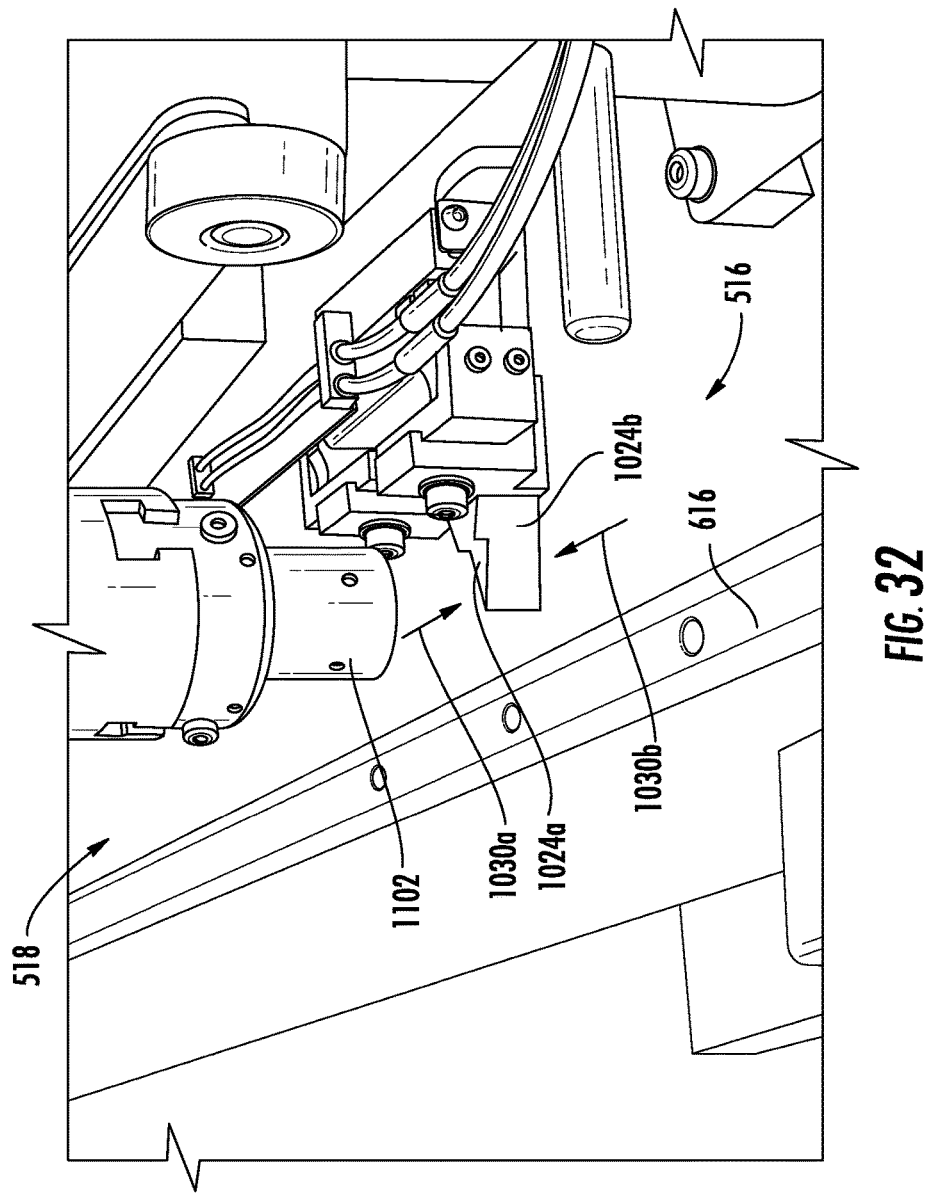
Figure 33:
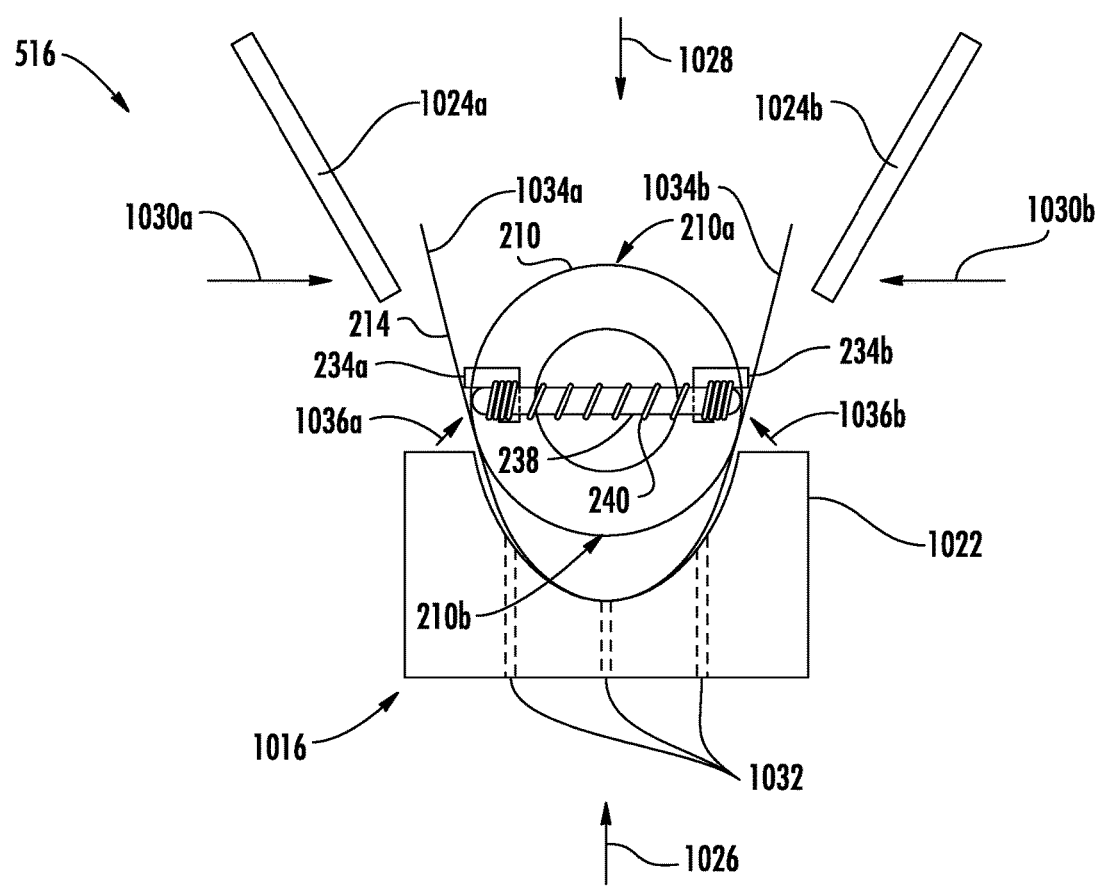
Figure 34:
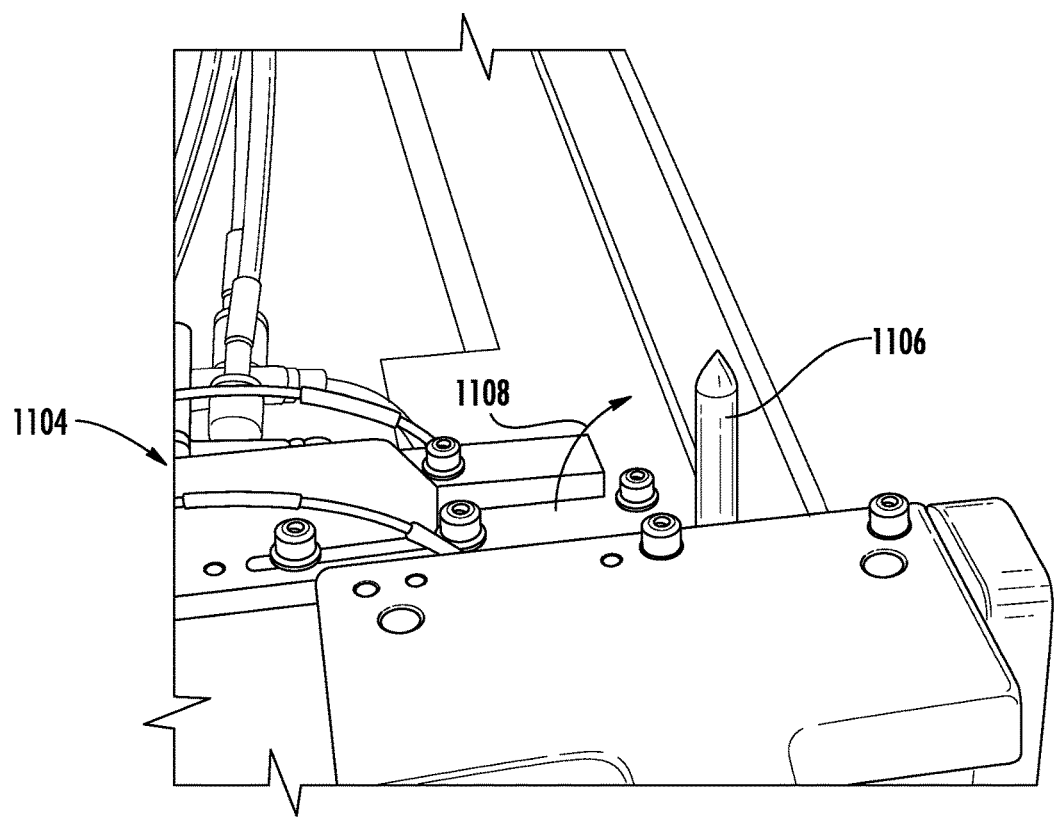
Figure 35:
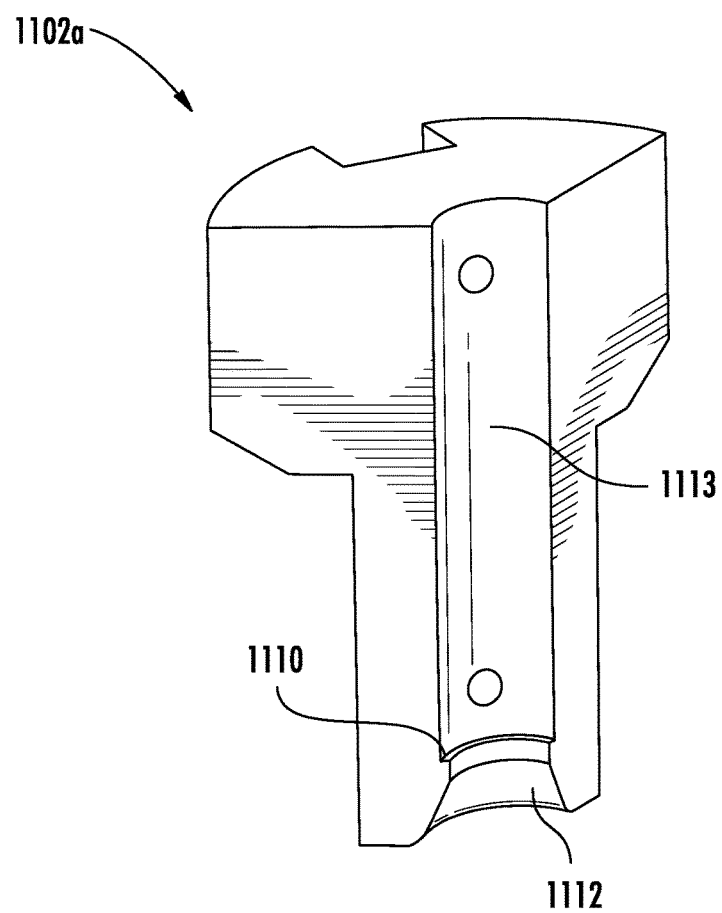
Figure 36:
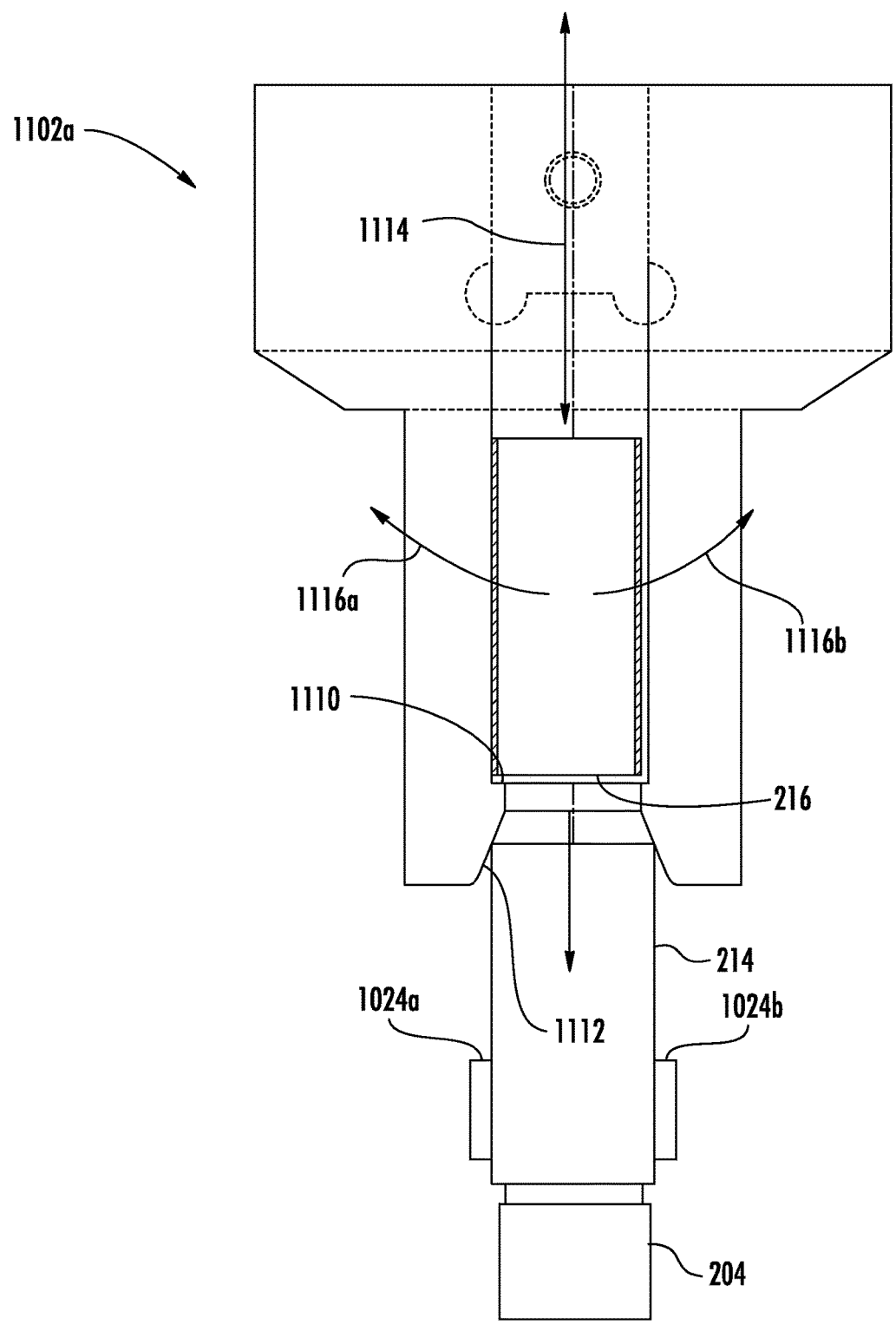
Figure 36A:
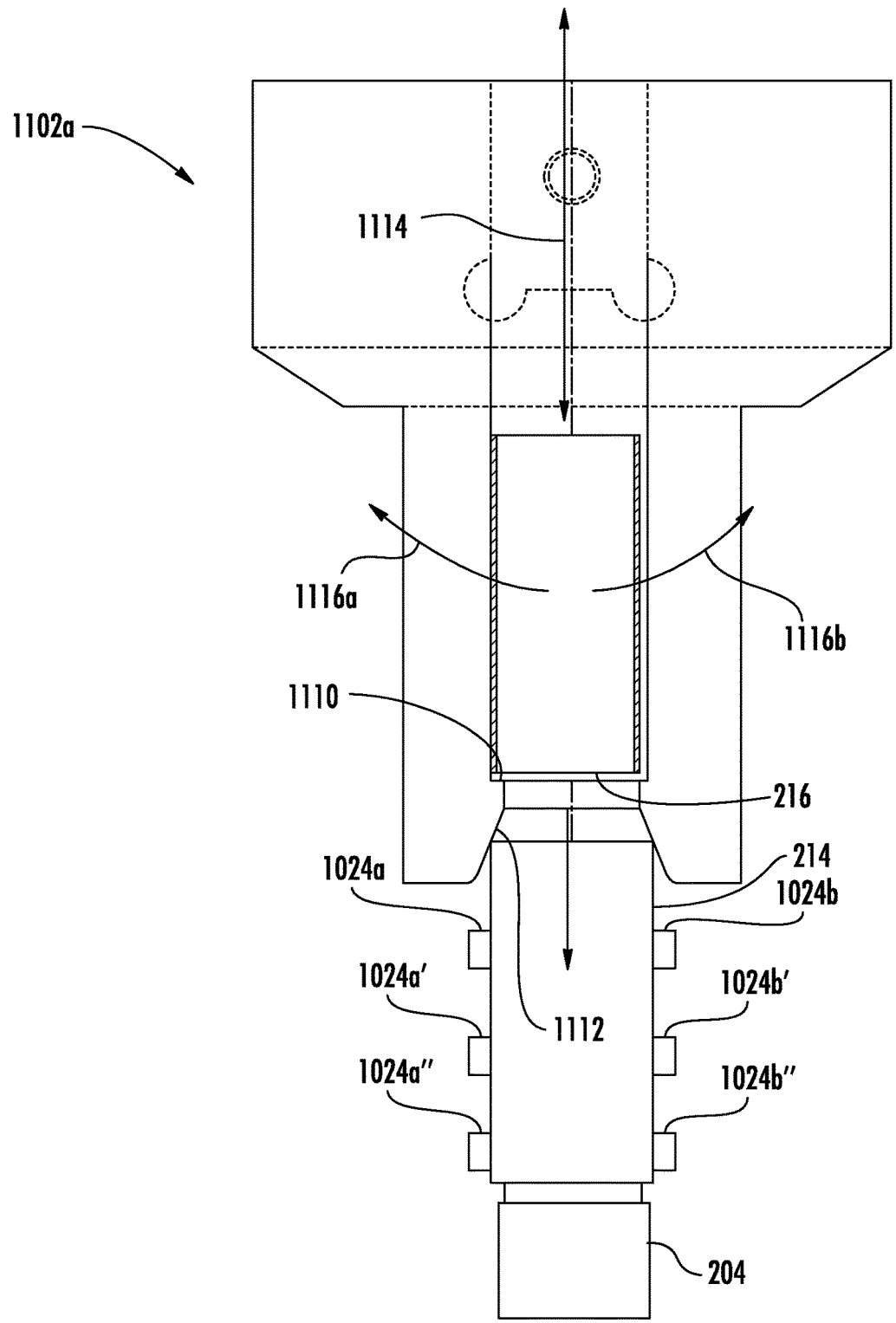
Figure 37:
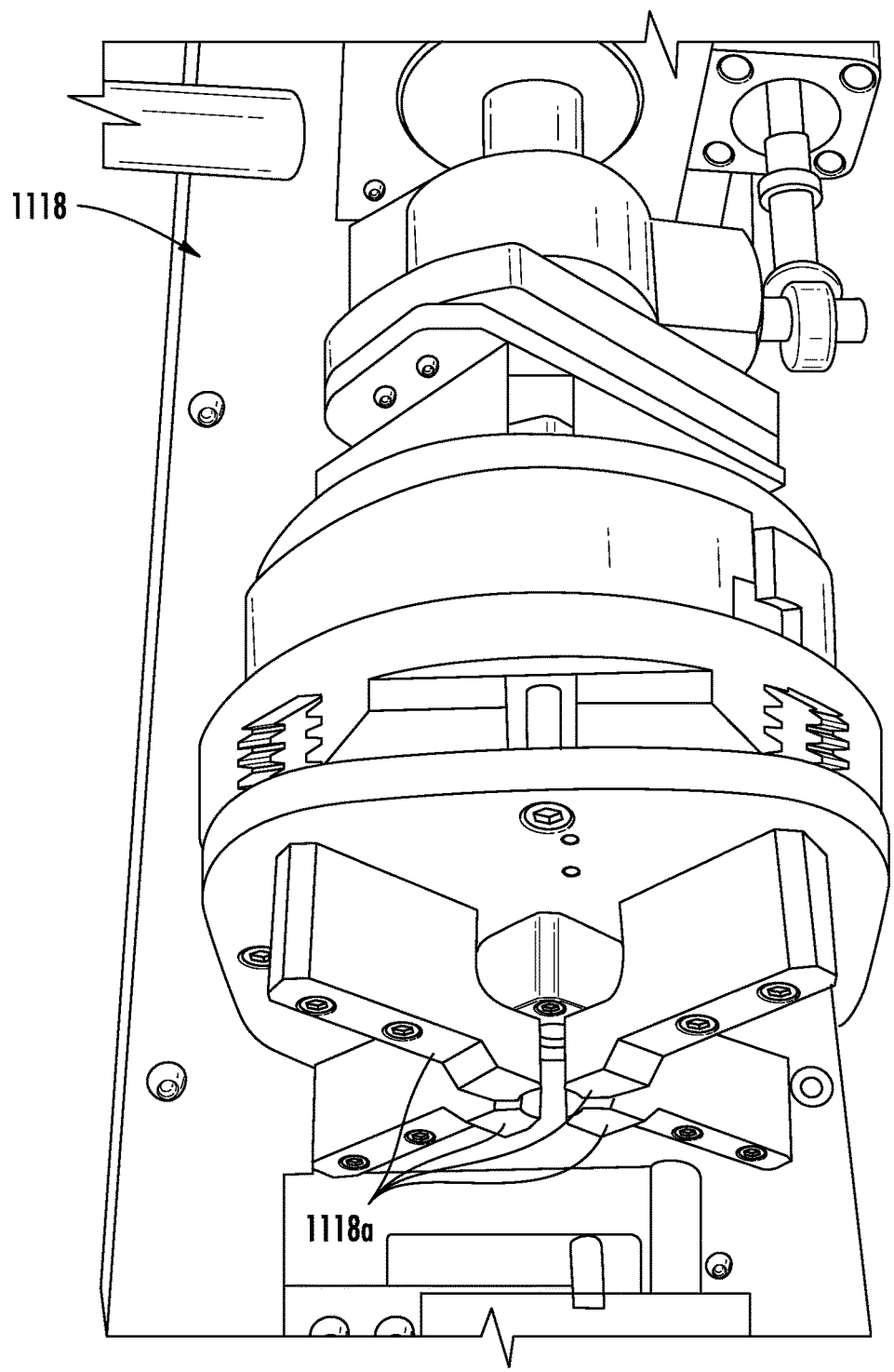
Figure 38:
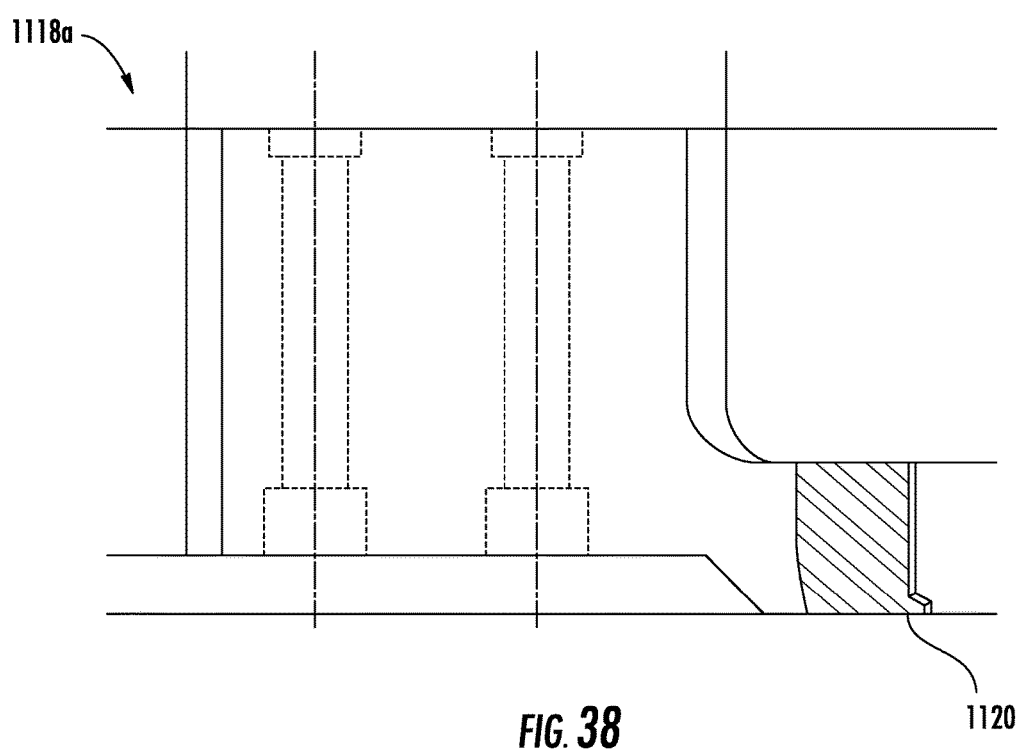
Figure 39:
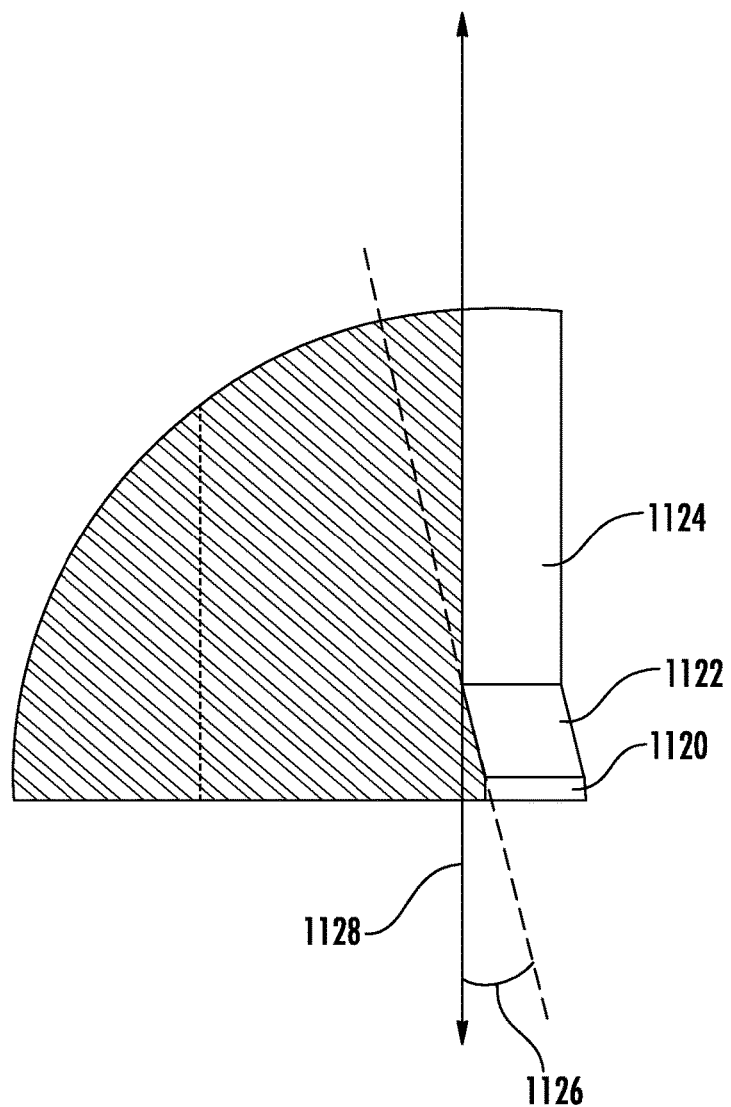
Figure 40:
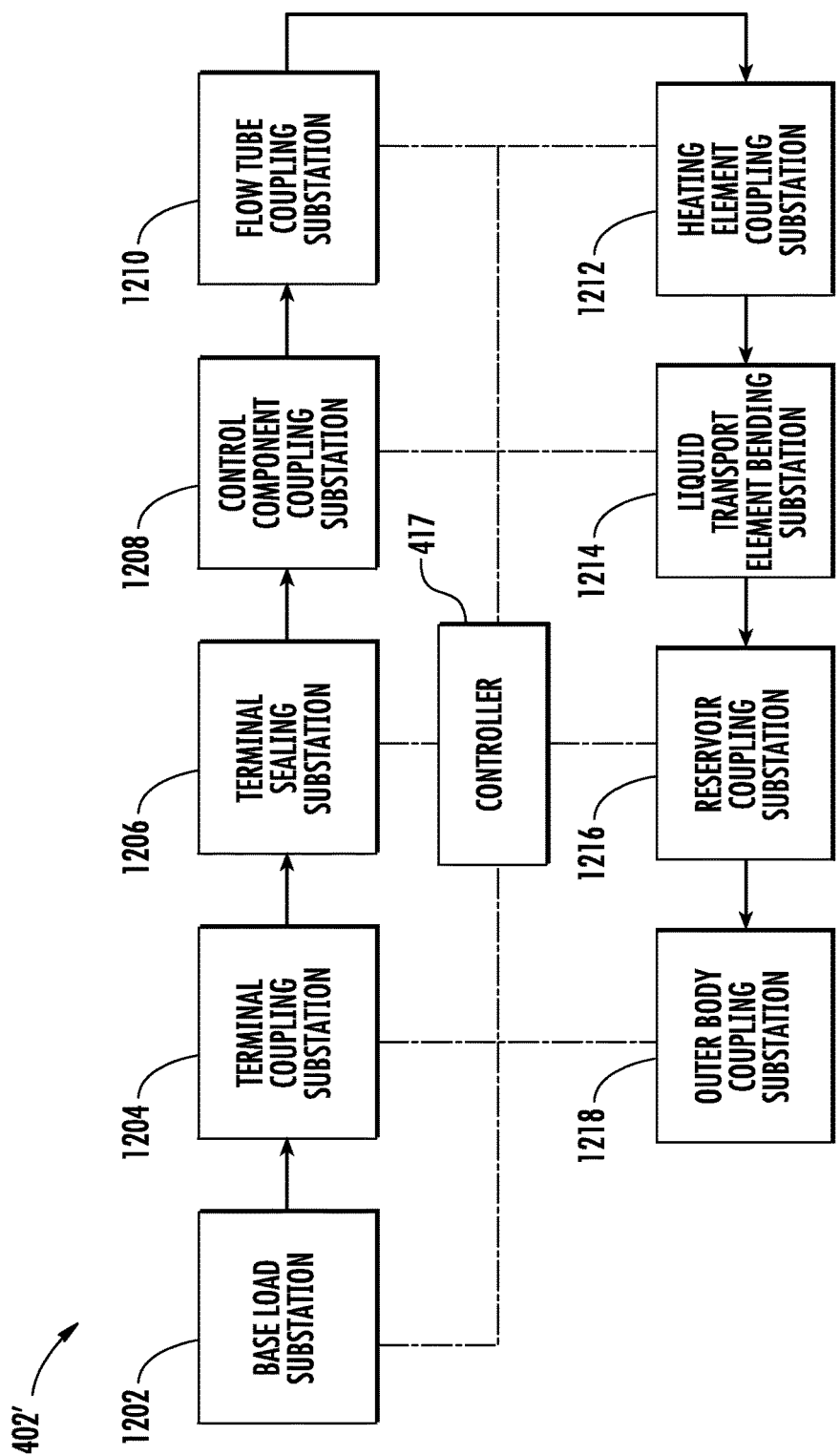
Figure 41:
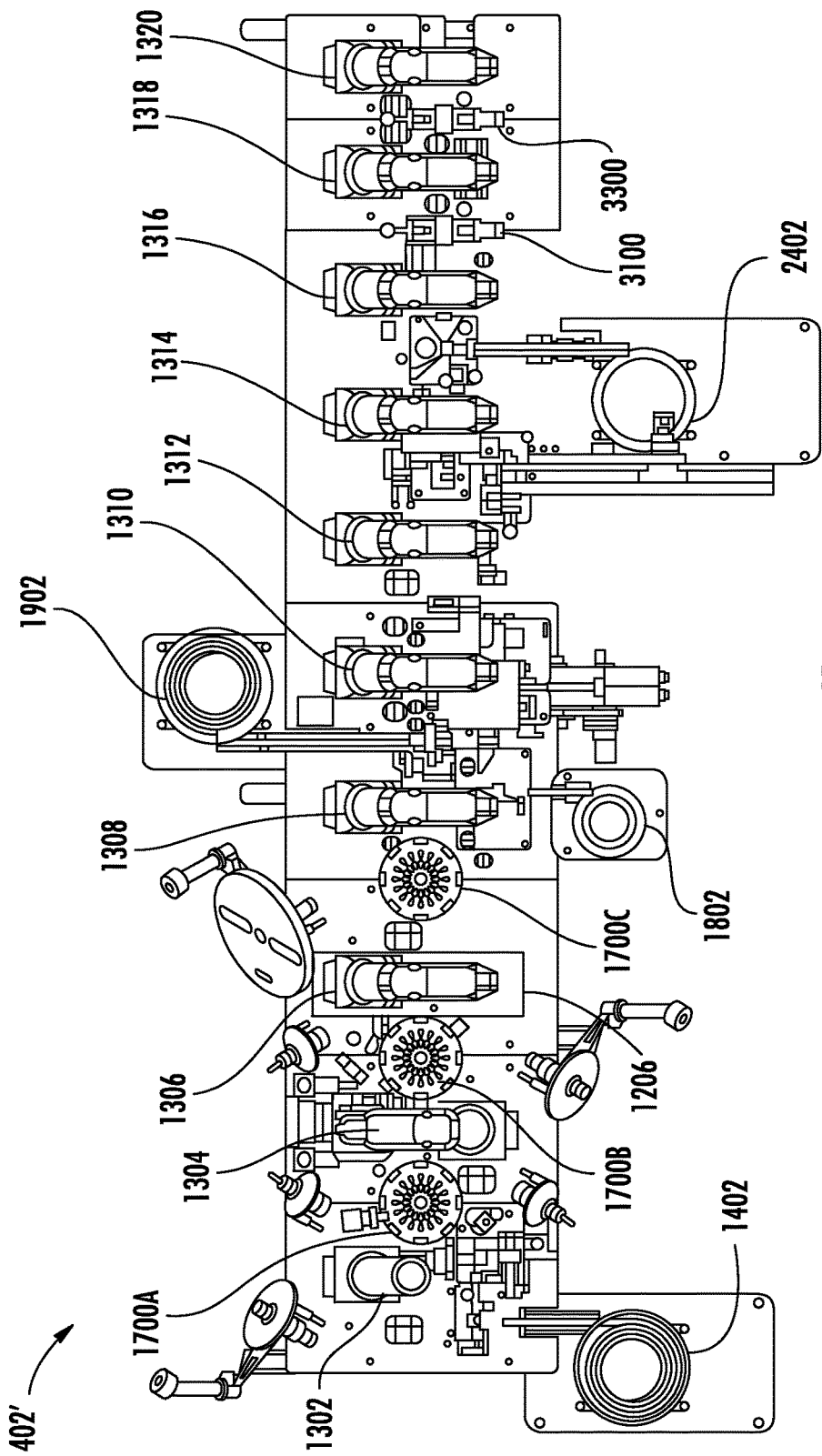
Figure 42:
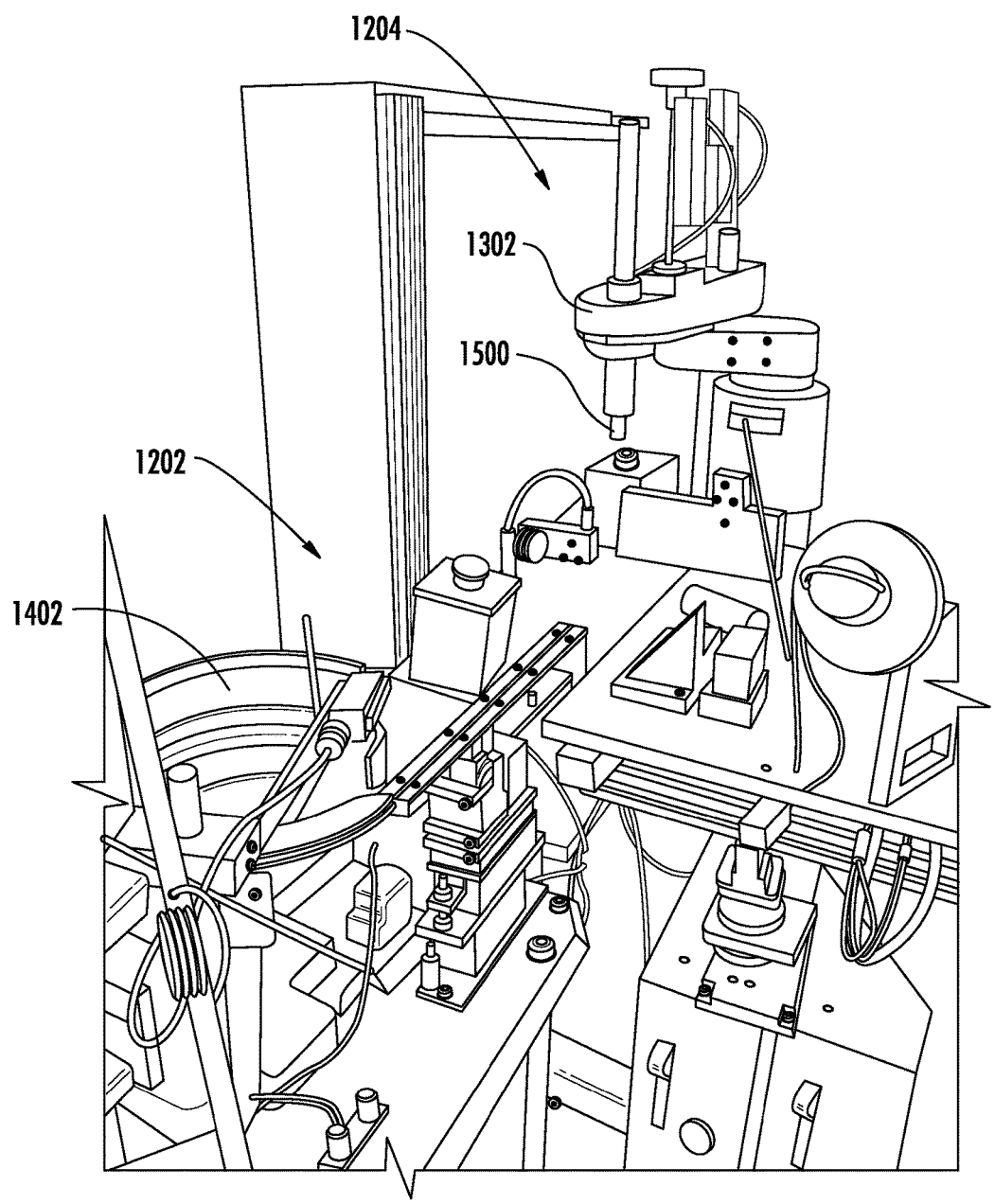
Figure 43:
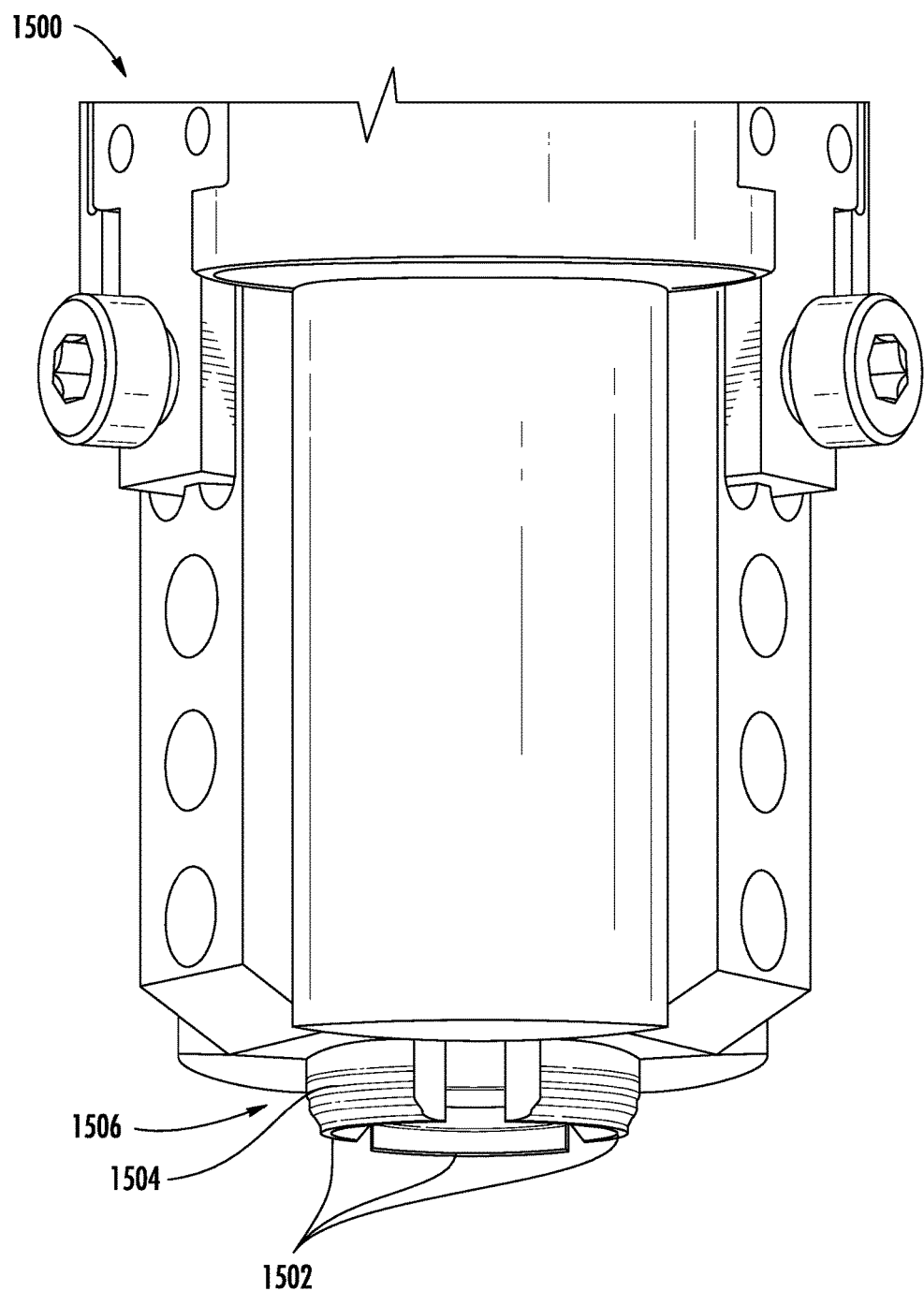
Figure 44:
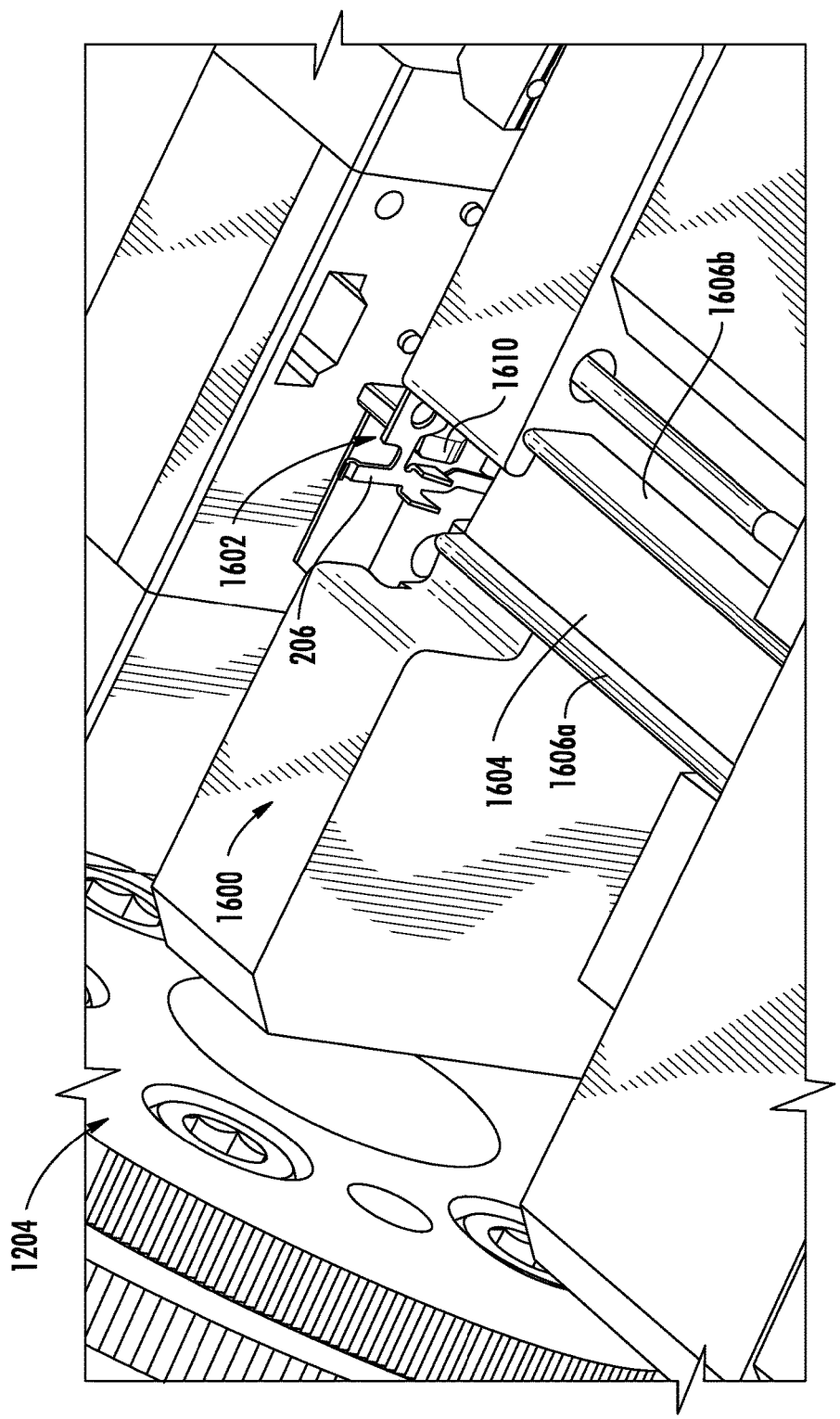
Figure 44A:
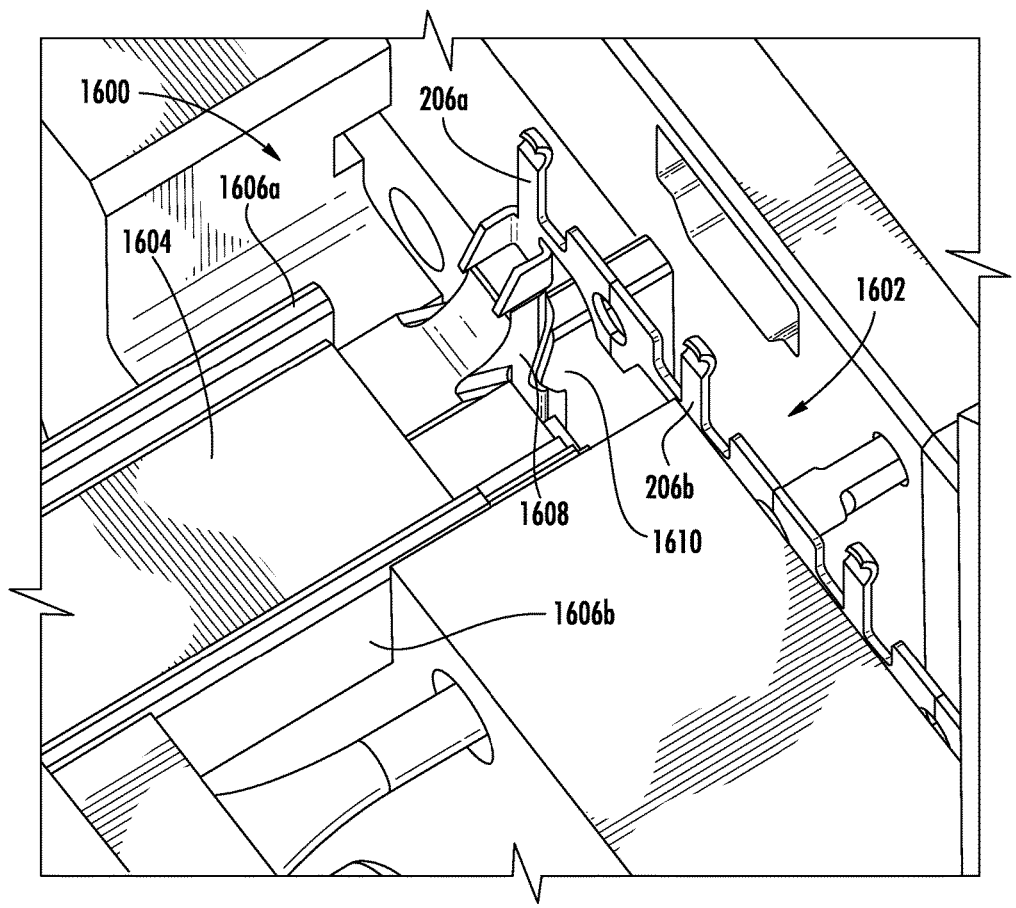
Figure 45:
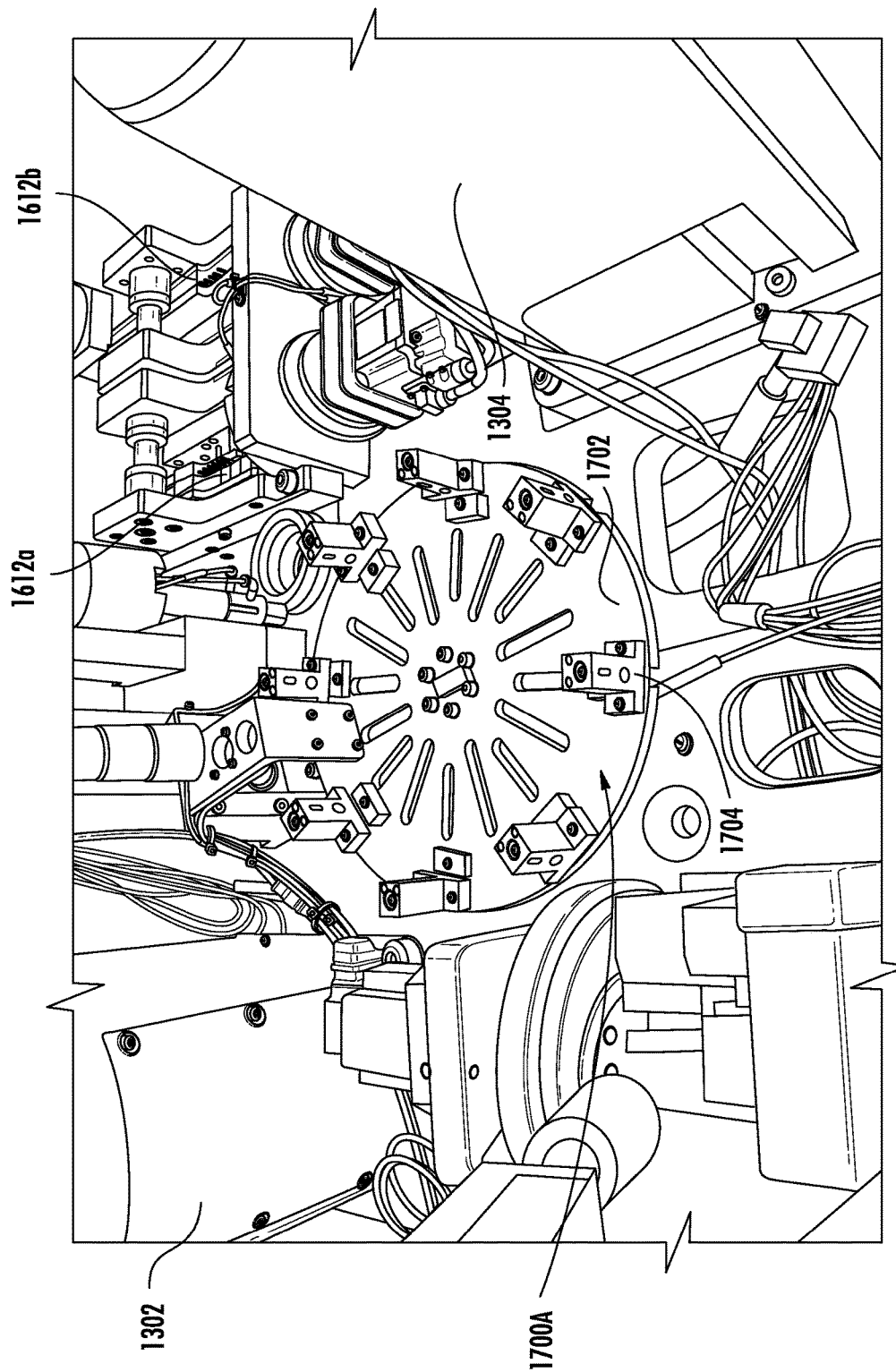
Figure 46:
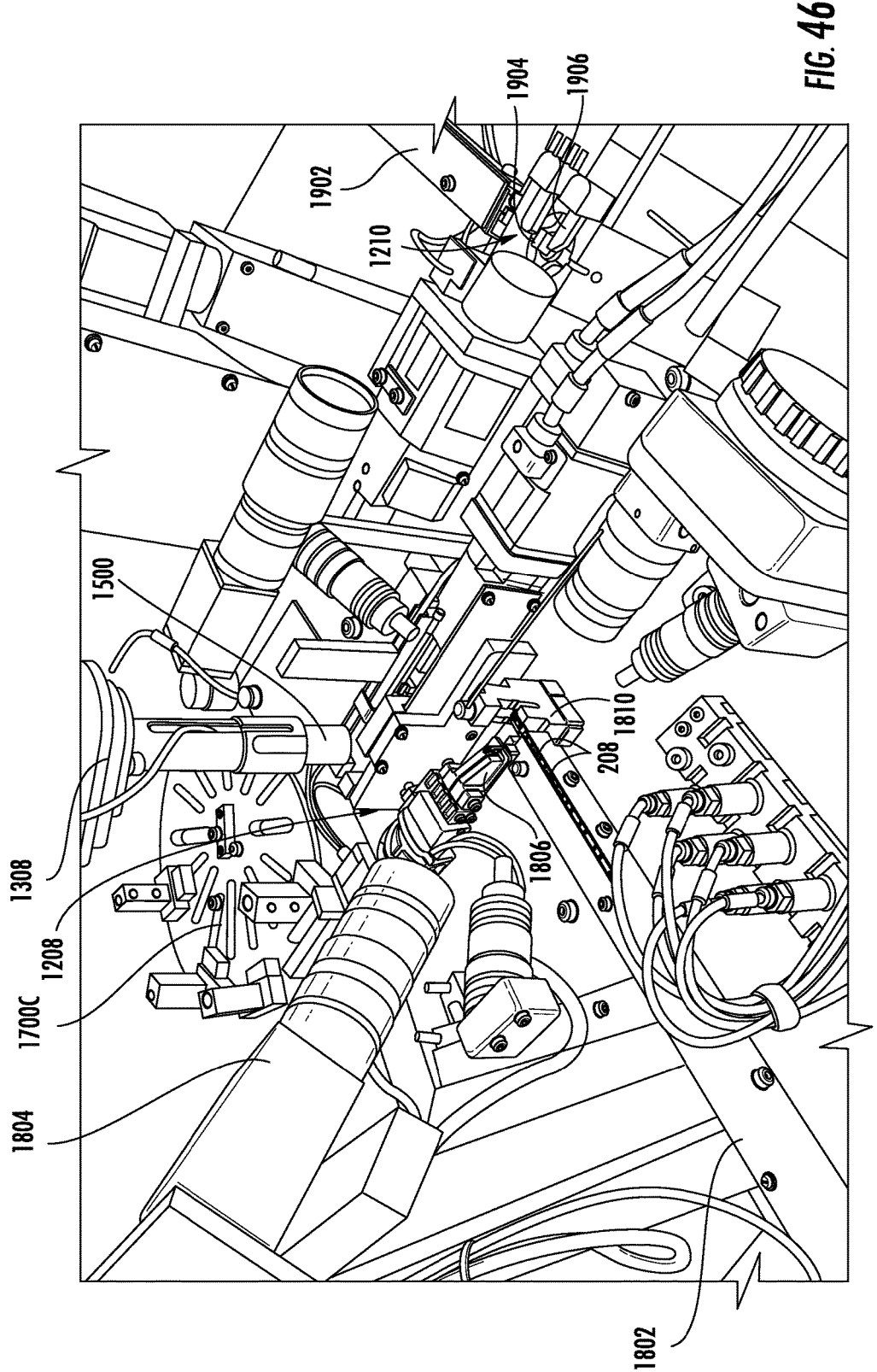
Figure 47:
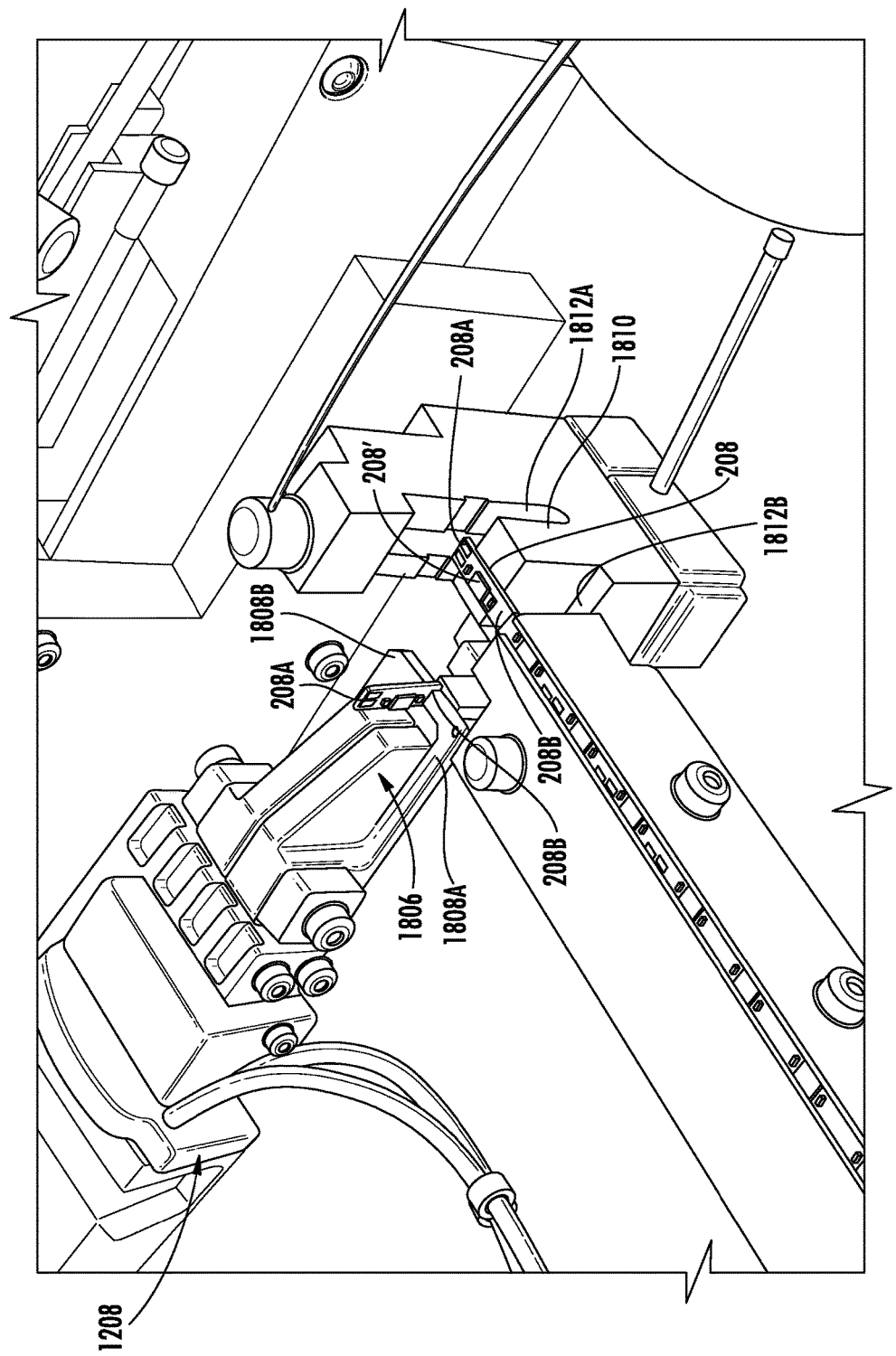
Figure 48:
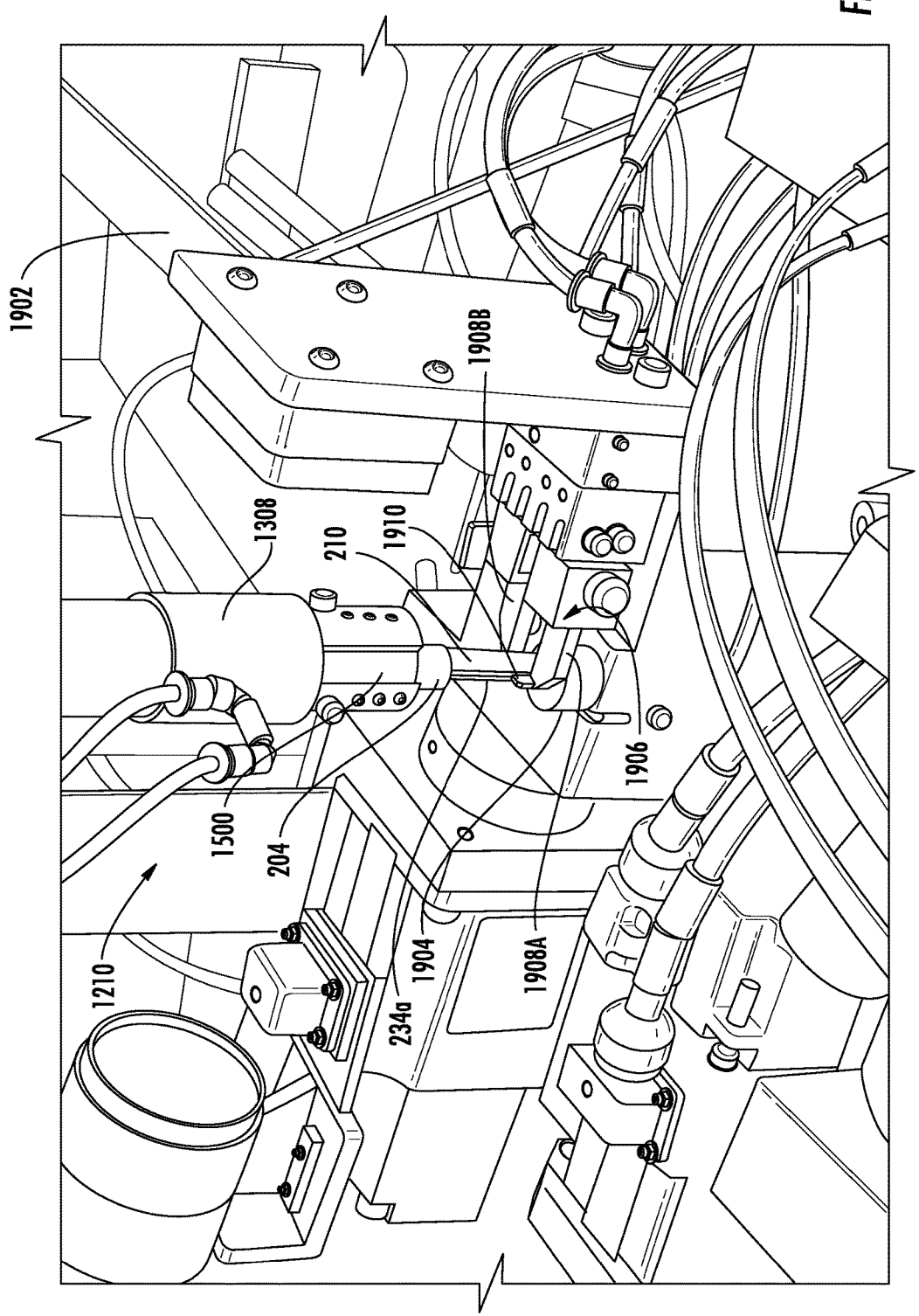
Figure 49:
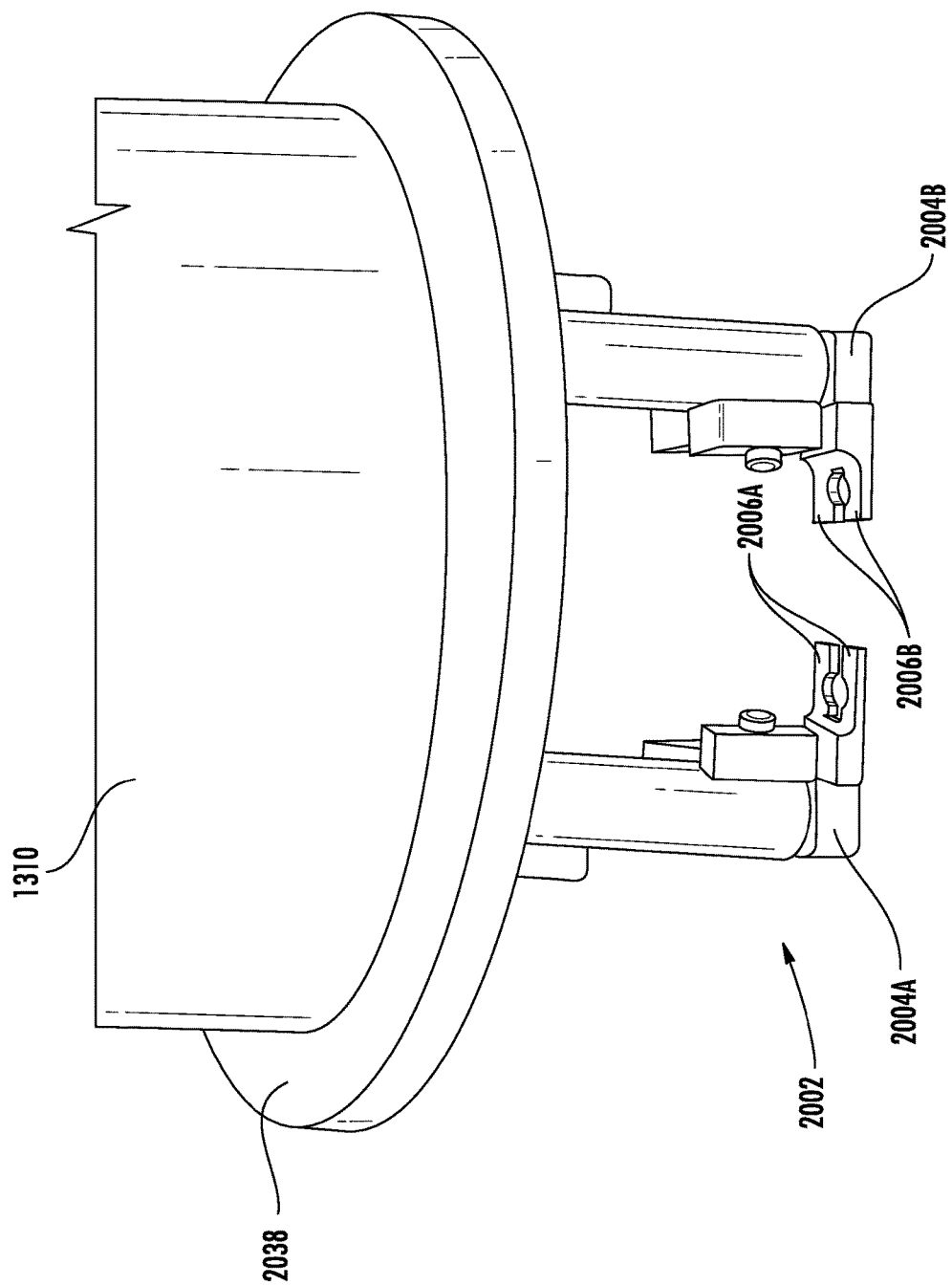
Figure 50:
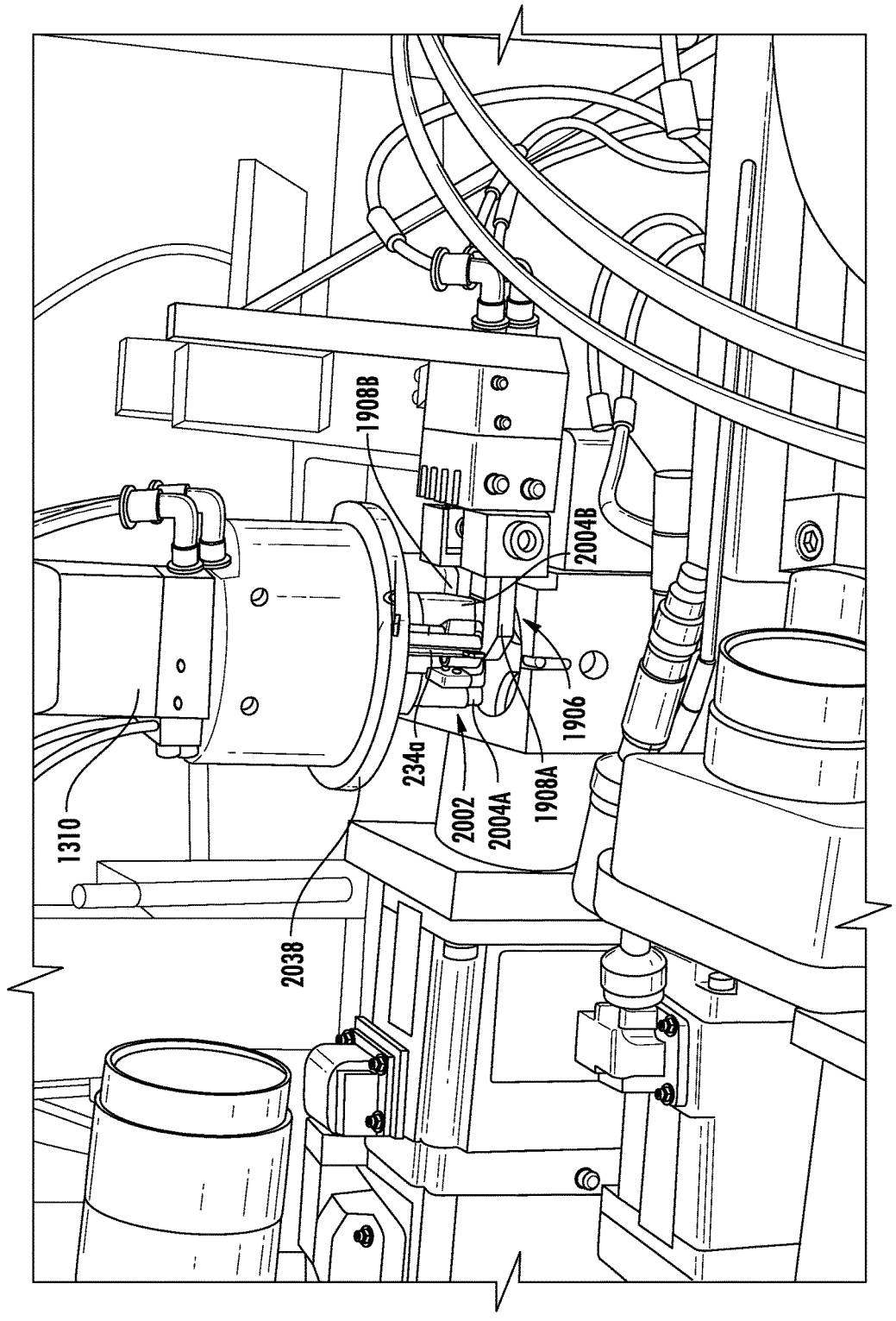
Figure 51:
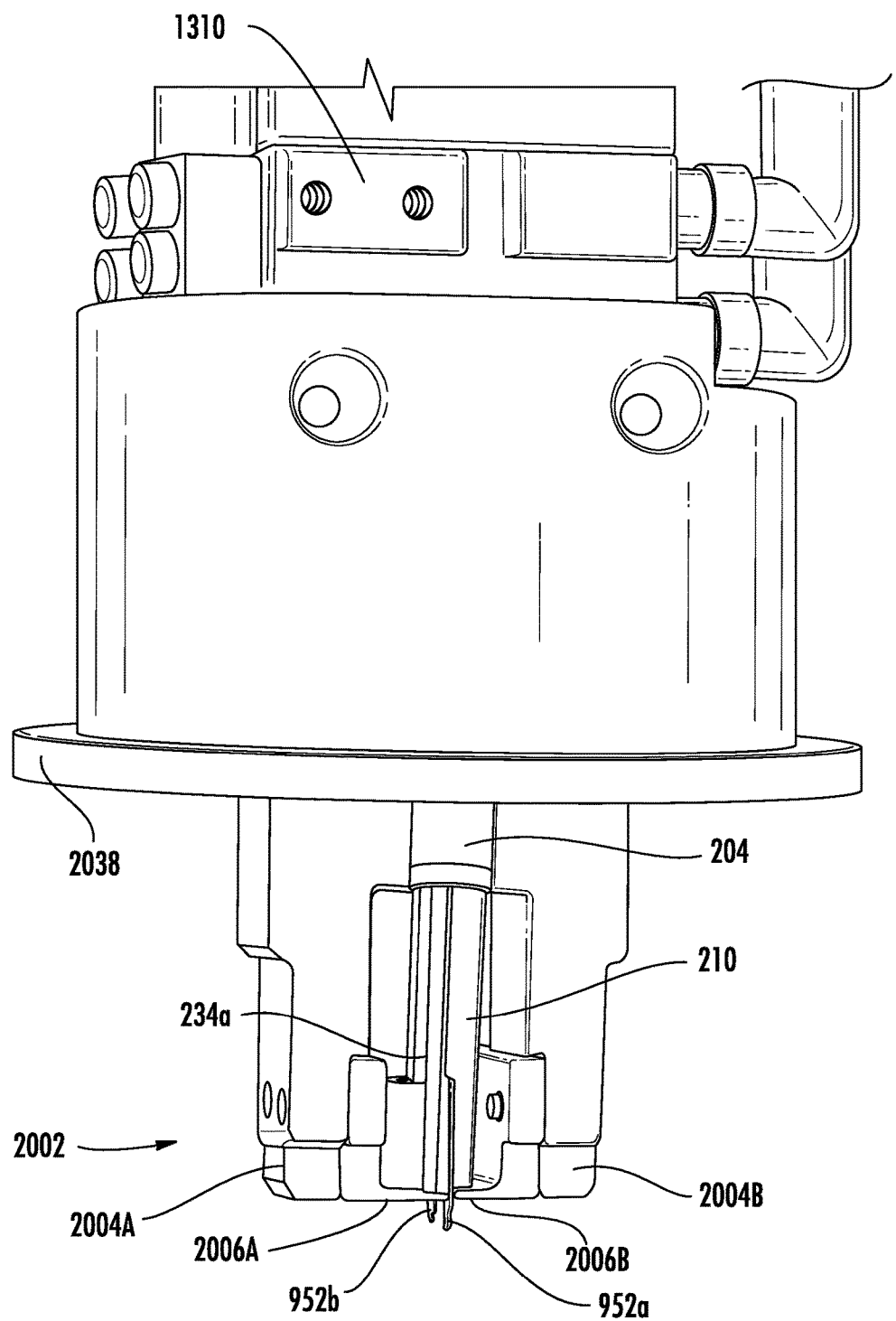
Figure 52:
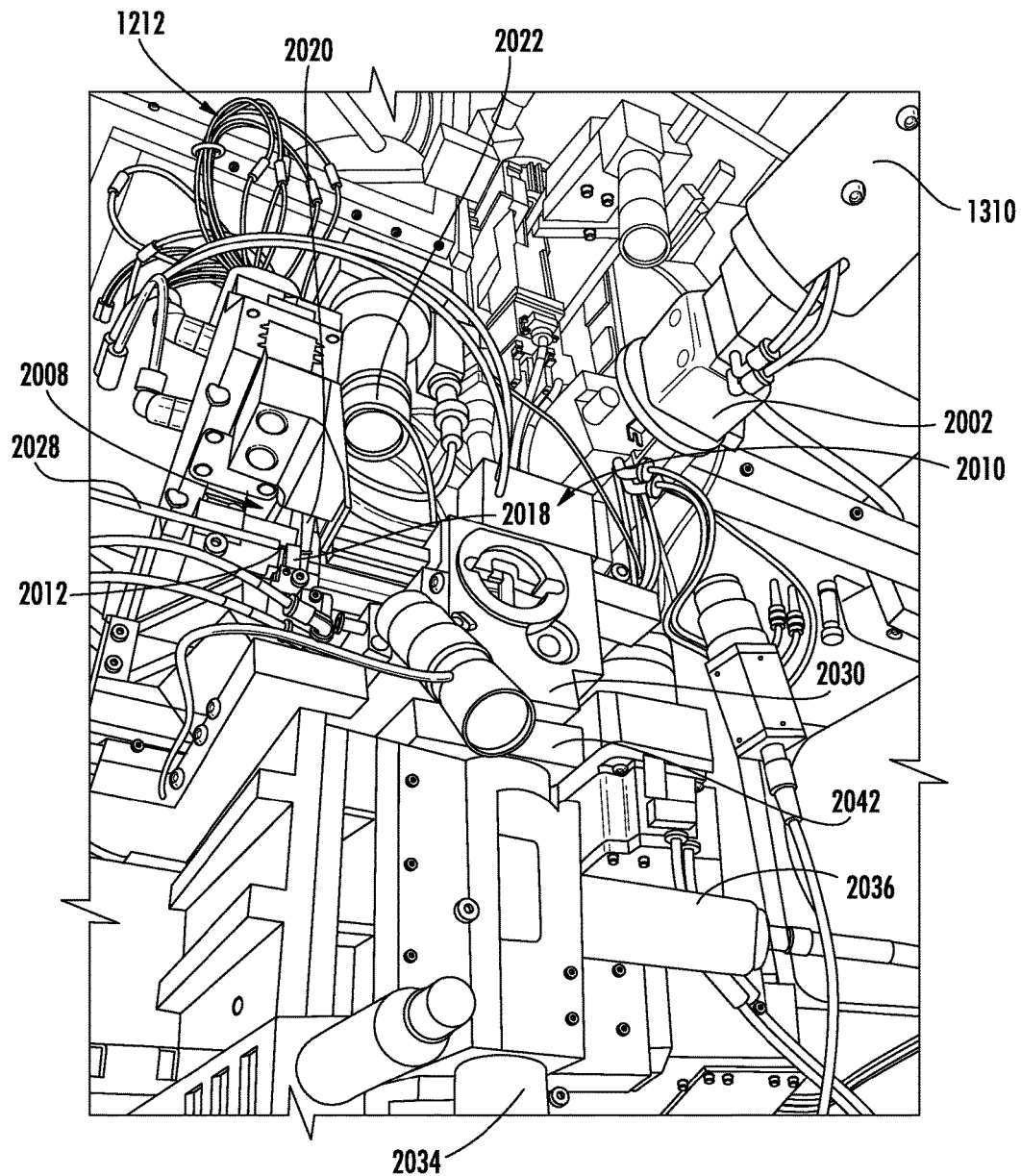
Figure 53:
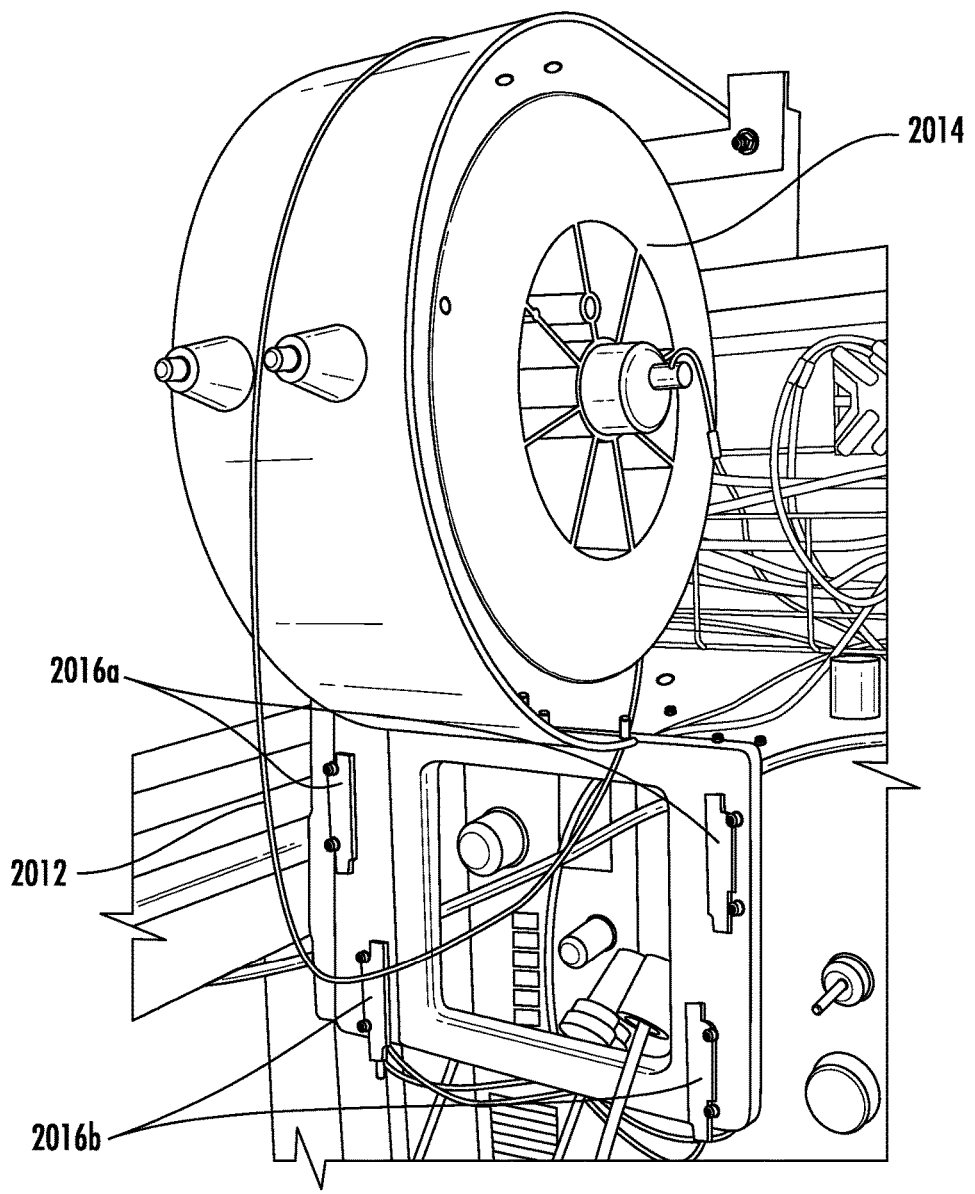
Figure 54:
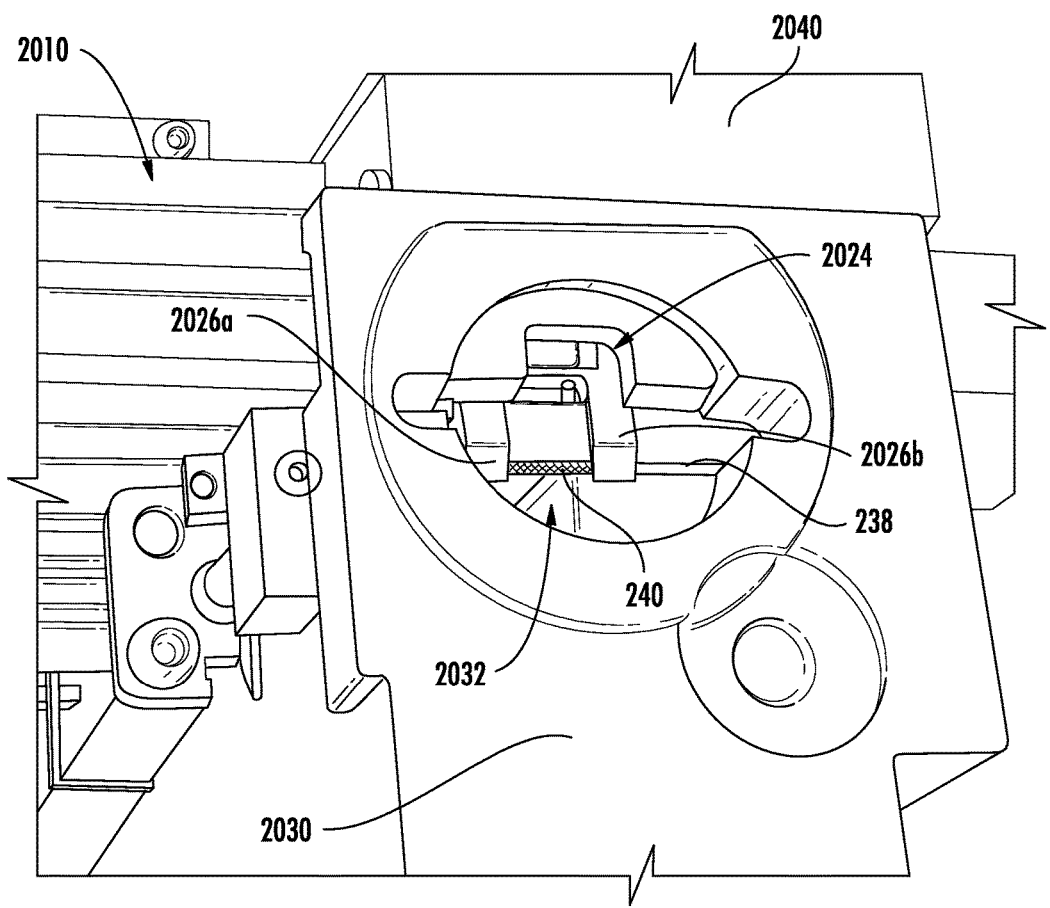
Figure 55:
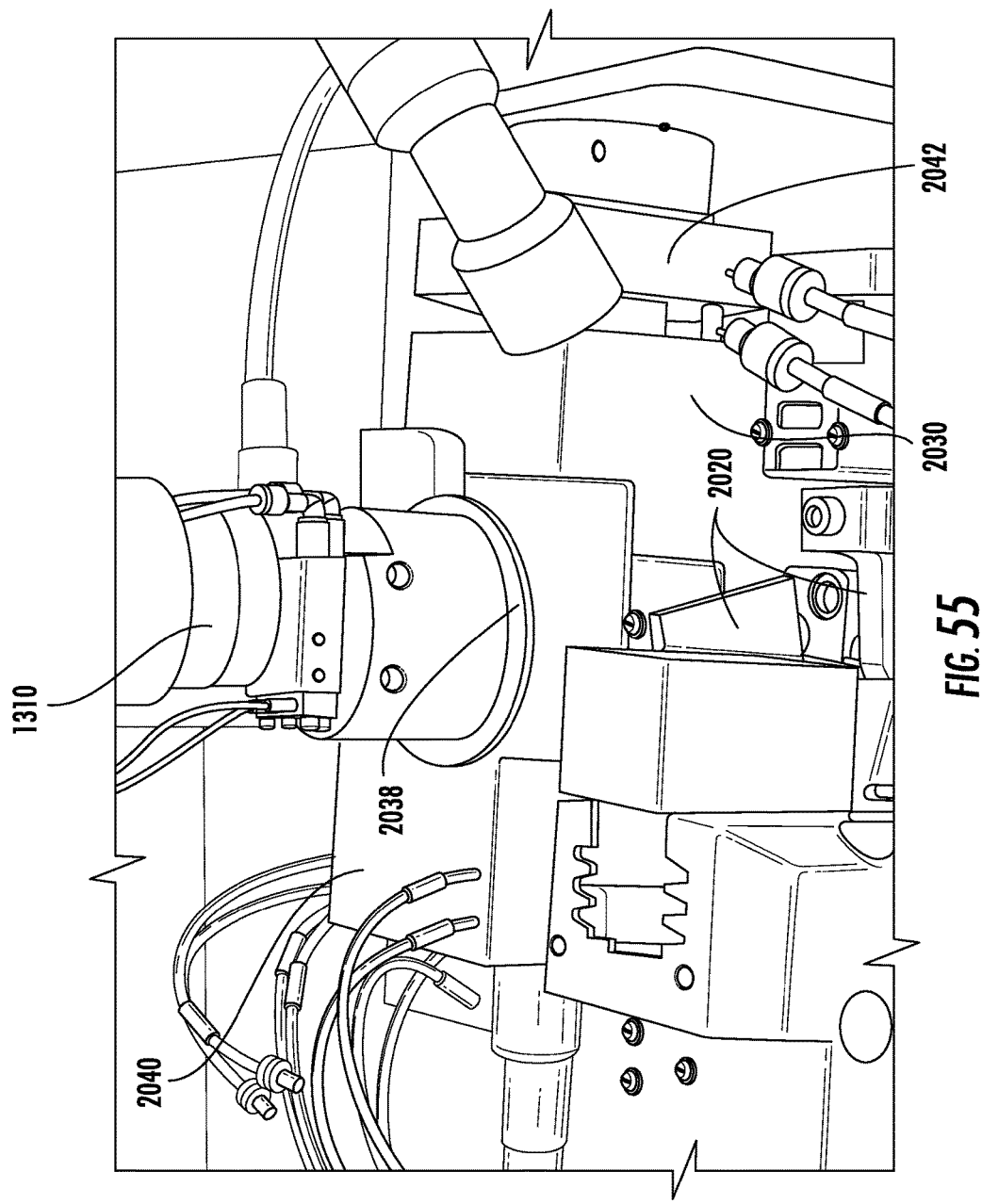
Figure 56:
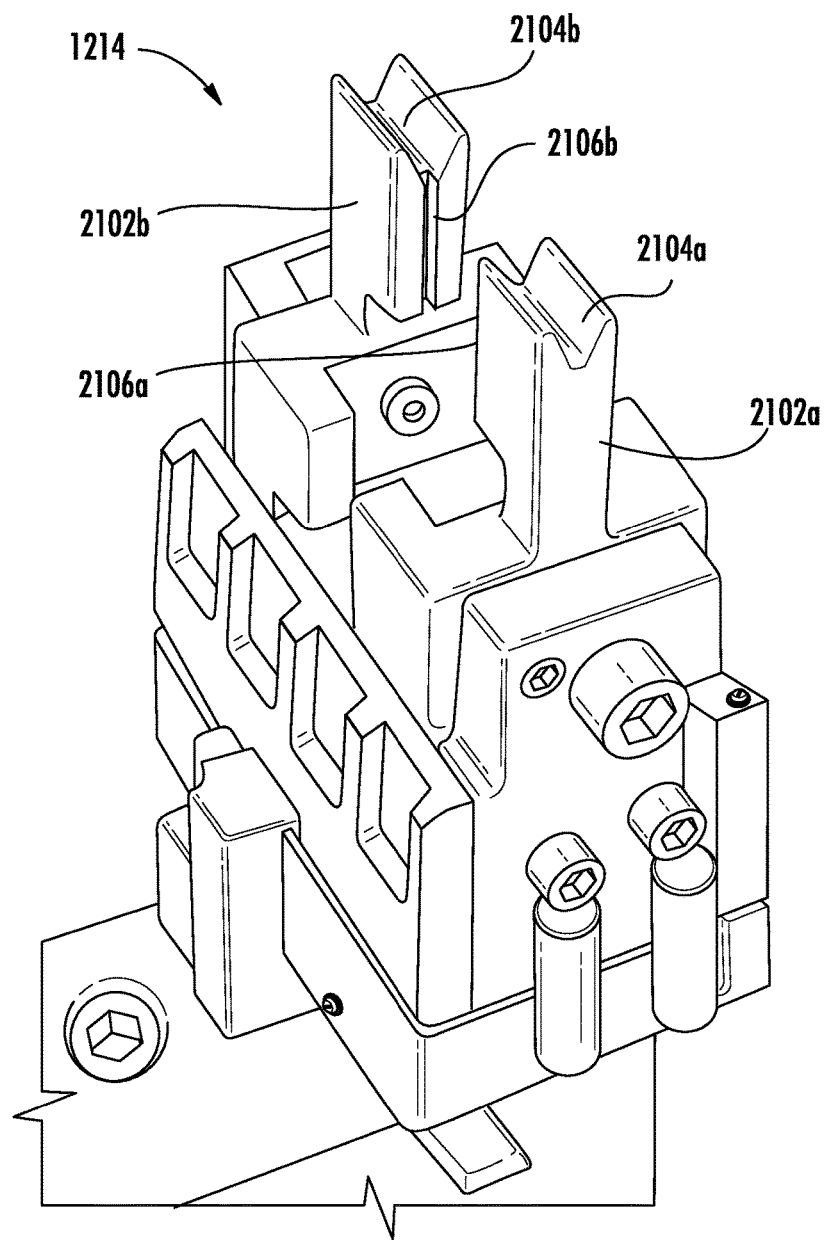
Figure 57:
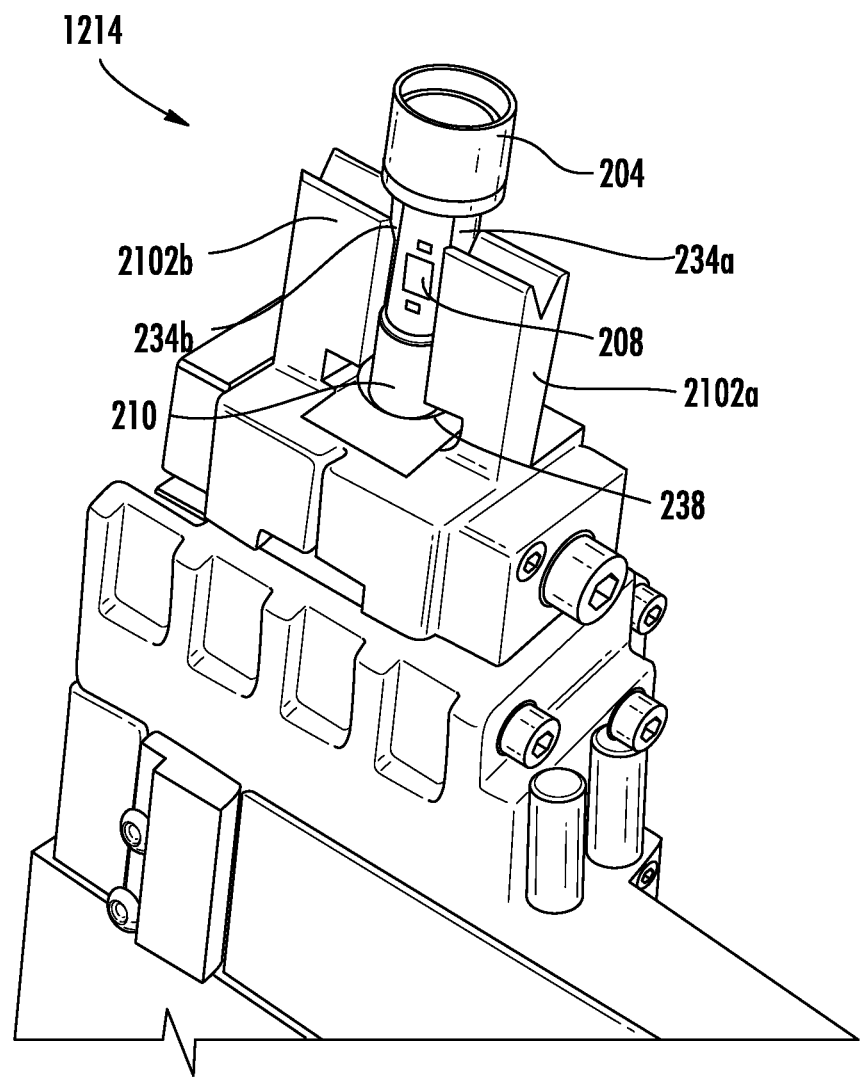
Figure 58:
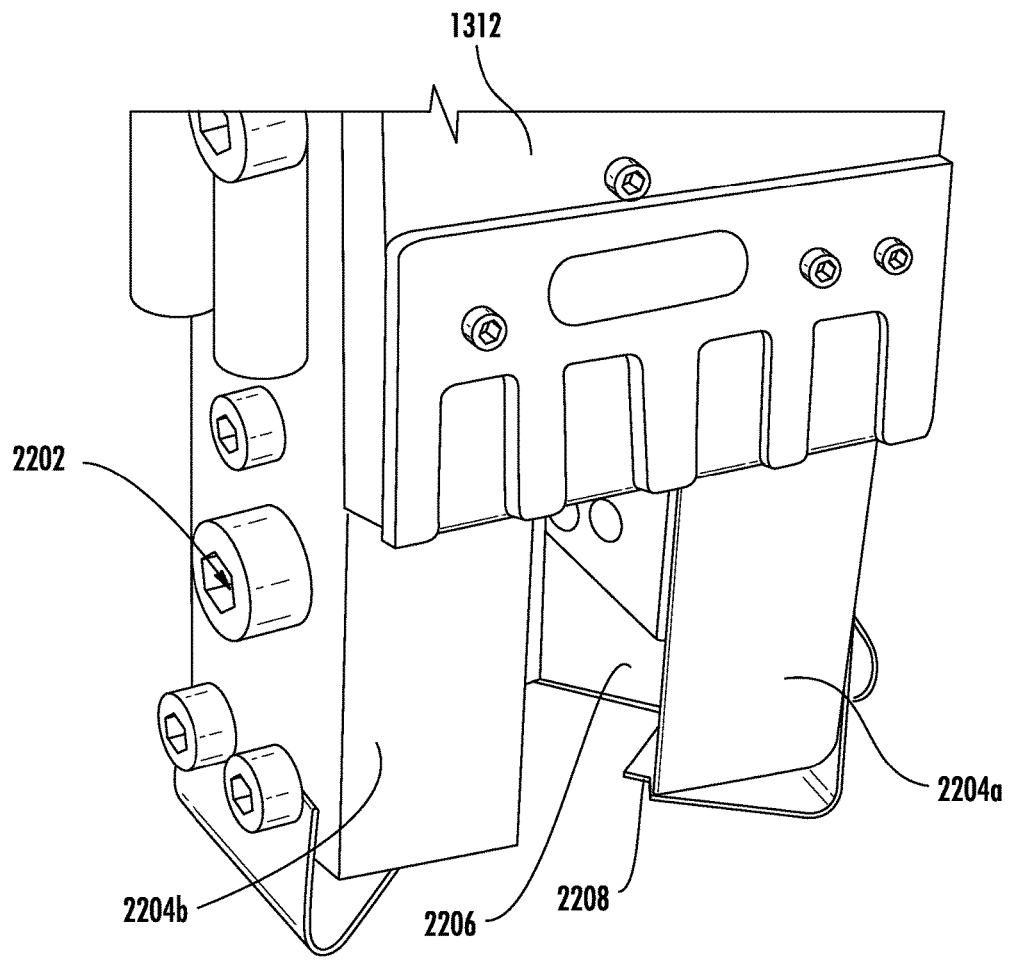
Figure 59:
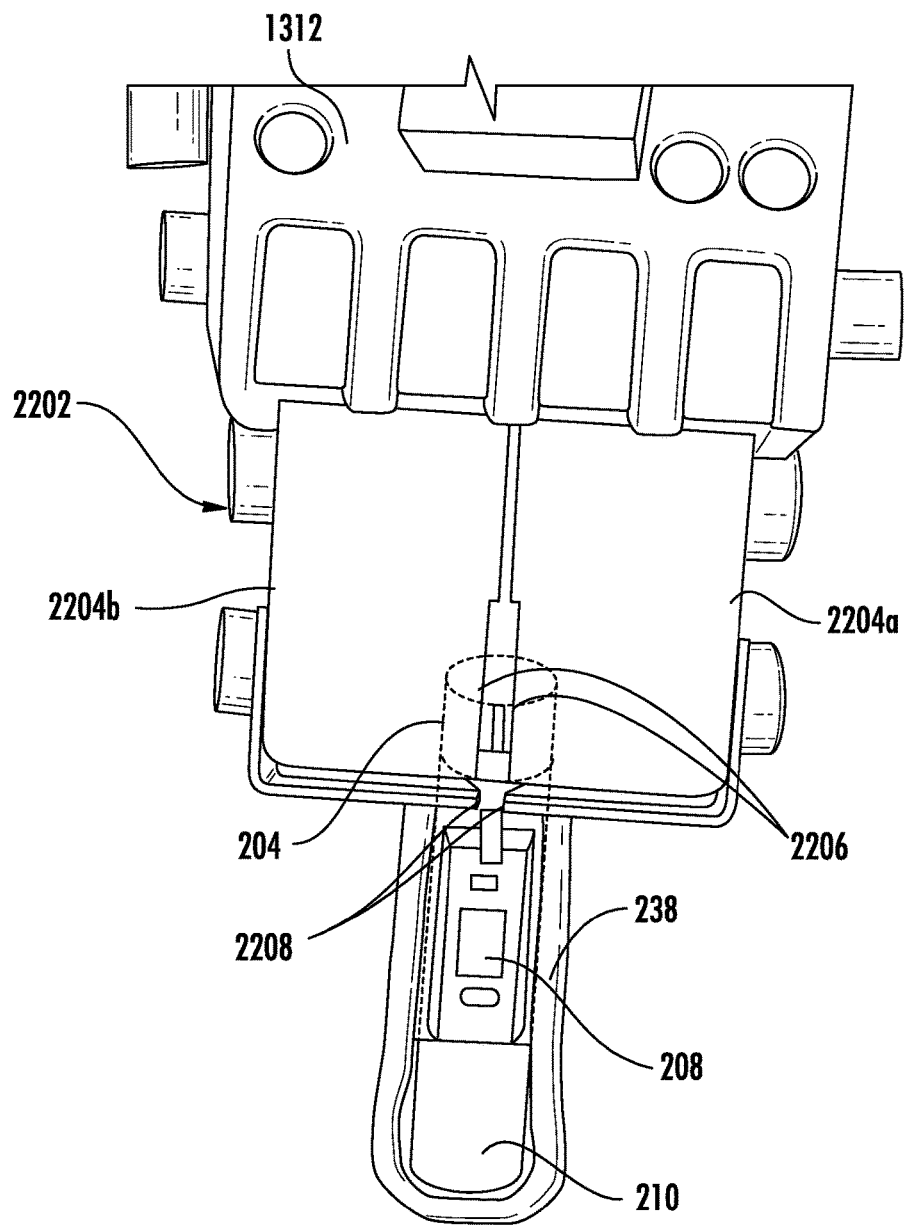
Figure 60:
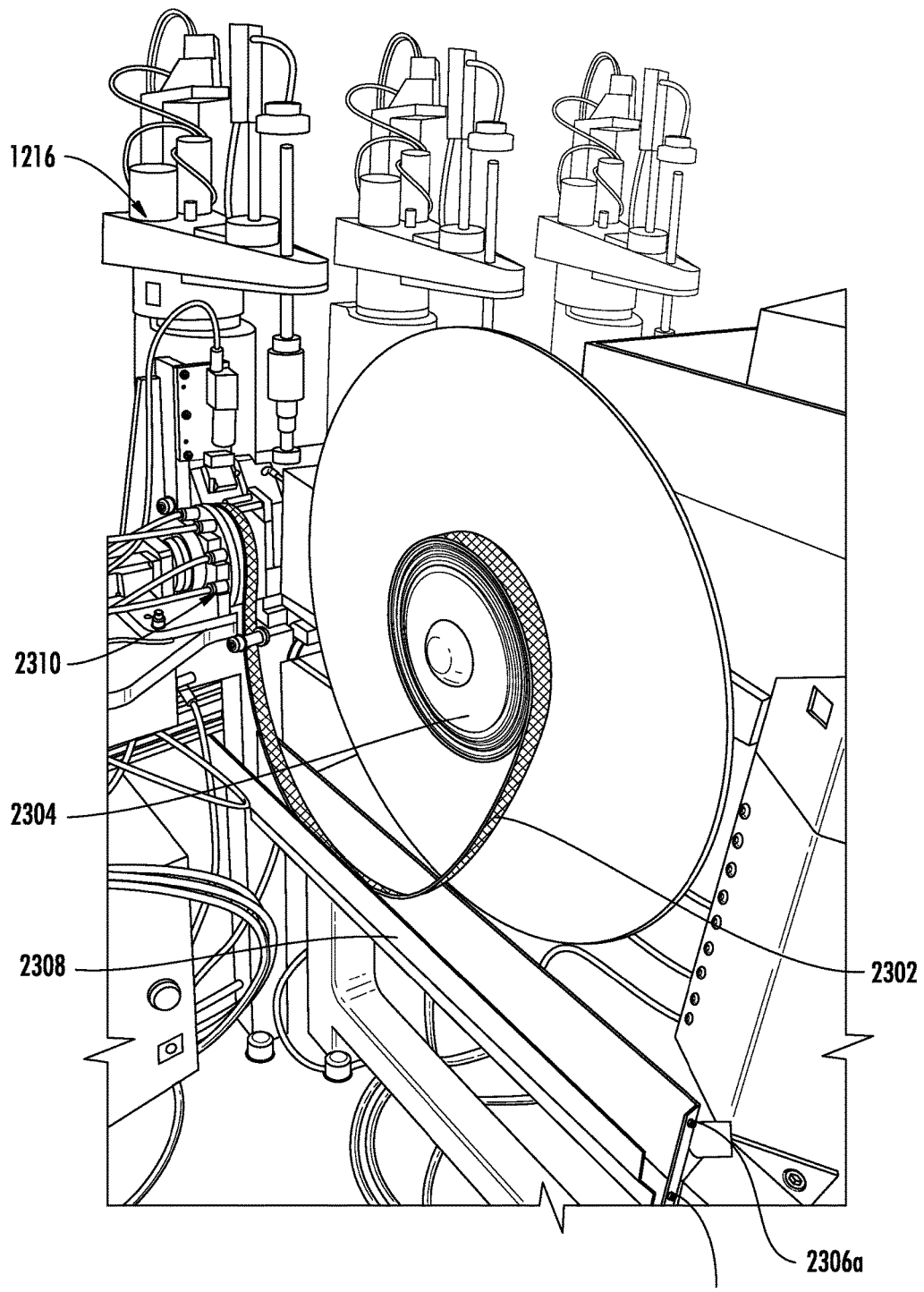
Figure 61:
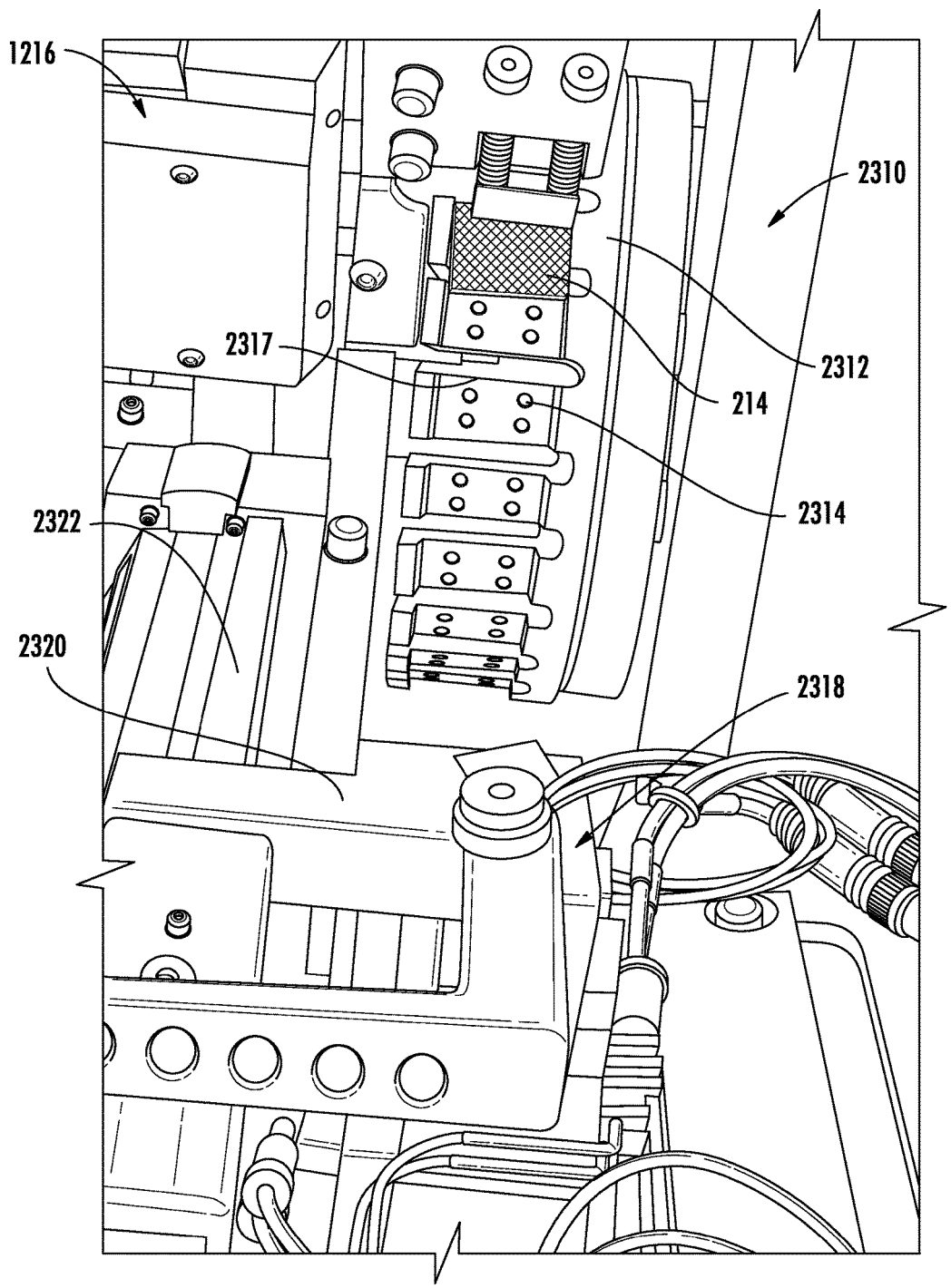
Figure 62:
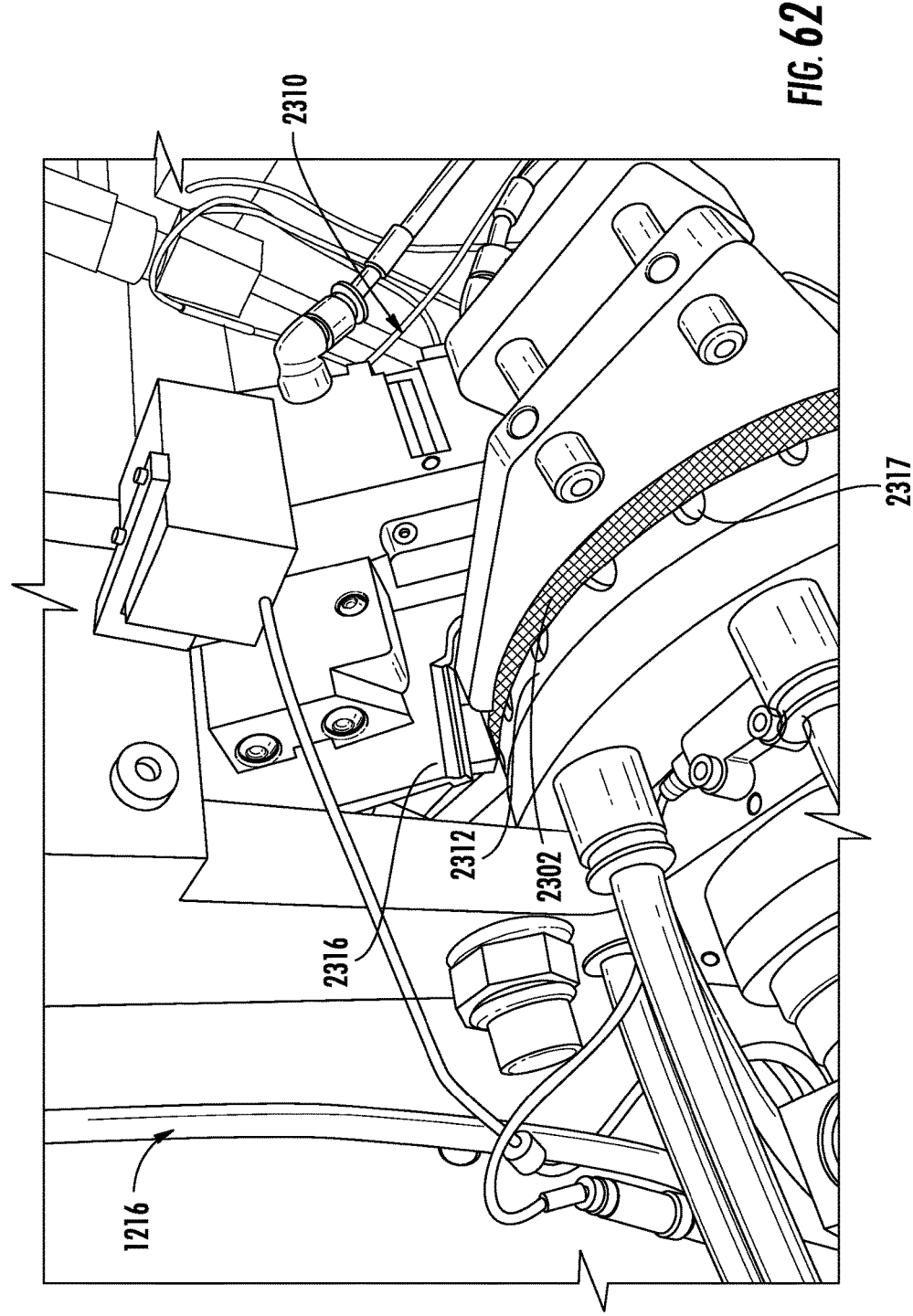
Figure 63:
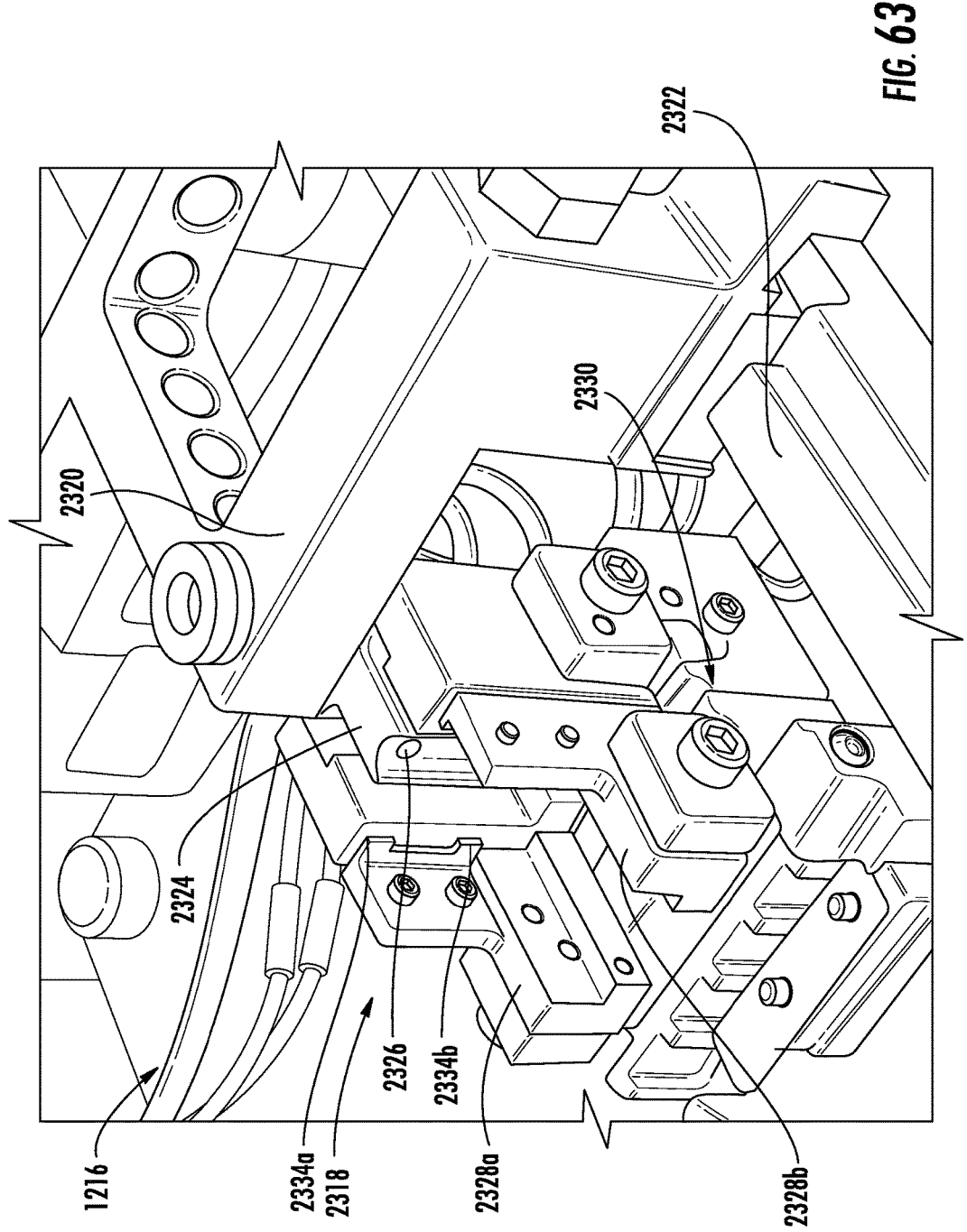
Figure 64:
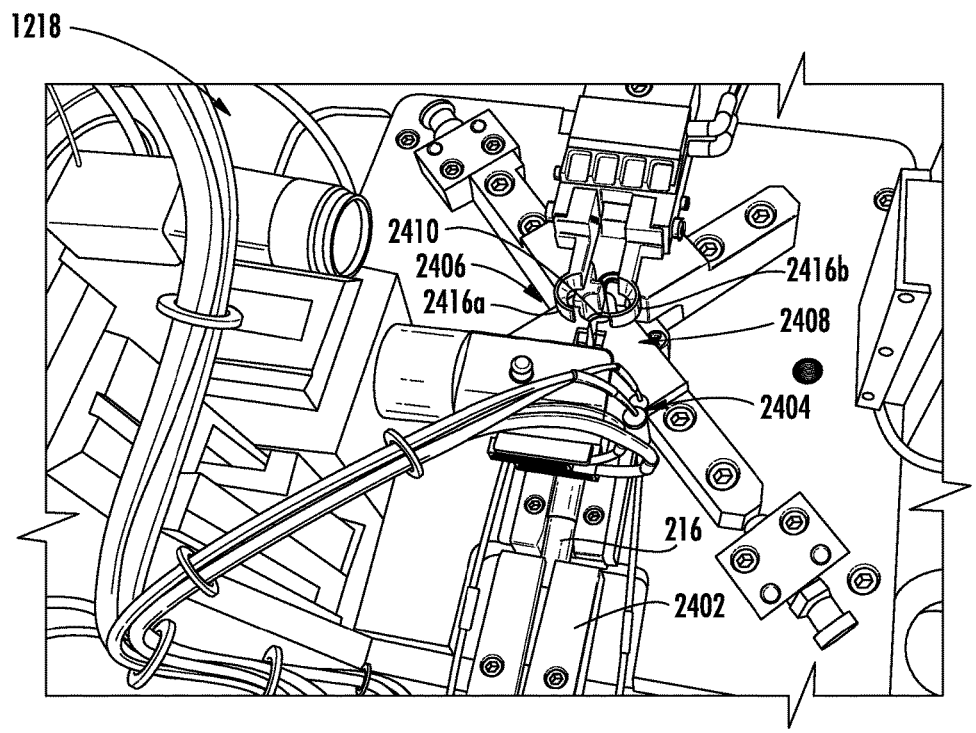
Figure 65:
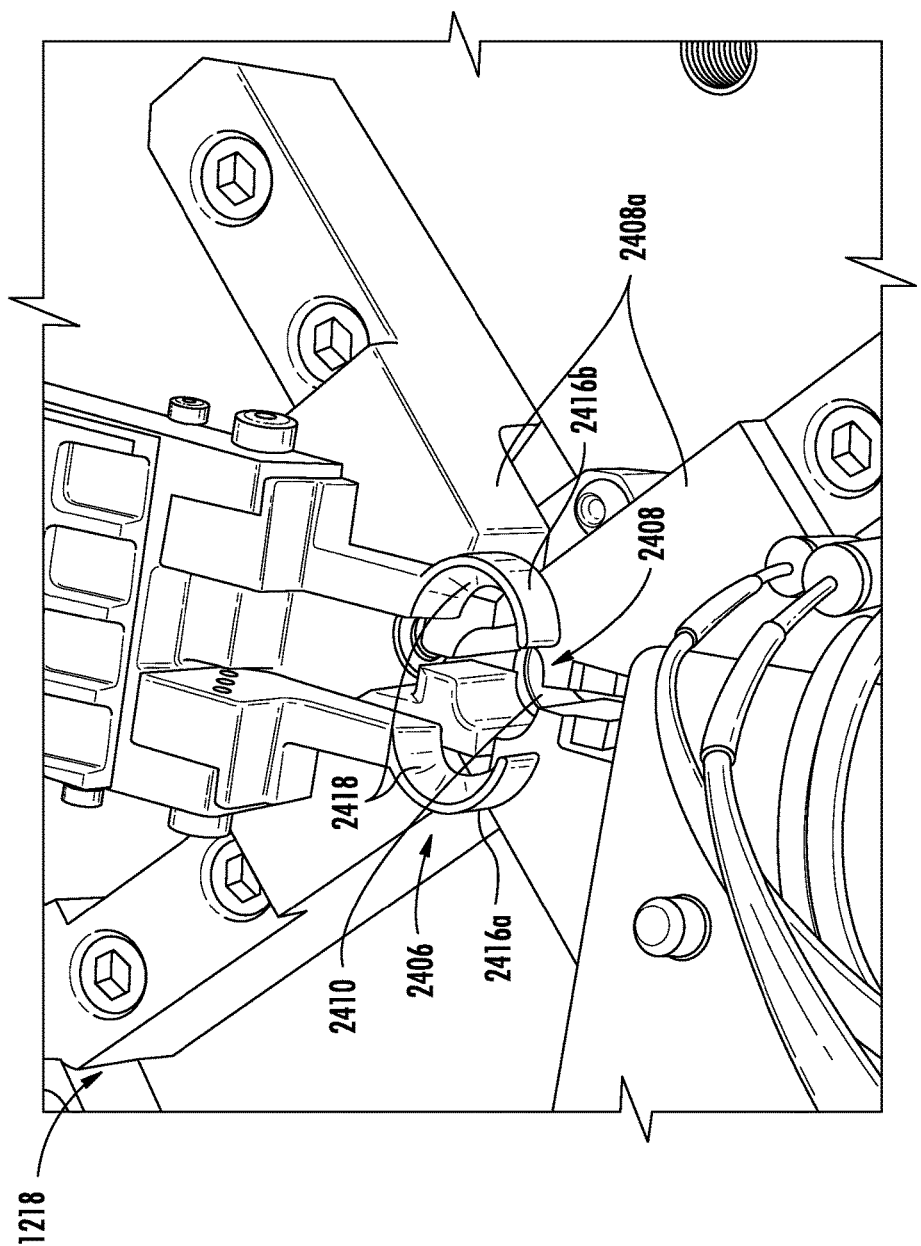
Figure 66:
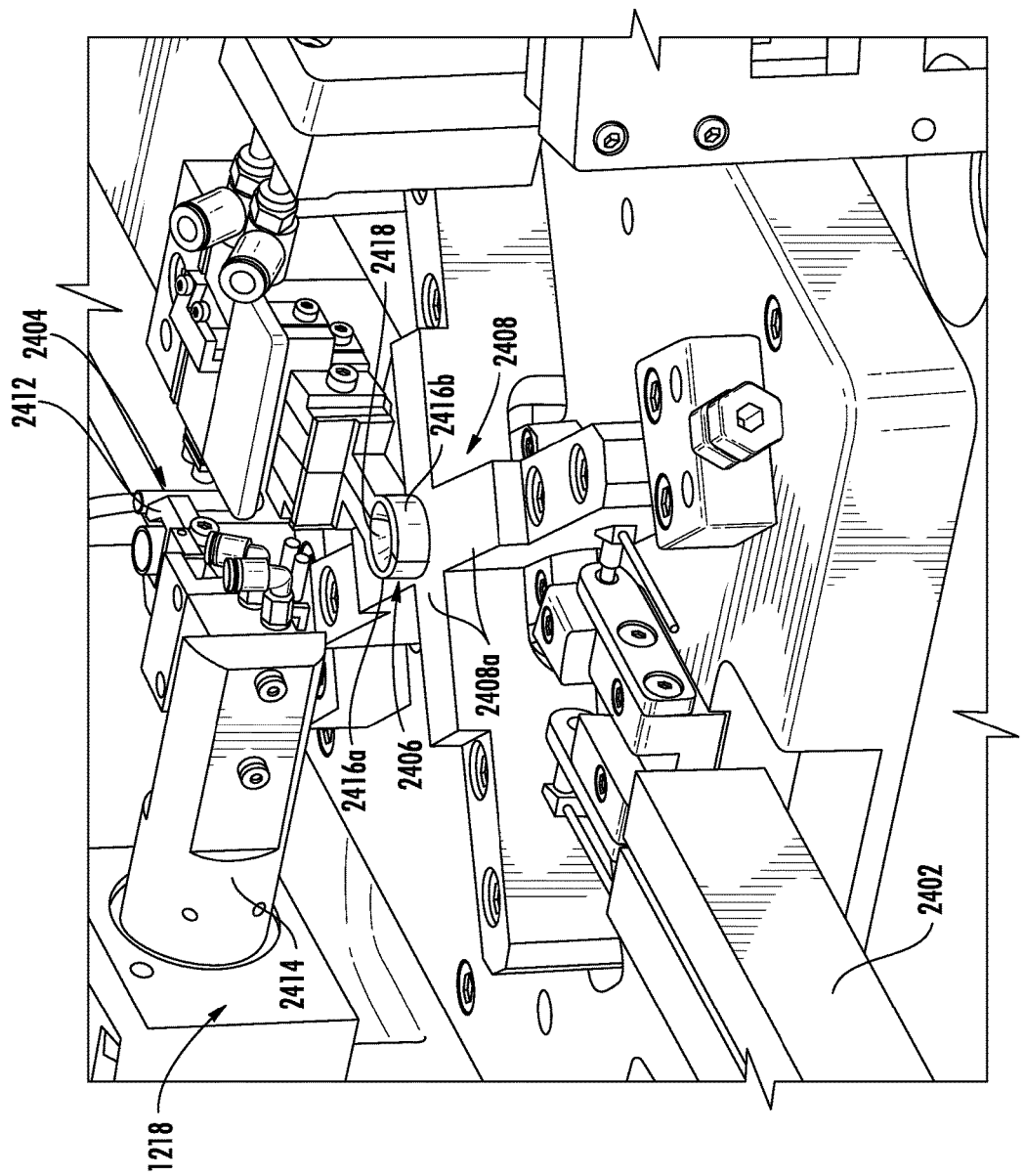
Figure 67:
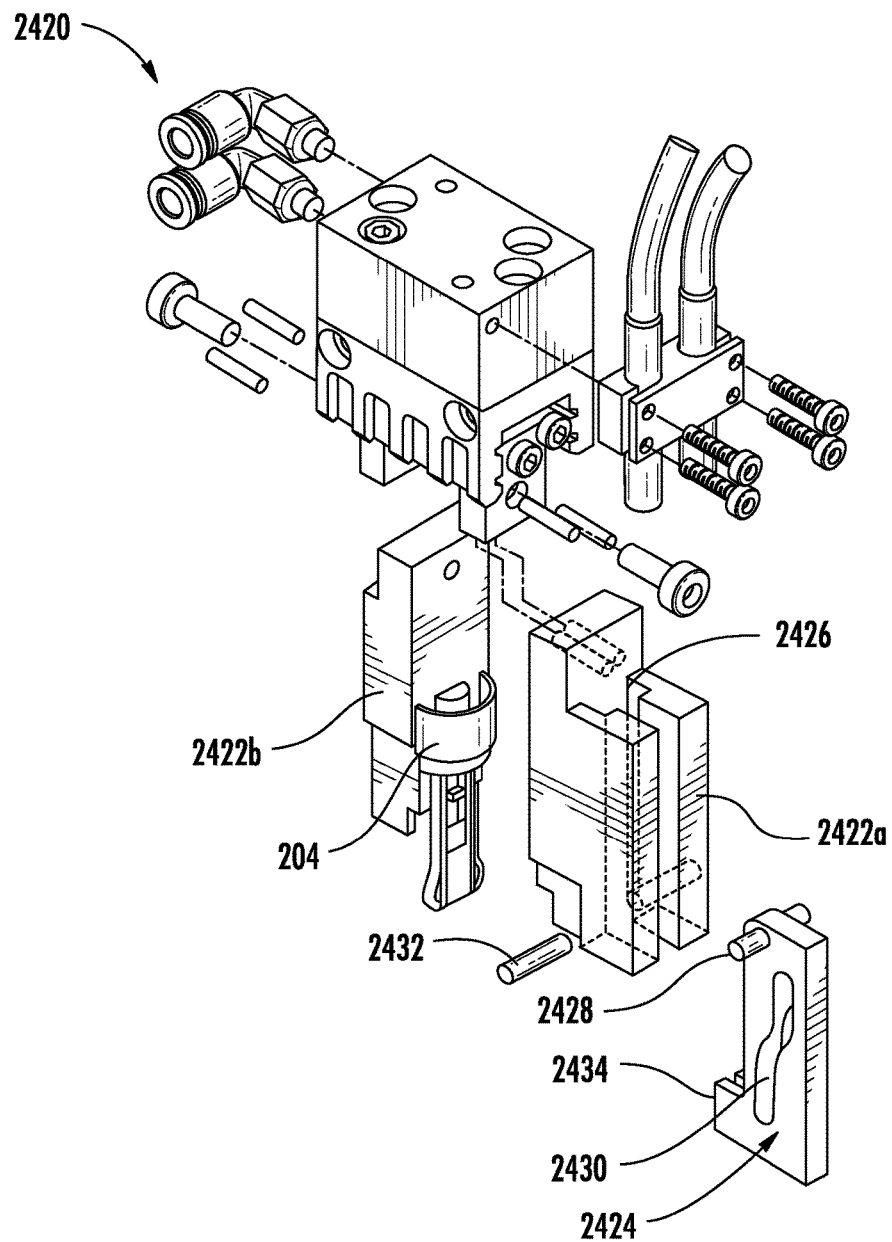
Figure 68:
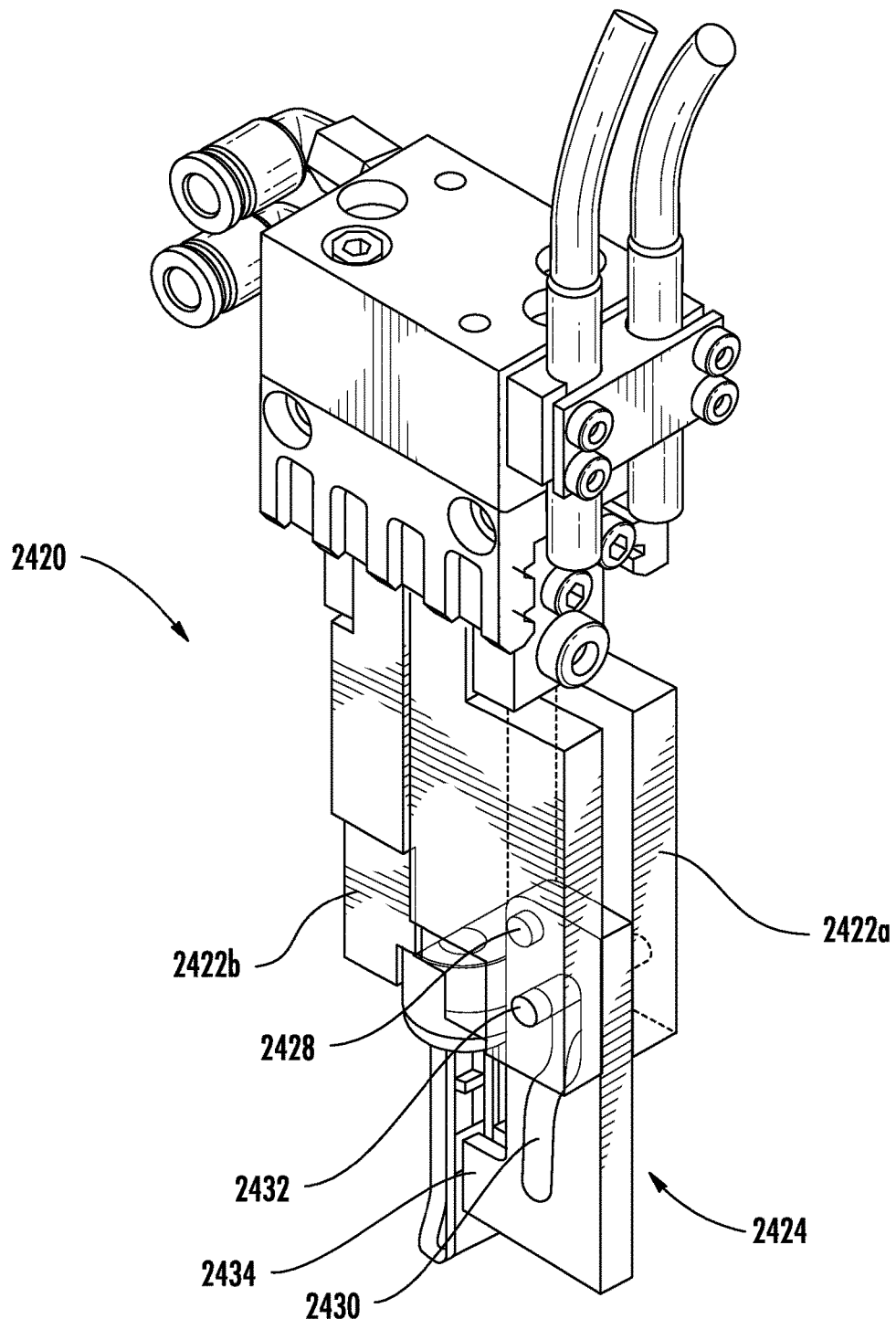
Figure 69:
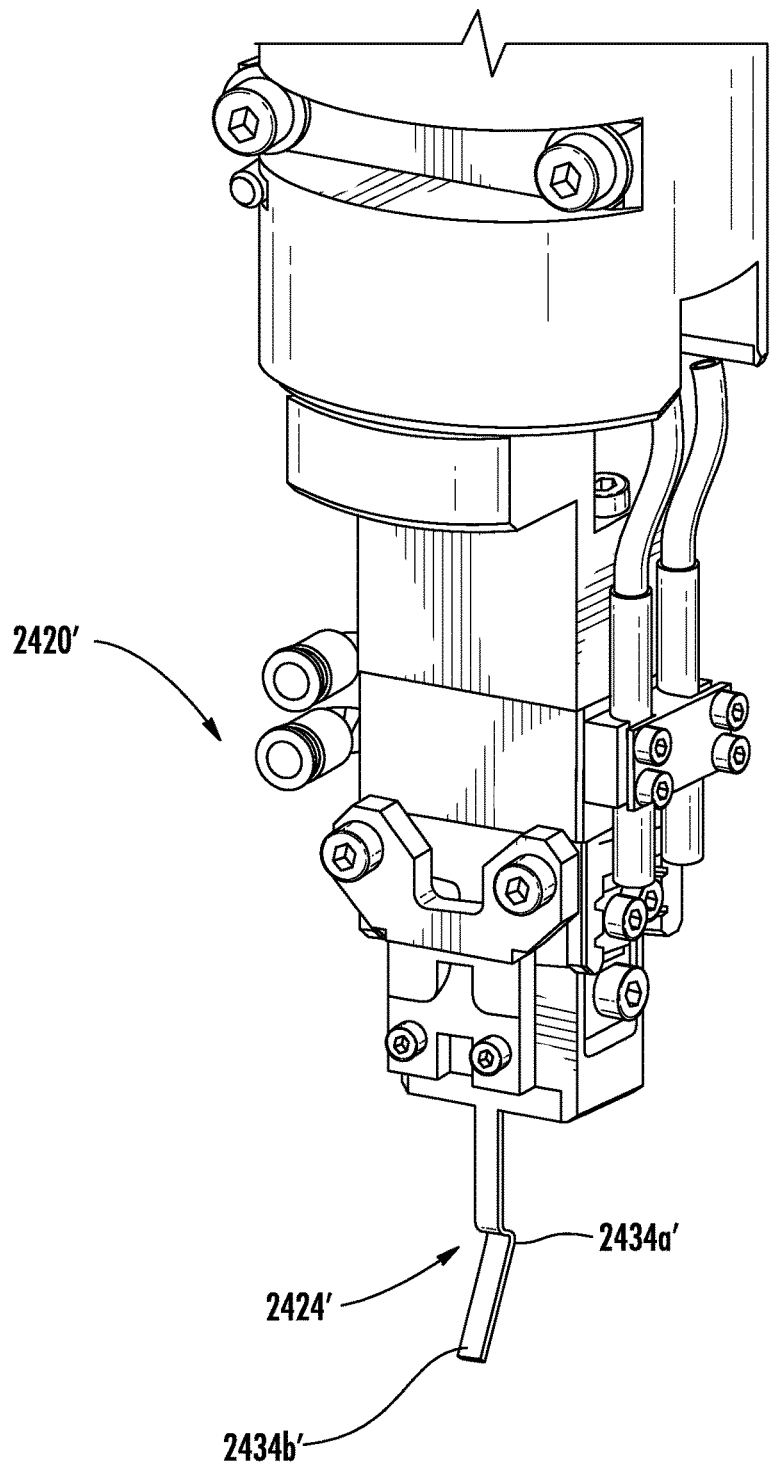
Figure 70:
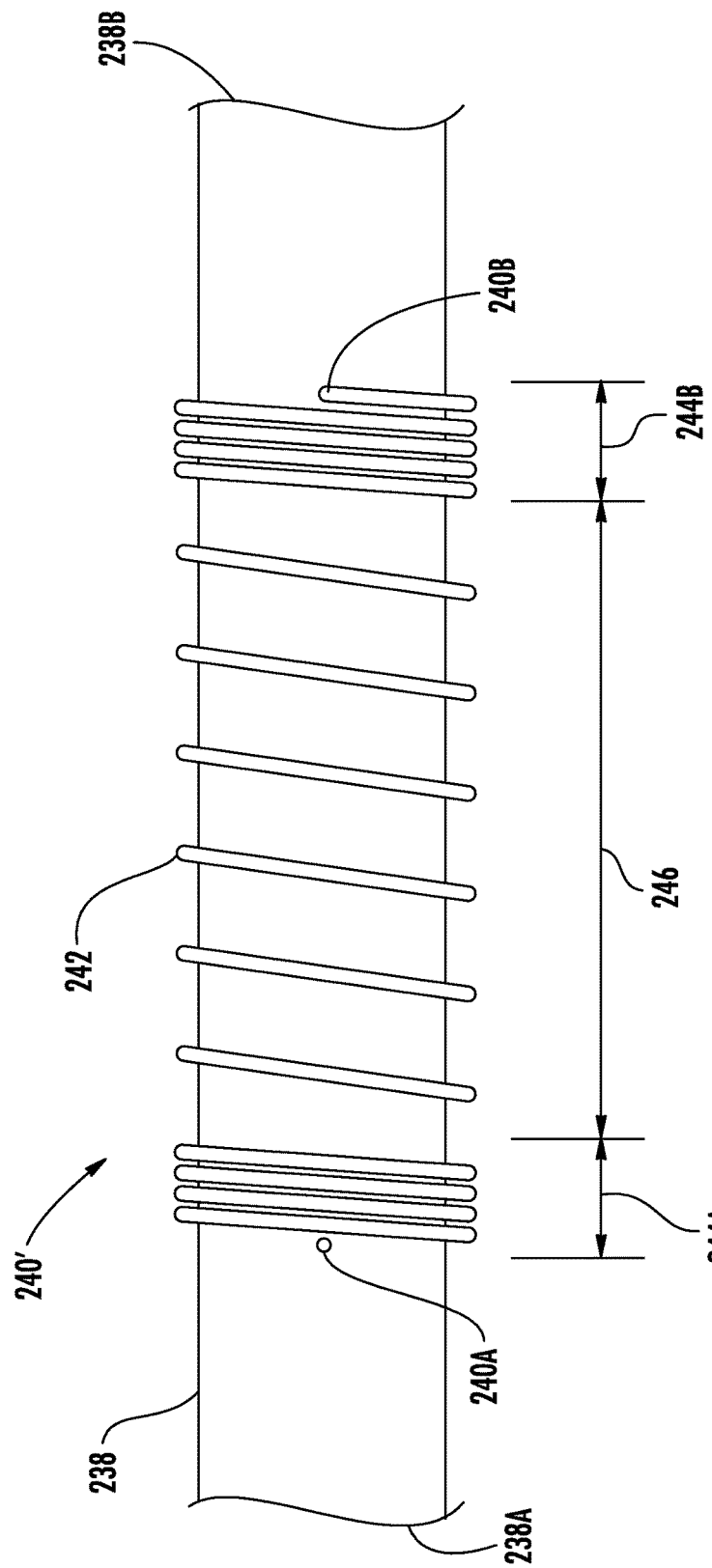
Figure 71:
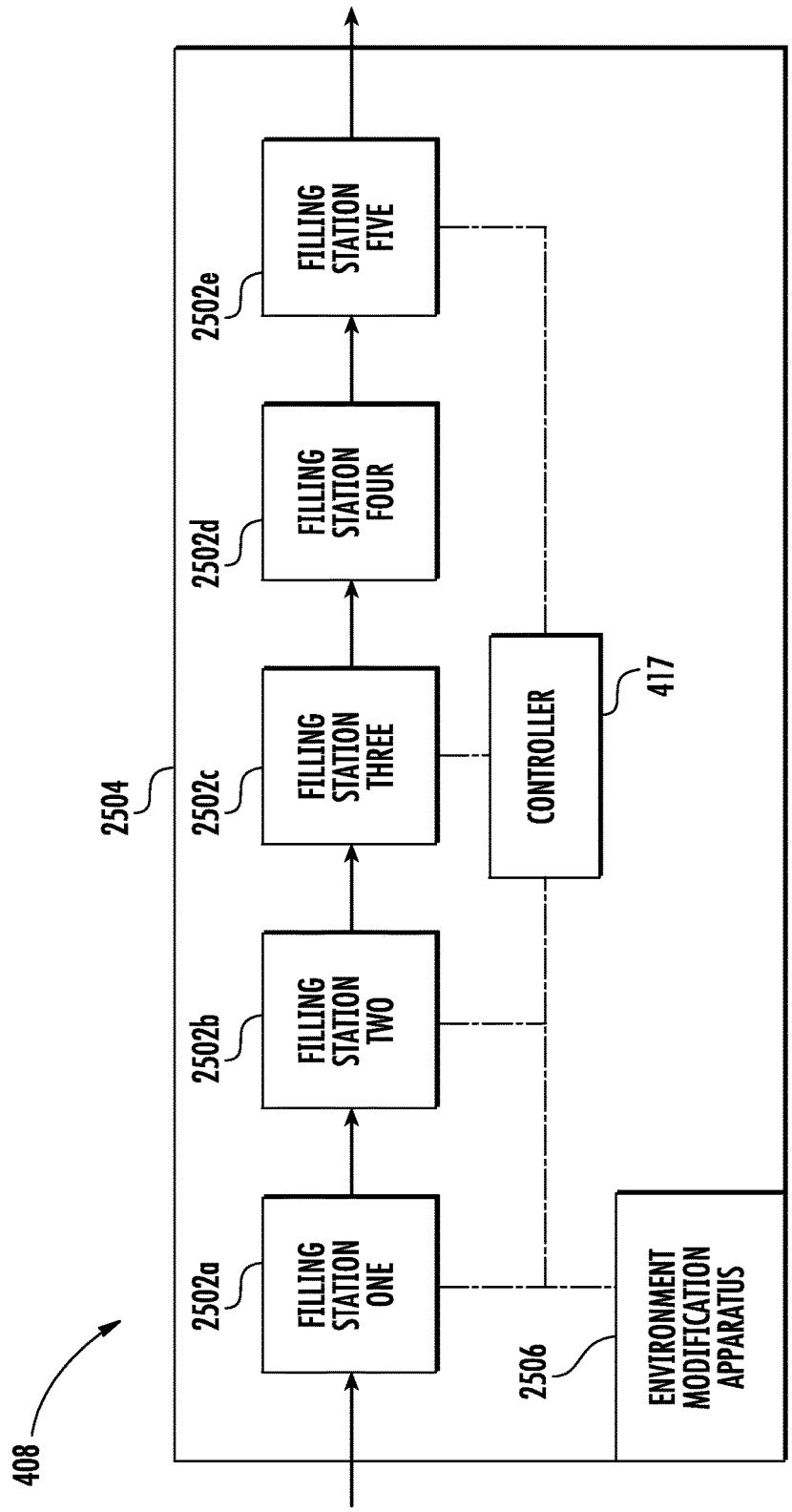
Figure 72:
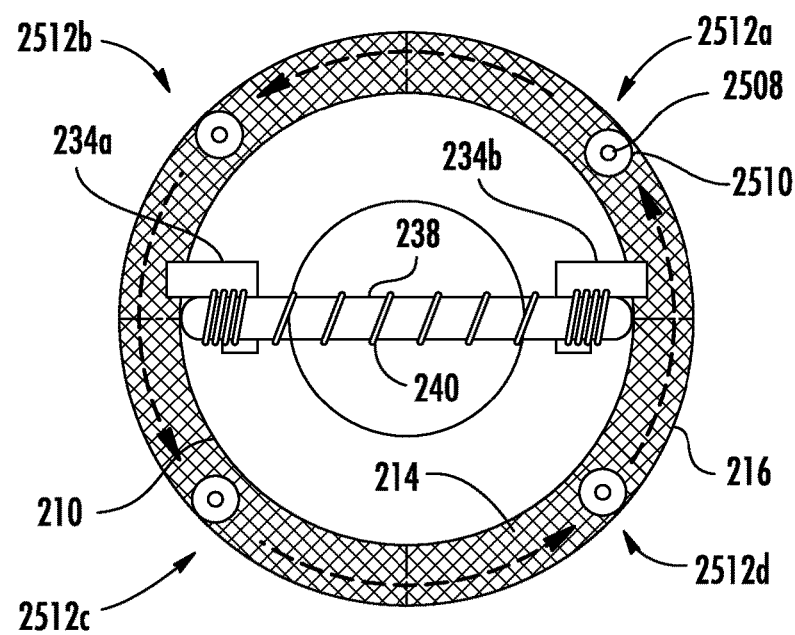
Figure 73:
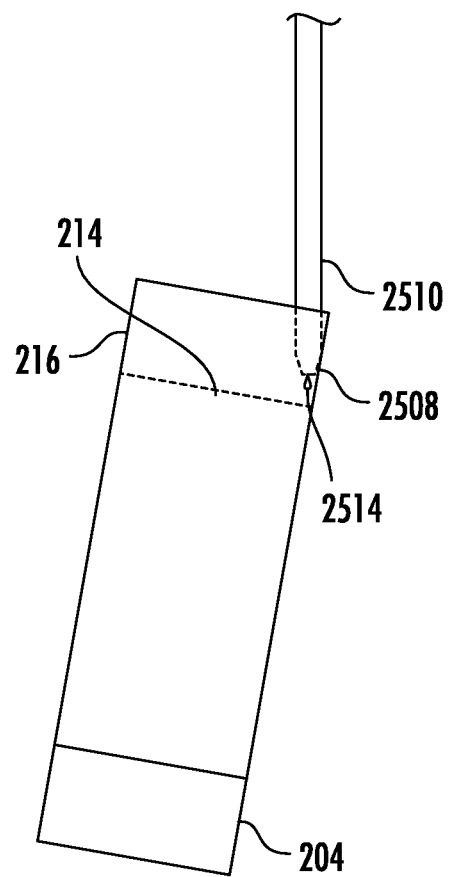
Figure 74:
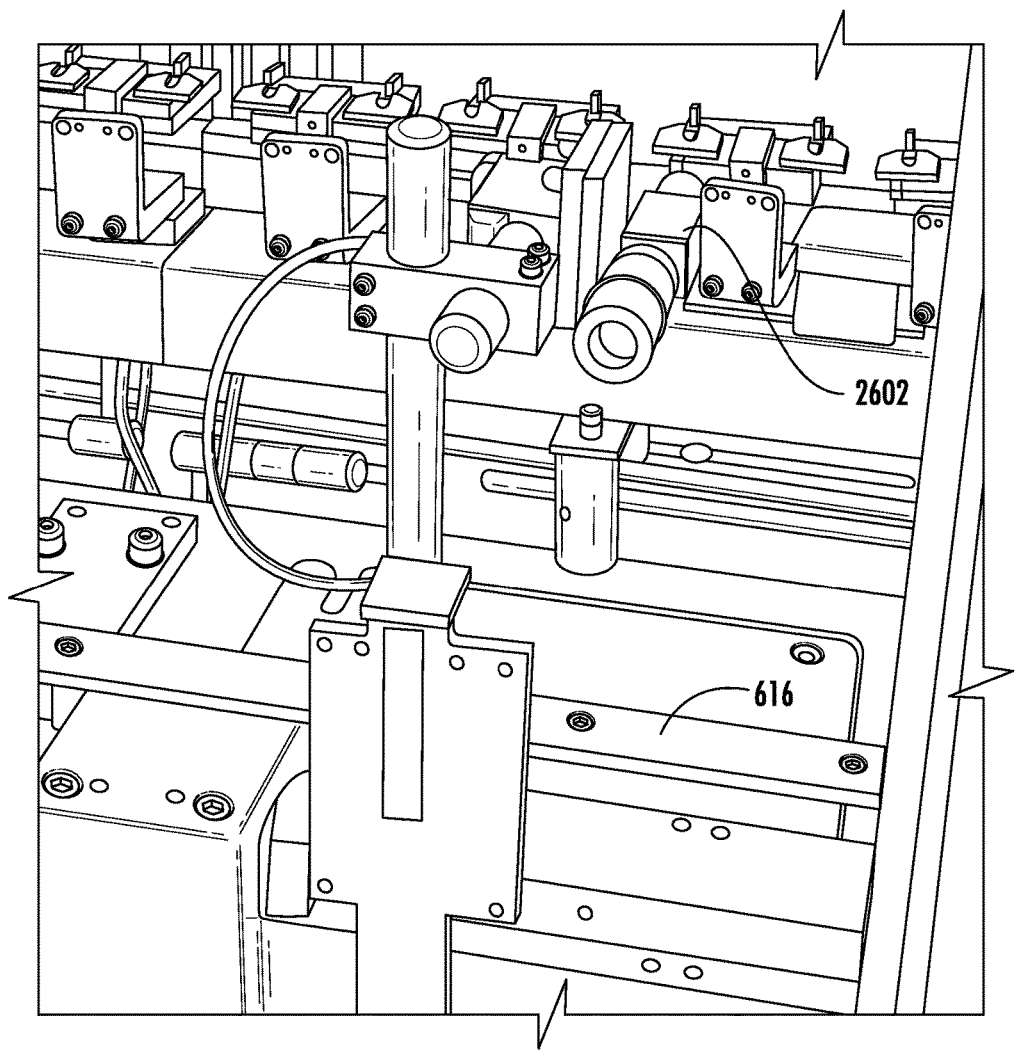
Figure 75:
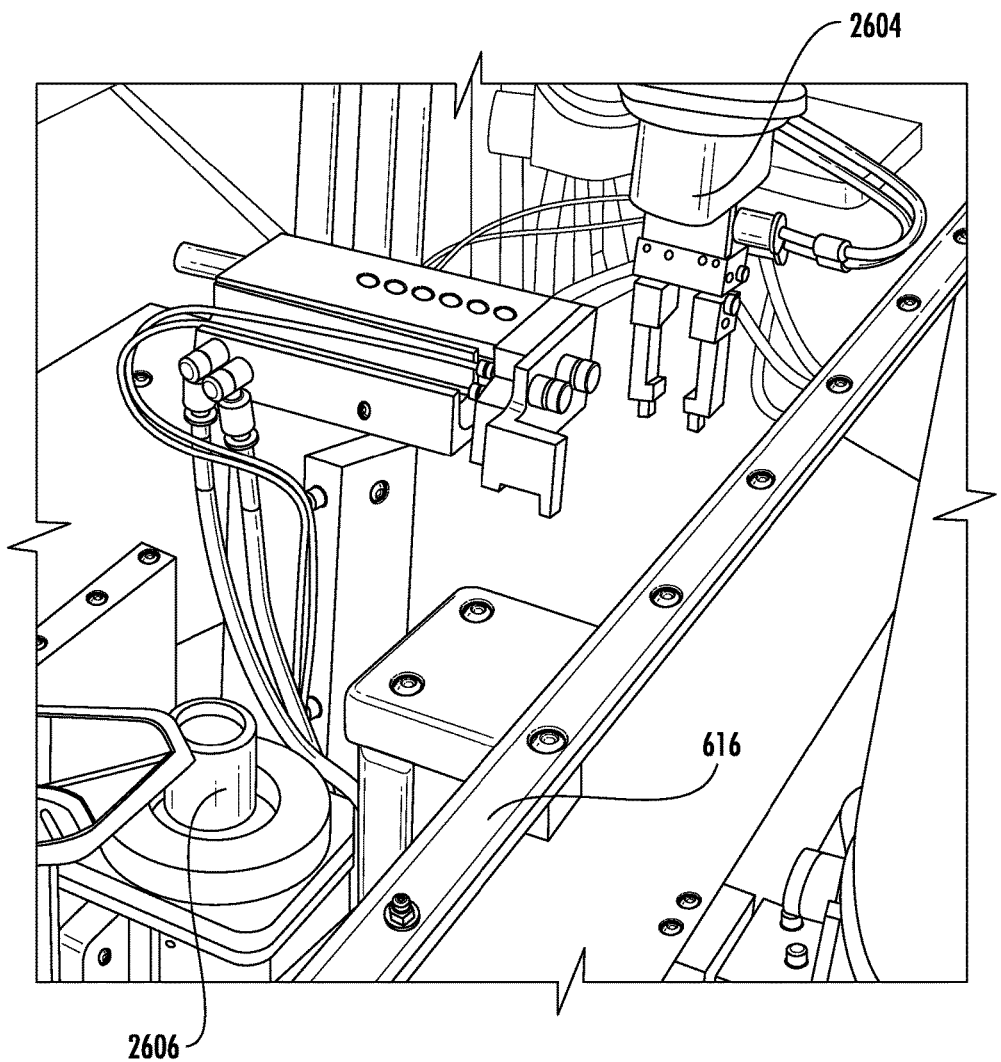
Figure 76:
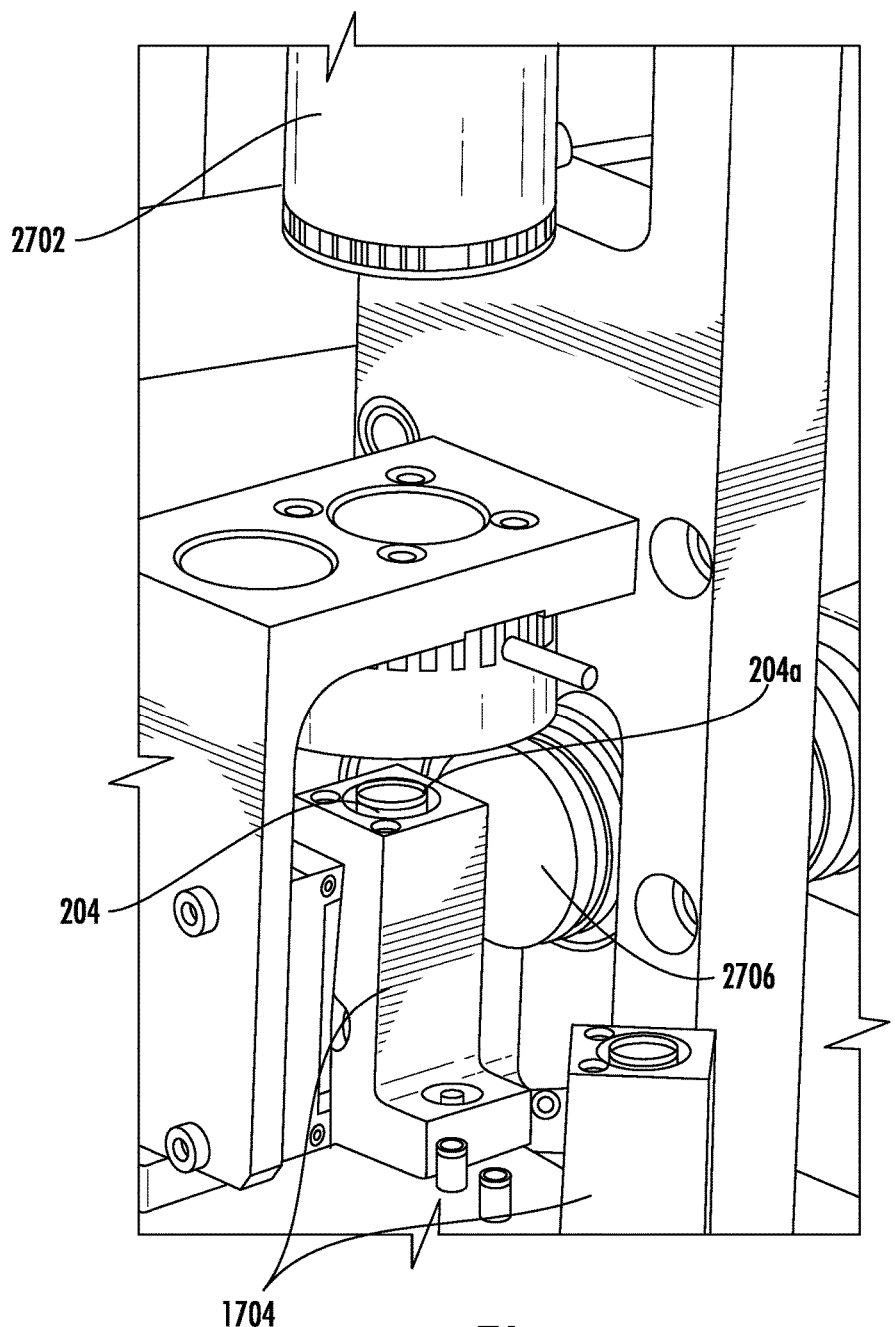
Figure 77:
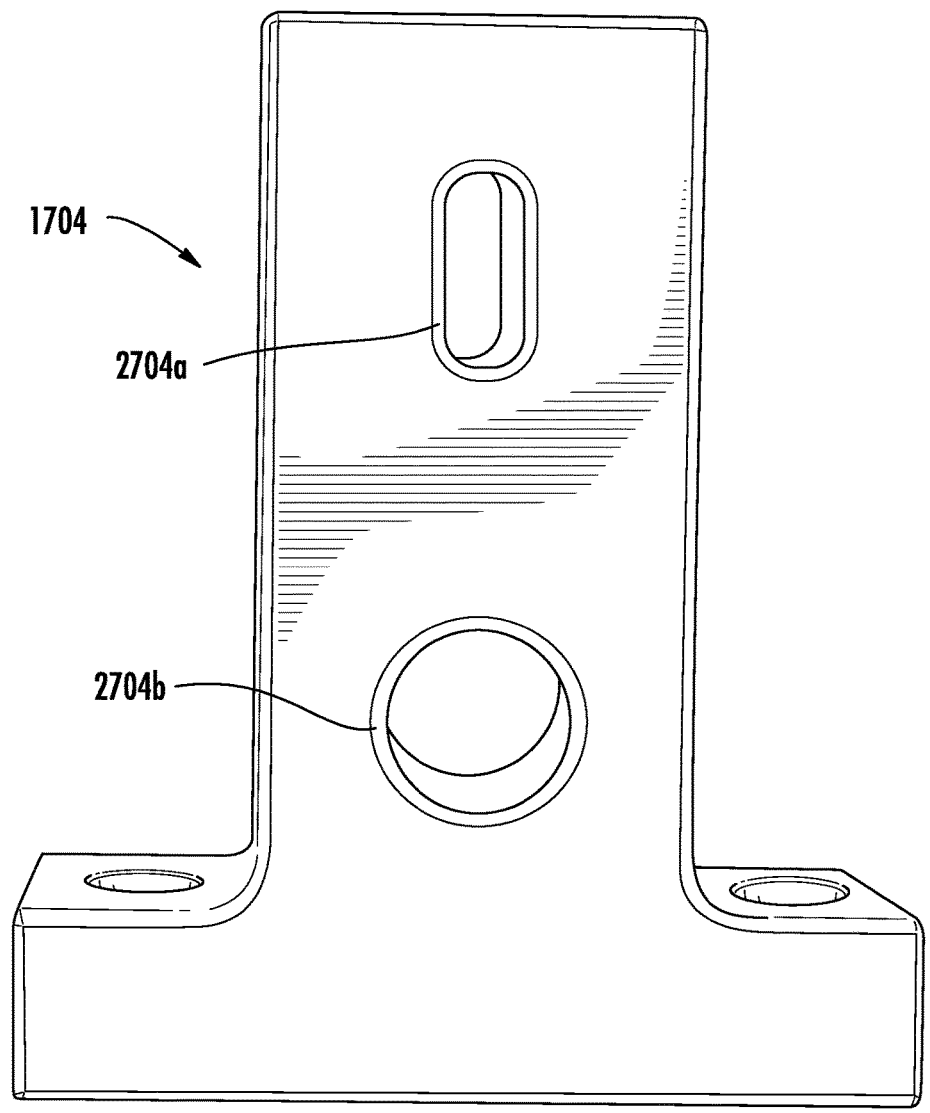
Figure 78:
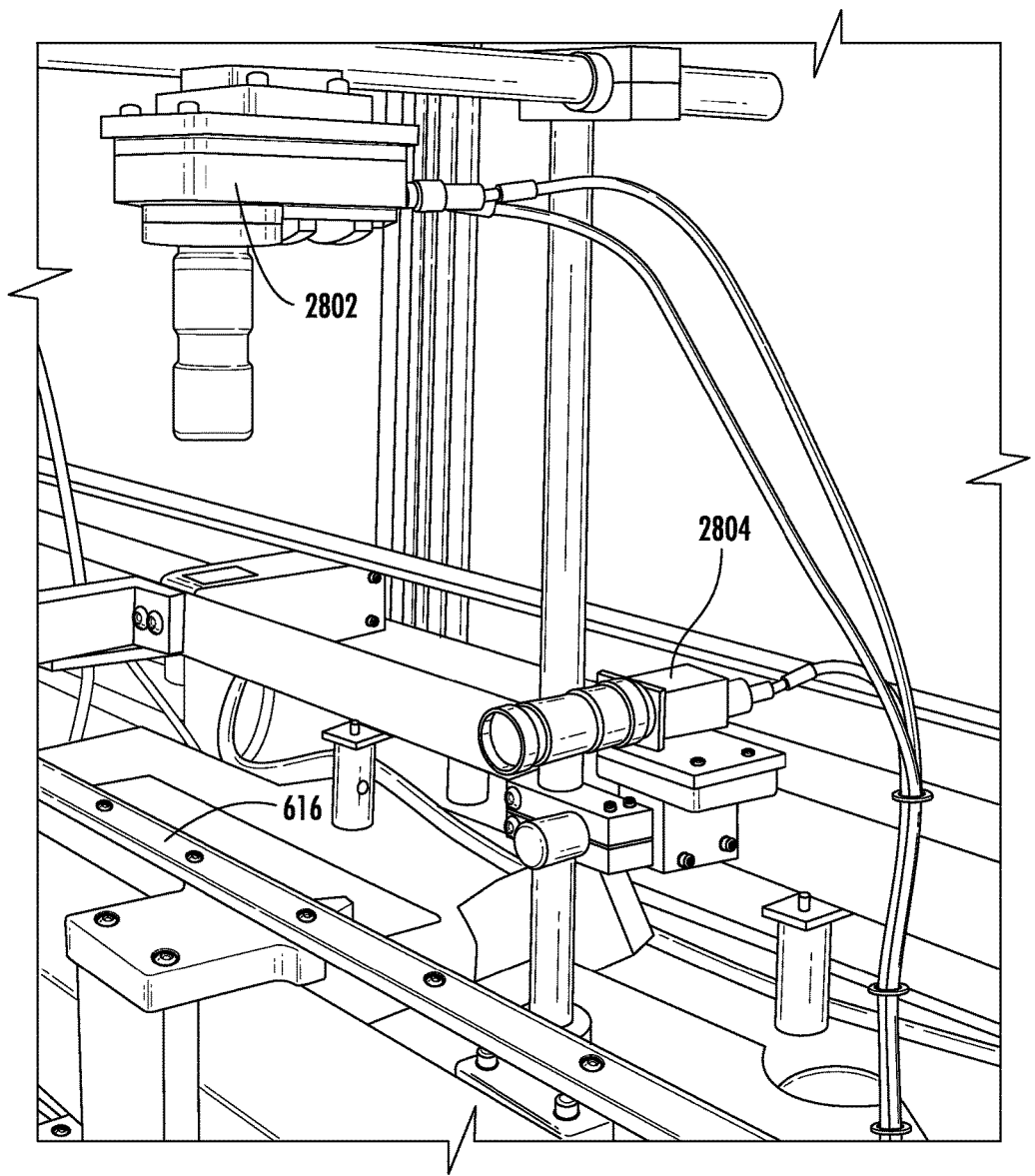
Figure 79:
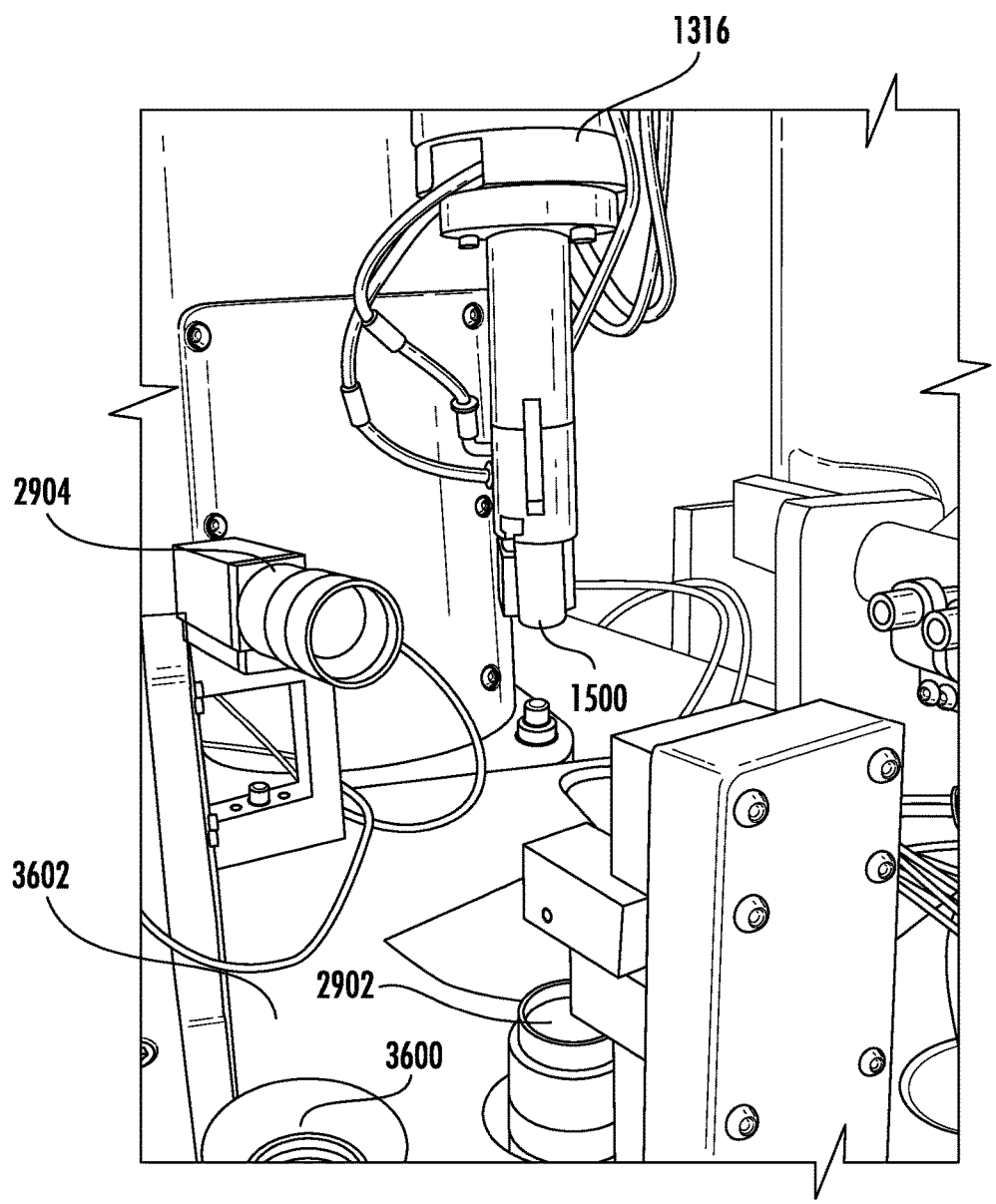
Figure 80:
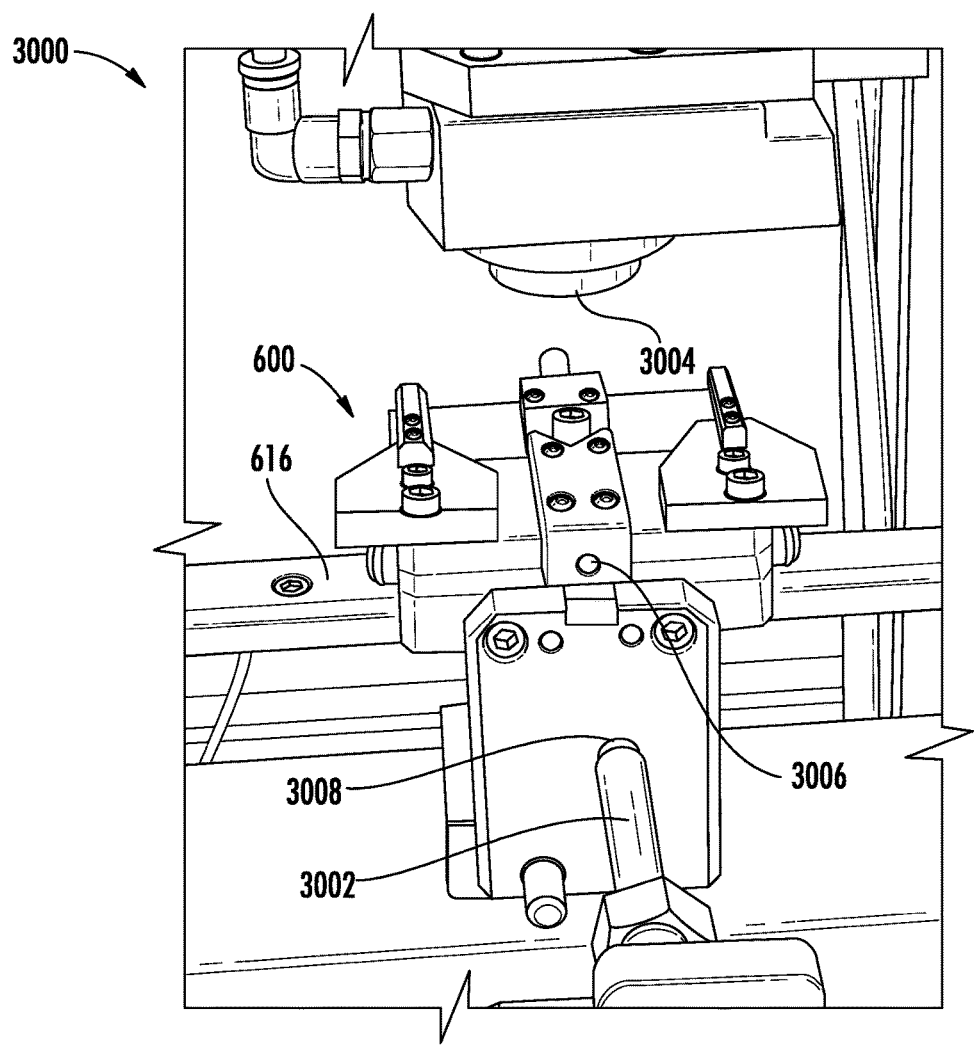
Figure 81:
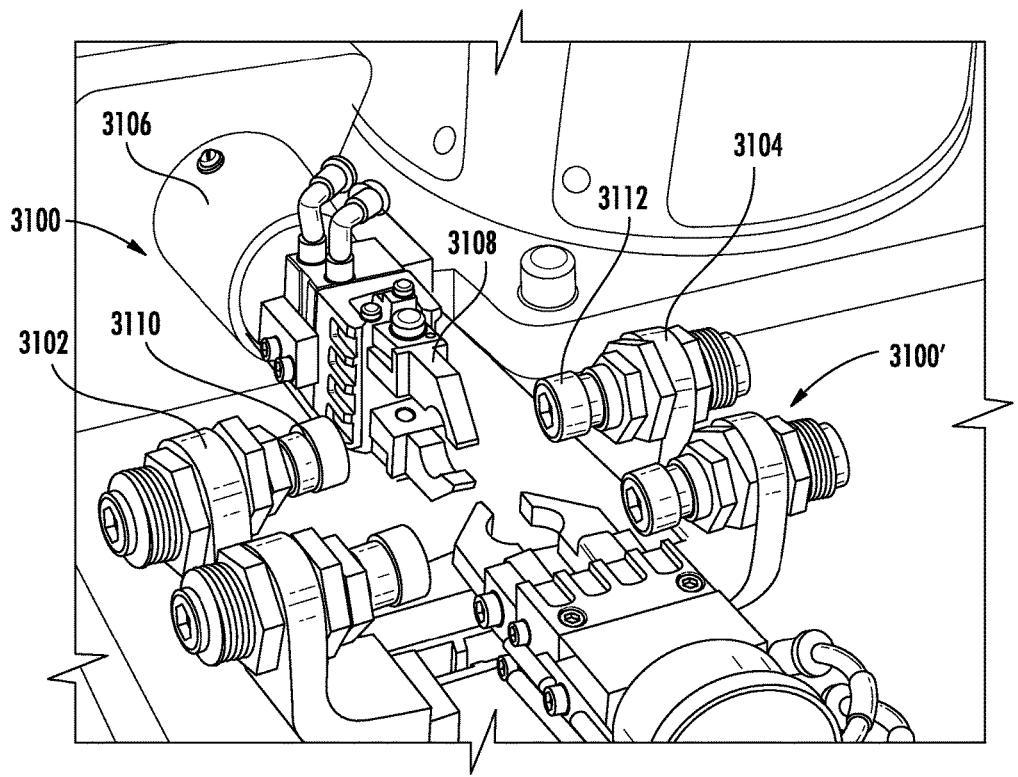
Figure 82:
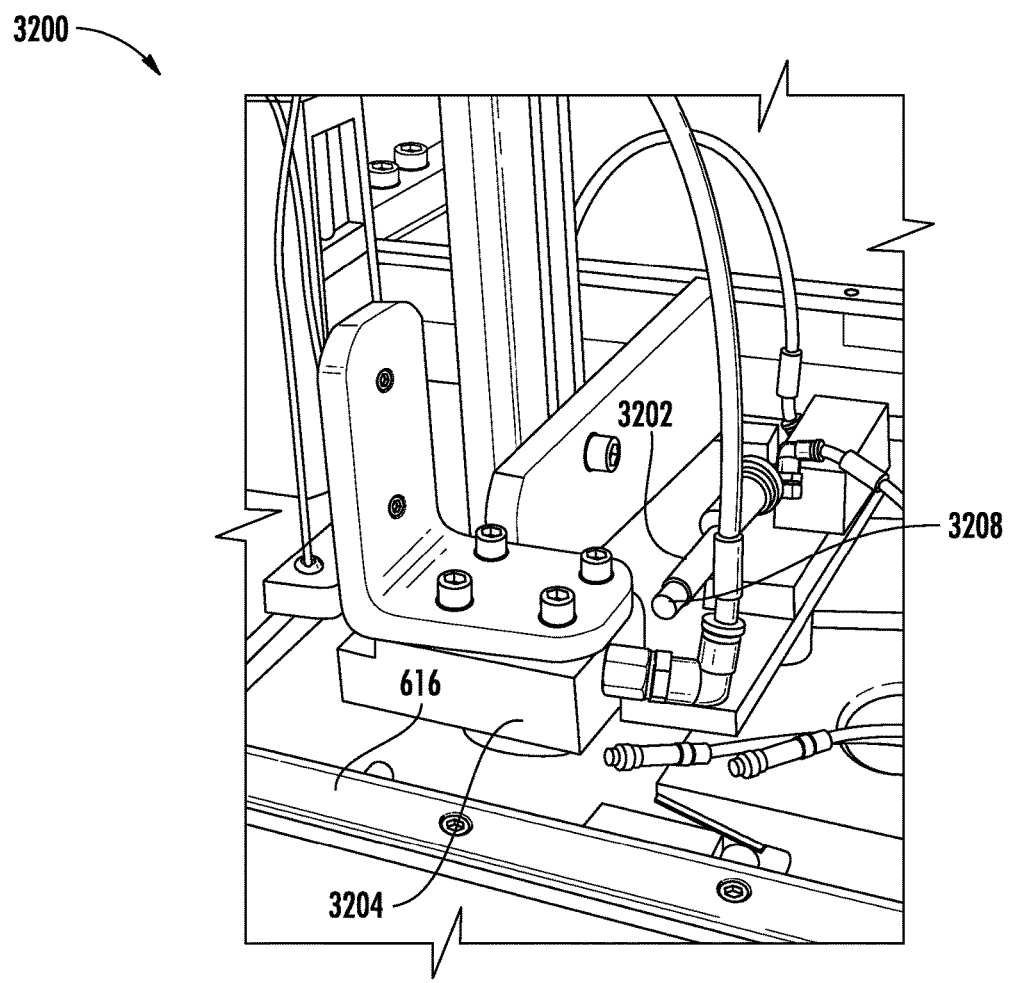
Figure 83:
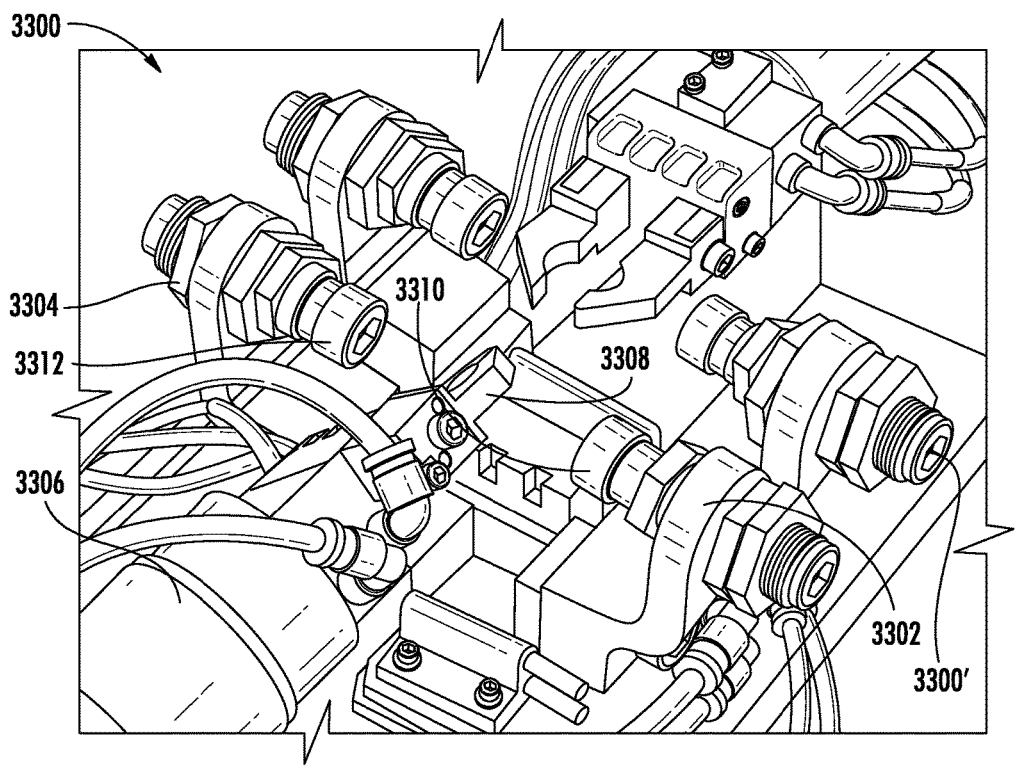
Figure 84:
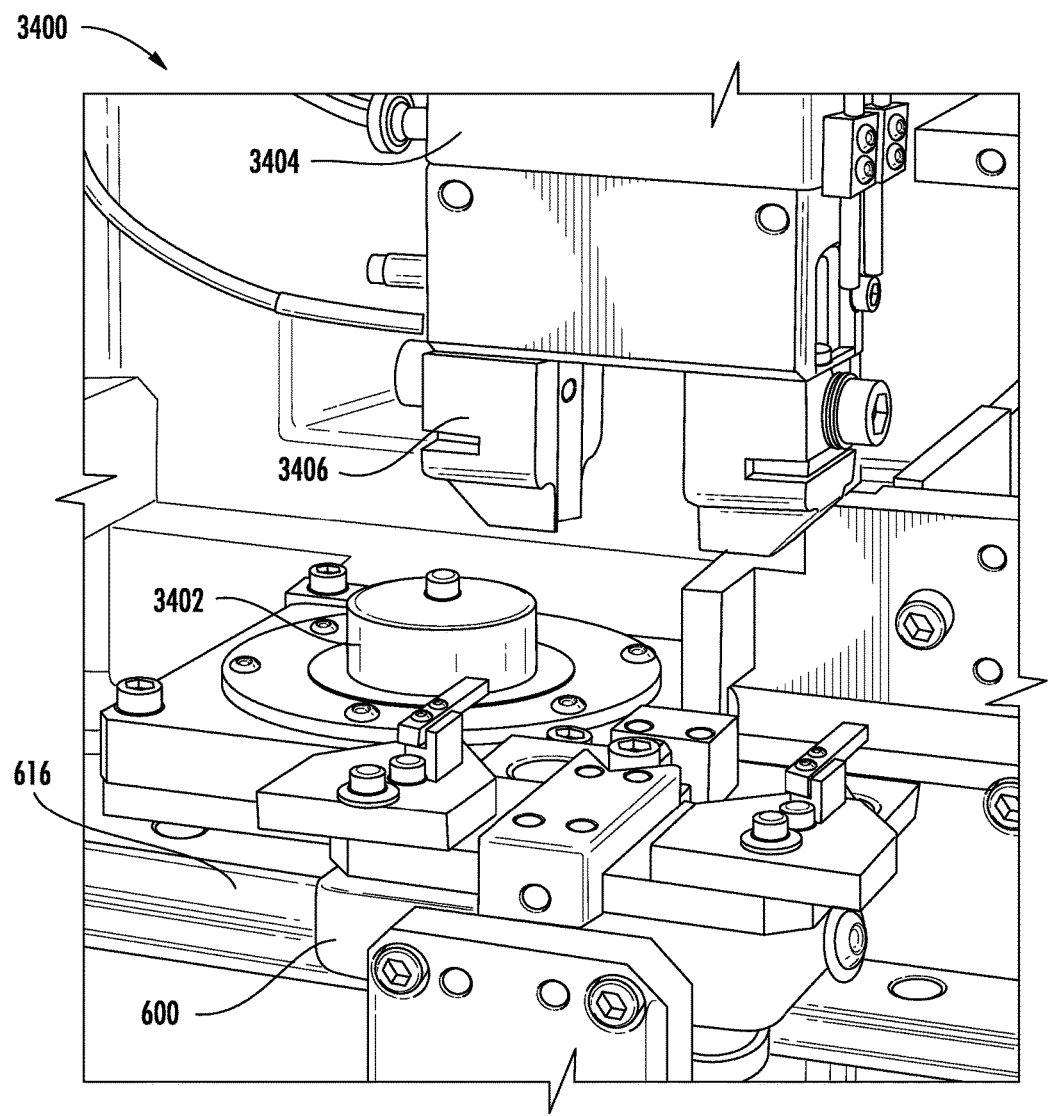
Figure 85:
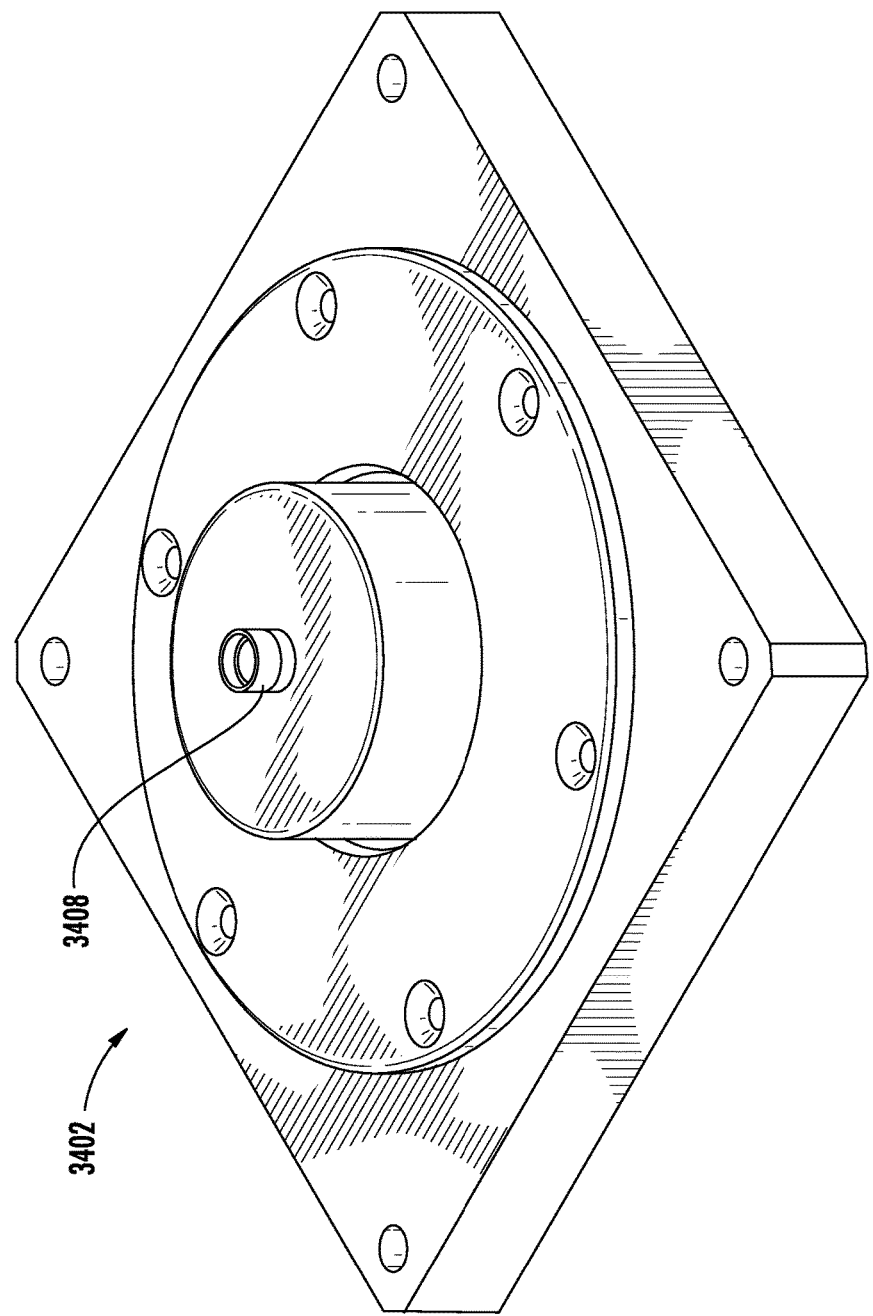
Figure 86:
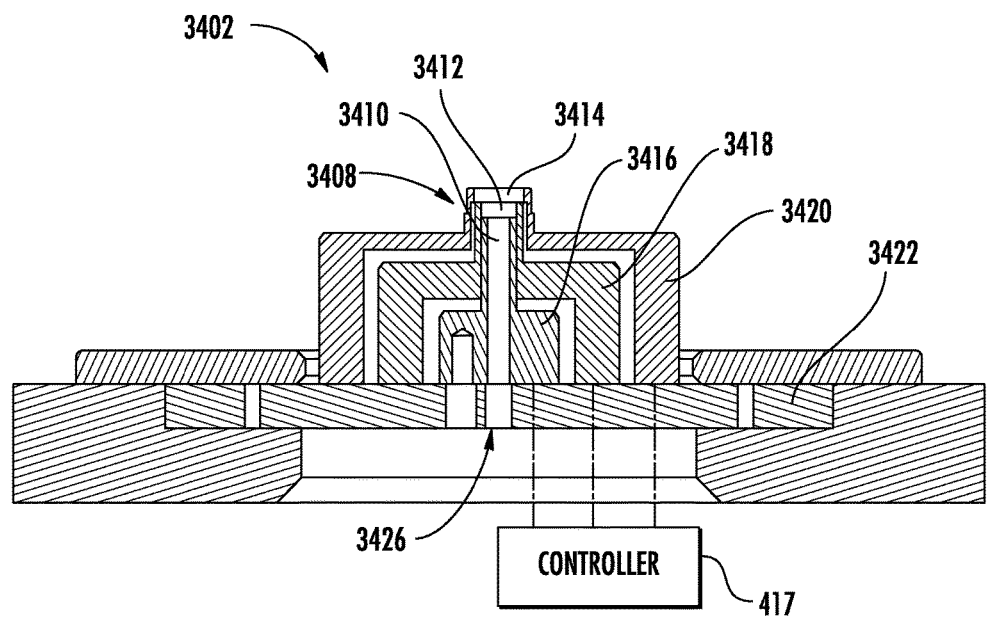
Figure 87:
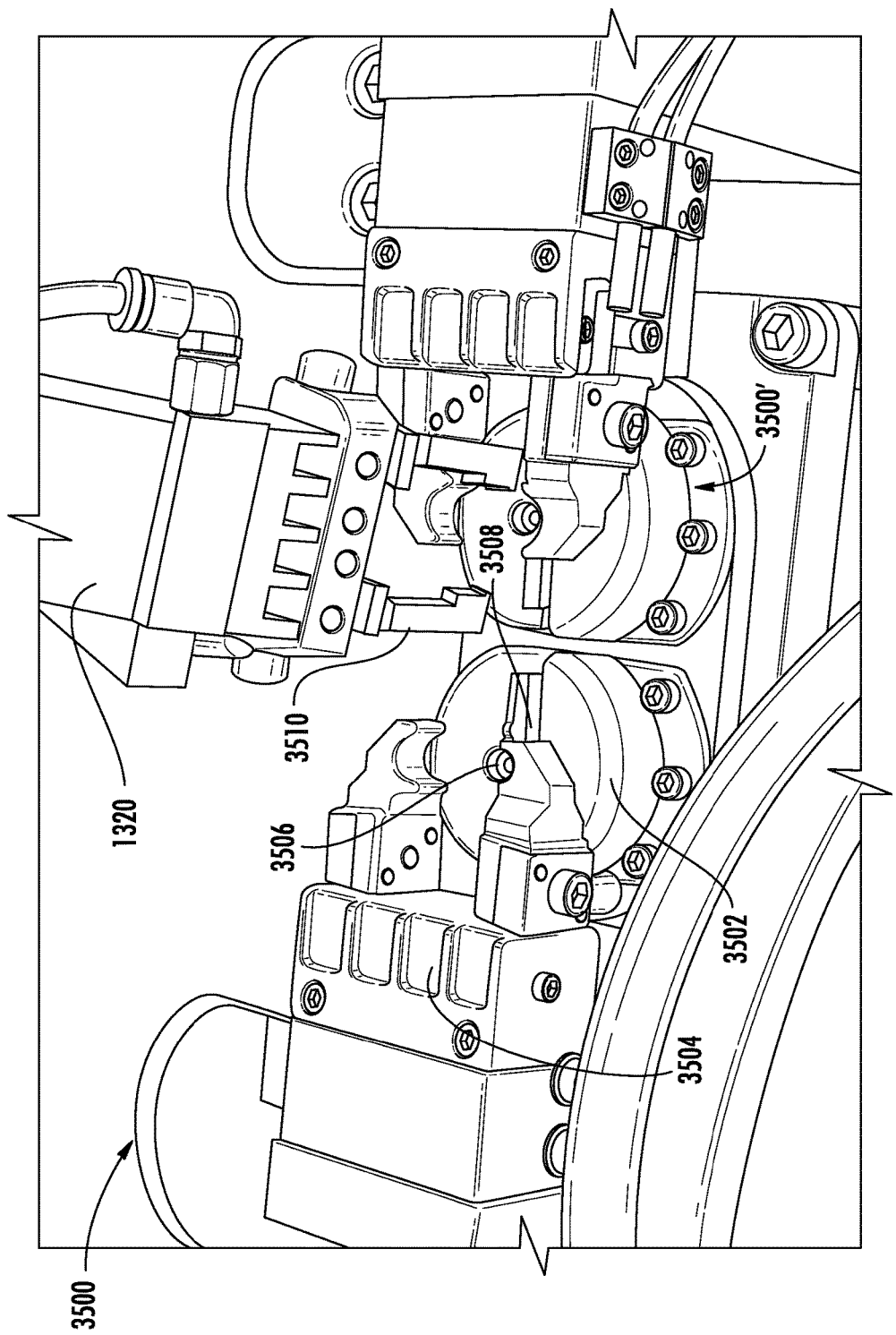
Figure 89:
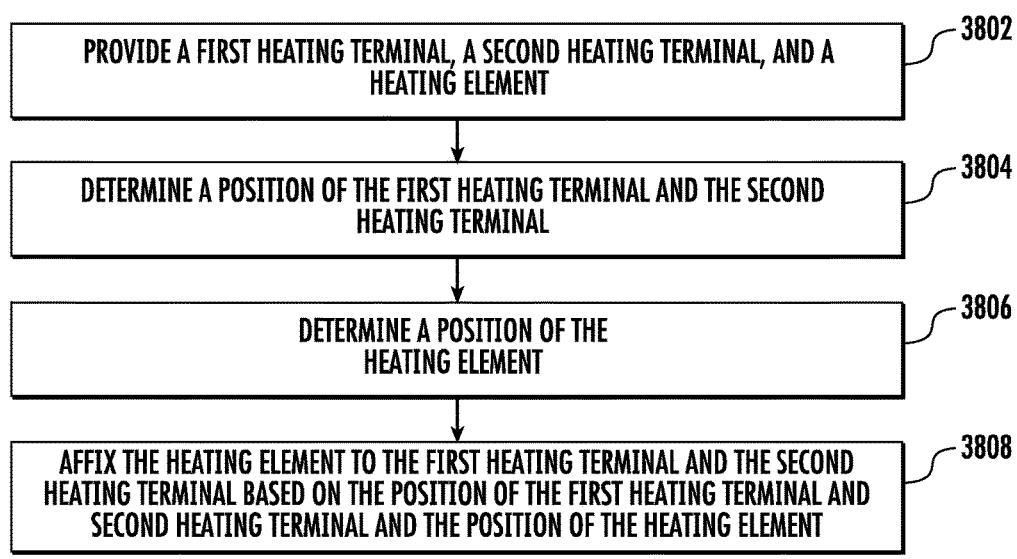
Figure 91:
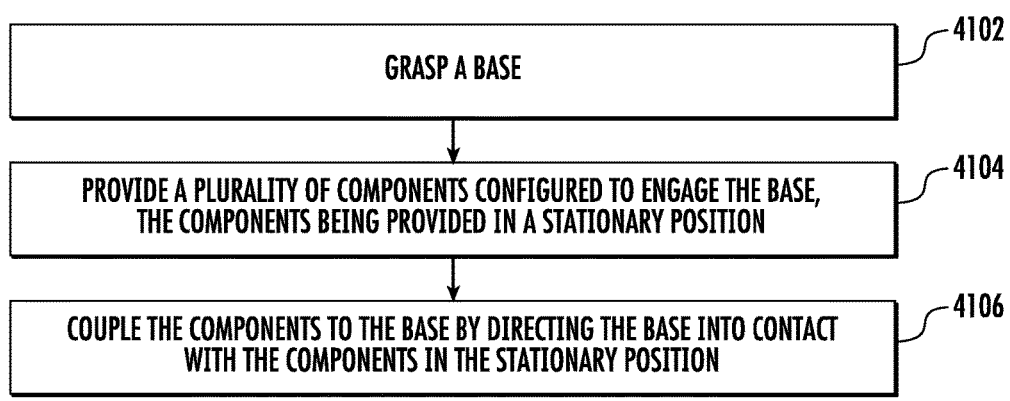
Figure 92:
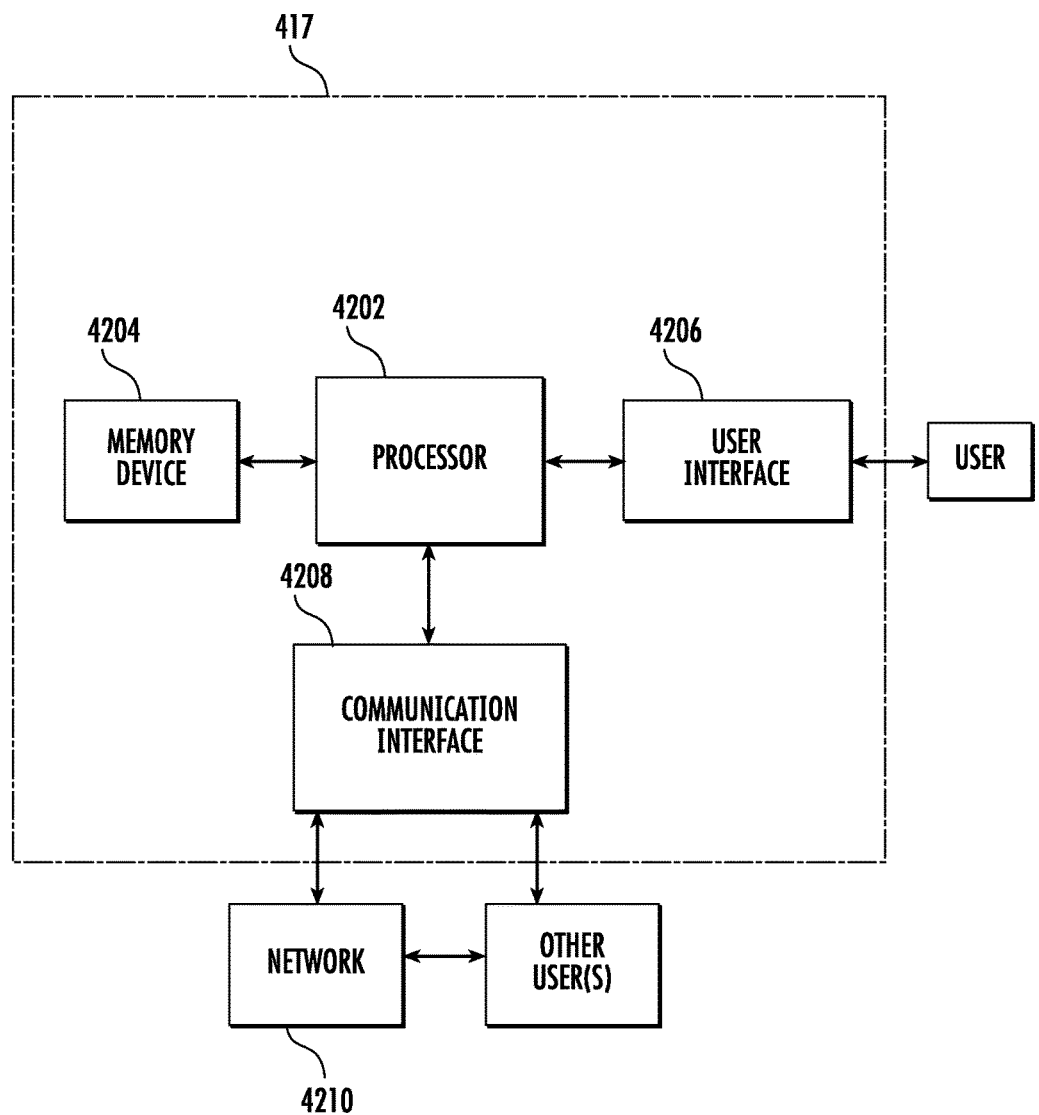

Having thus described the disclosure in the foregoing general terms, reference will now be made to the accompanying drawings, which are not necessarily drawn to scale, and wherein:

FIG. 1 illustrates an aerosol delivery device comprising a cartridge and a control body, the cartridge being illustrated in an exploded configuration and the control body being illustrated in an assembled configuration according to an example embodiment of the present disclosure;

FIG. 2 illustrates the control body of FIG. 1 in an exploded configuration according to an example embodiment of the present disclosure;

FIG. 3 schematically illustrates a system for producing cartridges for an aerosol delivery device including a cartridge assembly subsystem, a cartridge filling subsystem, a cartridge capping subsystem, a cartridge labeling subsystem, and an inspection subsystem according to an example embodiment of the present disclosure;

FIG. 4 schematically illustrates a first embodiment of the cartridge assembly subsystem of FIG. 3 according to an example embodiment of the present disclosure;

FIG. 5 illustrates a perspective view of a carriage of the cartridge assembly subsystem of FIG. 4 according to an example embodiment of the present disclosure;

FIG. 6 illustrates the carriage of FIG. 5 with a base held therein according to an example embodiment of the present disclosure;

FIG. 7 illustrates a side view of the carriage of FIG. 5 with an engagement mechanism disengaged therefrom according to an example embodiment of the present disclosure;

FIG. 8 illustrates a rear view of the carriage of FIG. 5 with the engagement mechanism engaged therewith according to an example embodiment of the present disclosure;

FIG. 9 illustrates a perspective view of a substantially continuous terminal input comprising a plurality of terminals according to an example embodiment of the present disclosure;

FIG. 10 illustrates a perspective view of the terminal sealing substation of the cartridge assembly subsystem of FIG. 4 according to an example embodiment of the present disclosure;

FIG. 11 illustrates an enlarged perspective view of sealant dispensers of the terminal sealing substation of FIG. 10 according to an example embodiment of the present disclosure;

FIG. 12 illustrates a perspective view of a heating element coupling substation of the cartridge assembly subsystem of FIG. 4 according to an example embodiment of the present disclosure;

FIG. 13 illustrates a perspective view of a substantially continuous heating element input of the cartridge assembly subsystem of FIG. 4 according to an example embodiment of the present disclosure;

FIG. 14 illustrates a perspective view of a preparing portion of the heating element coupling substation of FIG. 12 according to an example embodiment of the present disclosure;

FIG. 15 schematically illustrates the preparing portion of the heating element coupling substation of FIG. 14 according to an example embodiment of the present disclosure;

FIG. 16 illustrates an alternate perspective view of the preparing portion of the heating element coupling substation of FIG. 12 according to an example embodiment of the present disclosure;

FIG. 17 illustrates a perspective view of a welding portion of the heating element coupling substation of FIG. 12 according to an example embodiment of the present disclosure;

FIG. 18 illustrates an enlarged perspective view of the welding portion of the heating element coupling substation of FIG. 17 according to an example embodiment of the present disclosure;

FIG. 19 schematically illustrates a terminal fixation mechanism of the welding portion of the heating element coupling substation of FIG. 17 in an open configuration according to an example embodiment of the present disclosure;

FIG. 20 schematically illustrates the terminal fixation mechanism of FIG. 19 in an intermediate configuration according to an example embodiment of the present disclosure;

FIG. 21 schematically illustrates the terminal fixation mechanism of FIG. 19 in a closed configuration according to an example embodiment of the present disclosure;

FIG. 22 schematically illustrates an alternate embodiment of the terminal fixation mechanism of FIG. 19 in an open configuration according to an example embodiment of the present disclosure;

FIG. 23 schematically illustrates alignment of a heating element with heating terminals according to an example embodiment of the present disclosure;

FIG. 24 schematically illustrates welding the heating element to the heating terminals of FIG. 23 according to an example embodiment of the present disclosure;

FIG. 25 illustrates a perspective view of a liquid transport element held in a bent configuration according to an example embodiment of the present disclosure;

FIG. 26 illustrates a perspective view of a reservoir coupling substation of the cartridge assembly subsystem of FIG. 4 according to an example embodiment of the present disclosure;

FIG. 27 illustrates a perspective view of a moveable clamp of the reservoir coupling substation of FIG. 26 at an upper limit during dispensing of a substantially continuous reservoir substrate input according to an example embodiment of the present disclosure;

FIG. 28 illustrates a perspective view of the moveable clamp of FIG. 27 at a lower limit during dispensing of the substantially continuous reservoir substrate input according to an example embodiment of the present disclosure;

FIG. 29 illustrates a perspective view of a transfer mechanism of the reservoir coupling substation of FIG. 26 during receipt of a reservoir substrate according to an example embodiment of the present disclosure;

FIG. 30 illustrates a perspective view of the transfer mechanism of FIG. 29 proximate fingers of the reservoir coupling substation of FIG. 26 according to an example embodiment of the present disclosure;

FIG. 31 illustrates a perspective view of movement of the fingers of the reservoir coupling subsystem of FIG. 26 toward the transfer mechanism of FIG. 29 according to an example embodiment of the present disclosure;

FIG. 32 illustrates clamping of the fingers of the reservoir coupling substation of FIG. 26 according to an example embodiment of the present disclosure;

FIG. 33 schematically illustrates wrapping a reservoir substrate about a heating element using the reservoir coupling substation of FIG. 26 according to an example embodiment of the present disclosure;

FIG. 34 illustrates an outer body supply mechanism of an outer body coupling substation of the cartridge assembly subsystem of FIG. 4 according to an example embodiment of the present disclosure;

FIG. 35 illustrates a section of a tool configured to direct an outer body over the reservoir substrate of the outer body coupling substation of FIG. 34 according to an example embodiment of the present disclosure;

FIG. 36 illustrates directing an outer body over a reservoir substrate using the fingers of the reservoir coupling subsystem of FIG. 26 according to an example embodiment of the present disclosure;

FIG. 36A illustrates directing an outer body over a reservoir substrate using multiple pairs of fingers according to an alternate example embodiment of the present disclosure;

FIG. 37 illustrates a perspective view of a crimper of the outer body coupling substation of FIG. 34 according to an example embodiment of the present disclosure;

FIG. 38 illustrates a side view of a section of the crimper of FIG. 37 according to an example embodiment of the present disclosure;

FIG. 39 illustrates an enlarged partial perspective view of a section of the crimper of FIG. 37 according to an example embodiment of the present disclosure;

FIG. 40 schematically illustrates a second embodiment of the cartridge assembly subsystem of FIG. 3 according to an example embodiment of the present disclosure;

FIG. 41 illustrates an overhead view of the cartridge assembly subsystem of FIG. 40 according to an example embodiment of the present disclosure;

FIG. 42 illustrates a perspective view of a terminal coupling substation of the cartridge assembly subsystem of FIG. 40 according to an example embodiment of the present disclosure;

FIG. 43 illustrates a perspective view of a base gripper of the terminal coupling substation of FIG. 42 according to an example embodiment of the present disclosure;

FIG. 44 illustrates a perspective view of a die of the terminal coupling substation of FIG. 42 according to an example embodiment of the present disclosure;

FIG. 44A illustrates an enlarged perspective view of the die of FIG. 44;

FIG. 45 illustrates a transfer member of the terminal coupling substation of FIG. 42 according to an example embodiment of the present disclosure;

FIG. 46 illustrates a perspective view of a control component coupling substation of the cartridge assembly subsystem of FIG. 40 according to an example embodiment of the present disclosure;

FIG. 47 illustrates an enlarged perspective view of the control component coupling substation of FIG. 46 according to an example embodiment of the present disclosure;

FIG. 48 illustrates a perspective view of a flow tube coupling substation of the cartridge assembly subsystem of FIG. 40 according to an example embodiment of the present disclosure;

FIG. 49 illustrates a side view of a terminal gripper of the cartridge assembly subsystem of FIG. 40 according to an example embodiment of the present disclosure;

FIG. 50 illustrates a perspective view of the terminal gripper of FIG. 49 gripping heating terminals according to an example embodiment of the present disclosure;

FIG. 51 illustrates an enlarged side view of the terminal gripper of FIG. 49 gripping heating terminals according to an example embodiment of the present disclosure;

FIG. 52 illustrates a perspective view of a heating element coupling substation of the cartridge assembly subsystem of FIG. 40 according to an example embodiment of the present disclosure;

FIG. 53 illustrates a spool of a substantially continuous heating element input of the heating element coupling substation of FIG. 52 according to an example embodiment of the present disclosure;

FIG. 54 illustrates a perspective view of a welding portion of the heating element coupling substation of FIG. 52 according to an example embodiment of the present disclosure;

FIG. 55 illustrates a side view of the welding portion of the heating element coupling substation of FIG. 52 during welding according to an example embodiment of the present disclosure;

FIG. 56 illustrates a liquid transport element bending substation of the cartridge assembly subsystem of FIG. 40 according to an example embodiment of the present disclosure;

FIG. 57 illustrates the liquid transport element bending substation of FIG. 56 with a partially assembled cartridge received therein according to an example embodiment of the present disclosure;

FIG. 58 illustrates a perspective view of a base and wick gripper of the cartridge assembly subsystem of FIG. 40 according to an example embodiment of the present disclosure;

FIG. 59 illustrates a side view of the base and wick gripper of FIG. 58 gripping a partially assembled cartridge according to an example embodiment of the present disclosure;

FIG. 60 illustrates a spool of a substantially continuous reservoir substrate input of a reservoir coupling substation of the cartridge assembly subsystem of FIG. 40 according to an example embodiment of the present disclosure;

FIG. 61 illustrates a perspective view of a singulation unit of the reservoir coupling substation of FIG. 60 according to an example embodiment of the present disclosure;

FIG. 62 illustrates an alternate perspective view of the singulation unit of the reservoir coupling substation of FIG. 61 according to an example embodiment of the present disclosure;

FIG. 63 illustrates a perspective view of a wrapping mechanism of the reservoir coupling substation of the cartridge assembly subsystem of FIG. 40 according to an example embodiment of the present disclosure;

FIG. 64 illustrates an overhead view of the outer body coupling substation of the cartridge assembly subsystem of FIG. 40 according to an example embodiment of the present disclosure;

FIG. 65 illustrates an enlarged overhead view of the outer body coupling substation of FIG. 64 with a tool configured to receive the partially assembled cartridge therethrough in an open configuration according to an example embodiment of the present disclosure;

FIG. 66 illustrates an enlarged overhead view of the outer body coupling substation of FIG. 64 with the tool configured to receive the partially assembled cartridge therethrough in a closed configuration according to an example embodiment of the present disclosure;

FIG. 67 illustrates an exploded view of a reservoir gripper of the outer body coupling substation of FIG. 64 according to an example embodiment of the present disclosure;

FIG. 68 illustrates the reservoir gripper of FIG. 67 in an assembled configuration according to an example embodiment of the present disclosure;

FIG. 69 illustrates an alternate embodiment of a reservoir gripper of the outer body coupling substation of FIG. 64 including a finger according to an example embodiment of the present disclosure;

FIG. 70 illustrates an enlarged perspective view of a heating element formed by directing a wire through a liquid transport element and wrapping the wire thereabout according to an example embodiment of the present disclosure;

FIG. 71 schematically illustrates the cartridge filling subsystem of FIG. 3 according to an example embodiment of the present disclosure;

FIG. 72 illustrates an overhead view of a partially assembled cartridge during filling and prior to coupling of a mouthpiece thereto according to an example embodiment of the present disclosure;

FIG. 73 illustrates a cartridge during filling according to an example embodiment of the present disclosure;

FIG. 74 illustrates a side view camera of the inspection subsystem of FIG. 3 configured to inspect a distance to which terminals extend from a base according to an example embodiment of the present disclosure;

FIG. 75 illustrates an end view camera of the inspection subsystem of FIG. 3 configured to inspect a radial position of terminals according to an example embodiment of the present disclosure;

FIG. 76 illustrates side and end view cameras of the inspection subsystem of FIG. 3 configured to inspect terminal height and radial position according to an alternate embodiment of the present disclosure;

FIG. 77 illustrates a side view of a fixture of the inspection subsystem of FIG. 3 configured to facilitate inspection of terminals according to an embodiment of the present disclosure;

FIG. 78 illustrates side and end view cameras of the inspection subsystem of FIG. 3 configured to inspect an outer body of a cartridge according to an example embodiment of the present disclosure;

FIG. 79 illustrates side and end view cameras of the inspection subsystem of FIG. 3 configured to inspect an outer body of a cartridge according to an alternate example embodiment of the present disclosure;

FIG. 80 illustrates a perspective view of a blow-through station of the inspection subsystem of FIG. 3 according to an example embodiment of the present disclosure;

FIG. 81 illustrates a perspective view of a blow-through station of the inspection subsystem of FIG. 3 according to an alternate example embodiment of the present disclosure;

FIG. 82 illustrates perspective view of a pressure drop station of the inspection subsystem of FIG. 3 according to an example embodiment of the present disclosure;

FIG. 83 illustrates a perspective view of a pressure drop station of the inspection subsystem of FIG. 3 according to an alternate example embodiment of the present disclosure;

FIG. 84 illustrates a perspective view of an electrical test station of the inspection subsystem of FIG. 3 including a test fixture according to an example embodiment of the present disclosure;

FIG. 85 illustrates an enlarged perspective view of the test fixture of FIG. 84 according to an example embodiment of the present disclosure;

FIG. 86 illustrates a sectional view through the test fixture of FIG. 84 according to an example embodiment of the present disclosure;

FIG. 87 illustrates a perspective view of an electrical test station of the inspection subsystem of FIG. 3 including a test fixture according to an alternate example embodiment of the present disclosure;

FIG. 88 schematically illustrates a method for assembling a cartridge for an aerosol delivery device according to an example embodiment of the present disclosure FIG. 89 schematically illustrates a method for assembling an atomizer for an aerosol delivery device according to an example embodiment of the present disclosure;

FIG. 90 schematically illustrates a cartridge filling method according to an example embodiment of the present disclosure;

FIG. 91 schematically illustrates a method for assembling a cartridge for an aerosol delivery device according to an example embodiment of the present disclosure; and FIG. 92 schematically illustrates a controller according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to aerosol delivery devices and methods and equipment for assembly thereof. Aerosol delivery devices according to the present disclosure may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising an outer body or shell containing one or more reusable components (e.g., a rechargeable battery and various electronics for controlling the operation of that article), and at the other end and removably attached thereto an outer body or shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices, such as those representative products listed above in the present disclosure. For example, an embodiment of an aerosol delivery device comprising multiple outer bodies and a coupler is described in U.S. patent application Ser. No. 14/170,838, filed Feb. 3, 2014, to Bless et al., which is incorporated herein by reference in its entirety, as noted above.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device can vary. In specific embodiments, the aerosol precursor composition can be located near an end of the article (e.g., within a cartridge, which in certain circumstances can be replaceable and disposable), which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices, such as those representative products listed above in the present disclosure.

An aerosol delivery device incorporates a battery or other electrical power source to provide current flow sufficient to provide various functionalities to the article, such as powering of a heater, powering of control systems, powering of indicators, and the like. The power source can take on various embodiments. Preferably, the power source is able to deliver sufficient power to rapidly heat the heating element to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

One example embodiment of an aerosol delivery device 100 is illustrated in FIG. 1. In particular, FIG. 1 illustrates a partially exploded view of an aerosol delivery device 100 including a cartridge 200 and a control body 300. The cartridge 200 and the control body 300 can be permanently or detachably aligned in a functioning relationship. Various mechanisms may connect the cartridge 200 to the control body 300 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 200 and the control body 300 are in an assembled configuration.

In specific embodiments, one or both of the cartridge 200 and the control body 300 may be referred to as being disposable or as being reusable. For example, the control body 300 may have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 200 may comprise a single-use cartridge, as disclosed in U.S. patent application Ser. No. 13/603,612, filed Sep. 5, 2012, which is incorporated herein by reference in its entirety.

FIG. 2 illustrates an exploded view of the control body 300 of the aerosol delivery device 100 according to an example embodiment of the present disclosure. As illustrated, the control body 300 may comprise a coupler 302, an outer body 304, a sealing member 306, an adhesive member 308 (e.g., KAPTON® tape), a flow sensor 310 (e.g., a puff sensor or pressure switch), a control component 312, a spacer 314, an electrical power source 316 (e.g., a battery, which may be rechargeable), a circuit board with an indicator 318 (e.g., a light emitting diode (LED)), a connector circuit 320, and an end cap 322. Examples of electrical power sources are described in U.S. Pat. App. Pub. No. 2010/0028766 by Peckerar et al., the disclosure of which is incorporated herein by reference in its entirety.

With respect to the flow sensor 310, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. application Ser. No. 13/837,542 to Ampolini et al., filed Mar. 15, 2013, which is incorporated herein by reference in its entirety.

In one embodiment the indicator 318 may comprise one or more light emitting diodes. The indicator 318 can be in communication with the control component 312 through the connector circuit 320 and illuminate, for example, during a user drawing on a cartridge coupled to the coupler 302, as detected by the flow sensor 310. The end cap 322 may be adapted to make visible the illumination provided thereunder by the indicator 318. Accordingly, the indicator 318 may illuminate during use of the aerosol delivery device 100 to simulate the lit end of a smoking article. However, in other embodiments the indicator 318 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; and U.S. patent application Ser. No. 13/841,233, filed Mar. 15, 2013, each of which is incorporated herein by reference in its entirety. A variety of the materials disclosed by the foregoing documents may be incorporated into the present devices in various embodiments, and all of the foregoing disclosures are incorporated herein by reference in their entireties.

Returning to FIG. 1, the cartridge 200 is illustrated in an exploded configuration. As illustrated, the cartridge 200 may comprise a base shipping plug 202, a base 204, a control component terminal 206, an electronic control component 208, a flow tube 210, an atomizer 212, a reservoir substrate 214, an outer body 216, a label 218, a mouthpiece 220, and a mouthpiece shipping plug 222 according to an example embodiment of the present disclosure. The base 204 may be coupled to a first end of the outer body 216 and the mouthpiece 220 may be coupled to an opposing second end of the outer body to enclose the remaining components of the cartridge 200 therein. The base 204 may be configured to engage the coupler 302 of the control body 300. In some embodiments the base 204 may comprise anti-rotation features that substantially prevent relative rotation between the cartridge and the control body as disclosed in U.S. patent application Ser. No. 13/840,264, filed Mar. 15, 2013, which is incorporated herein by reference in its entirety.

The base shipping plug 202 may be configured to engage and protect the base 204 prior to use of the cartridge 200. Similarly, the mouthpiece shipping plug 222 may be configured to engage and protect the mouthpiece 220 prior to use of the cartridge 200. The control component terminal 206, the electronic control component 208, the flow tube 210, the atomizer 212, and the reservoir substrate 214 may be retained within the outer body 216. The label 218 may at least partially surround the outer body 216 and include information such as a product identifier thereon.

The atomizer 212 may comprise a first heating terminal 234a and a second heating terminal 234b, a liquid transport element 238 and a heating element 240. In this regard, the reservoir substrate 214 may be configured to hold an aerosol precursor composition. The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference in their entireties. Other aerosol precursors which may be employed in the aerosol delivery device of the present disclosure include the aerosol precursors included in the VUSE® product by R. J. Reynolds Vapor Company, the BLU™ product by Lorillard Technologies, the Mistic Menthol product by Mistic Ecigs, and the Vype product by CN Creative Ltd. Also desirable are the so-called "Smoke Juices" for electronic cigarettes that have been available from Johnson Creek Enterprises LLC. Additional exemplary formulations for aerosol precursor materials that may be used according to the present disclosure are described in U.S. Pat. Pub. No. 2013/0008457 to Zheng et al., the disclosure of which is incorporated herein by reference in its entirety.

The reservoir substrate 214 may comprise a plurality of layers of nonwoven fibers formed into the shape of a tube encircling the interior of the outer body 216 of the cartridge 200. Thus, liquid components, for example, can be sorptively retained by the reservoir substrate 214. The reservoir substrate 214 is in fluid connection with the liquid transport element 238. Thus, the liquid transport element 238 may be configured to transport liquid from the reservoir substrate 214 to the heating element 240 via capillary action.

As illustrated, the liquid transport element 238 may be in direct contact with the heating element 240. As further illustrated in FIG. 1, the heating element 240 may comprise a wire defining a plurality of coils wound about the liquid transport element 238. In some embodiments the heating element 240 may be formed by winding the wire about the liquid transport element 238 as described in U.S. patent application Ser. No. 13/708,381, filed Dec. 7, 2012, which is incorporated herein by reference in its entirety. Further, in some embodiments the wire may define a variable coil spacing, as described in U.S. patent application Ser. No. 13/827,994, filed Mar. 14, 2013, which is incorporated herein by reference in its entirety. Various embodiments of materials configured to produce heat when electrical current is applied therethrough may be employed to form the heating element 240. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic).

However, various other embodiments of methods may be employed to form the heating element 240, and various other embodiments of heating elements may be employed in the atomizer 212. For example, a stamped heating element may be employed in the atomizer, as described in U.S. patent application Ser. No. 13/842,125, filed Mar. 15, 2013, which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. patent application Ser. No. 13/602,871, filed Sep. 4, 2012, which is incorporated herein by reference, as noted above.

A variety of heater components may be used in the present aerosol delivery device. In various embodiments, one or more microheaters or like solid state heaters may be used. Embodiments of microheaters that may be utilized are further described herein. Further microheaters and atomizers incorporating microheaters suitable for use in the presently disclosed devices are described in U.S. patent application Ser. No. 13/602,871, filed Sep. 4, 2012, which is incorporated herein by reference in its entirety.

The first heating terminal 234a and the second heating terminal 234b (e.g., positive and negative terminals) at the opposing ends of the heating element 240 are configured to form an electrical connection with the control body 300 when the cartridge 200 is connected thereto. Further, when the control body 300 is coupled to the cartridge 200, the electronic control component 208 may form an electrical connection with the control body through the control component terminal 206. The control body 300 may thus employ the electronic control component 208 to determine whether the cartridge 200 is genuine and/or perform other functions. Further, various examples of electronic control components and functions performed thereby are described in U.S. patent application Ser. No. 13/647,000, filed Oct. 8, 2012, which is incorporated herein by reference in its entirety.

During use, a user may draw on the mouthpiece 220 of the cartridge 200 of the aerosol delivery device 100. This may pull air through an opening in the control body 300 or in the cartridge. For example, in one embodiment an opening may be defined between the coupler 302 and the outer body 304 of the control body 300, as described in U.S. patent application Ser. No. 13/841,233; Filed Mar. 15, 2013, which is incorporated herein by reference in its entirety. However, the flow of air may be received through other parts of the aerosol delivery device 100 in other embodiments. As noted above, in some embodiments the cartridge 200 may include the flow tube 210. The flow tube 210 may be configured to direct the flow of air received from the control body 300 to the heating element 240 of the atomizer 212.

A sensor in the aerosol delivery device 100 (e.g., a puff or flow sensor in the control body 300) may sense the puff. When the puff is sensed, the control body 300 may direct current to the heating element 240 through a circuit including the first heating terminal 234a and the second heating terminal 234b. Accordingly, the heating element 240 may vaporize the aerosol precursor composition directed to an aerosolization zone from the reservoir substrate 214 by the liquid transport element 238. Thus, the mouthpiece 220 may allow passage of air and entrained vapor (i.e., the components of the aerosol precursor composition in an inhalable form) from the cartridge 200 to a consumer drawing thereon.

Various other details with respect to the components that may be included in the cartridge 200, are provided, for example, in U.S. patent application Ser. No. 13/840,264, filed Mar. 15, 2013, which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow tube, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 3 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 4 thereof illustrates a perspective view of a base with an anti-rotation mechanism; FIG. 5 thereof illustrates a perspective view of a coupler with an anti-rotation mechanism; and FIG. 6 thereof illustrates a sectional view through the base of FIG. 4 thereof and the coupler of FIG. 5 thereof in an engaged configuration.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

Note further that portions of the cartridge 200 illustrated in FIG. 1 are optional. In this regard, by way of example, the cartridge 200 may not include the flow tube 210, the control component terminal 206, and/or the electronic control component 208 in some embodiments.

In another embodiment substantially the entirety of the cartridge may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the battery and controller. An example embodiment of a carbon-based cartridge is provided in U.S. Pat. App. Pub. No. 2013/0255702 to Griffith et al., which is incorporated herein by reference in its entirety.

As described above, cartridges of aerosol delivery devices may include a number of components. Some of the components may be relatively small and/or relatively delicate. Accordingly, precise manufacturing techniques may be required to form the aerosol delivery devices. In this regard, aerosol delivery devices have traditionally been formed via manual assembly. However, use of manual labor to assemble aerosol delivery devices suffers from certain detriments. In this regard, the quality of aerosol delivery devices produced via manual labor is only as good as the workers performing the labor. Further, even skilled workers may make errors from time-to-time. Additionally, manual labor may be relatively costly. Accordingly, as result of these issues and other issues associated with the production of aerosol delivery devices via manual labor, it may be desirable to produce aerosol delivery devices in an automated manner. Accordingly, automated production of cartridges for aerosol delivery devices is discussed hereinafter, which may provide enhanced repeatability, lower costs, and/or avoid other issues noted above.

In this regard, FIG. 3 schematically illustrates an embodiment of a system 400 for producing cartridges (e.g., the above-described cartridges 200) for an aerosol delivery device (e.g., the above-described aerosol delivery device 100). Note that the above described aerosol delivery device 100 is provided by way of example. In this regard, the methods, systems, and apparatuses described herein may be employed to form various embodiments of cartridges that differ from the above described cartridges in one or more respects.

As illustrated, the system 400 may include various subsystems that perform particular functions in the formation of the completed cartridges 200. Note that although the subsystems are illustrated as being separate from one another, the subsystems may overlap. For example, in some embodiments common equipment may perform two or more functions (e.g., assembly and filling or capping and labeling, etc.), rather than the particular functions being performed by separate equipment.

Further, the various subsystems and portions thereof are separately usable. In this regard, although the subsystems and portions thereof are generally described herein as being usable together, this is by way of example. Accordingly, any of the subsystems or portions thereof described herein may be usable by themselves or in any combination with some or all of the other subsystems and portions thereof described herein. Thus, for example, although an example embodiment of a cartridge filling subsystem is described hereinafter as being employed to fill cartridges filled by embodiments of cartridge assembly subsystems disclosed herein, the cartridge filling subsystem may be employed to fill cartridges formed by other subsystems and/or the cartridges assembled by the cartridge assembly subsystems may be filled by other cartridge filling subsystems. Further, although particular embodiments of portions of the subsystems are disclosed hereinafter, these embodiments are provided for example purposes only. Accordingly, in some embodiments the subsystems may include fewer or additional portions. Thus, each portion of each subsystem, and each portion of the overall system is not required in all embodiments.

As illustrated, the subsystems may include a cartridge assembly subsystem 402 configured to form unfilled cartridges 404 from components 406 (e.g., the base 204, the heating terminals 234a, 234b, etc.). A cartridge filling subsystem 408 may fill the unfilled cartridges 404 to produce filled cartridges 410. A cartridge capping subsystem 412 may cap the filled cartridges 410 to produce capped cartridges 414. A cartridge labeling subsystem 416 may apply labels to the capped cartridges 414 to complete the completed cartridges 200.

The system 400 may additionally include an inspection subsystem 418. The inspection subsystem 418 may inspect the components 406, the unfilled cartridges 404, the filled cartridges 410, the capped cartridges 414, and/or the completed cartridges 200. Further, in some embodiments the cartridges may be inspected at intermediate states of completion at one or more of the cartridge assembly subsystem 402, the cartridge filling subsystem 408, the cartridge capping subsystem 412, and the cartridge labeling subsystem 416. Accordingly, the cartridges 200 and components thereof may be inspected before, during, and after completion thereof.

The system my further at least one controller 417. The controller 417 may be configured to control the cartridge assembly subsystem 402, the cartridge filling subsystem 408, the cartridge capping subsystem 412, and/or the cartridge labeling subsystem 416. In this regard, the controller may be configured to receive data from one or more of the sensors described herein and output instructions based thereon, in addition to otherwise directing the operations described herein.

Note that some or all of the system 400 may be automated. In this regard, as described hereinafter, robotic apparatuses may be employed in some embodiments of the system 400. The robotic apparatuses may be provided from various robotic manufacturers including, by way of example, DENSO Robotics of Long Beach, Calif., FANUC of Rochester Hills, Mich., Mitsubishi Electric Automation of Vernon Hills, Ill., and Siemens Automation Technology of Munich, Germany.

An example embodiment of the cartridge assembly subsystem 402 is illustrated in FIG. 4. Note that the particular embodiments of substations and positions thereof may vary from those described below and illustrated in FIG. 4. Further, the particular operations employed as well as the order thereof may also vary. In this regard, the equipment employed to assemble a cartridge may depend on the particular configuration of the end-product cartridge. In this regard, the cartridge 200 described above and referenced hereinafter is discussed for example purposes only. Additionally, although the description generally refers to the portions of the cartridge assembly subsystem 402 as substations, it should be understood that the various assembly operations discussed herein may be performed by a single device, apparatus, or substation, or distributed across multiple devices, apparatuses, and substations. Accordingly, the description provided below is for example purposes only, and the equipment and operations and order thereof employed may vary without departing from the scope of the disclosure. Further, it should be understood that various substations and operations performed at each of the substations should be viewed as individual inventive aspects. In this regard, although the individual substations and operations are generally described herein as being part of a system, each of the substations may operate independently of the other substations discussed herein and/or be combined with other substations.

By way of example, the cartridge assembly subsystem 402 may include a base load substation 502, a terminal coupling substation 504, a terminal sealing substation 506, a control component coupling substation 508, a flow tube coupling substation 510, a heating element coupling substation 512, a liquid transport element bending substation 514, a reservoir coupling substation 516, and an outer body coupling substation 518. As illustrated, the controller 417 may be configured to control one or more of the substations 502-518 of the cartridge assembly subsystem 402. Briefly, the base load substation 502 may be configured to receive a base (e.g., the base 204) and orient the base for assembly with the various other components of the cartridge. The terminal coupling substation 504 may be configured to couple one or more terminals (e.g., the first and second heating terminals 234a,b and the control component terminal 206) to the base. The terminal sealing substation 506 may be configured to seal one or more of the terminals with respect to the base to prevent fluid ingress or egress between the base and the terminal(s). The control component coupling substation 508 may be configured to couple a control component (e.g., the electronic control component 208) to the control component terminal. The flow tube coupling substation 510 may be configured to couple a flow tube (e.g., the flow tube 210) to the control component, the first and second heating terminals, and/or other components. The heating element coupling substation 512 may be configured to couple a heating element (e.g., the heating element 240) to the heating terminals. The liquid transport element bending station 514 may be configured to bend a liquid transport element (e.g., the liquid transport element 238) about the heating terminals. The reservoir coupling substation 516 may be configured to couple a reservoir substrate (e.g., the reservoir substrate 214) to the liquid transport element. Further, the outer body coupling substation 518 may be configured to couple an outer body (e.g., the outer body 216) to the base.

The cartridge assembly subsystem 402 may assemble the cartridge (e.g., the cartridge 200) in a variety of manners. For example, in one embodiment the cartridge may be assembled generally upwardly from a base. In other words, components may be inserted into or otherwise coupled to the base to build up the cartridge therefrom.

In this regard, as illustrated in FIGS. 5 and 6, in one embodiment a transport system may include carriages 600, which may also be referred to as "pods" or "nests," which may be employed to assemble the cartridges 200. FIG. 5 illustrates an empty carriage 600, whereas FIG. 6 illustrates the carriage after a base 204 is loaded therein. As illustrated, the carriages 600 may include a clamping mechanism 602. The clamping mechanism 602 may include a displaceable piston 604 defining a head 606 at an end thereof. A biasing mechanism may bias the displaceable piston 604 toward a groove 608. Accordingly, as illustrated in FIG. 6, the head 606 of the displaceable piston 604 may cooperate with the groove 608 to retain the base 204 therein. In this regard, the groove 608 may be V-shaped in order to center the base 204 in the groove.

Various embodiments of biasing mechanisms may be employed, such as magnets, hydraulic or pneumatic cylinders, etc. However, in the illustrated embodiment a rod 610 may be received in a mount 612. The mount 612, which may also function to align the piston 604 with respect to the groove 608, may include a spring therein that biases the rod 610 toward the head 606 of the piston. Accordingly, the head 606 of the piston 604 may be biased toward the groove 608 to retain the base 204 therein. Further, the piston 604 may include a handle 614 at an end thereof opposite from the head 606. The handle 614 may be configured to allow for grasping thereof, via automated or manual methods, to oppose the force provided by the biasing mechanism to thereby release the base 204.

The transport system may further comprise a rail 616 or other mechanism configured to provide for movement of the carriages between a plurality of substations. The carriages 600 may be mounted to the rail 616 using wheels 618 (see, e.g., FIG. 5). The carriages 600 may be moved along the rail 616 by driving the wheels 618. Alternatively, magnetic propulsion may be employed to move the carriages 600. However, the wheels 618 may still be provided in order to hold the carriages on the rail 616. In this regard, as illustrated in FIGS. 7 and 8, a magnetic track 620 may cause the carriage 600 to move. More particularly, the carriage 600 may further comprise a magnet 622. The magnetic track 620 may change polarity in relation to the position of a magnet 622 coupled to the carriage 600 such that attractive and/or repulsive forces between the magnetic track 620 and the magnet cause the carriage to move. Thus, the carriages 600 may be transferred between various substations. In this regard, a plurality of the carriages 600 may be provided. The carriages 600 may be configured to move between the various substations described hereinafter. In this regard, the carriages 600 may be disposed at various locations along the path defined by the rail during assembly of the cartridges such that any given time, the carriages may be distributed along the length of the rail. Thereby, multiple cartridges may be constructed simultaneously.

It may be desirable to stop or slow down movement of the carriages 600 at one or more of the substations while one or more operations are conducted in order to simplify coupling parts of the cartridge to the base. Further, in some embodiments it may be desirable to lock the carriages 600 in a predefined position to substantially prevent movement of the carriages at one or more of the substations. In this regard, magnetic locking of a position of the carriage may be insufficient to properly lock a carriage in place because magnetic locking may still allow for some movement of the carriage. Accordingly, a locking apparatus may be employed to temporarily restrain movement of each carriage 600 along the rail 616.

The locking apparatus may include a locator mechanism 624 coupled to each carriage 600. In the illustrated embodiment, the locator mechanism 624 comprises first and second pegs 626. Further, the locking apparatus may comprise an engagement mechanism 628, which may be positioned at each location at which locking the carriage 600 in place is desired. Thus, the engagement mechanism 628 may be located at a fixed position relative to the longitudinal length of the rail 616. However, the engagement mechanism 628 may be configured to move into contact with the locator mechanism 624 (e.g., via a pneumatic piston, hydraulic piston, or linear motor) to lock the carriage 600 in place.

In the illustrated embodiment, the engagement mechanism 628 comprises a cylinder 630. Accordingly, as the engagement mechanism 628 is directed upwardly, the cylinder 630 may contact one or both of the pegs 626 of the locator mechanism 624. Thereby, the pegs 626 may deflect from the cylinder 630 such that the locator mechanism 624 becomes centered with respect to the engagement mechanism 628. Further, in one embodiment the cylinder 630 may comprise a roller or wheel configured to rotate to facilitate centering between the pegs 626 by allowing the cylinder to rotate when brought into contact with one of the pegs, rather than scraping thereagainst. Regardless of whether or not the cylinder 630 rotates, any imprecision in the initial stopping point of the carriage 600 may be accounted for by the centering effect created by the interaction between the pegs 626 of the locator mechanism 624 and the cylinder of the engagement mechanism 628. Accordingly, movement of the carriage 600 along the rail 616 may be restrained by interaction between the fixed engagement mechanism 628 and the locator mechanism 624 coupled to the carriage.

Note that locking apparatus may comprise various other mechanisms configured to center the carriage with respect to the engagement mechanism. For example, the locator mechanism may comprise a vertically oriented groove. Alternatively or additionally, the engagement mechanism may comprise an angled member such as a triangle.

Accordingly, the carriages 600 may be employed to transport the base 204 to various substations at which various components are assembled thereto. Thereby, the base 204 may be loaded into the carriage 600 as illustrated in FIGS. 6 and 8 at the base load substation 502. Thereafter, other components may be assembled with the base 204 (e.g., by directing the components downwardly into contact with the base) to assemble the cartridge.

In this regard, as described above, the control component terminal 206 and the first and second heating terminals 234a,b may be inserted into the base 204 at the terminal coupling substation 504. In some embodiments the first heating terminal 234a, the second heating terminal 234b, and/or the control component terminal 206 may be provided from substantially continuous inputs. More particularly, the first heating terminal 234a may be supplied from a substantially continuous first heating terminal input, the second heating terminal 234b may be supplied from a substantially continuous second heating terminal input, and/or the control component terminal 206 may be supplied from a substantially continuous control component terminal input. Note that the term substantially continuous, as used herein in relation to certain specified inputs, refers to a configuration in which the referenced input defines a strip, chain, or other grouping of interconnected underlying components such that individual components may be singulated therefrom.

By way of example, FIG. 9 illustrates a substantially continuous first heating terminal input 700 comprising a plurality of the first heating terminals 234a. In this regard, each of the first heating terminals 234a is connected to a substantially continuous carrier 702. In the illustrated embodiment, each of the first heating terminals 234a are connected to the carrier 702 by first and second couplers 704. However, a single coupler or additional couplers may be employed to hold the first heating terminals 234a to the carrier 702 in other embodiments. In some embodiments, as illustrated, the first heating terminals 234a, the couplers 704, and the carrier 702 may be integrally formed (e.g., from a strip of sheet metal).

The couplers 704 may be cut to release an individual first heating terminal 234a from the substantially continuous first heating terminal input 700. Further, the carrier 702 may comprise apertures 706, grooves, cutouts, or other mechanisms configured to facilitate movement of the substantially continuous first heating terminal input 700 such that individual first heating terminals 234a may be removed therefrom. In this regard, as illustrated in FIG. 9, a wheel 708 may include protrusions 710 configured to engage the apertures 706, such that rotation of the wheel 708 causes movement of the input 700 toward a location at which there individual first heating terminals 234a are removed therefrom. Note that although the above-provided description has been provided in terms of the first heating terminal 234a, in some embodiments the second heater terminal 234b and/or the control component terminal 206 may be supplied via substantially continuous inputs in similar manners.

After insertion into the base 204, the terminal sealing substation 506 may seal one or more of the terminals 206, 234a,b with respect to the base, in some embodiments, in order to prevent liquid ingress or egress past the terminals. However, in some embodiments only the heating terminals 234a,b may be sealed. For example, in the illustrated embodiment the control component terminal 206 may extend through, or be positioned adjacent to, an opening through the base 204 through which a user draws air through the cartridge 200 during use thereof. Accordingly, the control component terminal 206 may not be sealed with respect to the base 204 in order to prevent blocking the opening extending through the base. Further, the control component terminal 206 may not be in contact with the liquid-filled reservoir substrate 214, such that liquid egress past the control component terminal 206 may not be of concern.

FIG. 10 illustrates an example embodiment of the terminal sealing substation 506. The terminal sealing substation 506 may include one or more sealant dispensers 802a,b. In the illustrated embodiment first and second sealant dispensers 802a,b are employed to dispense a sealant provided by a pump 804 through one or more conduits 806. A robotic arm 808 may grasp the base 204 with a gripper 810. In this regard, the robotic arm 808 may position the base 204 such that the base is positioned in front of nozzles 812a,b of the sealant dispensers 802a,b. For example, the gripper 810 may grasp an external surface of the base 204 and remove the base 204 from the carriage 600. Thereafter, the robotic arm 808 may position the base 204 such that the terminals 206, 234a,b extend generally upwardly in a position proximate the sealant dispensers 802a,b. By grasping the outside of the base 204 in this manner, the gripper 810 of the robotic arm 808 may not interfere with dispensing the sealant because the gripper may not be positioned between the nozzles 812a,b and the terminals 206, 234a,b extending upwardly from the base.

As illustrated in FIG. 11, the sealant dispensers 802a,b may be positioned such that the nozzles 812a,b are at least partially directed toward one another. Thereby, the robotic arm 808 may position the base 204 and the terminals 206, 234a,b between the sealant dispensers 802a,b such that nozzles 812a,b may direct a sealant at opposing sides of the terminals. For example, droplets of the sealant may be ejected from the nozzles 812a,b toward opposing sides of the heating terminals 234a,b. More particularly, the nozzles 812a,b may direct the droplets of the sealant at an interface between the heating terminals 234a,b and the base 204.

In some embodiments the sealant may comprise a hot melt adhesive comprising polyolefins including atactic poly-alphaolefins, polyurethane, ethylene-vinyl acetate (EVA), metallocene polyalphaolefins, block copolymers, and/or polyamides. Thus, the terminal sealing substation 506 may further comprise a heater 814 (see, FIG. 10), which may melt the sealant. Further, the conduits 806 may be heated and/or insulted. Seals in the pump 804 and the sealant dispensers 802a,b may traditionally employ TEFLON® brand material for lubrication. However, a food-grade grease or lubricant may instead be employed in some embodiments, in order to advantageously employ food-grade manufacturing techniques in the production of the cartridge.

After the droplets of the liquid sealant contact the heating terminals 234a,b and/or the base 204, the droplets may dry in place relatively quickly. Further, the droplets may not contact one another. Thus, a complete seal around the full interface of the heating terminals 234a,b with the base 204 may not be formed by the initial application of the droplets of the sealant. Accordingly, the terminal sealing substation 506 may further comprise a re-melting device such as a hot air gun 816 configured to direct a flow of heated air at the sealant after application thereof to the heating terminals 234a,b and/or the base 204. Accordingly, the hot air from the hot air gun 816 may re-melt the sealant and blow the melted sealant around the heating terminals 234a,b such that the interface between the heating terminals and the base 204 is fully sealed around the perimeter of each of the heating terminals. In this regard, the hot air gun 816 may move relative to the base 204 and the heating terminals 234a,b. In some embodiments the hot air gun 816 may be configured to move. However, as illustrated, in another embodiment the hot air gun 816 may be stationary. Accordingly, the robotic arm 804 may move the base 204 relative to the hot air gun 816 such that hot air re-melts the sealant and directs the sealant around the interface between the heating terminals 234a,b and the base. Thus, the sealant may re-solidify and seal any gaps between the heating terminals 234a,b and the base 204.

Note that the terminal sealing substation 506 may additionally or alternatively seal the control component terminal 206 and/or any other component of the cartridge 200 with respect to the base 204. Additionally, although the re-melting device is described above as being the hot air gun 816, in other embodiments the sealant may be re-melted by other methods and other re-melting devices, such as by applying ultrasonic vibrations with an ultrasonic vibration device and/or applying radiant heat with a radiant heater. Further, although the sealant is described above as being a hot melt adhesive, various other embodiments of sealants may be employed. For example, the sealant may comprise an epoxy or an electrical potting material. After the heating terminals 234a,b are sealed, the base 204 may be returned to the carriage 600 by the robotic arm 608.

Thereafter, the control component coupling substation 508 may couple the electronic control component 208 to the control component terminal 206 (e.g., by vertically inserting the control component into a slot defined by the control component terminal). Then the flow tube coupling substation 510 may couple the flow tube 210 to the partially assembled cartridge. For example, the flow tube 210 may be inserted horizontally, such that the heating terminals 234a,b are slightly spread apart and then snap into place in longitudinal grooves defined in the flow tube, with a horizontal slot in the flow tube engaging the top of the electronic control component 208.

Next, the partially assembled cartridge may be transported to the heating element coupling substation 512 at which the heating element 240 may be coupled to the heating terminals 234a,b. In this regard, FIG. 12 illustrates an example embodiment of the heating element coupling substation 512. In the illustrated embodiment, the heating element coupling substation 512 includes a preparing portion 902, a welding portion 904, and a transport apparatus 905 configured to transport an individual heating element 240 wrapped about a liquid transport element 238 from the preparing portion 902 to the welding portion 904.

As illustrated in FIG. 13, in some embodiments the heating element and the liquid transport element may be supplied from a substantially continuous heating element input 906. In this regard, the substantially continuous heating element input 906 may comprise a plurality of the heating elements 240 wound about the liquid transport element 238. Examples of heating elements wound about liquid transport elements are provided in U.S. patent application Ser. No. 13/827,994, filed Mar. 14, 2013 and Ser. No. 13/708,381, filed Dec. 7, 2012, which are incorporated herein by reference in their entireties.

As illustrated, the substantially continuous heating element input 906 may be supplied from a spool 908 in some embodiments. The spool 908 may passively rotate as the substantially continuous heating element input 906 is pulled therefrom. Alternatively, the spool 908 may be actively rotated (e.g., by a motor) such that the spool rotates as the substantially continuous heating element input 906 is pulled therefrom. By either actively rotating the spool 908 or passively allowing the spool to substantially freely rotate as the substantially continuous heating element input 906 is pulled therefrom, tension in the substantially continuous heating element input may be controlled. In this regard, applying too much tension to the substantially continuous heating element input 906 may damage the heating elements 240 or the liquid transport element 238. For example, spacing of the coils of the heating elements 240 may be altered, which may make it difficult to attach the heating elements to the heating terminals. Further, too much tension in the liquid transport element 238 may cause breakage thereof, or stretching of the liquid transport element may reduce the diameter thereof and affect the ability of the liquid transport element to draw the aerosol precursor composition to the heating element 240. Accordingly, the substantially continuous heating element input 906 may be supplied to the preparing portion 902 without damaging the heating elements 240 or the liquid transport element 238 by controlling the tension therein.

FIG. 14 illustrates an enlarged view of the preparing portion 902 of the heating element coupling substation 512. Briefly, the preparing portion 902 of the heating element coupling substation 512 may be configured to prepare an individual heating element 240 coupled to an individual liquid transport element 238 for welding at the welding portion 904 of the heating element (see, e.g., coupling substation 512. In this regard, the preparing portion 902 of the heating element coupling substation 512 may be configured to singulate one heating element 240 and one liquid transport element 238, such that the heating element may thereafter be coupled to the heating terminals. In this regard, in one embodiment individual heating elements and liquid transport elements may be delivered to the preparing portion in a form ready for attachment to the heating terminals without performing additional operations thereon.

However, as described above, in the illustrated embodiment the substantially continuous heating element input 906 may include a coil of wire wrapped about a substantially continuous liquid transport element. Thereby, the substantially continuous heating element input 906 may be cut to remove an individual heating element 240 and liquid transport element 238 therefrom. In this regard, as illustrated, the preparing portion 902 of the heating element coupling substation 512 may include a dispenser 910, a cutter 912, and an imaging device 914 (e.g., a camera).

FIG. 15 schematically illustrates the preparing portion 902 of the heating element coupling substation 512. The dispenser 910 may be configured to dispense a length of the substantially continuous heating element input 906 from the spool 908 (see, FIG. 13). In this regard, the dispenser 910 may comprise a stationary portion 916 and a moveable portion 918. The moveable portion 918 may include a clamp 920 configured to grasp the substantially continuous heating element input 906 proximate an end thereof. The moveable portion 918 may be configured to move relative to the stationary portion 916 in a direction 922 such that the substantially continuous heating element input 906 is dispensed from the spool 908 (see, FIG. 13). For example, the dispenser 910 may comprise a hydraulic or pneumatic cylinder or a linear motor in some embodiments. The dispenser 910 may be configured to pull on the substantially continuous heating element input 906 until a desired length thereof has been dispensed.

In this regard, the imaging device 914 may be positioned and configured to capture images of the substantially continuous heating element input 906 as it is dispensed. The controller 417 (see, e.g., FIG. 3) may be in communication with the imaging device 914 and configured to analyze the images captured by the imaging device. Accordingly, the controller 417 may be configured to analyze the images captured by the camera 914 to identify the position of the substantially continuous heating element input 906 to determine a dispensed length thereof.

In this regard, the dispenser 910 may be configured to start dispensing the substantially continuous heating element input 906 and the controller 417 may analyze the images thereof and direct the dispenser to stop dispensing the substantially continuous heating element input when a desired length thereof has been dispensed. For example, the controller 417 may be configured to analyze the image captured by the imaging device 914 to detect coils or other features of the heating element 240. By way of further example, in one embodiment the controller 417 may be configured to detect a first contact portion 926 and a second contact portion 928 of the heating element 240, which are configured to engage the heating terminals. In one embodiment, the controller 417 may determine the position of inner edges 926a, 928a of the contact portions 926, 928 of the heating element 240. Thereby, the controller 417 may calculate a midpoint between the contact portions 926, 928 of the heating element 240 and allow the dispenser 910 to continue dispensing the substantially continuous heating element input 906 until the midpoint between the first contact portion 926 and the second contact portion 928 is aligned with the midpoint of the imaging device 914.

At this time, the controller 417 may direct the dispenser 910 to stop dispensing the substantially continuous heating element input 906. Additionally, the controller 417 may direct a transport apparatus 905 to grasp the substantially continuous heating element input 906. For example, the transport apparatus 905 may comprise a clamp 930 including first and second arms 932a, 932b configured to grasp the substantially continuous heating element input 906 outside of the contact portions 926, 928 of the heating element 240, which may allow the clamp to continue to hold the heating element during welding, as discussed below.

Further, the controller 417 may direct the cutter 912, which may comprise first and second blades 934a, 934b, to cut the substantially continuous heating element input 906 to singulate a heating element 240 and liquid transport element 238 having a desired length. In this regard, the imaging device 914 may be positioned such that when the midpoint between the first contact portion 926 and the second contact portion 928 of the heating element 240 is aligned with the midpoint of the imaging device, a distance between an end of the substantially continuous heating element input 906, as held by the clamp 920, and the blades 934a, 934b of the cutter 912 is equal to a desired length of a single heating element 240 and liquid transport element 238.

Note that the preparing portion 902 of the heating element coupling substation 512 may further comprise a tube 936. The substantially continuous heating element input 906 may be supplied through the tube 936 to the cutter 912. Accordingly, after the substantially continuous heating element input 906 is cut, the tube 936 may support the substantially continuous heating element input proximate a new end thereof. Thereby, the clamping mechanism 910 of the transport apparatus 905 may release from the singulated heating element 240 and liquid transport element 238 and grasp the new end of the substantially continuous heating element input 906, such that the above-described operations may be repeated by the preparing portion 902 of the heating element coupling substation 512, as illustrated in FIG. 16.

As further illustrated in FIG. 16, after a heating element 240 and liquid transport element 238 is singulated, the transport apparatus 905 may direct the heating element and liquid transport element to the welding portion 904 (see, e.g., FIG. 17). In this regard, the transport apparatus 905 may comprise a robotic arm 938 configured to move the clamp 930 between the preparing portion 902 and the welding portion 904 of the heating element coupling substation 512. Accordingly, the clamp 930 of the transport apparatus 905 may grasp the heating element 240 and liquid transport element 238 at the preparing portion 902 and continue to hold the heating element and liquid transport element when transported to the welding portion 904.

FIG. 17 illustrates the welding portion 904 of the heating element coupling substation 512. As illustrated, the welding portion 904 may include a laser 940, an imaging device 942 (e.g., a camera), a terminal fixation mechanism 944, and a gas dispenser 946. Briefly, the laser 940 may be configured to produce a laser beam to weld the heating element 240 to heating terminals. The imaging device 942 may be configured to capture images of the heating element 240 and the heating terminals. The terminal fixation mechanism 944 may be configured to grasp the first heating terminal and the second heating terminal during welding. The gas dispenser 946 may be configured to dispense an inert gas (e.g., argon) to improve the resultant weld (e.g., by preventing oxidation thereof).

Note that although the heating element is described herein as being attached to the heating terminals via laser welding, various other types of welding may be employed, such as arc welding, metal inert gas welding (MIG), tungsten inert gas welding (TIG), plasma welding, etc. More broadly, the heating element may be attached to the heating terminals via other methods, such as soldering and mechanical connections. Accordingly, it should be understood that various other embodiments of coupling methods and related equipment may be employed without departing from the scope of the present disclosure.

As described above, carriages 600 may travel along a rail 616 to various substations. In this regard, as further illustrated in FIG. 17, the rail 616 and magnetic track 620 may extend to and past the welding portion 904 of the heating element coupling substation 512 in some embodiments. Accordingly, the carriages may deliver the base, with heating terminals coupled thereto, to the welding portion 904 of the heating element coupling substation 512. For example, as described above, the heating terminals, control component terminal, control component, and flow tube may be assembled to the base when the carriages reach the welding portion 904 of the heating element coupling substation 512.

However, in order to facilitate welding the heating terminals to the heating element, it may be desirable to align the heating terminals in a desired configuration. In this regard, as illustrated in FIG. 18, the terminal fixation mechanism 944 may comprise first and second cooperating portions 948a, 948b. The cooperating portions 948a, 948b of the terminal fixation mechanism 944 may be configured to grasp the first heating terminal and the second heating terminal such that a first heating terminal tab and a second heating terminal tab thereof are substantially coplanar. Alternatively, or additionally, the cooperating portions 948a, 948b of the terminal fixation mechanism 944 may be configured to adjust a spacing between the first heating terminal and the second heating terminal. As illustrated, the cooperating portions 948a, 948b of the terminal fixation mechanism 944 may respectively define a groove 950 configured to receive the heating terminals therein.

FIGS. 19-21 schematically illustrate operation of the terminal fixation mechanism 944. FIG. 19 illustrates the cooperating portions 948a, 948b of the terminal fixation mechanism 944 in an initial separated configuration. The initial separated configuration may allow the heating terminals 234a, 234b to be received between the cooperating portions 948a, 948b thereof. Thereafter, as illustrated in FIG. 20, one or both of the cooperating portions 948a, 948b may move such that the cooperating portions move toward one another. As the cooperating portions 948a, 948b move relatively toward each other, the grooves 950 may cooperate to adjust the spacing between the heating terminals 234a, 234b. For example, the heating terminals 234a, 234b may be moved toward one another, as illustrated. Accordingly, as illustrated in FIG. 21, the spacing of the heating terminals 234a, 234b may be adjusted to match a desired spacing when the cooperating portions 948a, 948b clamp against opposing sides of the heating terminals. Further, by clamping the heating terminals 234a, 234b on opposing sides between the cooperating portions 948a, 948b, the heating terminals may be held by the terminal fixation mechanism 944 such that heating terminal tabs thereof are coplanar, which may facilitate welding of the heating element thereto.

Note that in the embodiment illustrated in FIGS. 19-21, the grooves 950 defined in the cooperating portions 948a, 948b are configured to move the heating terminals 234a, 234b toward one another. However, in another embodiment, as illustrated in FIG. 22, the terminal fixation mechanism 944' may include first and second cooperating portions 948a', 948b' including grooves 950' that are configured to adjust the spacing between heating terminals 234a, 234b by moving each of the heating terminals either toward or away from the other heating terminal, depending on the initial position of the heating terminals. Accordingly, the heating terminals 234a may be centered by providing grooves 950' configured to move each heating terminal 234a, 234b in either of two directions. Alternatively, as may be understood, the grooves may be configured to only move the terminals away from one another in another embodiment. Thus, the selection of the particular shape and functionality of the grooves of the cooperating portions of the terminal fixation mechanism may depend on the initial configuration of the heating terminals at the time the base and heating terminals reach the terminal heating element coupling substation 512.

While the heating terminals 234a, 234b are clamped in plane at a desired spacing using the terminal fixation mechanism 944, the transport apparatus 905 may hold the singulated heating element 240 and liquid transport element 238 with the clamp 930 such that the heating element is in view of the imaging device 942 (see, FIG. 17). For example, as illustrated in FIG. 23, the clamp 930 may initially hold the heating element 240 and liquid transport element 238 above the heating terminals 234a, 234b such that the heating element is in view of the imaging device 942 and thereby the imaging device may determine the position of the heating element. By way of further example, as described above, the controller 417 (see, e.g., FIG. 3) or a separate controller may determine the position of the inner edges 926a, 928a of the contact portions 926, 928 of the heating element 240 from the images captured by the imaging device 942. Accordingly, the midpoint between the contact portions 926, 928 of the heating element 240 may be determined.

Similarly, the location of the heating terminals 234a, 234b may be determined. In this regard, as illustrated in FIG. 23, the heating terminals 234a, 234b may respectively comprise a heating terminal tab 952a, 952b at an end thereof configured to be welded to one of the contact portions 926, 928 of the heating element 240. Accordingly, the positions of the heating terminal tabs 952a, 952b may be determined. For example, inner edges 954a, 954b of the heating terminals 234a, 234b may be identified by the controller 417 (or another controller) from the images captured by the imaging device 942. Thereby, the controller 417 may determine the midpoint between the heating terminal tabs 952a, 952b.

Thus, the transport apparatus 905 may move the heating element 240 and the liquid transport element in position for welding the heating element to the heating terminals 234a, 234b. In this regard, the controller 417 may direct the transport apparatus 905 to align the midpoint between the first heating terminal tab 952a and the second heating terminal tab 952b with the midpoint between the first contact portion 926 and the second contact portion 928. Further, the controller 417 may direct the transport apparatus 905 to bring the heating element 240 into engagement with the heating terminal tabs 952a, 952b. In particular, the transport apparatus 905 may engage the first contact portion 926 of the heating element 240 with the first heating terminal tab 952a and engage the second contact portion 928 with the second heating terminal tab 952b. In some embodiments the controller 417 may direct the transport apparatus 905 to press the heating element 240 against the heating terminal tabs 952a, 952b such that the heating terminals 234a, 234b are displaced slightly (e.g., a distance from about 0.002 inches to about 0.006 inches, and preferably about 0.004 inches). In this regard, by pressing the heating element 240 against the heating terminal tabs 952a, 952b (e.g., in a direction perpendicular to a substantially planar front face thereof, contact between the heating element and the heating terminals 234a, 234b may be assured.

Accordingly, as illustrated in FIG. 24, the laser 940 may weld the heating element 240 to the heating terminals 234a, 234b. The laser 940 may weld the heating element 240 to the first heating terminal 234a and the second heating terminal 234b by directing a laser beam at the first heating terminal tab 952a and at the second heating terminal tab 952b. As illustrated in FIG. 24, the laser beams may be directed at a backside of the first heating terminal tab 952a and the second heating terminal tab 952b opposite from the heating element 240. Accordingly, energy from the laser beams may heat the heating terminal tabs 952a, 952b to cause the heating terminal tabs to weld to the contact portions 926, 928 of the heating element, thereby completing the atomizer 202 (see, e.g., FIG. 1). In the illustrated embodiment, the laser is directed at first and second locations 956a, 956b on each heating terminal tab 952a, 952b to provide a relatively more secure weld. However, the laser beams may be directed at a greater or lesser number of locations in other embodiments. Note that by directing the laser beams at the heating terminal tabs 952a, 952b, issues with respect to damaging the heating element 240 may be avoided by indirectly, rather than directly applying heat to the heating element.

Note that the heating element 240 illustrated in FIG. 23 comprises a wire defining a variable coil spacing. The variable coil spacing may be employed to provide the contact portions 926, 928 with a relatively tight coil spacing. This relatively tight coil spacing at the contact portions 926, 928 may facilitate welding the heating terminals 234a, 234b thereto by providing more wire material at these locations to which the heating terminals may be affixed.

A center portion 929 of the heating element 240, defined between the contact portions 926, 928, may function to produce heat when current is supplied therethrough via the heating terminals 234a, 234b. The spacing of the coils at the center portion 929 of the heating element 240 may be greater than the spacing of the coils at the contact portions 926, 928 since the center portion is not employed for affixation to the heating terminals 234a, 234b. However, the spacing of the coils at the center portion 929 of the heating element 240 may be less than a spacing of optional coils at outer portions 931a, 931b of the wire positioned outside of the contact portions 926, 928 of the heating element. In this regard, the outer portions 931a, 931b may not produce heat or facilitate affixation to the heating terminals 234a, 234b, and hence the spacing of the coils may be relatively large in order to decrease material usage of the wire in the formation of the heating element 240. Rather, the outer portions 931a, 931b may be provided for ease of manufacturing the substantially continuous heating element input 906 (see, e.g., FIG. 13) in some embodiments. Various other details with respect to atomizers employing variable coil spacing are provided in U.S. patent application Ser. No. 13/827,994, filed Mar. 14, 2013, which, as noted above, is incorporated herein by reference in its entirety.

Note further that the above-described coil spacing, which may be applicable to any of the atomizers described herein, may not be uniform throughout each portion of the wire. In this regard, some variation may exist in the coil spacing in one or more of the portions of the wire. For example, the spacing of the coils may vary across the center portion of the heating element. Accordingly, by way of further example, the differences in coil spacing described above may refer to the average coil spacing for each of the portions of the wire.

Following welding, the carriage 600 with the partially assembled cartridge 200 may be directed to the liquid transport element bending substation 514. The liquid transport element bending substation 514 may be configured to bend the liquid transport element 238 such that the ends thereof extend down the heating element terminals 234a, 234b. However, the liquid transport element 238 and/or the wire wound thereon may be somewhat resilient and tend to bend back to an initial straight configuration following bending thereof.

In this regard, as illustrated in FIG. 25, in some embodiments the carriages 600 may further comprise pivotable arms 632a, 632b configured to engage the ends of the liquid transport element 238 such that the ends of the liquid transport element are held against the heating terminals 234a, 234b. In this regard, the pivotable arms 632a, 632b may be configured to apply a force to the liquid transport element 238 to hold the liquid transport element against the heating terminals 234a, 234b. For example, magnets and/or a spring may be configured to bias each of the pivotable arms 632a, 632b toward the liquid transport element 238. In this regard, in the illustrated embodiment, the pivotable arms 632a, 632b may include magnetic members 634a, 634b that cooperate with stationary magnetic base members 636a, 636b of the carriage 600 to bias the pivotable arms 632a, 632b against the liquid transport element 238. However, various other biasing mechanisms may be employed in other embodiments.

Following bending of the liquid transport element 238 and retention of the liquid transport element in the bent configuration with the pivotable arms 632a, 632b, the carriage 600 may be directed to the reservoir coupling substation 516. As illustrated in FIG. 26, the reservoir coupling substation 516 may include a spool 1002. The spool 1002 may be configured to supply a substantially continuous reservoir substrate input 1004 from which individual reservoir substrates may be cut. Tension in the substantially continuous reservoir substrate input 1004 may be controlled to prevent stretching the reservoir substrate material, which may affect the liquid storage and transport characteristics thereof. In this regard, rather than being pulled from the spool 1002, the substantially continuous reservoir substrate input 1004 may be actively dispensed from the spool 1002 (e.g., by a belt 1006)

in some embodiments. However, the substantially continuous reservoir substrate input 1004 may be passively dispensed in other embodiments.

FIGS. 27 and 28 illustrate singulation of individual reservoir substrates from the substantially continuous reservoir substrate input 1004 supplied from the spool 1002. In this regard, as illustrated, the reservoir coupling substation 516 may further comprise a moveable clamp 1008 and a stationary clamp 1009. The moveable clamp 1008 may be configured to pull a predefined quantity of the substantially continuous reservoir substrate input 1004 downwardly into a cutter 1010. In this regard, FIG. 27 illustrates the moveable clamp 1008 at an upper limit, where it grips the substantially continuous reservoir substrate input 1004. FIG. 28 illustrates the moveable clamp 1008 at a lower limit. When the moveable clamp 1008 reaches the lower limit, the moveable clamp has moved a predefined length of the substantially continuous reservoir substrate input 1004 into the cutter 1010, which cuts the substantially continuous reservoir substrate input to define an individual reservoir substrate having a desired length.

Further, when the moveable clamp 1008 reaches the lower limit, the stationary clamp 1009 grips the substantially continuous reservoir substrate input 1004. Accordingly, the substantially continuous reservoir substrate input 1004 is prevented from moving during cutting thereof into an individual reservoir having a desired length. Further, the stationary clamp 1009 may prevent undesirable upward movement of the substantially continuous reservoir substrate input 1004 by continuing to hold the substantially continuous reservoir substrate input as the moveable clamp 1008 returns to the upper limit. Once the moveable clamp 1008 reaches the upper limit and grips the substantially continuous reservoir input 1004, the stationary clamp 1009 may release the substantially continuous reservoir substrate input to allow the moveable clamp to pull the predefined quantity of the substantially continuous reservoir substrate input downwardly into the cutter 1010, as described above.

Following singulation, a transfer mechanism 1012 may receive the reservoir substrate. As illustrated in FIGS. 28 and 29, the transfer mechanism 1012 may include a head portion 1014 configured to releasably retain the reservoir substrate. In some embodiments the head portion 1014 of the transfer mechanism 1012 may be configured to apply vacuum to the reservoir substrate thereon. In this regard, the head portion 1014 may define a plurality of apertures to which vacuum is applied. However, in other embodiments the reservoir may be retained on the transfer mechanism 1012 by a clamp or other mechanical mechanisms.

As illustrated in FIG. 29, the transfer mechanism 1012 may be configured to receive the reservoir substrate from the cutter 1010 and transport the reservoir substrate to a wrapping mechanism 1016. In this regard, the transfer mechanism 1012 may travel along a longitudinal path 1018 and then a lateral path 1020 to transfer the reservoir substrate to the wrapping mechanism 1016. The wrapping mechanism 1016 may comprise a head portion 1022 configured to receive the reservoir substrate. The head portion 1022 of the wrapping mechanism 1016 may employ vacuum to hold the reservoir substrate. In this regard, the head portion 1022 of the wrapping mechanism 1016 may define a plurality of apertures at an inner surface thereof to which vacuum is applied. In some embodiments, during transfer of the reservoir substrate from the head portion 1014 of the transfer mechanism 1012 to the head portion 1022 of the wrapping mechanism 1016, vacuum at the head portion of the transfer mechanism may switch to a positive pressure. Accordingly, air directed out of the head portion 1014 of the transfer mechanism 1012 may push the reservoir substrate toward the head portion 1022 of the wrapping mechanism 1016 which may securely engage the reservoir substrate using vacuum applied thereto.

After receiving the reservoir substrate from the transfer mechanism 1012, the wrapping mechanism 1016 may spin around (e.g., about 180 degrees) such that the head portion 1022 thereof is positioned proximate the rail 616, as illustrated in FIG. 30. In this regard, the carriage 600 may deliver the partially assembled cartridge to the reservoir coupling substation 516. For example, the partially assembled cartridge may define the configuration described above and illustrated in FIG. 25 in which the liquid transport element 238 is bent and held in place by the pivotable arms 632a, 632b.

FIGS. 30-32 illustrate movement of portions of the reservoir coupling substation 516 during addition of the reservoir substrate to the cartridge. Note that the carriage and components of the cartridge coupled thereto are not illustrated in FIGS. 30-32 for clarity purposes. However, as illustrated in FIGS. 30-32, the reservoir coupling substation 516 may further comprise fingers 1024a, 1024b, which may cooperate with the head portion 1022 of the wrapping mechanism 1016 to wrap the reservoir substrate about the components of the cartridge. Briefly, FIG. 30 illustrates movement of the head portion 1022 of the wrapping mechanism 1016 in a direction 1026 toward a position at which the cartridge would be located. As illustrated in FIG. 31, the fingers 1024a, 1024b may then move in a direction 1028 toward a position at which the cartridge would be located. Further, as illustrated in FIG. 32, the fingers 1024a, 1024b may move in directions 1030a, 1030b toward one another. As additionally illustrated in FIG. 32, the wrapping mechanism 1016 may move away from the fingers 1024a, 1024b at this time.

The interaction of the wrapping mechanism 1016 and the fingers 1024a, 1024b of the reservoir coupling substation 516 with the reservoir substrate 214 is schematically illustrated in FIG. 33. As illustrated, the reservoir substrate 214 may be held to the head portion 1022 of the wrapping mechanism 1016 by vacuum applied through apertures 1032 extending therethrough. Accordingly, first and second ends 1034a, 1034b of the reservoir substrate 214 may extend around opposing sides of the flow tube 210 and/or other components of the cartridge. In this regard, an inner surface of the head portion 1022 of the wrapping mechanism 1016 may define a curved configuration that causes the ends 1034a, 1034b of the reservoir substrate 214 to extend around the flow tube 210 in a manner whereby they may be grasped by the fingers 1024a, 1024b. More particularly, the inner surface of the head portion 1022 of the wrapping mechanism 1026 may define a partial elliptical configuration, such that the ends 1034a, 1034b of the reservoir substrate 214 remain in close proximity to the flow tube 210 when wrapped thereabout and may be grasped by the fingers 1024a, 1024b.

The flow tube 210 may be asymmetrical. In this regard, the flow tube 210 may define a shortened side 210a and an elongated side 210b (see, e.g., FIG. 1). As illustrated in FIG. 33, the wrapping mechanism 1016 may be configured such that the head portion 1022 thereof is directed toward the elongated side 210b of the flow tube 210. In this regard, the elongated side 210b of the flow tube 210 may contact the reservoir substrate 214 and facilitate wrapping the reservoir substrate thereabout in an even manner, whereas wrapping the reservoir substrate about the shortened side 210a of the flow tube may result in uneven wrapping of the reservoir substrate or damage to underlying components such as the control component.

Note further that the heating terminals 234a, 234b may be oriented relative to the wrapping mechanism 1016 such that when the reservoir substrate 214 is wrapped about the partially assembled cartridge, the liquid transport element 238 is forced into further engagement with the heating terminals. In this regard, as illustrated by arrows 1036a, 1036b, the liquid transport element 238 may be pressed by the reservoir substrate 214 into inner corners defined by the heating elements 234a, 234b. More particularly, as illustrated, the heating elements 234a, 234b may include substantially perpendicularly extending walls defines an "L-shape," and the liquid transport element 238 may be forced into an inner corner between the two walls. Accordingly, wrapping the reservoir substrate 214 about the partially assembled cartridge may assist in positioning the liquid transport element 238 in a desired position (e.g., a position wherein the liquid transport element extends substantially parallel to a longitudinal length of the heating terminals 234a, 234b).

The fingers 1024a, 1024b may be configured to engage the reservoir substrate 214 and further wrap the reservoir substrate about the flow tube 210 and/or the remainder of the partially assembled cartridge. For example, as illustrated in FIGS. 32 and 33, the fingers 1024a, 1024b may be configured to move in directions 1030a, 1030b toward one another such that the reservoir substrate 214 is pinched around the flow tube 210 and/or other components of the partially assembled cartridge. In some embodiments the fingers 1024a, 1024b may be directed toward one another substantially simultaneously. For example, this may be employed in embodiments of cartridges in which the ends 1034a, 1034b of reservoir substrate 214 form a butt-joint, or do not otherwise overlap. However, in embodiments in which the ends 1034a, 1034b of the reservoir substrate 214 overlap, one of the fingers 1024a, 1024b may move before and/or faster than the other finger, such that one of the ends may wrap around the flow tube 210 and then the other end of the reservoir substrate may wrap about that end.

After the reservoir substrate 214 is wrapped about the flow tube 210 and the atomizer 212 and/or other components of the cartridge, the outer body coupling substation 518 may couple the outer body to the base. In this regard, as illustrated in FIGS. 30-32, in some embodiments the outer body coupling substation 518 may include an outer body coupling tool 1102, which may be positioned proximate the fingers 1024a, 1024b.

Further, the outer body coupling substation 518 may include an outer body supply mechanism 1104, as illustrated in FIG. 34. The outer body supply mechanism 1104 may include a pivoting prong 1106. The pivoting prong 1106 may be configured to receive an outer body 216 (see, e.g., FIG. 1) directed thereto in an initial substantially horizontal configuration and then pivot, as indicated by arrow 1108, such that the outer body received thereon extends substantially vertically. Thereby, the outer body coupling tool 1102 may be directed over the outer body 216 such that the outer body may be received therein.

The outer body coupling tool 1102 may comprise multiple sections (e.g. two or more sections) which cooperate to receive the outer body 216 by radially separating from one another. In this regard, FIG. 35 illustrates a perspective view of a section 1102a of the outer body coupling tool 1102. As illustrated, each section 1102a may define a lip 1110 configured to retain the outer body 216 in the outer body coupling tool 1102 when the sections of the outer body coupling tool are radially contracted toward one another. In this regard, the outer body coupling tool 1102 may include a body receiving portion 1113 defining an inner radius that is at least as large as an outer radius of the outer body 216 and an inner radius of the lip 1110 may be less than the outer radius of the outer body.

Accordingly, as illustrated in FIG. 36, the outer body 216 may be retained in the outer body coupling tool 1102 by the lip 1110. As further illustrated in FIG. 36, the outer body coupling tool 1102 may facilitate placement of the outer body 216 over the reservoir substrate 214. In this regard, each section 1102a the outer body coupling tool 1002 may define a funnel portion 1112. The funnel portion 1112 may be configured to reduce an outer dimension of the reservoir substrate 214 such that the outer dimension of the reservoir substrate is less than or equal to an internal dimension of the outer body 216 to facilitate insertion of the reservoir substrate into the outer body. In this regard, the reservoir substrate 214 may comprise a flexible, fabric-like material, which may stick out in certain directions, making it difficult to directly insert the reservoir substrate 214 into the outer body 216 when the reservoir substrate is wrapped about the flow tube 210 and/or other components of the cartridge. Thus, the funnel portion 1112 may define a minimum inner radius that is less than or equal to the inner radius of the outer body. Accordingly, when the outer body coupling tool 1102 presses down over the reservoir substrate 214, the reservoir substrate may be compacted by the funnel portion 1112 such that it slides relatively easily into the outer body 216.

As illustrated, in some embodiments one or both of the fingers 1024a, 1024b may engage the reservoir substrate 214 such that the reservoir substrate remains at least partially wrapped about the atomizer when beginning to insert the reservoir substrate through the outer body coupling tool 1002 into the outer body 216. In this regard, the finger(s) 1024a, 1024b may prevent the reservoir substrate 214 from unwrapping as the outer body 216 is inserted over the reservoir substrate. However, the fingers 1024a, 1024b may release from the reservoir substrate 214 after the outer body 216 has received the reservoir substrate a predefined distance therein (e.g., when the reservoir substrate is halfway into the outer body), at which time risk of the reservoir substrate unwrapping is substantially reduced.

Note that in some embodiments multiple sets of fingers 1024a, 1024b, 1024a', 1024b', 1024a", 1024b" may be employed to hold the reservoir substrate 214 in the wrapped configuration, as illustrated in FIG. 36A. Thus, the fingers 1024a, 1024b, 1024a', 1024b', 1024a", 1024b" may be sequentially released as the reservoir substrate 214 is inserted through the outer body coupling tool 1002 into the outer body 216. For example, a first set of fingers 1024a, 1024b may be released, followed by a second set of fingers 1024a', 1024b', followed by a third set of fingers 1024a", 1024b" as the reservoir substrate 214 is inserted into the outer body 216. By employing multiple sets of fingers at differing positions along a longitudinal length of the partially assembled cartridge, the reservoir substrate may more securely be retained in the wrapped configuration during insertion into the outer body, such that issues with respect to the reservoir substrate moving from the wrapped configuration may be avoided.

Further, in some embodiments the outer body coupling tool 1102 may twist during insertion of the reservoir substrate 214 through the outer body coupling tool into the outer body 216, as illustrated in FIGS. 36 and 36A. In particular, the outer body coupling tool 1102 may twist about a longitudinal axis 1114 thereof. Accordingly, friction between the funnel portion 1112 of the outer body coupling tool 1102 and the reservoir substrate 214 may be reduced. In some embodiments the outer body coupling tool 1102 may twist in a single direction about the longitudinal axis 1114. In another embodiment the outer body coupling tool 1102 may oscillate between rotating in first and second opposing directions 1116a, 1116b during insertion, which may reduce the chance for movement of the reservoir substrate 214 during insertion through the outer body coupling tool into the outer body 216. Note that in some embodiments the sections 1102a of the outer body coupling tool 1102 may clamp on the outer body 216 such that the outer body rotates with the outer body coupling tool. Thus, friction between the outer body 216 and the reservoir substrate 214 may be reduced. Accordingly, twisting movement of outer body 216 with respect to the reservoir substrate 214 may further facilitate insertion of the reservoir substrate into the outer body.

Following insertion of the reservoir substrate 214 and the other components of the cartridge into the outer body 216, the outer body may be coupled to the base 204. In this regard, the outer body coupling substation 518 may further comprise a crimper 1118, as illustrated in FIG. 37. In some embodiments the crimper 1118 may comprise multiple sections 1118a. For example, in the embodiment illustrated in FIG. 37, the crimper 1118 comprises four sections 1118a, which may be substantially identical. In this regard, use of a crimper comprising four or more sections may crimp the outer body more evenly than crimpers defining fewer sections, such that leaks between the outer body and the base may be avoided. However, in other embodiments, the number of sections may vary. For example, two or more sections may be employed.

FIG. 38 illustrates one of the sections 1118a of the crimper 1118. As illustrated, each section 1118a may include a lip 1120 configured to crimp the outer body 216. FIG. 39 illustrates an enlarged view of section A from FIG. 38. As illustrated, in FIG. 39, an angled portion 1122 may extend from the lip 1120 to an inner surface 1124 of the section 1118a of the crimper 1118. In some embodiments the angled portion 1122 of the sections 1118a may define an angle 1126 with respect to a longitudinal axis 1128 of the crimper 1118 along which the crimper receives the outer body 216 from about 10 degrees to about 15 degrees and preferably about 12 degrees. In this regard, the angled portion 1122 may provide for a smooth transition from a crimp formed in the outer body 216 by the lip 1120 to the remainder of the outer body. Thereby, leaks between the outer body 216 and the base 204 may be substantially avoided.

Accordingly, FIGS. 4-39 illustrate one embodiment of a cartridge assembly subsystem 402. However, as may be understood, various other embodiments of cartridge assembly subsystems may be employed to assemble cartridges in accordance with embodiments of the present disclosure. In this regard, FIG. 40 schematically illustrates a cartridge assembly subsystem 402' according to another embodiment of the present disclosure.

As illustrated, the cartridge assembly subsystem 402' may include a base load substation 1202, a terminal coupling substation 1204, a terminal sealing substation 1206, a control component coupling substation 1208, a flow tube coupling substation 1210, a heating element coupling substation 1212, a liquid transport element bending substation 1214, a reservoir coupling substation 1216, and an outer body coupling substation 1218. Further, the controller 417 may be configured to control one or more of the substations 1202-1218 of the cartridge assembly subsystem 402'. Accordingly, the cartridge assembly subsystem 402' may be similar to the cartridge assembly subsystem 402 described above and illustrated in FIGS. 4-39. Thus, the description provided hereinafter relating to the cartridge assembly subsystem 402' will focus primarily on differences with respect to the previously described cartridge assembly subsystem 402 for brevity purposes.

In this regard, the cartridge assembly subsystem 402 described above generally assembled cartridges upwardly from a carriage 600 transported between various subsystems. More particularly, the carriage 600 would generally pause at each substation, such that the base 204 was in a stationary position with the components moved into contact therewith from above.

However, the cartridge assembly subsystem 402' described hereinafter differs in that the base 204 is generally directed into contact with stationary components to form a cartridge. In particular, the base 204 may be inverted and directed generally downwardly to engage the components therewith to form the cartridge in some embodiments. FIG. 41 illustrates an overhead view of one embodiment of the cartridge assembly subsystem 402'. In this regard, robots (e.g., robotic arms) may be configured to hold the base 204 and direct the base into contact with the components during assembly therewith to form cartridges.

For example, as illustrated in FIG. 41, a plurality of robots may be employed to move the base 204 into engagement with various components to assemble the cartridge. The robots may interact with the components of the cartridge and each other to perform various assembly operations such that each robot may not be specifically associated with only one of the substations 1202-1218 illustrated in FIG. 40. However, as illustrated in FIG. 41, in one embodiment the cartridge assembly subsystem 402' may include a control component terminal robot 1302, a heating terminal robot 1304, a robotic arm 1306, a control component and flow tube robot 1308, a heating element robot 1310, a reservoir substrate robot 1312, and an outer body robot 1314.

As illustrated in FIG. 42, the base load substation 1202 may include a base supply 1402 configured to supply the base 204. In some embodiments the base supply 1402 may comprise a vibratory bowl feeder. Further, the base supply 1402 may orient the bases 204 for grasping. In this regard, an attachment end 204a of the base (see, FIG. 1) may be oriented upwardly by the base supply 1202.

As noted above, in some embodiments portions of the cartridge assembly subsystem 402' may be configured to grasp the base 204 such that the base is inverted during assembly of the cartridge. Additionally or alternatively, portions of the cartridge assembly subsystem 402' may be configured to grasp an internal surface 204a' of an attachment end 204a of the base 204 (see, FIG. 1) configured to engage a control body. In order to grasp the internal surface 204a' of an attachment end 204a of the base 204, appropriate grippers may be employed.

In this regard, FIG. 43 illustrates a base gripper 1500 that may be employed by robots of the cartridge assembly subsystem 402'. As illustrated, the base gripper 1500 may define multiple sections 1502. The sections 1502 may be configured to contract (e.g., move radially inward toward one another) during insertion into the attachment end 204a of the base 204, and expand (e.g., move radially move outwardly away from one another) after inserted into the attachment end of the base. A plurality of protrusions 1504 or other features (e.g., recesses) on an outer surface 1506 of each of the sections 1502 may assist in gripping the base 204. For example, the protrusions 1504 may be configured to engage recesses defined in the internal surface 204a' of the attachment end 204a of the base 204. In this regard, the outer surfaces 1506 of the sections 1502 of the base gripper 1500 may be configured to correspond to the shape of the internal surface 204a' of the attachment end 204a of the base 204. Accordingly, the base gripper 1500 may securely, and releasably, engage the base 204.

The terminal coupling substation 1204 may comprise the control component terminal robot 1302. As illustrated in FIG. 42, the control component terminal robot 1302 may include the base gripper 1500. Thereby, the control component terminal robot 1302 may grasp a base 204 supplied by the base supply 1402. Accordingly, the control component terminal robot 1302 may couple the control component terminal to the base.

In this regard, as illustrated in FIG. 44, the terminal coupling substation 1204 may further comprise a die 1600 configured to prepare the control component terminal 206 for attachment to the base 204. For example, the control component terminal 206 may be cut from a substantially continuous control component terminal input 1602. In this regard, a cutter 1604 may cut the control component terminal 206 from the substantially continuous control component terminal input 1602.

FIG. 44A illustrates an enlarged view of the die 1600. As illustrated in FIG. 44A, the die 1600 may further comprise first and second pressure pads 1606a, 1606b, which may be positioned on opposing sides of the cutter 1604. The pressure pads 1606a, 1606b may extend into contact with, and press against the substantially continuous control component terminal input 1602 as the cutter 1604 cuts a control component terminal 206 therefrom. More particularly, the first pressure pad 1606a may press against a first control component terminal 206a, which is cut from the substantially continuous control component terminal input 1602 by the cutter 1604, and the second pressure pad 1606b may press against a second control component terminal 206b which is next in line to be separated from the substantially continuous control component terminal input. Accordingly, the first control component terminal 206a may be held in place while being cut from the substantially continuous control component terminal input 1602, and the second control component terminal 206b, which then becomes the first control component terminal at the end of the substantially continuous control component terminal input, are both held in place.

Following singulation, the first control component terminal 206a may be held in a stationary position to facilitate coupling with the base 204. More particularly, the first control component terminal 206a may be pinched between backing member 1608 and an opposing pressure pad 1610. In this regard, one or both of the opposing pressure pad 1610 and the backing member 1608 may move toward the first control component terminal 206a such that the first control component terminal is pinched therebetween. As illustrated, the opposing pressure pad 1610 and the backing member 1608 may define a contour that matches each of the control component terminals 206, such that the control component terminal may be securely held in place without affecting the shape of the control component terminal. Thereby, the base 204 may be directed into contact with the singulated control component terminal 206. For example, the control component terminal robot 1302 may direct the base 204 downwardly into contact with the stationary control component terminal 206, such that the control component terminal engages the base.

The terminal coupling substation 1204 may further comprise the heating terminal robot 1304. In this regard, after the control component terminal robot 1302 couples the control component terminal 206 to the base 204, the control component terminal robot may transfer the base to the heating terminal robot 1304. In some embodiments a transfer member may facilitate transfer of the base 204 from the control component robot 1302 to the heating terminal robot 1304.

As illustrated in FIG. 45, in one embodiment the transfer member 1700A comprises a wheel 1702 which rotates to deliver the base 204 from the control component terminal robot 1302 to the heating terminal robot 1304. The transfer member 1700A may further comprise one or more fixtures 1704 coupled to the wheel 1702. Accordingly, the control component terminal robot 1302 may deposit the base 204 in one of the fixtures 1704, the transfer member 1700A may rotate, and the heating terminal robot 1304 may grasp the base in the fixture and remove the base therefrom.

In this regard, by depositing the base 204 in the fixture 1704, the base may be positioned such that the heating terminal robot 1304 may grasp the base in substantially the same manner as that employed by the control component terminal robot 1302 to grasp the base. For example, the heating terminal robot 1304 may include a base gripper, such as the above-described base gripper 1500. Thereby, the base 204 may be directed by the heating terminal robot 1304 into contact with the first and second heating terminals 234a, 234b (see, e.g., FIG. 1). More particularly, as illustrated in FIG. 45, first and second dies 1612a, 1612b may cut the first and second heating terminals 234a, 234b from first and second substantially continuous control component terminal inputs, which may be substantially similar to the substantially continuous first heating terminal input 700 described above. Thereby, after engaging the first and second heating terminals 234a, 234b with the base 204, the heating terminal robot 1304 may deposit the base in a second transfer member 1700B (see, e.g., FIG. 41), which may be substantially similar to the transfer member 1700A described above.

The base 204 may then be engaged by the robotic arm 1306. The robotic arm 1306 may deposit the base 204 on a third transfer member 1700C, which may be substantially similar to the previously-described transfer members 1700A, 1700B. Further, in some embodiments the robotic arm 1306 may comprise part of the terminal sealing substation 1206, in embodiments in which sealing of the heating terminals 234a, 234b with respect to the base 204 is employed. In this regard, the terminal sealing substation 1206 may function in substantially the same manner as the terminal sealing substation 506 described above, wherein the robotic arm 1306 functions in substantially the same manner as the robotic arm 808 (see, e.g., FIG. 10). In some embodiments, one or both of the robotic arms 808, 1306 may employ the above-described base gripper 1500 to engage the base 204 during the sealing process.

Regardless of whether or not the terminal sealing substation 1206 is employed, the robotic arm 1306 may deposit the base 204 on the third transfer member 1700C. Thereafter, the base 204 may be directed to the control component coupling substation 1208 and the flow tube coupling substation 1210. In the illustrated embodiment, both the control component coupling substation 1208 and the flow tube coupling substation 1210 include and employ the control component and flow tube robot 1308.

In this regard, as illustrated in FIG. 46 the control component and flow tube robot 1308 may be configured to engage the base 204 at the third transfer member 1700C. For example, as illustrated, the control component and flow tube robot 1308 may include a gripper such as the base gripper 1500. Thereby, the control component and flow tube robot 1308 may transfer the base 204 to the control component coupling substation 1208.

Further, the control coupling substation 1208 may include a control component supply 1802 (see, FIG. 41) configured to supply the electronic control component 208. In some embodiments the control component supply 1802 may comprise a vibratory bowl feeder. Further, the control component supply 1802 may orient the electronic control component 208 in a desired manner. For example as illustrated in FIG. 47, each of the electronic control components 208 may be oriented such that a chip 208' (e.g., a memory chip) or other portion of the electronic control component is oriented upwardly. In this regard, the first and second major sides of the electronic control component 208 may be asymmetrical, which may facilitate orientation by the control component supply 1802 such that the chip 208' extends upwardly.

As further illustrated in FIG. 47, the electronic control component 208 may define first and second opposing longitudinal ends 208A, 208B. A connector at the first end 208A of the electronic control component 208 may be configured to engage the control component terminal 206. In this regard, as illustrated in FIG. 46, an imaging device 1804 (e.g., a camera) may be configured to determine whether the first end 208A is at the front or rear of the electronic control component 208 in terms of the direction that the electronic control components are supplied by the control component supply 1802.

Accordingly, as illustrated in FIG. 47, based on the determined orientation of the electronic control component 208, a control component gripper 1806 may grasp the second end 208B of the electronic control component. In this regard, the control component gripper 1806 may include first and second fingers 1808A, 1808B configured to pinch the second end 208B of the control component 208 therebetween. As illustrated, the first and second fingers 1808A, 1808B may be relatively narrow. In this regard, the control component supply 1802 may direct the control components 208 to a support member 1810. The support member 1810 may define first and second slots 1812A, 1812B configured to respectively align with one of the first and second ends 208A, 208B of an electronic control component 208 when the electronic control component is received on the support member. Accordingly, the grippers 1808A, 1808B may extend into one of the slots 1812A, 1812B in the support member 1810 and grasp the second end 208B of the control component 208.

Thereby, as further illustrated in FIG. 47, the control component gripper 1806 may rotate the electronic control component 208 such that the first end 208A thereof points upwardly. Accordingly, the control component and flow tube robot 1308 may direct the base 204 downwardly such that the first send 208A of the electronic control component 208 engages the control component terminal 206. In some embodiments the connector (e.g., a contact patch) at the first end 208A of the electronic control component 208 may be located on only one of the major sides of the electronic control component and the control component terminal 206 may be asymmetrical and configured to engage only that particular side. Accordingly, the control component and flow tube robot 1308 may rotate the base 204 such that a desired rotational alignment of the electronic control component 208 and the control component terminal 206 is achieved when the base 204 is directed downwardly toward the electronic control component.

After coupling of the electronic control component 208 to the control component terminal 206, the base 204 may be directed by the control component and flow tube robot 1308 to the flow tube coupling substation 1210. As illustrated in FIG. 41, the flow tube coupling substation 1210 may include a flow tube supply 1902 configured to supply the flow tube 210. In some embodiments the flow tube supply 1902 may comprise a vibratory bowl feeder. Further, the flow tube supply 1902 may orient the flow tube 210 in a desired manner.

The flow tube coupling substation 1210 may further comprise a base 1904, as illustrated in FIGS. 46 and 48. The base 1904 may define an upwardly extending protrusion configured to mate with an inner portion of the flow tube 210 to support the flow tube thereon. Thereby, the control component and flow tube robot 1308 may direct the base 204 downwardly toward the flow tube 210. Accordingly, the flow tube 210 may be received between the heating terminals 234a, 234b and engage the control component 208. As illustrated in FIG. 48, a flow tube gripper 1906 may grasp the partially assembled cartridge. More particularly, the flow tube gripper 1906 may include a pair of arms 1908A, 1908B each including an extension 1910 configured to press the heating terminals 234a, 234b against the flow tube 210. Thus, the flow tube gripper 1906 may indirectly hold the flow tube 210 in place by pressing the heating terminals 234a, 234b against the flow tube. By grasping the partially assembled cartridge in this manner, the base gripper 1500 of the control component and flow tube robot 1308 may release and retract from the base 204 while the partially assembled cartridge is securely held in place.

Thereafter, the heating element robot 1310 may engage the partially assembled cartridge. In this regard, as illustrated in FIG. 49, the heating element robot 1310 may include a terminal gripper 2002. As illustrated, the terminal gripper 2002 may include first and second arms 2004A, 2004B. The first arm 2004A of the terminal gripper 2002 may include a first pair of prongs 2006A and the second arm 2004B of the terminal gripper may include a second pair of prongs 2006B.

In this regard, as illustrated in FIG. 50, the terminal gripper 2002 may be configured to engage the heating terminals 234a, 234b. However, as noted above, the partially assembled cartridge may be held in place by the flow tube gripper 1906. Thus, the terminal gripper 2002 may be configured to avoid contacting the flow tube gripper 1906. For example, as illustrated, the terminal gripper 2002 may be configured to extend at least partially between the arms 1908a, 1908b of the flow tube gripper 1906. In this regard, the heating element robot 1310 may rotate such that the first and second arms 2004A, 2004B of the terminal gripper 2002 extend perpendicularly to the first and second arms 1908A, 1908B of the flow tube gripper 1906.

Accordingly, as illustrated in FIG. 51, the terminal gripper 2002 may grip the partially assembled cartridge. In particular, the first pair of prongs 2006A and the second pair of prongs 2006B may pinch the heating terminals 234a, 234b therebetween. More particularly, one of the first pair of prongs 2006A and one of the second pair of prongs 2006B may press against opposing sides of the first heating terminal 234a such that the first heating terminal is held therebetween. Similarly, one of the first pair of prongs 2006A and one of the second pair of prongs 2006B may press against opposing sides of the second heating terminal 234b such that the second heating terminal is held therebetween. As illustrated, the prongs 2006A, 2006B may engage the heating terminals 234a, 234b such that the heating terminal tabs 952a, 952b are exposed. For example, when the base 204 is oriented such that the heating terminals 234a, 234b extend downwardly therefrom, the prongs 2006A, 2006B may engage the heating terminals slightly above the heating terminal tabs 952a, 952b.

Further, by grasping the heating terminals 234a, 234b in the above-described manner, the heating terminal tabs 952a, 952b may be configured in a desired position for attachment of the heating element thereto. In this regard, as described above, the flow tube gripper 1906 may press the heating terminals 234a, 234b against the flow tube 210. Thereby, when the terminal gripper 2002 grasps the heating terminals 234a, 234b, the heating terminal tabs 952a, 952b may define a desired separation therebetween, as defined by the width of the flow tube 210. Further, when the terminal gripper 2002 presses against opposing sides of each of the heating terminal tabs 952a, 952b with the prongs 2006A, 2006B, the heating terminal tabs may be aligned.

The heating element coupling substation 1212 may include the above-described heating element robot 1310. Additionally, as illustrated in FIG. 52, the heating element coupling substation 1212 may include a preparing portion 2008 and a welding portion 2010. The preparing portion 2008 and the welding portion 2010 may function in substantially the same manner as the preparing portion 902 and the welding portion 904 described above (see, e.g., FIG. 12). In this regard, as illustrated in FIG. 53, in some embodiments the heating element may be supplied from a substantially continuous heating element input 2012. The substantially continuous heating element input 2012 may comprise a plurality of the heating elements 240 wound about the liquid transport element 238 as described, for example, in U.S. patent application Ser. No. 13/827,994, filed Mar. 14, 2013 and Ser. No. 13/708,381, filed Dec. 7, 2012, which are incorporated herein by reference in their entireties.

As illustrated, the substantially continuous heating element input 2012 may be supplied from a spool 2014 in some embodiments. The spool 2014 may passively rotate as the substantially continuous heating element input 2014 is pulled therefrom. Alternatively, the spool 2014 may be actively driven (e.g., by a motor) such that the spool rotates as the substantially continuous heating element input 2012 is pulled therefrom. By either actively rotating the spool 2014 or passively allowing the spool to substantially freely rotate as the substantially continuous heating element input 2012 is pulled therefrom, tension in the substantially continuous heating element input may be controlled to avoid damage thereto.

In one embodiment the position of the substantially continuous heating element input 2012 may be monitored such that the spool 2014 may actively supply the substantially continuous heating element input to maintain a desired amount of slack therein. For example, as illustrated in FIG. 53, in one embodiment an upper sensor 2016a and a lower sensor 2016b may be provided, with the substantially continuous heating element input 2012 draped off the spool 2014 such that it extends between the sensors 2016a, 2016b. In one embodiment the sensors 2016a, 2016b may each include a light emitter and a light detector, which may detect when an object blocks the light from reaching the light detector. Accordingly, the spool 2014 may be actively driven based on detection of the substantially continuous heating element input 2012. For example, if the upper sensor 2016a detects a blockage of light caused by the substantially continuous heating element input 2012, the spool 2014 may be directed to rotate or rotate more quickly. Conversely, if the lower sensor 2016b detects a blockage of the light caused by the substantially continuous heating element input 2012, the spool 2014 may be directed to rotate more slowly or stop. Accordingly, tension in the substantially continuous heating element input 2012 may be controlled. For example, the controller 417 may be in communication with the sensors 2016a, 2016b and configured to direct the spool 2014 to rotate as described above.

As noted above, the preparing portion 2008 of the heating element coupling substation 1212 may be substantially similar to the preparing portion 902 described above. In this regard, the preparing portion 2008 may be configured to prepare an individual heating element 240 coupled to the liquid transport element 238 for welding. Accordingly, the preparing portion 2008 will not be described in detail.

Briefly, however, as illustrated in FIG. 52, the preparing portion 2008 may include a dispenser 2018, a cutter 2020, and an imaging device 2022 (e.g., a camera). Thereby, the dispenser 2018 may pull on the substantially continuous heating element input 2012 until a controller determines that a desired length of the substantially continuous heating element input 2012 has been dispensed, based on images captured by the camera 2022. In this regard, the controller may determine the center of the heating element in the same manner as described above. Thereby, a transport apparatus 2024 (see, FIG. 54) may grasp the substantially continuous heating element input 2012 such that the heating element 240 is centered between first and second arms 2026a, 2026b thereof.

The cutter 2020 may cut the substantially continuous heating element input 2012 to singulate an individual heating element 240 and liquid transport element 238. A new end of the substantially continuous heating element input 2012 may be supported by a tube 2028, as illustrated in FIG. 52, such that the end is ready for grasping by the dispenser 2018 in order to repeat the above-described process.

As illustrated in FIG. 54, the welding portion 2010 may comprise a housing 2030. The transport apparatus 2024 may transport the singulated heating element 240 and liquid transport element 238 into a chamber 2032 defined by the housing 2030. Further, as illustrated in FIG. 55, the heating element robot 1310 may come into contact with the housing 2030. More particularly, the heating element robot 1310 may direct at least the heating terminal tabs 952a, 954b of the heating terminals 234a, 234b into the chamber 2032 defined by the housing.

Accordingly as illustrated in FIG. 52, an imaging device 2034 (e.g., a camera) may captures images of the heating element 240 and the heating terminal tabs 952a, 954b of the heating terminals 234a, 234b. Thereby, a controller may direct the transfer apparatus 2024 and the heating element robot 1030 to respectively align a center of the heating element 240 and a center of the heating terminals 234a, 234b with a center of the imaging device 2034. Thus, the heating element robot 1030 may press the heating terminal tabs 952a, 952b against the contact portions 926, 928 of the heating element 240 (see, e.g., FIG. 23). An upward-looking imaging device may be employed to determine the horizontal position of the heating terminals 234a, 234b relative to the heating element 240 such that contact therebetween may be established. A laser 2036 may direct laser beams against the backs of the heating terminal tabs 952a, 952b such that the heating element 240 is welding to the heating terminals 234a, 234b in substantially the same manner as described above. In this regard, a gas dispenser (e.g., a fitting coupled to a bottom of the housing 2030) may be configured to dispense an inert gas (e.g., argon) into the chamber 2032 to improve the resultant weld (e.g., by preventing oxidation thereof).

Further, the chamber 2032 defined by the housing 2030 may be substantially sealed before welding the heating element 240 to the first heating terminal 234a and the second heating terminal 234b. In this regard, as illustrated in FIG. 55, the heating element robot 1310 may include a sealing member 2038 configured to engage the housing 2030. In this regard, when the heating terminals 234a, 234b are inserted into the housing 2030, the sealing member 2038 of the heating element robot 1310 may seal thereagainst. Similarly, a second sealing member 2040 may seal the transport apparatus 2024 to the housing 2030 when the transport apparatus directs a heating element 240 into the chamber 2032 and a third sealing member 2042 may create a seal between the camera 2034 and/or the laser 2036 and the housing 2030. Accordingly, by substantially sealing closed the chamber 2032 defined by the housing, issues with respect to the laser beam exiting the chamber may be averted. Additionally, use of the substantially sealed chamber 2032 may facilitate usage of the inert gas by at least partially retaining the inert gas in the chamber 2032. Further, as noted above, various alternate attachment methods, including various other types of welding, may be employed to couple the heating element to the heating terminals.

Following welding, the partially assembled cartridge may be transported to the liquid transport element bending substation 1214. In this regard, the heating element robot 1310 may transport the partially assembled cartridge thereto in some embodiments. FIG. 56 illustrates an example embodiment of the liquid transport element bending substation 1214. As illustrated, the liquid transport element bending substation 1214 may include first and second upright members 2102a, 2102b. Upper channels 2104a, 2104b and side channels 2106a, 2106b may be defined in the upright members 2102a, 2102b.

The heating element robot 1310 may be configured to direct the partially assembled cartridge between the upright members 2102a, 2102b of the liquid transport element bending substation 1214. More particularly, the heating element robot 1310 may orient the partially assembled cartridge such that the liquid transport element 238 enters the upper channels 2104a, 2104b. As the partially assembled cartridge is inserted down between the upright members 2102a, 2102b, the liquid transport element 238 may begin to bend and enter the side channels 2106a, 2106b defined at inner surfaces of the upright members. Further, as illustrated in FIG. 57, the upright members 2102a, 2102b may pinch toward one another such that the liquid transport element 238 bends more and comes into contact with the heating terminals 234a, 234b.

Once the liquid transport element 238 is bent, the reservoir substrate robot 1312 may grasp the partially assembled cartridge. As illustrated in FIG. 58, the reservoir substrate robot 1312 may include a base and wick gripper 2202. The base and wick gripper 2202 may include first and second portions 2204a, 2204b. Each of the portions 2204a, 2204b may include a base gripper section 2206. For example, in the illustrated embodiment the base gripper sections 2206 comprise v-notches that cooperate to center the base 204 therein. Further, each of the portions 2204a, 2204b may include a wick gripper section 2208 configured to engage the liquid transport element 238.

In this regard, FIG. 59 illustrates the base and wick gripper 2202 engaged with the partially assembled cartridge. As illustrated, the base 204 may be received between the base gripper sections 2206. Further, the wick gripper section 2208 may pinch against ends of the liquid transport element 238. Accordingly, the base and wick gripper 2202 may retain the liquid transport element 238 in the bent configuration.

The reservoir substrate robot 1312 may thus transport the partially assembled cartridge, with the liquid transport element 238 in the bent configuration, to the reservoir coupling substation 1216, where the reservoir substrate 214 is coupled thereto. Accordingly, the reservoir substrate 214 may be prepared for attachment to the partially assembled cartridge. In this regard, as illustrated in FIG. 60, a substantially continuous reservoir substrate input 2302 may be supplied from a spool 2304 in some embodiments. The spool 2304 may passively rotate as the substantially continuous reservoir substrate input 2302 is pulled therefrom. Alternatively, the spool 2304 may be actively driven (e.g., by a motor) such that the spool rotates as the substantially continuous reservoir substrate input 2302 is pulled therefrom. By either actively rotating the spool 2304 or passively allowing the spool to substantially freely rotate as the substantially continuous reservoir substrate input 2302 is pulled therefrom, tension in the substantially continuous reservoir substrate input may be controlled to avoid damage thereto.

In one embodiment the position of the substantially continuous reservoir substrate input 2302 may be monitored such that the spool 2304 may actively supply the substantially continuous reservoir substrate input to maintain a desired amount of slack therein. For example, as illustrated in FIG. 60, in one embodiment an upper sensor 2306a and a lower sensor 2306b may be provided, with the substantially continuous reservoir substrate input 2302 draped off the spool 2304 such that it extends between the sensors 2306a, 2306b. In one embodiment the sensors 2306a, 2306b may each include a light emitter and a light detector, which may be positioned at opposing ends of a trough 2308, and which may detect when an object blocks the light from reaching the light detector. Accordingly, the spool 2304 may be actively driven based on detection of the substantially continuous reservoir substrate input 2302. For example, if the upper sensor 2306a detects a blockage of light caused by the substantially continuous reservoir substrate input 2302, the spool 2304 may be directed to rotate or rotate more quickly. Conversely, if the lower sensor 2306b detects a blockage of the light caused by the substantially continuous reservoir substrate input 2302, the spool 2304 may be directed to stop or rotate more slowly. Accordingly, tension in the substantially continuous reservoir substrate input 2302 may be controlled. For example, the controller 417 may be in communication with the sensors 2306a, 2306bb and configured to direct the spool 2304 to rotate as described above.

The substantially continuous reservoir substrate input 2302 may be supplied from the spool 2304 to a singulation unit 2310. As illustrated in FIG. 61, the singulation unit 2310 may comprise a rotary wheel 2312 defining a plurality of apertures 2314 at an outer surface thereof. The apertures 2314 may be configured to apply vacuum to the substantially continuous reservoir substrate input 2302 such that the substantially continuous reservoir substrate input is retained thereon. Further, the singulation unit 2310 may include a cutter 2316, as illustrated in FIG. 62. The cutter 2316 may be configured to cut the substantially continuous reservoir substrate input 2302 at predetermined intervals in order to provide individual reservoir substrates 214. For example, a portion of the cutter 2316 may extend through cutouts 2317 defined in the rotary wheel 2312 in order to cut the reservoir substrate without damaging the rotary wheel. Thus, for example, the rotary wheel 2312 may rotate in stepped increments corresponding to a desired length of the individual reservoir substrates and corresponding to a distance between centers of the cutouts 2317. As illustrated in FIG. 61, after being cut from the substantially continuous reservoir substrate input 2302, the singulated reservoir substrate 214 may be retained on the rotary wheel 2312 by vacuum applied through the apertures 2314. However, the rotary wheel 2312 may be configured to transfer the reservoir substrate 214 to a wrapping mechanism 2318.

In this regard, as illustrated in FIG. 63, the wrapping mechanism 2318 may include a moveable slide 2320 configured to move on a track 2322. The moveable slide 2320 may comprise a head portion 2324 with one or more apertures 2326 defined therein. Thereby, the moveable slide 2320 may move along the track 2322 such that the head portion 2324 comes into proximity to the rotary wheel 2312. Thus, a reservoir substrate 214 may be transferred from the rotary wheel 2312 to the head portion 2324 of the moveable slide 2320. For example, vacuum may be applied to the apertures 2326 in the head portion 2324. Thereby, when vacuum is relieved from the apertures 2314 in the rotary wheel 2312 holding the reservoir substrate 214 and/or positive pressure is applied through the apertures in the rotary wheel, the reservoir substrate may be transferred to the head portion 2324 of the moveable slide 2320. In this regard, the rotary wheel 2312 may be configured such that vacuum ceases or positive pressure is applied to the apertures 2314 as the apertures reach a specified angular position corresponding to a position at which the head portion 2324 of the moveable slide 2320 comes into proximity therewith.

After transfer of a reservoir substrate 214 to the head portion 2324 of the moveable slide 2320, the moveable slide may begin moving back to an initial starting position. The reservoir substrate robot 1312 may bring the partially assembled cartridge into contact with the reservoir substrate 214 held by the head portion 2324 of the moveable slide 2320. Then the reservoir substrate robot 1312 and the moveable slide 2320 may move in a synchronized manner in the same direction until the moveable portion reaches the position illustrated in FIG. 63. At this point, first and second arms 2328a, 2328b of a wrapping member 2330 may pinch together towards one another, which may cause the reservoir substrate 214 to wrap around the partially assembled cartridge. The arms 2328a, 2328b may move at the same time (e.g., to create a butt joint at the ends of the reservoir substrate 214) or sequentially one after the other (e.g., to cause one end of the reservoir substrate to wrap around the other end). In this regard, the arms 2328a, 2328b may function in substantially the same manner as the arms 1024a, 1024b described above and illustrated in FIG. 33.

Following wrapping of the reservoir substrate 214, the partially assembled cartridge may be directed to the outer body coupling substation 1218 by the outer body robot 1314. As illustrated in FIG. 64, in addition to the outer body robot 1314, the outer body coupling substation 1218 may include an outer body supply 2402 configured to supply the outer body 216 204. In some embodiments the outer body supply 2402 may comprise a vibratory bowl feeder, as illustrated in FIG. 41.

The outer body supply 2402 may supply the outer bodies 216 to a transfer member 2404. The transfer member 2404 may be configured to grasp an individual outer body 216 and position the outer body for coupling to the partially assembled cartridge. In this regard, as illustrated in FIG. 65, the outer body coupling substation 1218 may include an outer body coupling tool 2406 configured to facilitate insertion of the reservoir substrate 214 into the outer body 216 and a crimper 2408 configured to crimp the outer body to the base 204 after the outer body extends over the reservoir substrate and engages the base. A chamber 2410 defined in the crimper 2408 may be configured to receive the outer body 216 such that the partially assembled cartridge may be inserted therein and then the outer body may be crimped to the base 204.

In order to deposit the outer body 216 in the chamber 2410, as illustrated in FIG. 66, the transfer member 2404 may include an outer body gripper 2412 and a rotary arm 2414. Thus, the outer body gripper 2412 may grasp an outer body 216 supplied by the outer body supply 2402. The outer body 216 may be supplied in a substantially horizontal configuration in some embodiments. Thereby, the rotary arm 2414 may rotate such that the outer body 216 is substantially vertical and positioned over the outer body coupling tool 2406 and the crimper 2408. The outer body gripper 2412 may release the outer body 216 such that it falls though the outer body coupling tool 2406 into the chamber 2410 defined by the crimper 2408.

In this regard, the outer body coupling tool 2406 may comprise a plurality of sections. For example, in the illustrated embodiment the outer body coupling tool 2406 comprises first and second sections 2416a, 2416b. The sections 2416a, 2416b of the outer body coupling tool 2406 may be moveable between an expanded configuration (see, e.g., FIGS. 64 and 65) in which the sections are radially separated from one another, and a contracted configuration (see, FIG. 66), in which the sections are in contact with one another. Each section 2416a, 2416b the outer body coupling tool 2406 may define a funnel portion 2418. The funnel portions 2418 may cooperate to define a funnel, as illustrated in FIG. 66, when the sections 2416a, 2416b are in the closed configuration. Accordingly, when the partially assembled cartridge is directed into contact therewith, the outer body coupling tool 2406 may reduce an outer dimension of the reservoir substrate 214 such that the outer dimension of the reservoir substrate is less than or equal to an internal dimension of the outer body 216 to facilitate insertion of the reservoir substrate into the outer body. In this regard, the reservoir substrate 214 may comprise a flexible, fabric-like material, which may stick out in certain directions, making it difficult to directly insert the reservoir substrate 214 into the outer body 216 when the reservoir substrate is wrapped about the flow tube 210 and/or other components of the cartridge. Thus, the funnel portions 2418 may define a funnel having a minimum inner radius that is less than or equal to the inner radius of the outer body 216. Accordingly, when the outer body robot 1314 presses the partially assembled cartridge down through the outer body coupling tool 2406, the reservoir substrate 214 may be compacted by the funnel portions 2418 such that it slides relatively easily into the outer body 216.

The outer body robot 1314 may include a gripper configured to facilitate the above-described insertion of the partially assembled cartridge through the outer body coupling tool 2406 into the outer body 216. In this regard, FIG. 67 illustrates an exploded view of a reservoir gripper 2420 and FIGS. 68 and 69 illustrates the gripper in an assembled configuration according to an example embodiment of the present disclosure. As illustrated, the reservoir gripper 2420 may include first and second body portions 2422a, 2422b. The first and second body portions 2422a, 2422b may be configured to releasably clamp the base 204 therebetween in order to hold the partially assembled cartridge.

Further, the reservoir substrate gripper 2420 may include a finger 2424 configured to retain the reservoir substrate 214 in the wrapped configuration. Note that the reservoir substrate is not illustrated in FIGS. 67 and 68 for clarity purposes. The finger 2424 may be moveably coupled with respect to the first body portion 2422a of the reservoir substrate gripper 2420. The reservoir substrate gripper 2420 may be provided with various features configured to facilitate movement of the finger 2424 in the manner described below. However, in the illustrated embodiment the first body portion 2422a of the reservoir substrate gripper 2420 includes a channel 2426. The channel 2426 may be configured to receive a protrusion or pin 2428 at an upper portion of the finger 2424. The channel 2426 may be substantially straight in some embodiments. Further, the finger 2424 may comprise an elongated aperture 2430 configured to receive a protrusion or pin 2432 coupled to the first body portion 2422a. As illustrated, in some embodiments the elongated aperture 2430 may generally define a path that extends upward and away from a tip 2434 of the finger 2424.

The finger 2424 may be configured to retain the reservoir substrate 214 in the wrapped configuration. In this regard, the tip 2434 of the finger 2424 may be configured to press against the wrapped reservoir substrate 214 while the outer body robot 1314 transports the partially assembled cartridge to the outer body coupling substation 1218. In this regard, as illustrated in FIG. 63, the arms 2328a, 2328b of the wrapping mechanism 2318 may each include upper and lower protrusions 2334a, 2334b, which may assist in the above-described wrapping operations. Further, the protrusions 2334a, 2334b from one arm 2328a may contact the protrusions 2334a, 2334b on the opposing arm 2328b when the arms are moved toward one another such that a gap exists between the arms when the reservoir substrate is in the wrapped configuration.

Thereby, while the arms 2328a, 2328b hold the reservoir substrate in the wrapped configuration, the outer body robot 1314 may engage the partially assembled cartridge with the reservoir substrate gripper 2420. More particularly, the first and second body portions 2422a, 2422b may engage the base 204 of the partially assembled cartridge. Further, the tip 2434 of the finger 2424 may extend between or below the protrusions 2334a, 2334b to engage the reservoir substrate proximate a location at which the ends thereof overlap or meet at a joint. Accordingly, when the arms 2328a, 2328b of the wrapping mechanism 2318 retract, the reservoir substrate gripper 2420 may retain the reservoir substrate 214 in the wrapped configuration by pressing against the reservoir substrate.

Accordingly, the partially assembled cartridge may include the reservoir substrate 214 wrapped thereabout when insertion through the outer body coupling tool 2406 into the outer body 216 begins. However, the finger 2424 may be configured to release from the reservoir substrate 214 during insertion of the partially assembled cartridge into the outer body 216. In this regard, as the outer body robot 1314 inserts the partially assembled cartridge through the outer body coupling tool 2406, the finger 2424 of the reservoir substrate gripper 2420 may contact the outer body coupling tool. Accordingly, the first body portion 2422a may continue moving toward the outer body coupling tool 2406 while the finger 2424 remains in contact with the outer body coupling tool. Accordingly, the finger 2424 may move along a path relative to the first body portion 2422a defined by the interaction between the channel 2426 and the pin 2428 and between the elongated aperture 2430 and the pin 2432. Accordingly, the upper portion of the finger 2424 may remain substantially stationary as a result of the channel 2426 being substantially straight. However, a lower portion of the finger 2424 may be directed outward, away from the reservoir substrate 214 and the remainder of the partially assembled cartridge as a result of the elongated aperture 2430 defining a path that extends upward and away from the tip 2434 of the finger. Accordingly, the tip 2434 of the finger 2424 may deflect away from and release the reservoir substrate 214 as the outer body robot 1314 inserts the partially assembled cartridge through the outer body coupling tool 2406.

Note that the particular embodiment of the reservoir substrate gripper 2420 may vary while still operating in a manner similar to that described above. For example, FIG. 69 illustrates an alternate embodiment of a reservoir substrate gripper 2420'. The reservoir substrate gripper 2420' may be configured to grasp the base 204 of a partially assembled cartridge in a manner similar to the reservoir substrate gripper 2420 described above. Further, the reservoir substrate gripper 2420' may include a finger 2424' configured to releasably retain the reservoir substrate 214 in the wrapped configuration. In this regard, an innermost portion 2434a' of the finger 2424' may be configured to press against the reservoir substrate 214. However, an outermost portion 2434b' may be configured to deflect outside of, and away from the outer body coupling tool 2406 when the outer body robot 1314 directs the partially assembled cartridge through the outer body coupling tool. In this regard, as a result of the deflection, the finger 2424' may release from the reservoir substrate 214. Accordingly, insertion of the partially assembled cartridge through the outer body coupling tool 2406 may be accomplished in substantially the same manner.

Once the partially assembled cartridge is inserted into the outer body 216, the crimper 2408 may crimp the outer body to the base 204. In this regard, as illustrated in FIGS. 65 and 66, the crimper 2408 may comprise multiple sections 2408a. For example, the crimper 2408 may comprise at least four sections 2408a, which may facilitate production of a tight seal between the base and the outer body 216. Each of the sections 2408a may include a lip, angled portion, and some or all of the features of the crimper 1118 described above (see, FIGS. 37-39). Accordingly, the sections 2408a may move from an open configuration (see, e.g., FIG. 65) to a closed configuration (see, e.g., FIG. 66) to crimp the outer body 216 to the base 204. Note, however, the crimper 2408 may be inverted relative to the above described crimper 1118. Further the crimper 2408 may be configured to hold the outer body 216 during the insertion of the partially assembled cartridge through the outer body coupling tool 2406. Accordingly, the crimper 2408 may differ from the above-described crimper 1118 in one or more respects.

Note that the above-described cartridge assembly subsystems 402, 402' may be combined and modified in a number of manners without varying from the scope of the present disclosure. In this regard, the heating element has been generally described above as being provided as a substantially continuous coil of wire wound about a substantially continuous liquid transport element. Thus, preparation of individual heating elements 240 and liquid transport elements 238 involved cutting a substantially continuous input into sections. However, in other embodiments the heating elements may be formed by the cartridge assembly subsystem.

For example, as illustrated in FIG. 70, in one embodiment a heating element 240' may be formed by providing a liquid transport element 238 and coupling a wire 242 thereto to form the heating element. By way of further example, in one embodiment an end 240A of the wire 242 may be inserted through the liquid transport element 238. Thereafter, one or both of the liquid transport element 238 and the wire 242 may be rotated to define the coils of the heating element 240'. Further, a second end 240B of the wire 242 may be inserted back through the liquid transport element 238 such that both the first end 240A and the second end 240B of the wire are held in place and the heating element is held in the coiled configuration. Alternatively, one or both of the ends of the wire may be welded to an adjacent coil to hold the heating element in place and in the coiled configuration.

Accordingly, the above-described process may produce a heating element 240' coupled to a liquid transport element 238, which may form a completed atomizer when heating terminals (e.g., heating terminals 234a, 234b) are coupled thereto (e.g., in via the processes disclosed herein). In this regard, as described above, the wire 242 may extend at least partially through the liquid transport element 238 at one or both of first and second ends 240A, 240B of the wire. Thus, the ends of the wire 242 may extend through the liquid transport element 238 substantially transversely to a longitudinal length of the liquid transport element. The liquid transport element 238 may extend between first and second opposing ends 238A, 238B. However, the wire 242 may not extend to the opposing ends of the liquid transport element (note that a section of the transport element is shown in FIG. 70, rather than a full length thereof) in order to prevent inclusion of unnecessary wire, as described below. The heating element 240' may comprise two contact portions 244A, 244B positioned proximate the ends of the wire 242 and a center portion 246 positioned between the contact portions. As illustrated, the contact portions 244A, 244B may define a first coil spacing and the center portion 246 may define a second coil spacing, wherein the second coil spacing is greater than the first coil spacing. As described elsewhere herein with respect to another embodiment of a heating element, this may facilitate attachment of the heating element to the heating terminals at the contact portions. Further, by forming the heating element 240' in a manner whereby the wire 242 terminates at the contact portions 244A, 244B of the heating element, less of the wire 242 may be required to form the heating element, as compared to embodiments in which the wire extends along substantially the entire length of the liquid transport element. In this regard, wire positioned outside of the heating terminals may be wasted material in a completed atomizer, since wire at these locations would not function to facilitate coupling to the heating terminals or produce heat.

Following attachment of the outer body 216 to the base, the partially assembled cartridge may be directed to the cartridge filling substation 408. The cartridge filling substation 408 may include one or more fill stations. As illustrated in FIG. 71, in one embodiment the cartridge filling substation 408 may include five filling stations 2502a-e. Further, in some embodiments the cartridge filling substation 408 may include an environment control housing 2504 in which the filling stations 2502a-e are positioned. Accordingly, an environment within the environment control housing 2504 may be controlled. Additionally, an environment modification apparatus 2506 may be configured to affect the environment within the environment control housing 2504. In some embodiments the controller 417 may be configured to control one or more of the stations 2502a-e and/or the environment modification apparatus 2506 of the cartridge filling substation 408.

In one embodiment the environment modification apparatus 2506 may comprise a dehumidifier configured to affect the ambient environment within the environment control housing 2504. By way of additional example, the environment modification apparatus 2506 may be configured to control the ambient environment within the environment control housing 2504 such that the ambient environment defines a relative humidity of less than about 60%, preferably less than about 50% and most preferably less than about 40%. By controlling the humidity in this manner, issues with respect to the aerosol precursor composition absorbing ambient moisture, which may undesirably dilute the aerosol precursor composition and/or overfill the cartridge, may be avoided.

FIG. 72 illustrates an overhead view of a partially assembled cartridge, during filling and prior to coupling of a mouthpiece thereto. As illustrated, an outlet 2508 of a filling device 2510 (e.g., a filling needle) may be positioned in proximity to a plurality of angular portions 2512a-d (e.g., quadrants) of the reservoir substrate 214, wherein the angular portions are defined relative to a longitudinal axis extending through the cartridge. For example, as illustrated in FIG. 72, the outlet 2508 of the filling device 2510 may be sequentially positioned at a first angular portion 2512a, followed by a second angular portion 2512b, a third angular portion 2512c, and a fourth angular portion 2512d. Directing the aerosol precursor composition at a plurality of angular positions may increase a fill rate of the reservoir substrate 214 with the aerosol precursor composition. In this regard, the absorbency rate of the reservoir composition 214 may be less than a flow rate out of the outlet 2508 of the filling device 2510. Accordingly, by moving the outlet 2508 to various angular portions 2512a-d, each angular portion may receive a flow of the aerosol precursor composition, to avoid issues with respect to a single angular portion of the reservoir substrate 214 being unable to absorb the aerosol precursor composition at the rate at which the filling device 2510 dispenses the aerosol precursor composition.

In one embodiment, the outlet 2508 of the filling device 2510 may be sequentially moved from each of the first through fourth angular portions 2512a-d at filling station one 2502a. Thereafter, filling stations two through five 2502b-e may position the outlet 2508 of the filling device 2510 at one of the angular portions. For example, filling station two 2502b may position the outlet 2508 of the filling device 2510 at the first angular portion 2512a, filling station three 2502c may position the outlet 2508 of the filling device 2510 at the second angular portion 2512b, filling station four 2502d may position the outlet 2508 of the filling device 2510 at the third angular portion 2512c, and filling station five 2502e may position the outlet 2508 of the filling device 2510 at the fourth angular portion 2512d. Accordingly, the cartridge may be transported between the filling stations 2502a-e and the flow of the aerosol precursor composition may be directed to at least one of the angular portions 2512a-d of the reservoir substrate 214 at each of the filling stations.

Further, as illustrated in FIG. 73, the outlet 2508 of the filling device 2510 may remain out of contact with the reservoir substrate 214 while directing a flow of an aerosol precursor composition 2514 through the outlet of the filling device at each of the angular portions of the reservoir substrate. In this regard, by avoiding contact with the reservoir substrate 214, damage thereto may be avoided. Further, as illustrated in FIGS. 72 and 73, the filling device 2510 may be configured to press against an inner surface of the outer body 216 when filling at each of the angular portions 2512a-d. Accordingly, the cartridge may tilt slightly and the aerosol precursor composition 2514 may be directed down the internal surface of the outer body 216, such that the reservoir substrate 214 may be filled at a relatively faster rate.

After filling, the cartridge may be directed to the cartridge capping subsystem 412, at which the mouthpiece 220 is coupled to the outer body 216. The outer body 216 may be crimped to the mouthpiece 220 using a crimper substantially similar to the above-described crimpers in order to prevent leakage between the outer body and the mouthpiece. Further, the cartridge labeling subsystem 416 may apply a label 218 to the cartridge in some embodiments.

Various quality control measures may be employed to ensure that the completed cartridges 200 are suitably constructed. In this regard, as noted above and illustrated in FIG. 3, the system 400 may additionally include an inspection subsystem 418, which may inspect the components 406, the unfilled cartridges 404, the filled cartridges 410, the capped cartridges 414, and/or the completed cartridges 200. Further, in some embodiments the cartridges may be inspected at intermediate states of completion at one or more of the cartridge assembly subsystem 402, the cartridge filling subsystem 408, the cartridge capping subsystem 412, and the cartridge labeling subsystem 416. Accordingly, the cartridges and components thereof may be inspected before, during, and after completion thereof.

In this regard, imaging devices (e.g., cameras) may be employed at a variety of locations to ensure that the above-described processes are being performed as desired, within specifications. Thus, cameras and/or other inspection equipment may be employed at a plurality of locations within the system 400. However, inspection at certain locations may be of particular importance.

In this regard, it may be important to inspect the position of the terminals 206, 234a, 234b after insertion into the base 204. For example, one or more cameras may be configured to inspect a radial position of each of the terminals 206, 234a, 234b (e.g., with respect to a center of the base 204). The radial position of the terminals 206, 234a, 234b may be determined at an attachment end 204a of the base 204. In this regard, proper radial position of the terminals 206, 234a, 234b may facilitate attachment of the cartridge 200 to the control component 300. Further, one or more cameras may be employed to inspect the distance to which the terminals 206, 234a, 234b extend from the base 204. The distance to which the terminals 206, 234a, 234b extend from the base 204 may be determined at an inner end 204b (see, FIG. 1) in some embodiments. In this regard, extension of the terminals 206, 234a, 234b to the proper distance from the inner end 204b of the base 204 may be important for ensuring a proper coupling of the heating element 240 thereto.

In the cartridge assembly subsystem 402, the terminals 206, 234a, 234b are downwardly inserted into the base 204. Accordingly, inspection of the distance to which the terminals 206, 234a, 234b extend from the inner end 204b of the base 204 may be conducted while the base is held in the carriage 600 traveling on the rail 616. In this regard, as illustrated in FIG. 74, a side view camera 2602 may be configured to capture images of a side profile of the partially assembled cartridge following coupling of one or more of the terminals 206, 234a, 234b to the base 204. Thereby, a controller may be configured to determine a distance to which one or more of the terminals 206, 234a, 234b extend from the base 204.

However, as a result of the attachment end 204a of base 204 being downwardly oriented toward the carriage 600, the base may be removed from the carriage to inspect the radial position of the terminals 206, 234a, 234b. In this regard, as illustrated in FIG. 75, a removal robot 2604 may be configured to remove the partially assembled cartridge from the carriage 600 and move the partially assembled cartridge over an end view camera 2606. Accordingly, images captured by the end view camera 2604 may be analyzed by a controller to determine a radial position of one or more of the terminals 206, 234a, 234b. Alternatively, an aperture extending through the carriage 600 may allow for inspection of the radial position of the terminals 206, 234a, 234b at the attachment end 204a of the base 204. Further, note that in some embodiments a separate camera may be provided for each terminal in order to focus on each particular terminal. In other embodiments a camera may be employed to inspect multiple terminals, for example by adjusting the focus of the camera.

In the second embodiment of the cartridge assembly subsystem 402', the cartridge is generally assembled with the base 204 oriented in an opposing manner such that components coupled thereto extend downwardly therefrom. In this regard, as illustrated in FIG. 76, the fixtures 1704 of one or more of the transfer members 1700A-C may be employed to facilitate inspection of the terminals 206, 234a, 234b. For example, the fixtures 1704 may hold the base 204 such that the attachment end 204a thereof extends upwardly. Accordingly, an end view camera 2702 positioned above the base 204 may inspect the radial position of the terminals 206, 234a, 234b.

Further, as illustrated in FIG. 77, the fixtures 1704 may include one or more apertures 2704a, 2704b extending therethrough. Accordingly, as illustrated in FIG. 76, a side view camera 2706 may be positioned to look through one or more of the apertures 2704a, 2704b to determine a distance to which the terminals 206, 234a, 234b extend from the inner end 204b of the base 204. In some embodiments a separate camera may be provided for each terminal in order to focus on each particular terminal. In other embodiments a camera may be employed to inspect multiple terminals, for example by adjusting the focus of the camera.

The inspection subsystem 418 may additionally include one or more cameras configured to inspect the partially assembled cartridge following crimping of the outer body 216 to the base 204. For example, as illustrated in FIG. 78, when inspecting the first embodiment of the cartridge assembly subsystem 402, the inspection subsystem 418 may include an end view camera 2802 configured to capture images inside of the outer body 216. In this regard, the end view camera 2802 may be positioned above the rail 616 downstream of the crimper 1118, such that when a carriage 600 is directed under the end view camera, the end view camera may capture one or more images of the inside of the outer body 216. Thereby, a controller may determine whether or not the reservoir substrate 214 is present, which is a desired condition, or missing, which is an undesired condition.

Further, the cartridge assembly subsystem 402 may include a side view camera 2804 configured to capture images of a side of the partially assembled cartridge. In this regard, the side view camera 2804 may be positioned beside the rail 616 such that the side view camera may capture images of the partially assembled cartridge held by the carriage 600. In this regard, a controller may be configured to analyze the images captured by the side view camera 2804 to determine whether a crimp in the outer body 216 produced by the crimper 1118 is proper (e.g., when the crimp is proper the outer body may be substantially flush with the base 204) and further the controller may determine whether the reservoir substrate 214 sticks out of the outer body (e.g., at the interface between the outer body and the base), which is an undesired condition, or contained within the outer body, which is a desired condition.

As illustrated in FIG. 79, when inspecting the second embodiment of the cartridge assembly subsystem 402', the inspection subsystem 418 may include an end view camera 2902 configured to capture images inside of the outer body 216 and a side view camera 2904 configured to capture images of the side of the partially assembled cartridge such that a controller may analyze the images of the partially assembled cartridge in the manner described above. Further, an outer body inspection robot 1316 may be employed to receive the partially assembled cartridge from the crimper 2408 and direct the partially assembled cartridge to a position at which the end view camera 2902 and the side view camera 2904 may capture images of the partially assembled cartridge. Further, the outer body inspection robot 1316 may include the base gripper 1500 in some embodiments, which may facilitate gripping the base 204 in the manner described above.

The inspection subsystem 418 may additionally include a blow-through station. The blow-through station may be configured to direct a flow of air through the cartridge to purge the flow path defined therethrough. In this regard, although not expected, the blow-through station may remove any dust or debris from the flow path through the cartridge. By way of example, FIG. 80 illustrates a blow-through station 3000 that may be employed with the first embodiment of the cartridge assembly subsystem 402. As illustrated, the blow-through station 3000 may include a first connector 3002 and a second connector 3004. In one embodiment, the first connector 3002 may be configured to engage an aperture 3006 in the carriage 600 in communication with the attachment end 204a of the base 204. In this regard, the first connector may include an elastomeric seal 3008 configured to engage the aperture 3006 in the carriage 600 in some embodiments. Further, the second connector 3004 may be configured to engage an end of the outer body 216 opposite from the base 204, for example via an elastomeric seal.

The connectors 3002, 3004 may be at differing pressures. Accordingly, a pressure differential applied across the cartridge through the connectors 3002, 3004 may cause a flow of air to be directed therethrough. In some embodiments the first connector 3002 may be at a higher pressure than the second connector 3004 such that air flows through the cartridge in the same direction as would occur during normal use of the cartridge. For example, vacuum may be applied to the second connector 3004, whereas the first connector 3002 may be ambient pressure. Accordingly, any debris in the cartridge may be removed.

FIG. 81 illustrates an embodiment of a blow-through station 3100 which may be included with the second embodiment of the cartridge assembly subsystem 402'. As illustrated, the blow-through station 3100 may include a first connector 3102 and a second connector 3104. Further, the blow-through station 3100 may include a rotatable arm 3106 and an outer body gripper 3108. The outer body inspection robot 1316 may move the partially assembled cartridge to the blow-through station 3100. Thus, the outer body gripper 3108 may grasp the outer body 216 of the partially assembled cartridge and the rotatable arm 3106 may rotate the partially assembled cartridge into place between the connectors 3102, 3104. The connectors 3102, 3104 may contract against the ends of the cartridge to form a seal therewith. For example, the connectors 3102, 3104 may respectively include an elastomeric seal 3110, 3112 that facilitate formation of connections with the attachment end 204a of the base 204 and the opposite end of the outer body 216. Following completion of the blow-through in the manner described above, connectors 3102, 3104 may retract and the rotatable arm 3106 may rotate the partially assembled cartridge such that the cartridge may be grasped and moved to an additional station. Note that, as illustrated, an additional blow-through station 3100', which may be substantially similar to the blow-through station 3100 may be provided in order to increase throughput.

Further, the inspection subsystem 418 may additionally include a pressure drop station. The pressure drop station 418 may be configured to detect a pressure drop associated with directing airflow through the partially assembled cartridge. Accordingly, a pressure drop associated with the cartridge may be determined and compared to a desired pressure drop to ensure that there are not any obstructions or leaks in the cartridge.

In some embodiments the pressure drop station may be substantially similar to the flow-through station. In this regard, FIG. 82 illustrates a pressure drop station 3200 that may be employed with the first embodiment of the cartridge assembly subsystem 402. As illustrated, the pressure drop station 3200 may include a first connector 3202 and a second connector 3204. In one embodiment, the first connector 3202 may be configured to engage an aperture in the carriage (see, e.g., aperture 3006 in carriage 600 FIG. 80) in communication with the attachment end 204a of the base 204. In this regard, the first connector 3202 may include an elastomeric seal 3208 configured to engage the aperture in the carriage in some embodiments. Further, the second connector 3204 may be configured to engage an end of the outer body 216 opposite from the base 204, for example via an elastomeric seal.

One of the connectors 3202, 3204 may supply air to the cartridge at a known flow rate and/or pressure. Further, the flow rate and/or the pressure of the air traveling through the other of the connectors 3202, 3204 may be tested to determine the pressure drop associated with the cartridge. Thereby, the pressure drop may be compared to a desired pressure drop.

FIG. 83 illustrates an embodiment of a pressure drop station 3300 which may be included with the second embodiment of the cartridge assembly subsystem 402'. As illustrated, the pressure drop station 3300 may include a first connector 3302 and a second connector 3304. Further, the pressure drop station 3300 may include a rotatable arm 3306 and an outer body gripper 3308. Accordingly, an inspection robot 1318 (see, FIG. 41) may move the partially assembled cartridge from the blow-through station 3100 to the pressure drop station 3300. Thus, the outer body gripper 3308 may grasp the outer body 216 of the partially assembled cartridge and the rotatable arm 3306 may rotate the partially assembled cartridge into place between the connectors 3302, 3304, which may move together to seal against the ends of the cartridge. For example, the connectors 3302, 3304 may respectively include an elastomeric seal 3310, 3312 that facilitate formation of connections with the attachment end 204a of the base 204 and the opposite end of the outer body 216. Following completion of the pressure drop test in the manner described above, the connectors 3302, 3304 may retract and the rotatable arm 3106 may rotate the partially assembled cartridge such that the cartridge may be grasped and moved to an additional station. Note that, as illustrated, an additional pressure drop station 3300', which may be substantially similar to the pressure drop station 3300 may be provided in order to increase throughput.

Further, the inspection subsystem 418 may additionally include an electrical test station. In this regard, FIG. 84 illustrates an embodiment of an electrical test station 3400 that may be included with the first embodiment of the cartridge assembly subsystem 402. As illustrated, the electrical test station 3400 may include a test fixture 3402. Further, electrical test station 3400 may include a robotic arm 3404 configured to move the partially assembled cartridge from the carriage to the test fixture 3402 and back. The robotic arm 3404 may include an outer body gripper 3406, which may be configured to grasp an outer surface of the outer body 216.

FIG. 85 illustrates an enlarged view of the test fixture 3402. As illustrated, the test fixture 3402 may comprise a receptacle 3408 configured to engage the base 204 of the cartridge. FIG. 86 illustrates a cross-sectional view through the test fixture 3402. In this regard, the receptacle 3408 may define a shape and size that is similar to that of the coupler 302 of the control body 300. However, the receptacle 3408 may be relatively shorter than the coupler 302 in order to avoid damaging optional crush members in the base 204. Further, the receptacle 3408 may not include anti-rotation features, such that the cartridge may engage the base 204 at any rotational position.

As illustrated, the test fixture 3402 may comprise a plurality of electrical contacts coupled to the receptacle 3408 and configured to engage terminals of the cartridge. For example, a first electrical contact 3410 may be configured to engage the first heating terminal 234a, a second electrical contact 3412 may be configured to engage the second heating terminal 234b, and a third electrical contact 3414 may be configured to engage a control component terminal 206. The first electrical contact 3410 may be defined by a first body portion 3416, the second electrical contact 3412 may be defined by a second body portion 3418, and the third electrical contact 3414 may be defined by a third body portion 3420. The body portions 3416, 3418, 3420 may be formed from conductive and relatively hard material, such as hardened steel, in order to withstand repeated use and allow for electrical communication therethrough in the manner described below.

Each of the body portions 3416, 3418, 3420 may be coupled to a nonconductive member 3422, which may be formed from any of a variety of nonconductive materials such as plastic. Further, the body portions 3416, 3418, 3420 may be electrically insulated from another by avoiding direct contact therebetween. In this regard, the body portions 3416, 3418, 3420 may be positioned such that air gaps are defined therebetween. For example, the body portions 3416, 3418, 3420 may be coupled to the nonconductive member 3422 such that the body portions are spaced apart from one another when coupled to the nonconductive member. Alternatively or additionally, nonconductive spacers may be placed between the body portions 3416, 3418, 3420.

The test fixture 3402 may be in communication with a controller such as the above-described controller 417 (see, e.g., FIG. 3). The controller 417 may be configured to communicate with the cartridge through the electrical contacts 3410, 3412, 3414 when the base of the cartridge is engaged with the receptacle 3402. Thereby, the cartridge may be tested and various other functions may be performed. For example, the controller 417 may be configured to determine a resistance of the atomizer of the cartridge and compare the resistance to a desired resistance. In some embodiments the resistance of the atomizer may preferably be from 1.5 ohms to about 3.5 ohms and more preferably from about 2.1 ohms to about 3.0 ohms, which may correspond to an atomizer configured to produce a desired amount of heat. Further, the controller 417 may be configured to determine if the atomizer is shorted to the outer body of the cartridge. In this regard, the controller 417 may check to make sure that a resistance between the outer body and one or more of the terminals 206, 234a, 234b is greater than about one mega ohm. For example, current may be applied through the outer body gripper 3406 to the outer body 216 of the cartridge and the controller 417 may detect any current reaching one or more of the terminals 206, 234a, 234b to determine the resistance between the terminals and the outer body. In this regard, in an improperly assembled cartridge the atomizer may touch the outer body, which could cause current to be transferred therebetween.

The test fixture 3402 may further comprise an aperture 3426 configured to provide for a flow of air through the base 204 of the cartridge. Accordingly, in some embodiments the test fixture 3402 may be employed to perform the above-described flow-through and/or pressure drop operations. Thus, for example, the aperture 3426 in the test fixture may be in communication with a first connector and the outer body gripper 3406 may include a second connector, such that an air flow may be provided through a cartridge held by the test fixture 3402 and the outer body gripper.

Further, the controller 417 may be configured to transmit program code instructions to the electronic control component 208 of the cartridge through the third electrical contact 3414 and the control component terminal 206. Accordingly, for example, a heating profile defining when and how much current to apply to the atomizer upon detection of a puff may be written to the electronic control component 208. Additionally, the program code instructions may include an authentication code, which may be employed to verify that the cartridge is authentic. The controller 417 may be further configured to read program code instructions stored on the electronic control component 208 and determine whether the program code instructions stored on the electronic control component correspond to desired program code instructions. For example, reading the stored program code instructions may be employed to ensure that the proper heating profile and authentication code are stored. A unique identifier associated with the electronic control component 208 may also be read therefrom, which may be employed to record information regarding the cartridge (e.g., manufacture date, heater profile, authentication code, etc.) in a database. The controller 417 may also initialize the electronic control component 208 such that the electronic control component directs current to the atomizer upon detection of a first puff, rather than a second puff, which may occur when the electronic control component is not initialized.

FIG. 87 illustrates an embodiment of an electrical test station 3500 that may be included in the inspection subsystem 418 with the second embodiment of the cartridge assembly subsystem 402'. Cartridges may be delivered to the electrical test station 3500 by the above-described inspection robot 1318. In this regard, the inspection robot 1318 may deposit the cartridges on a test fixture 3502. A gripper 3504 may be configured to press and hold the cartridge on a receptacle 3506 of the test fixture 3502. The functionality and structure of the test fixture 3502 may be substantially similar to the above-described test fixture 3402. Accordingly, description thereof will not be repeated. However, the test fixture 3502 may further comprise a slot 3508 positioned on opposing sides of the receptacle 3506. The slot 3508 may be configured to receive a gripper 3510 of a test fixture robot 1320 such that the gripper may grasp beneath the base to remove the cartridge from the receptacle. Accordingly, the gripper 3510 may pull the cartridge off of the receptacle 3506. Note that, as illustrated, an additional test fixture 3500', which may be substantially similar to the test fixture 3500 may be provided in order to increase throughput.

In some embodiments the inspection subsystem 418 may additionally include a quality assurance station. The quality assurance station may be positioned at any point in the assembly process. For example, the quality assurance station may be positioned downstream of the crimper 1118, 2408 that crimps the outer body 216 to the base 204. However, the quality assurance station may be configured to receive partially assembled cartridges in various states of completion. In this regard, the various substations of the cartridge assembly subsystems 402, 402' may be configured to direct the cartridges to quality assurance station in any of the various states of completion occurring during the assembly thereof. Thus, for example, a base 204 with the terminals 206, 234a, 234b coupled thereto may be directed to the quality assurance station without the electronic control component, flow tube, reservoir substrate, and outer body coupled thereto. By way of further example, the carriages 600 of the first embodiment of the cartridge assembly subsystem 402 may skip various stations, and/or some of the robots of the second embodiment of the cartridge assembly subsystem 402' may transfer the partially assembled cartridge to the quality assurance station without performing operations thereon. The partially assembled cartridges directed to the quality assurance station may be inspected manually, or via automated processes, to ensure that the cartridges are being properly assembled. In some embodiments the partially assembled cartridges, defining various states of completion, may be directed to the quality assurance substation at predefined intervals, such that partially assembled cartridges in each of various states of completion, may be regularly inspected.

The inspection subsystem 418 may be configured to dispose of defective cartridges that fail to meet certain predefined standards, as described above. For example, after a partially assembled cartridge is identified as defective in the first embodiment of the cartridge assembly subsystems 402, the carriage 600 holding the defective cartridge may skip the remaining assembly stations and direct the cartridge to a reject station at which the defective cartridge is removed therefrom (e.g., via a vacuum hose) for disposal. By way of further example, after a partially assembled cartridge is identified as defective in the second embodiment of the cartridge assembly subsystems 402', a robot proximate the location at which the cartridge is determined to be defective may drop the defective cartridge in a waste receptacle. For example, FIG. 79 illustrates a receptacle 3600 in a table 3602 supporting the cartridge assembly subsystems 402' in which defective cartridges may be deposited (e.g., following inspection of the terminals 206, 234a, 234b). In this regard, a receptacle may be associated with each location at which the cartridges are inspected such that the defective cartridges may be immediately disposed of.

The inspection subsystem 418 may additionally inspect the cartridges following filling at the cartridge filling subsystem 408, capping at the cartridge capping subsystem 410, and/or labeling at the cartridge labeling subsystem 412. For example, the inspection subsystem 418 may be configured to detect leaks in the cartridge after filling. By way of further example, the inspection subsystem 418 may include a camera over which the filled cartridges are lifted and the captured images may be compared to stored images of known acceptable cartridges that do not have leaks. Additional cameras may ensure that the mouthpiece 220 is properly crimped to the outer body 216. For example, the crimp associated with attachment of the mouthpiece 220 to the outer body 216 may be inspected in substantially the same manner as the crimp employed to attach the base 204 to the outer body. Further, following application of the label 218 to the outer body 216, a camera may inspect the placement of the label to ensure that it is properly positioned.

A method for assembling a cartridge for an aerosol delivery device is also provided. As illustrated in FIG. 88, the method may comprise providing a reservoir substrate extending at least partially about an atomizer at operation 3702. Further, the method may include providing an outer body configured to at least partially receive the reservoir substrate and the atomizer therein at operation 3704. Additionally, the method may include inserting the reservoir substrate through a tool into the outer body, the tool defining a funnel portion configured to reduce an outer dimension of the reservoir substrate such that the outer dimension of the reservoir substrate is less than or equal to an internal dimension of the outer body to facilitate insertion of the reservoir substrate into the outer body at operation 3706.

In some embodiments the method may additionally include twisting the tool relative to the reservoir substrate while inserting the reservoir substrate through the tool into the outer body at operation 3706. Providing the reservoir substrate extending at least partially about the atomizer at operation 3702 may comprise wrapping the reservoir substrate at least partially about the atomizer prior to inserting the reservoir substrate through the tool into the outer body at operation 3706. Wrapping the reservoir substrate at least partially about the atomizer may comprise directing a flow of air at the reservoir substrate.

The method may further comprise engaging the reservoir substrate with one or more fingers such that the reservoir substrate remains at least partially wrapped about the atomizer when beginning to insert the reservoir substrate through the tool into the outer body at operation 3706. Further, the method may include releasing the one or more fingers from the reservoir substrate when the reservoir substrate is inserted to a predetermined depth in the tool. Releasing the one or more fingers may comprise deflecting the one or more fingers away from the reservoir substrate by contacting the one or more fingers with the tool. Further, releasing the one or more fingers may comprise sequentially releasing the fingers. The method may further comprise coupling the atomizer to a base prior to wrapping the reservoir substrate at least partially about the atomizer and coupling the outer body to the base after inserting the reservoir substrate through the tool into the outer body at operation 3706. Additionally, the method may include supplying the reservoir substrate from a substantially continuous reservoir substrate input and controlling a tension in the substantially continuous reservoir substrate input.

A method for assembling an atomizer for an aerosol delivery device is also provided. As illustrated in FIG. 89, the method may include providing a first heating terminal, a second heating terminal, and a heating element at operation 3802. Further, the method may include determining a position of the first heating terminal and the second heating terminal at operation 3804. The method may also include determining a position of the heating element at operation 3806. Additionally, the method may include affixing the heating element to the first heating terminal and the second heating terminal (e.g., such that an electrical connection is established therebetween) based on the position of the first heating terminal and the second heating terminal and the position of the heating element at operation 3808.

Determining the position of the first heating terminal and the second heating terminal at operation 3804 may comprise determining a midpoint between a first heating terminal tab and a second heating terminal tab. The heating element may comprise a first contact portion and a second contact portion, and determining the position of the heating element at operation 3806 may comprise determining a midpoint between the first contact portion and the second contact portion. The method may further comprise aligning the midpoint between the first heating terminal tab and the second heating terminal tab with the midpoint between the first contact portion and the second contact portion, engaging the first contact portion with the first heating terminal tab, and engaging the second contact portion with the second heating terminal tab.

The method may further comprise clamping the first heating terminal and the second heating terminal such that the first heating terminal tab and the second heating terminal tab are substantially coplanar. Clamping the first heating terminal and the second heating terminal may comprise adjusting a spacing between the first heating terminal and the second heating terminal. Affixing the heating element to the first heating terminal and the second heating terminal at operation 3808 may comprise directing a plurality of laser beams at the first heating terminal tab and at the second heating terminal tab. Directing the laser beams at the first heating terminal tab and at the second heating terminal tab may comprise directing the laser beams at a backside of the first heating terminal tab and the second heating terminal tab opposite from the heating element. The method may further comprise inserting the heating element, the first heating terminal, and the second heating terminal into a substantially sealed chamber before directing the laser beams at the first heating terminal tab and at the second heating terminal tab.

Providing the heating element at operation 3802 may comprise supplying the heating element from a substantially continuous heating element input and controlling a tension in the substantially continuous heating element input. The method may further comprise coupling the heating element to a liquid transport element. Coupling the heating element to the liquid transport element may comprise inserting an end of the heating element through the liquid transport element and rotating at least one of the heating element and the liquid transport element such that the heating element winds about the liquid transport element. Providing the first heating terminal and the second heating terminal at operation 3802 may comprise supplying the first heating terminal from a substantially continuous first heating terminal input and supplying the second heating terminal from a substantially continuous second heating terminal input.

In some embodiments the heating element may comprise a wire wound about a liquid transport element. The wire may comprise two contact portions, a center portion, and two outer portions positioned outside of the contact portions, the two contact portions and the center portion of the wire defining the heating element. The contact portions may define a first coil spacing, the center portions may define a second coil spacing, and the outer portions may define a third coil spacing. The third coil spacing may be greater than the second coil spacing and the second coil spacing may be greater than the first coil spacing. Further, affixing the heating element to the first heating terminal and the second heating terminal at operation 3808 may comprise affixing the contact portions to the first heating terminal and the second heating terminal.

A cartridge filling method is also provided. As illustrated in FIG. 90, the method may include providing a cartridge for an aerosol delivery device comprising a reservoir substrate positioned in an outer body at operation 4002. Further, the method may include sequentially positioning an outlet of a filling device in proximity to a plurality of angular portions of the reservoir substrate at operation 4004. The method may additionally include directing a flow of an aerosol precursor composition through the outlet of the filling device at each of the angular portions of the reservoir substrate at operation 4006.

In some embodiments the outlet of the filling device may remain out of contact with the reservoir substrate. Further, the method may include transporting the cartridge between a plurality of filling stations, wherein the flow of the aerosol precursor composition is directed to at least one of the angular portions of the reservoir substrate at each of the filling stations. Additionally, the flow of the aerosol precursor composition may be directed at each of the angular portions of the reservoir substrate at a first one of the filling stations. The flow of the aerosol precursor composition is respectively directed to one of the angular portions of the reservoir substrate at a remainder of the filing stations. The method may further comprise controlling an ambient environment in which the cartridge is filled such that the ambient environment defines a relative humidity of less than about 40%.

A method for assembling a cartridge for an aerosol delivery device is also provided. As illustrated in FIG. 91, the method may include grasping a base at operation 4102. Further, the method may include providing a plurality of components configured to engage the base, the components being provided in a stationary position at operation 4104. Additionally, the method may include coupling the components to the base by directing the base into contact with the components in the stationary position at operation 4106.

Grasping the base at operation 4102 may comprise grasping an internal surface of an attachment end of the base configured to engage a control body. Directing the base into contact with the components in the stationary position at operation 4106 may comprise directing the base downwardly into contact with the components. The method may further comprise inserting the base into a fixture and inspecting a position of first and second heating terminals coupled to the base through the fixture.

As noted above, the system 400 may include a controller 417. The controller 417 may be configured to execute computer code for performing the operations described herein. In this regard, as illustrated in FIG. 92, the controller 417 may comprise a processor 4202 that may be a microprocessor or a controller for controlling the overall operation thereof. In one embodiment the processor 4202 may be particularly configured to perform the functions described herein. The controller 417 may also include a memory device 204. The memory device 4204 may include non-transitory and tangible memory that may be, for example, volatile and/or non-volatile memory. The memory device 4204 may be configured to store information, data, files, applications, instructions or the like. For example, the memory device 4204 could be configured to buffer input data for processing by the processor 4202. Additionally or alternatively, the memory device 4204 may be configured to store instructions for execution by the processor 4202.

The controller 417 may also include a user interface 4206 that allows a user to interact therewith. For example, the user interface 4206 can take a variety of forms, such as a button, keypad, dial, touch screen, audio input interface, visual/image capture input interface, input in the form of sensor data, etc. Still further, the user interface 4206 may be configured to output information to the user through a display, speaker, or other output device. A communication 4208 interface may provide for transmitting and receiving data through, for example, a wired or wireless network 4210 such as a local area network (LAN), a metropolitan area network (MAN), and/or a wide area network (WAN), for example, the Internet.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

As noted above, the controller 417 may be configured to execute computer code for performing the above-described operations. In this regard, an embodiment of a non-transitory computer readable medium for storing computer instructions executed by a processor in a controller (e.g. controller 417) configured assemble a cartridge for an aerosol delivery device is provided. The non-transitory computer readable medium may comprise program code instructions for providing a reservoir substrate extending at least partially about an atomizer; program code instructions for providing an outer body configured to at least partially receive the reservoir substrate and the atomizer therein; and program code instructions for inserting the reservoir substrate through a tool into the outer body, the tool defining a funnel portion configured to reduce an outer dimension of the reservoir substrate such that the outer dimension of the reservoir substrate is less than or equal to an internal dimension of the outer body to facilitate insertion of the reservoir substrate into the outer body.

The computer readable medium may further comprise program code instructions for twisting the tool relative to the reservoir substrate while inserting the reservoir substrate through the tool into the outer body. The program code instructions for providing the reservoir substrate extending at least partially about the atomizer may comprise program code instructions for wrapping the reservoir substrate at least partially about the atomizer prior to inserting the reservoir substrate through the tool into the outer body. The program code instructions for wrapping the reservoir substrate at least partially about the atomizer may comprise program code instructions for directing a flow of air at the reservoir substrate. The computer readable medium may further comprise program code instructions for engaging the reservoir substrate with one or more fingers such that the reservoir substrate remains at least partially wrapped about the atomizer when beginning to insert the reservoir substrate through the tool into the outer body. The computer readable medium may further comprise program code instructions for releasing the one or more fingers from the reservoir substrate when the reservoir substrate is inserted to a predetermined depth in the tool. The program code instructions for releasing the one or more fingers may comprise program code instructions for deflecting the one or more fingers away from the reservoir substrate by contacting the one or more fingers with the tool. The program code instructions for releasing the one or more fingers may comprise program code instructions for sequentially releasing the fingers. The computer readable medium may further comprise program code instructions for coupling the atomizer to a base prior to wrapping the reservoir substrate at least partially about the atomizer; and program code instructions for coupling the outer body to the base after inserting the reservoir substrate through the tool into the outer body. The computer readable medium may further comprise program code instructions for supplying the reservoir substrate from a substantially continuous reservoir substrate input; and program code instructions for controlling a tension in the substantially continuous reservoir substrate input.

In an additional embodiment, a non-transitory computer readable medium for storing computer instructions executed by a processor in a controller (e.g. controller 417) configured to assemble an atomizer for an aerosol delivery device may comprise program code instructions for providing a first heating terminal, a second heating terminal, and a heating element; program code instructions for determining a position of the first heating terminal and the second heating terminal; program code instructions for determining a position of the heating element; and program code instructions for affixing the heating element to the first heating terminal and the second heating terminal based on the position of the first heating terminal and the second heating terminal and the position of the heating element. The program code instructions for determining the position of the first heating terminal and the second heating terminal may comprise program code instructions for determining a midpoint between a first heating terminal tab and a second heating terminal tab.

In some embodiments the heating element may comprise a first contact portion and a second contact portion, and the program code instructions for determining the position of the heating element may comprise program code instructions for determining a midpoint between the first contact portion and the second contact portion. The computer readable medium may further comprise program code instructions for aligning the midpoint between the first heating terminal tab and the second heating terminal tab with the midpoint between the first contact portion and the second contact portion; program code instructions for engaging the first contact portion with the first heating terminal tab; and program code instructions for engaging the second contact portion with the second heating terminal tab. The computer readable medium may additionally include program code instructions for clamping the first heating terminal and the second heating terminal such that the first heating terminal tab and the second heating terminal tab are substantially coplanar. The program code instructions for clamping the first heating terminal and the second heating terminal may comprise program code instructions for adjusting a spacing between the first heating terminal and the second heating terminal. The program code instructions for affixing the heating element to the first heating terminal and the second heating terminal may comprise program code instructions for directing a laser beam at the first heating terminal tab and at the second heating terminal tab. The program code instructions for directing the laser beam at the first heating terminal tab and at the second heating terminal tab may comprise program code instructions for directing the laser beam at a backside of the first heating terminal tab and the second heating terminal tab opposite from the heating element. The computer readable medium may further comprise program code instructions for inserting the heating element, the first heating terminal, and the second heating terminal into a substantially sealed chamber before directing the laser beam at the first heating terminal tab and at the second heating terminal tab. The program code instructions for providing the heating element may comprise program code instructions for supplying the heating element from a substantially continuous heating element input; and program code instructions for controlling a tension in the substantially continuous heating element input. The computer readable medium may further comprise program code instructions for coupling the heating element to a liquid transport element. The program code instructions for coupling the heating element to the liquid transport element may comprise program code instructions for inserting an end of the heating element through the liquid transport element; and program code instructions for rotating at least one of the heating element and the liquid transport element such that the heating element winds about the liquid transport element. The program code instructions for providing the first heating terminal and the second heating terminal may comprise program code instructions for supplying the first heating terminal from a substantially continuous first heating terminal input; and program code instructions for supplying the second heating terminal from a substantially continuous second heating terminal input. The heating element may comprise a wire wound about a liquid transport element. The wire may comprise two contact portions, a center portion, and two outer portions positioned outside of the contact portions, the two contact portions and the center portion of the wire may define the heating element, wherein the contact portions define a first coil spacing, the center portion defines a second coil spacing, and the outer portions define a third coil spacing, the third coil spacing being greater than the second coil spacing and the second coil spacing being greater than the first coil spacing, and wherein affixing the heating element to the first heating terminal and the second heating terminal comprises affixing the contact portions to the first heating terminal and the second heating terminal.

In an additional embodiment, a non-transitory computer readable medium for storing computer instructions executed by a processor in a controller (e.g. controller 417) configured to fill a cartridge may comprise program code instructions for providing a cartridge for an aerosol delivery device comprising a reservoir substrate positioned in an outer body; program code instructions for sequentially positioning an outlet of a filling device in proximity to a plurality of angular portions of the reservoir substrate; and program code instructions for directing a flow of an aerosol precursor composition through the outlet of the filling device at each of the angular portions of the reservoir substrate. The outlet of the filling device may remain out of contact with the reservoir substrate. The computer readable medium may further comprise program code instructions for transporting the cartridge between a plurality of filling stations, wherein the flow of the aerosol precursor composition is directed to at least one of the angular portions of the reservoir substrate at each of the filling stations. The flow of the aerosol precursor composition may be directed at each of the angular portions of the reservoir substrate at a first one of the filling stations. The flow of the aerosol precursor composition may be respectively directed to one of the angular portions of the reservoir substrate at a remainder of the filing stations. The computer readable medium may further comprise program code instructions for controlling an ambient environment in which the cartridge is filled such that the ambient environment defines a relative humidity of less than about 40%.

In an additional embodiment, a non-transitory computer readable medium for storing computer instructions executed by a processor in a controller (e.g. controller 417) configured to assemble a cartridge for an aerosol delivery device may comprise program code instructions for grasping a base; program code instructions for providing a plurality of components configured to engage the base, the components being provided in a stationary position; and program code instructions for coupling the components to the base by directing the base into contact with the components in the stationary position. The program code instructions for grasping the base may comprise program code instructions for grasping an internal surface of an attachment end of the base configured to engage a control body. The program code instructions for directing the base into contact with the components in the stationary position may comprise program code instructions for directing the base downwardly into contact with the components. The computer readable medium may further comprise program code instructions for inserting the base into a fixture; and program code instructions for inspecting a position of first and second heating terminals coupled to the base through the fixture.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A method for assembling a cartridge for an aerosol delivery device, the method comprising:
    wrapping a reservoir substrate at least partially about an atomizer;
    providing an outer body configured to at least partially receive the reservoir substrate and the atomizer therein;
    and inserting the reservoir substrate and the atomizer through a tool into the outer body, the tool defining a funnel portion configured to reduce an outer dimension of the reservoir substrate such that the outer dimension of the reservoir substrate is less than or equal to an internal dimension of the outer body to facilitate insertion of the reservoir substrate into the outer body;
    the method further comprising engaging the reservoir substrate with one or more fingers such that the reservoir substrate remains at least partially wrapped about the atomizer when beginning to insert the reservoir substrate through the tool into the outer body; and
    releasing the one or more fingers from the reservoir substrate when the reservoir substrate is inserted to a predetermined depth in the tool, wherein releasing the one or more fingers comprises deflecting the one or more fingers away from the reservoir substrate by contacting the one or more fingers with the tool.

2. The method of claim 1, further comprising twisting the tool relative to the reservoir substrate while inserting the reservoir substrate through the tool into the outer body.

3. The method of claim 1, wherein wrapping the reservoir substrate at least partially about the atomizer comprises directing a flow of air at the reservoir substrate.

4. The method of claim 1, further comprising coupling the atomizer to a base prior to wrapping the reservoir substrate at least partially about the atomizer; and coupling the outer body to the base after inserting the reservoir substrate through the tool into the outer body.

5. The method of claim 1, further comprising supplying the reservoir substrate from a substantially continuous reservoir substrate input; and controlling a tension in the substantially continuous reservoir substrate input.

6. A method for assembling a cartridge for an aerosol delivery device, the method comprising:

wrapping a reservoir substrate at least partially about an atomizer;

providing an outer body configured to at least partially receive the reservoir substrate and the atomizer therein;

and inserting the reservoir substrate and the atomizer through a tool into the outer body, the tool defining a funnel portion configured to reduce an outer dimension of the reservoir substrate such that the outer dimension of the reservoir substrate is less than or equal to an internal dimension of the outer body to facilitate insertion of the reservoir substrate into the outer body;

the method further comprising engaging the reservoir substrate with fingers such that the reservoir substrate remains at least partially wrapped about the atomizer when beginning to insert the reservoir substrate through the tool into the outer body; and sequentially releasing the fingers from the reservoir substrate when the reservoir substrate is inserted to a predetermined depth in the tool.

* * * * *